US008969325B2

(12) United States Patent
Dart et al.

(10) Patent No.: US 8,969,325 B2
(45) Date of Patent: Mar. 3, 2015

(54) TRPV1 ANTAGONISTS

(71) Applicant: AbbVie Inc., North Chicago, IL (US)

(72) Inventors: Michael J. Dart, Highland Park, IL (US); Philip R. Kym, Libertyville, IL (US); Eric A. Voight, Pleasant Prarie, WI (US); Anurupa Shrestha, Gurnee, IL (US); Jerome F. Daanen, Racine, WI (US); Tammie K. Jinkerson, Pleasant Prairie, WI (US); Ryan G. Keddy, Beach Park, IL (US); Sridhar Peddi, Schaumburg, IL (US); Arthur Gomtsyan, Vernon Hills, IL (US); Michael E. Kort, Lake Bluff, IL (US); Gregory A. Gfesser, Lindenhurst, IL (US); Kevin R. Woller, Antioch, IL (US); Derek W. Nelson, Highland Park, IL (US)

(73) Assignee: AbbVie Inc., North Chicago, IL (US)

( * ) Notice: Subject to any disclaimer, the term of this patent is extended or adjusted under 35 U.S.C. 154(b) by 72 days.

(21) Appl. No.: 13/716,862

(22) Filed: Dec. 17, 2012

(65) Prior Publication Data
US 2013/0172334 A1     Jul. 4, 2013

Related U.S. Application Data

(60) Provisional application No. 61/577,394, filed on Dec. 19, 2011, provisional application No. 61/704,823, filed on Sep. 24, 2012.

(51) Int. Cl.
C07D 405/12    (2006.01)
C07D 215/38    (2006.01)
C07D 239/80    (2006.01)
C07D 413/12    (2006.01)
C07D 491/052   (2006.01)
A61K 31/192    (2006.01)
A61K 31/4704   (2006.01)
A61K 31/4709   (2006.01)
A61K 31/517    (2006.01)
A61K 31/538    (2006.01)
A61K 45/06     (2006.01)
C07D 413/14    (2006.01)
C07D 215/227   (2006.01)
C07D 265/36    (2006.01)

(52) U.S. Cl.
CPC ............ C07D 405/12 (2013.01); C07D 413/14 (2013.01); C07D 215/227 (2013.01); C07D 239/80 (2013.01); C07D 413/12 (2013.01); C07D 491/052 (2013.01); C07D 265/36 (2013.01); A61K 31/192 (2013.01); A61K 31/4704 (2013.01); A61K 31/4709 (2013.01); A61K 31/517 (2013.01); A61K 31/538 (2013.01); A61K 45/06 (2013.01); C07D 215/38 (2013.01)

USPC .......... 514/105; 544/230; 544/284; 544/286; 544/70; 546/15; 546/157; 514/230.5; 514/266.21; 514/266.24; 514/266.3; 514/278; 514/312

(58) Field of Classification Search
None
See application file for complete search history.

(56) References Cited

U.S. PATENT DOCUMENTS

| | | | |
|---|---|---|---|
| 6,353,011 | B1 | 3/2002 | Pershadsingh et al. |
| 6,993,311 | B2 | 1/2006 | Li et al. |
| 7,015,233 | B2 | 3/2006 | Gomtsyan et al. |
| 7,375,126 | B2 | 5/2008 | Gomtsyan et al. |
| 7,504,520 | B2 | 3/2009 | Gomtsyan et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 7,622,493 | B2 | 11/2009 | Brown et al. |

(Continued)

FOREIGN PATENT DOCUMENTS

EP    2128157 A1    7/2008
JP    201037422 A   2/2010

(Continued)

OTHER PUBLICATIONS

Apostolidis, A. et al., "Capsaicin Receptor TRPV1 in Urothelium of Neurogenic Human Bladders and Effect of Intravesical Resiniferatoxin," Urology, 65(2): 400-405 (2005).
Barone, F. C. et al., "Brain Cooling During Transient Focal Ischemia Provides Complete Neuroprotection," Neurosci. Biobehav. Rev., 21(1): 31-44 (1997).
Bernard, S. A. et al., "Treatment of Comatose Survivors of Out-of-Hospital Cardiac Arrest With Induced Hypothermia," N. Engl. J. Med., 346(8): 557-563 (2002).
Beylot, M. et al., "In vivo Studies of Intrahepatic Metabolic Pathways," Diabetes & Metabolism (Paris), 23: 251-257 (1997).

(Continued)

Primary Examiner — James D Anderson

(57) ABSTRACT

Disclosed herein are compounds of formula (I):

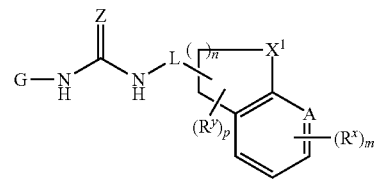

or pharmaceutically acceptable salts thereof, wherein $X^1$, L, $R^x$, $R^y$, G, Z, A, m, n, and p are as defined in the specification. Compositions comprising such compounds and methods for treating conditions and disorders using such compounds and compositions are also disclosed.

31 Claims, No Drawings

(56) References Cited

U.S. PATENT DOCUMENTS

| | | | |
|---|---|---|---|
| 7,875,627 | B2 | 1/2011 | Turner et al. |
| 7,910,751 | B2 | 3/2011 | Uchida et al. |
| 7,998,982 | B2 | 8/2011 | Vasudevan et al. |
| 8,026,256 | B2 | 9/2011 | Gomtsyan et al. |
| 8,084,616 | B2 | 12/2011 | Gomtsyan et al. |
| 2003/0109700 | A1 | 6/2003 | Ksander |
| 2006/0128689 | A1 | 6/2006 | Gomtsyan et al. |
| 2007/0099954 | A1 | 5/2007 | Gomtsyan et al. |
| 2008/0153871 | A1 | 6/2008 | Bayburt et al. |
| 2008/0287676 | A1 | 11/2008 | Gomtsyan et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |
| 2009/0137457 | A1 | 5/2009 | Harbeson |
| 2010/0016285 | A1 | 1/2010 | Uchida et al. |
| 2012/0245163 | A1 | 9/2012 | Gomtsyan et al. |
| 2013/0158067 | A1 | 6/2013 | Woller et al. |

FOREIGN PATENT DOCUMENTS

| | | |
|---|---|---|
| JP | 2011201777 A | 10/2011 |
| WO | 9507271 A1 | 3/1995 |
| WO | 9710223 A1 | 3/1997 |
| WO | 03097586 A1 | 11/2003 |
| WO | 2004046133 A1 | 6/2004 |
| WO | 2005016915 A1 | 2/2005 |
| WO | 2005040100 A1 | 5/2005 |
| WO | 2005099353 A2 | 10/2005 |
| WO | 2006008754 A1 | 1/2006 |
| WO | 2006065484 A2 | 6/2006 |
| WO | 2007010383 A1 | 1/2007 |
| WO | 2007042906 A1 | 4/2007 |
| WO | 2007121299 A2 | 10/2007 |
| WO | 2008040360 A2 | 4/2008 |
| WO | 2008040361 A2 | 4/2008 |
| WO | 2008059339 A2 | 5/2008 |
| WO | 2008079683 A2 | 7/2008 |
| WO | 2008091021 A1 | 7/2008 |
| WO | 2008110863 A1 | 9/2008 |
| WO | 2010004401 A1 | 1/2010 |
| WO | 2010010935 A1 | 1/2010 |
| WO | 2010016285 A1 | 2/2010 |
| WO | 2010045401 A1 | 4/2010 |
| WO | 2010045402 A1 | 4/2010 |

OTHER PUBLICATIONS

Blagojevic, N. et al., "Role of Heavy Water in Boron Neutron Capture Therapy," Dosimetry & Treatment Planning for Neutron Capture Therapy, Editors R. Zamenhof, G. Solares and O. Harling, Advanced Medical Publishing, Madison, WI. pp. 125-134 (1994).
Blake, M. I. et al., "Studies With Deuterated Drugs," J. Pharm. Sci. 64(3): 367-391 (1975).
Brickner, S. J. et al., "Synthesis and Antibacterial Activity of U-100592 and U-100766, Two Oxazolidinone Antibacterial Agents for the Potential Treatment of Multidrug-Resistant Gram-Positive Bacterial Infections," J Med Chem, 39(3): 673-679 (1996).
Burgard, A. et al., "Asymmetric synthesis of 4-amino-3,4-dihydro-2,2-dimethyl-2H-1-benzopyrans," Tetrahedron, 55(24): 7555-7562 (1999).
Caterina, M. J. et al., "The Vanilloid Receptor: A Molecular Gateway to the Pain Pathway," Annu. Rev. Neurosci., 24: 487-517 (2001).
Caterina, M. J. et al., "Impaired Nociception and Pain Sensation in Mice Lacking the Capsaicin Receptor," Science, 288(5464): 306-313 (2000).
Caterina, M. J. et al., "The Capsaicin Receptor: A Heat-Activated Ion Channel in the Pain Pathway," Nature, 389(6653): 816-824 (1997).
Coimbra, C. et al., "Moderate Hypothermia Mitigates Neuronal Damage in the Rat Brain When Initiated Several Hours Following Transient Cerebral Ischemia," Acta Neuropathol. 87(4): 325-331 (1994).
Colbourne, F. et al., "Prolonged but Delayed Postischemic Hypothermia: A Long-term Outcome Study in the Rat Middle Cerebral Artery Occlusion Model," J. Cereb. Blood Flow Metab., 20(1-2): 1702-1708 (2000).
Corey, E. J. et al., "An Efficient and Catalytically Enantioselective Route to (S)-(−)-Phenyloxirane" J. Org. Chem., 53(12): 2861-2863 (1988).
Cross, L. C. et al., "IUPAC 1974 Recommendations for Section E, Fundamental Stereochemistry," Pure Appl. Chem., 45: 13-30 (1976).
Czajka, D. M. et al., "Effect of Deuterium Oxide on the Reproductive Potential of Mice," Ann. N.Y. Acad. Sci., 84: 770-779 (1960).
Czajka, D. M. et al., "Physiological Effects of Deuterium on Dogs," Am. J. Physiol., 201(2): 357-362 (1961).
Davis, J. et al., "Vanilloid Receptor-1 is Essential for Inflammatory Thermal Hyperalgesia," Nature, 405: 183-187 (2000).
Fernihough, J. et al. "Regulation of Calcitonin Gene-Related Peptide and TRPV1 in a Rat Model of Osteoarthritis," Neurosci. Lett., 388(2): 75-80 (2005).
Foster, Allan B. "Deuterium Isotope Effects in the Metabolism of Drugs and Xenobiotics: Implications of Drug Design," Advances in Drug Research, vol. 14, pp. 2-36 (Bernard Testa, Editor), Academic press, London, 1985.
Garami, A. et al., "Contributions of Different Modes of TRPV1 Activation to TRPV1 Antagonist-Induced Hyperthermia" J. Neurosci., 30(4): 1435-1440 (2010).
Garrett, C. E. et al., "The Enantioselective Reduction of 2'-Fluoroacetophenone Utilizing a Simplified CBS-Reduction Procedure," Tetrahedron Asymmetry, 13(13): 1347-1349 (2002).
Gavva, N. R. et al., "Pharmacological Blockade of the Vanilloid Receptor TRPV1 Elicits Marked Hyperthermia in Humans" Pain, 136(1-2): 202-210 (2008).
Gavva, N. R. et al., "Repeated Administration of Vanilloid Receptor TRPV1 Antagonists Attenuates Hyperthermia Elicited by TRPV1 Blockade" J. Pharmacol. Exp. Ther., 323(1): 128-137 (2007).
Gavva, N. R. et al., "The Vanilloid Receptor TRPV1 is Tonically Activated in vivo and Involved in Body Temperature Regulation" J. Neurosci., 27(13): 3366-3374 (2007).
Geppetti, P. et al., "The Transient Receptor Potential Vanilloid 1: Role in Airway Inflammation and Disease," Eur. J. Pharmacol., 533(1-3): 207-214 (2006).
Gilchrist, H. D. et al., "Enhanced Withdrawal Responses to Heat and Mechanical Stimuli Following Intraplantar Injection of Capsaicin in Rats," Pain, 67(1): 179-188 (1996).
Gololobov, Yu. G. et al. "Sixty Years of Staudinger Reaction," Tetrahedron, 37(3): 437-72 (1981).
Gomtsyan, A. et al., "Identification of (R)-1-(5-tert-Butyl-2,3-dihydro-1H-inden-1-yl)-3-(1H-indazol-4-yl)urea (ABT-102) as a Potent TRPV1 Antagonist for Pain Management," J. Med. Chem, 2008, 51(3):392-395.
Greene, T. et al., Editor, Protective Groups in Organic Synthesis (3rd ed.), John Wiley & Sons, NY (1999), (20 pages, Table of Contents).
Grennan, D. M. et al., "Rheumatoid Arthritis," Textbook of Pain, 3$^{rd}$ Ed., Patrick Wall et al. Editors, Churchill Livingstone, pp. 397-407 (1994).
Hayes, P. et al. "Cloning and functional expression of a human orthologue of rat vanilloid receptor-1," Pain, 88(2): 205-215 (2000).
Higuchi, T. et al., "Pro-drugs as Novel Delivery Systems," vol. 14 of the A.C.S. Symposium Series; American Chemical Society, Washington, DC, 1975. (13 pages, Table of Contents).
Hogue, J. H. et al., "Pathophysiology and First-Line Treatment of Osteoarthritis," Ann. Pharmacother., 36(4): 679-686 (2002).
Holzer, M. et al., "Mild Therapeutic Hypothermia to Improve the Neurologic Outcome After Cardiac Arrest," N. Engl. J. Med., 346(8): 549-556 (2002).
Honore, P. et al., "A-425619 [1-isoquinolin-5-yl-3-(4-trifluoromethyl-benzyl)-urea], A Novel Transient Receptor Potential Type V1 Receptor Antagonist, Relieves Pathophysiological Pain Associated With Inflammation and Tissue Injury in Rats," J. Pharmacol. Exp. Ther., 314(1): 410-421 (2005).
Iida, T. et al., "Attenuated Fever Response in Mice Lacking TRPV1" Neurosci. Lett., 378(1): 28-33 (2005).

(56) References Cited

OTHER PUBLICATIONS

International Search Report and Written Opinion for International Application No. PCT/US2012/070159 dated Feb. 18, 2013 (13 pages).
Jia, Y. et al., "Anandamide Induces Cough in Conscious Guinea-Pigs Through VR1 Receptors," Br. J. Pharmacol., 137(6): 831-836 (2002).
Kato, S. et al., "Synthesis of Deuterated Mosapride Citrate," J. Labeled Comp. Radiopharmaceut., 36(10): 927-932 (1995).
Kawai, N. et al., "Effects of delayed intraischemic and postischemic hypothermia on a focal model of transient cerebral ischemia in rats," Stroke, 31: 1982-89; discussion 1989 (2000).
Kawanami, S. et al., "Practical Enantioselective Reduction of Ketones Using Oxazaborolidine Catalyst Generated in Situ From Chiral Lactam Alcohol and Borane," Tetrahedron, 59(42): 8411-8414 (2003).
Kort, M. E. et al., "2 TRPV1 Antagonists: Clinical Setbacks and Prospects for Future Development," Progress in Medicinal Chemistry, vol. 51, pp. 57-70, G. Lawton and D.R. Witty Editors, Elsevier B.V., (2012).
Kushner, D. J. et al., "Pharmacological Uses and Perspectives of Heavy Water and Deuterated Compounds," Can. J. Physiol. Pharmacol., 77(2): 79-88 (1999).
Lehto, S. G. et al., "Antihyperalgesic effects of (R,E)-N-(2-hydroxy-2,3-dihydro-1H-inden-4-yl)-3-(2-(piperidin-1-yl)-4-(trifluoromethyl)phenyl)-acrylamide (AMG8562), A Novel Transient Receptor Potential Vanilloid Type 1 Modulator That Does Not Cause Hyperthermia in Rats" J. Pharmacol. Exp. Ther., 326(1): 218-229 (2008).
Levine, J. et al., "Inflammatory Pain," Textbook of Pain, $3^{rd}$ Ed., Patrick Wall et al. Editors, Churchill Livingstone, pp. 45-56 (1994).
Lizondo, J et al., "Linezolid-Oxazolidinone Antibacterial" Drugs Future, 21(11): 1116-1123 (1996).
Maier, C. M. et al., "Delayed Induction and Long-Term Effects of Mild Hypothermia in a Focal Model of Transient Cerebral Ischemia: Neurological Outcome and Infarct Size," J. Neurosurg., 94(1): 90-96 (2001).
Maier, C. M. et al., "Optimal Depth and Duration of Mild Hypothermia in a Focal Model of Transient Cerebral Ischemia: Effects on Neurologic Outcome, Infarct Size, Apoptosis, and Inflammation," Stroke, 29: 2171-2180 (1998).
Mallesham, B et al., "Highly Efficient Cui-Catalyzed Coupling of Aryl Bromides With Oxazolidinones Using Buchwald's Protocol: A Short Route to Linezolid and Toloxatone," Org Lett, 5(7): 963-965 (2003).
Marsch, R. et al., "Reduced Anxiety, Conditioned Fear, and Hippocampal Long-Term Potentiation in Transient Receptor Potential Vanilloid Type 1 Receptor-Deficient Mice," J. Neurosci., 27(4): 832-839 (2007).
McCarthy, C. et al., "Osteoarthritis," Textbook of Pain, $3^{rd}$ Ed., Patrick Wall et al. Editors, Churchill Livingstone, pp. 387-395 (1994).
Meyer, R. A. et al., "Peripheral Neural Mechanisms of Nociception," Textbook of Pain, $3^{rd}$ Ed., Patrick Wall et al. Editors, Churchill Livingstone, pp. 13-44 (1994).
Millan, Mark J. "The Induction of Pain: An Integrative Review," Prog. Neurobiol., 57: 1-164 (1999). (Uploaded in 2 parts due to size).
Murata, Y. et al., "Peripheral and Central Distribution of TRPV1, Substance P and CGRP of Rat Corneal Neurons," Brain Res., 1085(1): 87-94 (2006).
Nolano, M. et al., "Topical Capsaicin in Humans: Parallel Loss of Epidermal Nerve Fibers and Pain Sensation," Pain, 81(1-2): 135-145 (1999).
Onesti, S. T. et al., "Transient Hypothermia Reduces Focal Ischemic Brain Injury in the Rat," Neurosurgery, 29(3): 369-373 (1991).
Ooboshi, H. et al., "Hypothermia Inhibits Ischemia-Induced Efflux of Amino Acids and Neuronal Damage in the Hippocampus of Aged Rats," Brain Res., 884(1): 23-30 (2000).
Prescott, David M., Editor, Methods in Cell Biology, vol. XIV, Academic Press, New York, N. Y., (1976), (12 pages, Table of Contents).
Reilly, R. M. et al., "Pharmacology of Modality-Specific Transient Receptor Potential Vanilloid-1 Antagonists That Do Not Alter Body Temperature," Journal of Pharmacology and Experimental Therapeutics, 342(2): 416-428 (2012).
Roche, Edward B., Editor, Bioreversible Carriers in Drug Design, American Pharmaceutical Association and Pergamon Press (1987), (4 pages, Table of Contents).
Sappington, R. M. et al., "TRPV1: Contribution to Retinal Ganglion Cell Apoptosis and Increased Intracellular Ca2+ With Exposure to Hydrostatic Pressure," Invest. Ophthalmol. Vis. Sci., 50(2): 717-728 (2009).
Steiner, A. A. et al., "Nonthermal Activation of Transient Receptor Potential Vanilloid-1 Channels in Abdominal Viscera Tonically Inhibits Autonomic Cold-Defense Effectors" J. Neurosci., 27(28): 7459-7468 (2007).
Suri, A. et al., "The Emerging Role of TRPV1 in Diabetes and Obesity," Trends Pharmacol. Sci., 29(1): 29-36 (2008).
Swanson, D. M. et al., "Identification and Biological Evaluation of 4-(3-trifluoromethylpyridin-2-yl)piperazine-1-carboxylic acid (5-trifluoromethylpyridin-2-yl)amide, a High Affinity TRPV1 (VR1) Vanilloid Receptor Antagonist" J. Med. Chem., 48(6): 1857-1872 (2005).
Szallasi, A. et al., "The Vanilloid Receptor TRPV1: 10 Years From Channel Cloning to Antagonist Proof-of-Concept" Nature Rev., 6: 357-373 (2007).
Tamayo, N. et al., "Design and Synthesis of Peripherally Restricted Transient Receptor Potential Vanilloid 1 (TRPV1) Antagonists" J. Med. Chem., 51(9): 2744-2757 (2008).
Tanuwidjaja, J. et al. "One-Pot Asymmetric Synthesis of Either Diastereomer of Tert-Butanesulfinyl-Protected Amines From Ketones," J. Org. Chem., 72(2): 626-629 (2007).
Thomson J. F., "Physiological Effects of D20 in Mammals," Ann. NY Acad. Sci., 84: 736-744 (1960).
Tzavara, E. et al., "Endocannabinoids Activate Transient Receptor Potential Vanilloid 1 Receptors to Reduce Hyperdopaminergia-Related Hyperactivity: Therapeutic Implications," Biol. Psych., 59: 508-515 (2006).
Voight, E. A. et al., "Transient receptor potential vanilloid-1 antagonists: a survey of recent patent literature," Expert Opinion Ther. Patents, 20(9): 1107-1122 (2010).
Voight, E. A. et al., "Efficient and General Asymmetric Synthesis of (R)-chroman-4-amine Salts," Tetrahedron Letters, 2010, 51(45): 5904-5907.
Watanabe N. et al , "Immunohistochemical Localization of Vanilloid Receptor Subtype 1 (TRPV1) in the Guinea Pig Respiratory System," Pulmonary Pharmacol. Ther., 18(3): 187-197 (2005).
Woolf, C. J. et al., "Neuronal Plasticity: Increasing the Gain in Pain," Science, 288(5472): 1765-1768 (2000).
Woolf, C. J. et al., "Implications of Recent Advances in the Understanding of Pain Pathophysiology for the Assessment of Pain in Patients," Pain Supp., 82(6): S141-S147 (1999).
Woolf, C. J. et al. "Neuropathic Pain: Aetiology, Symptoms, Mechanisms, and Management," Lancet, 353(9168): 1959-1964 (1999).
Yamashita, K. et al., "Mild Hypothermia Ameliorates Ubiquitin Synthesis and Prevents Delayed Neuronal Death in the Gerbil Hippocampus," Stroke, 22(12): 1574-1581 (1991).
Zhang, Y. et al., "The Effect of Intraischemic Mild Hypothermia on Focal Cerebral Ischemia/Reperfusion Injury," Acta Anaesthesiol. Sin., 39(2): 65-69 (2001).
Zhang, F. et al., "Transient Receptor Potential Vanilloid 1 Activation Induces Inflammatory Cytokine Release in Corneal Epithelium Through MAPK Signaling," J. Cell. Physiol., 213(3): 730-739 (2007).

TRPV1 ANTAGONISTS

CROSS REFERENCE TO RELATED APPLICATIONS

This application claims priority to U.S. Provisional Application No. 61/577,394 filed Dec. 19, 2011, and U.S. Provisional Application No. 61/704,823 filed Sep. 24, 2012, which are incorporated herein by reference in their entirety.

TECHNICAL FIELD

Described herein are ureas which are useful for treating pain, cough, bladder overactivity, urinary incontinence, or conditions and disorders modulated by the TRPV1 channel. Pharmaceutical compositions comprising said compounds and methods for treating pain, diabetic neuropathy, cough, asthma, bladder overactivity, urinary incontinence, anxiety, or conditions and disorders modulated by the TRPV1 channel are also included.

BACKGROUND

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as the transient receptor potential vanilloid-1 (TRPV1). TRPV1 is also known as vanilloid receptor-1 (VR1). The intradermal administration of capsaicin is characterized by an initial burning or hot sensation followed by a prolonged period of analgesia. The analgesic component of the TRPV1 receptor activation is thought to be mediated by a capsaicin-induced desensitization of the primary sensory afferent terminal. Thus, the long lasting anti-nociceptive effect of capsaicin has prompted the clinical use of capsaicin analogs as analgesic agents. Further, capsazepine, a capsaicin receptor antagonist, can reduce inflammation-induced hyperalgesia in animal models. TRPV1 receptors are also localized on sensory afferents, which innervate the bladder. Capsaicin or resiniferatoxin have been shown to ameliorate incontinence symptoms upon injection into the bladder.

The TRPV1 receptor has been called a "polymodal detector" of noxious stimuli since it can be activated in several ways. The receptor channel is activated by capsaicin and other vanilloids, and thus is classified as a ligand-gated ion channel. The TRPV1 receptor activation by capsaicin can be blocked by the competitive TRPV1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the TRPV1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The TRPV1 (−/−) mice also did not show reduced sensitivity to nerve injury-induced mechanical or thermal nociception. However, the TRPV1 knock-out mice were insensitive to the noxious effects of intradermal capsaicin, exposure to intense heat (50-55° C.), and failed to develop thermal hyperalgesia following the intradermal administration of carrageenan.

In the course of characterizing analgesic properties of structurally distinct TRPV1 antagonists, multiple investigators have observed core body temperature elevating ("hyperthermic") attributes of these compounds in rodent behavioral models of pain (Swanson, D. M. et al., *J. Med. Chem.*, 2005, 48, 1857; Gavva, N. R. et al., *J. Pharmacol. Exp. Ther.*, 2007, 323, 128; Steiner, A. A. et al., *J. Neurosci.*, 2007, 27, 7459; Tamayo, N. et al., *J. Med. Chem.*, 2008, 51, 2744; Gavva, N. R. et al., *J. Neurosci.*, 2007, 27, 3366). Often modest (0.5° C.), the associated temperature elevation can be considerably more robust (1-2° C.), and also has been reported preclinically in dogs and monkeys (Gavva, N. R. et al., *J. Pharmacol. Exp. Ther.*, 2007, 323, 128; Gavva, N. R. et al., *J. Neurosci.*, 2007, 27, 3366) and in human subjects in the course of clinical trials (Gavva, N. R. et al., *Pain*, 2008, 136, 202). These effects have the potential to be self-limiting; they are generally transient and attenuate with repeat dosing (Gavva, N. R. et al., *J. Pharmacol. Exp. Ther.*, 2007, 323, 128). The temperature effects are considered to be mechanism based (Iida, T. et al., *Neurosci. Lett.*, 2005, 378, 28) since TRPV1 null mice show no deficits in thermoregulation, even when dosed with antagonists that elevate temperature in wild-type mice (Steiner, A. A. et al., *J. Neurosci.*, 2007, 27, 7459; Garami, A. et al., *J. Neurosci.*, 2010, 30, 1435).

Efforts to understand and separate the nociceptive and thermoregulatory functions of TRPV1 have led to directed research to identify antagonists that afford analgesic benefit without affecting core body temperature (Lehto, S. G. et al., *J. Pharmacol. Exp. Ther.*, 2008, 326, 218) or imparting insensitivity to noxious heat, as observed in TRPV1 null mice (Caterina, M. J. et al., *Science*, 2000, 288, 306).

Certain chromane and indane derivatives that are TRPV1 modulators are reported in the following publications: WO 2005/040100, WO 2007/042906, WO 2008/059339, US 2006/0128689, WO 2007/121299, US 2008/0153871, WO 2008/110863, WO 2008/091021, WO 2007/010383, WO 2010/010935, WO 2010/045401, WO 2010/045402, U.S. Pat. No. 7,375,126, U.S. Pat. No. 7,015,233, U.S. Pat. No. 8,026,256, US 2008/0287676, and US 2007/0099954.

We describe herein certain TRPV1 antagonists that have little or no significant effect on the sensation of noxious heat.

SUMMARY OF THE INVENTION

One aspect is directed towards compounds of formula (I) or pharmaceutical salts, solvates, salts of solvates, or solvates of salts thereof,

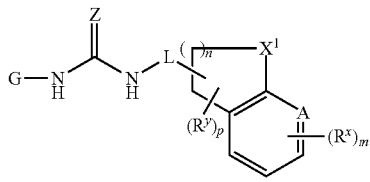

wherein
G is formula (i), (ii), or (iii)

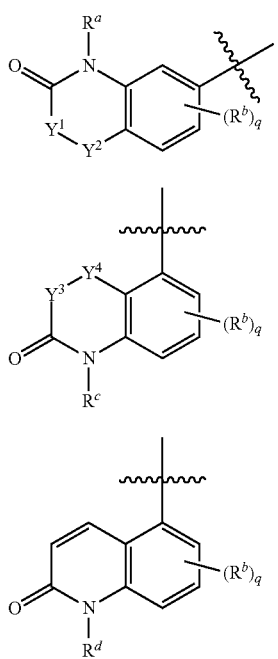

$R^a$ is hydrogen or alkyl;
$Y^1$ is $CH_2$ and $Y^2$ is O; or
$Y^1$ is $CR^{1a}R^{1b}$, and $Y^2$ is $CH_2$; wherein $R^{1a}$ is hydrogen, and $R^{1b}$ is hydrogen or $NR^{1c}R^{1d}$ wherein $R^{1c}$ is hydrogen or alkyl, and $R^{1d}$ is —($C_1$-$C_6$ alkylenyl)-OH or —($C_1$-$C_6$ alkylenyl)-O(alkyl), or $R^{1c}$ and $R^{1d}$, together with the nitrogen atom to which they are attached form a monocyclic ring selected from the group consisting of morpholinyl and oxazepanyl; or
$Y^1$ is $NR^1$ and $Y^2$ is $CH_2$; wherein $R^1$ is hydrogen, alkyl, or —($C_1$-$C_6$ alkylenyl)-OH,
$R^c$ is hydrogen or alkyl;
$Y^3$ is $CR^{3a}R^{3b}$, and $Y^4$ is O; wherein $R^{3a}$ and $R^{3b}$ are each independently hydrogen or alkyl; or
$Y^3$ and $Y^4$ are $CH_2$; or
$Y^3$ is $NR^3$ and $Y^4$ is $CH_2$; wherein $R^3$ is hydrogen or alkyl;
$R^d$ is hydrogen or alkyl;
$R^b$, at each occurrence, represents an optional substituent on the benzo moiety of the bicyclic rings of formula (i), (ii), and (iii), and is independently alkyl, halogen, or haloalkyl;
q is 0, 1, 2, or 3;
Z is O or S;
$X^1$ is $CH_2$, O, or $N(R^w)$ wherein $R^w$ is hydrogen, alkyl, or haloalkyl;
A is CH or N;

L is a bond or $CH_2$, and is bound to any one of the carbon atom of the ring containing $X^1$;
n is 1, 2, or 3;
m is 0, 1, 2, 3, or 4;
$R^x$, at each occurrence, represents optional substituent on any substitutable carbon atom of the ring containing A, and each $R^x$ is independently alkyl, halogen, haloalkyl, OH, O(alkyl), O(haloalkyl), $NH_2$, N(H)(alkyl), or N(alkyl)$_2$;
p is 0, 1, 2, 3, 4, 5, or 6; and
$R^y$, at each occurrence, represents optional substituent on any substitutable carbon atom of the ring containing $X^1$, and each $R^y$ is independently alkyl, haloalkyl, —($C_1$-$C_6$ alkylenyl)-O(alkyl), $G^1$, and —($C_1$-$C_6$ alkylenyl)-$G^1$; wherein each $G^1$ is the same or different, and is an aryl optionally substituted with 1, 2, 3, or 4 substituents independently selected from the group consisting of alkyl, halogen, haloalkyl, O(alkyl), and O(haloalkyl);
two $R^y$ groups that are attached to the same carbon atom, together with said carbon atom to which they are attached, optionally form a $C_3$-$C_6$ monocyclic cycloalkyl ring, wherein the monocyclic cyclcoalkyl ring is optionally substituted with 1, 2, or 3 substituents independently selected from the group consisting of alkyl, oxo, halogen, and haloalkyl.

Another aspect is related to methods for treating or preventing ischemia such as acute cerebral ischemia, cerebrovascular ischemia; pain such as acute pain, chronic pain, neuropathic pain, nociceptive pain, allodynia, inflammatory pain, inflammatory hyperalgesia, neuropathies, neuralgia, diabetic neuropathy, HIV-related neuropathy, nerve injury, rheumatoid arthritic pain, osteoarthritic pain, burns, back pain, eye pain, visceral pain, cancer pain (e.g. bone cancer pain), dental pain, headache, migraine, carpal tunnel syndrome, fibromyalgia, neuritis, sciatica, pelvic hypersensitivity, pelvic pain, post herpetic neuralgia, post operative pain, post stroke pain, and menstrual pain; bladder disease such as incontinence, bladder overactivity, micturition disorder, renal colic and cystitis; inflammation such as burns, rheumatoid arthritis and osteoarthritis; neurodegenerative disease such as stroke and multiple sclerosis; pulmonary disease such as asthma, cough, chronic obstructive pulmonary disease (COPD) and bronchi constriction; gastrointestinal disease such as gastro esophageal reflux disease (GERD), dysphagia, ulcer, irritable bowel syndrome (IBS), inflammatory bowel disease (IBD), colitis and Crohn's disease; emesis such as cancer chemotherapy-induced emesis, or obesity, said method comprising the step of administering a therapeutically effective amount of a compound described herein, or a pharmaceutically acceptable salt, prodrug, solvate, salt of a solvate, or solvate of a salt thereof, to a subject in need thereof, alone or in combination with an analgesic (e.g. acetaminophen, opioids such as, but not limited to, morphine), or a nonsteroidal anti-inflammatory drug (NSAID), or a combination thereof, and with or without a pharmaceutically acceptable carrier.

Another aspect relates to pharmaceutical compositions comprising therapeutically effective amount of a compound described herein or pharmaceutically acceptable salt, prodrug, solvate, salt of a solvate, or solvate of a salt thereof, in combination with a pharmaceutically acceptable carrier. Such compositions can be administered in accordance with methods described herein, typically as part of a therapeutic regimen for treatment or prevention of conditions and disorders related to TRPV1 activity. For example, the methods are useful for treating or preventing conditions described above. In one embodiment, the methods are useful for treating or preventing pain such as those delineated above. In one embodiment, the pain state is osteoarthritic pain.

Further, included herein are uses of present compounds or pharmaceutically acceptable salts, prodrugs, solvates, salts of solvates, or solvates of salts thereof, in the manufacture of medicaments for the treatment or prevention of the diseases or conditions described above, with or without a pharmaceutically acceptable carrier, and alone, or in combination with an analgesic (e.g. acetaminophen, opioids), or with a nonsteroidal anti-inflammatory drug (NSAID), or combinations thereof.

These and other objectives are described in the following paragraphs. These objectives should not be deemed to narrow the scope of the invention.

DETAILED DESCRIPTION OF THE INVENTION

Disclosed herein are compounds of formula (I)

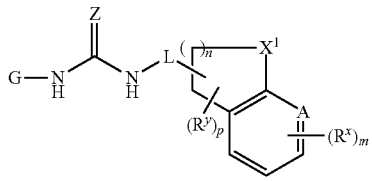

wherein $X^1$, L, $R^x$, $R^y$, G, Z, A, m, n, and p are as defined above in the Summary of the Invention and below in the Detailed Description. Compositions comprising such compounds and methods for treating conditions and disorders using such compounds and compositions are also disclosed.

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated from a reaction mixture.

A. DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkyl" as used herein, means a saturated, straight or branched hydrocarbon chain containing from 1 to 10 carbon atoms. In some instances, the number of carbon atoms in an alkyl moiety is indicated by the prefix "$C_x$—$C_y$", wherein x is the minimum and y is the maximum number of carbon atoms in the substituent. Thus, for example, "$C_1$-$C_6$ alkyl" refers to an alkyl substituent containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkylenyl" means a divalent group derived from a straight or branched, saturated hydrocarbon chain of 1 to 10 carbon atoms, for example, of 1 to 6 carbon atoms. The term "$C_1$-$C_6$ alkylenyl" means a divalent group derived from a straight or branched, saturated hydrocarbon chain of 1 to 6 carbon atoms. Examples of alkylene include, but are not limited to, —$CH_2$—, —C(H)($CH_3$)—, —$CH_2CH_2$—, —$CH_2CH_2CH_2$—, —$CH_2CH_2CH_2CH_2$—, and —$CH_2CH(CH_3)CH_2$—.

The term "aryl" as used herein, means phenyl or a bicyclic aryl. The bicyclic aryl is naphthyl, or a phenyl fused to a $C_3$-$C_6$ monocyclic cycloalkyl. Non-limiting examples of the aryl groups include dihydroindenyl (indanyl), naphthyl, and tetrahydronaphthalenyl. The bicyclic aryls are attached to the parent molecular moiety through any carbon atom contained within the bicyclic ring systems and can be unsubstituted or substituted.

The term "$C_3$-$C_6$ monocyclic cycloalkyl" means an optionally substituted monocyclic ring selected from the group consisting of cyclopropyl, cyclobutyl, cyclopentyl, and cyclohexyl, each of which is optionally substituted.

The term "haloalkyl" as used herein, means an alkyl group, as defined herein, in which one, two, three, four, five, six, or seven hydrogen atoms are replaced by halogen. The term "lower haloalkyl" means a $C_1$-$C_6$ alkyl group in which one, two, three, four, five, six, or seven hydrogen atoms are replaced by halogen. Representative examples of haloalkyl and lower haloalkyl include, but are not limited to, chloromethyl, fluoromethyl, 2-fluoroethyl, 2,2-difluoroethyl, trifluoromethyl, 2,2,2-trifluoroethyl, difluoromethyl, pentafluoroethyl, 2-chloro-3-fluoropentyl, and 2-iodoethyl.

The term "halogen" as used herein, means F, Cl, Br, or I.

The term "oxo" as used herein, means =O.

The terms "treat", "treating", and "treatment" refer to a method of alleviating or abrogating a disease or a condition and/or its attendant symptoms.

The terms "prevent", "preventing", and "prevention" refer to a method of preventing the onset of a disease and/or its attendant symptoms or barring a subject from acquiring a disease or a condition. As used herein, "prevent", "preventing" and "prevention" also include delaying the onset of a disease or a condition and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

B. COMPOUNDS

TRPV1 antagonists have formula (I) as described above.

Particular values of variable groups in compounds of formula (I) are as follows. Such values can be used where appropriate with any of the other values, definitions, claims or embodiments defined hereinbefore or hereinafter.

In certain compounds of formula (I) Z is O, such as those exemplified in formula (I-a)

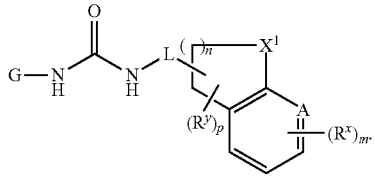
(I-a)

In certain compounds of formula (I) Z is S, such as those exemplified in formula (I-b)

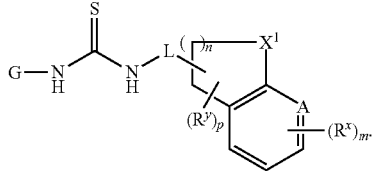
(I-b)

The variables $X^1$, L, $R^x$, $R^y$, G, A, m, n, and p of formula (I-a) and (I-b) are as disclosed in the Summary and embodiments described herein below.

In certain embodiments of compounds of formula (I), (I-a), and (I-b), n is 1 or 2.

In other embodiments, n is 1.

In other embodiments, n is 2.

In compounds of formula (I), (I-a), and (I-b), $X^1$, n, and L are as defined in the Summary. For example, in certain embodiments of compounds of formula (I) and (I-a), $X^1$ is $CH_2$, n is 1, and L is a bond. In the embodiments that $X^1$ is $CH_2$, n is 1, and L is a bond, the NH group of the urea moiety can be attached to the ring containing $X^1$ at a variety of positions, for example, the NH group can be attached to the second carbon atom relative to $X^1$. Such compounds can be exemplified by, but not limited to, those of formula (I-c)

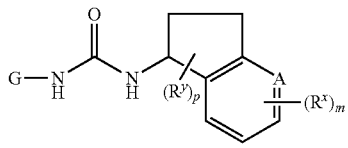
(I-c)

wherein the variables $R^x$, $R^y$, A, m, p, and G are as defined above in the Summary and embodiments herein.

In certain embodiments of compounds of formula (I), (I-a), and (I-b), $X^1$ is O or $N(R^w)$ and n is 2. In the embodiments wherein $X^1$ is O or $N(R^w)$ and n is 2, the variable L can be attached to the ring containing $X^1$ at various carbon atoms, for example, the L group can be attached to the $1^{st}$, $2^{nd}$, or $3^{rd}$ carbon atom relative to $X^1$. Compounds of formula (I) wherein $X^1$ is O and n is 2 can thus be exemplified by, but not limited to, those of formula (I-d), (I-e), and (I-f)

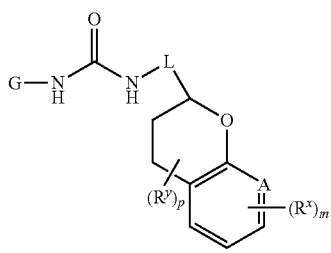
(I-d)

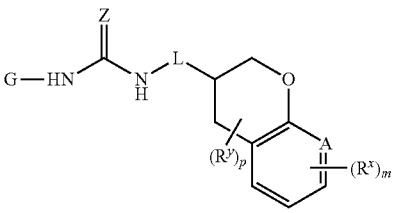
(I-e)

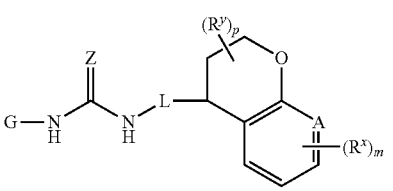
(I-f)

wherein the variables L, $R^x$, $R^y$, Z, A, G, m, and p are as defined above in the Summary and embodiments herein above and below. For example, in certain embodiments of compounds of formula (I), (I-a), (I-b), (I-d), and (I-e), L is $CH_2$. In certain embodiments of compounds of formula (I), (I-a), (I-b), (I-e), and (I-f), L is a bond.

In certain embodiments of compounds of formula (I), (I-a), and (I-b), $X^1$ is O and n is 2.

In other embodiments of compounds of formula (I), (I-a), and (I-b), $X^1$ is $N(R^w)$ and n is 2.

$R^w$ is as defined in the Summary, for example, in certain embodiments, $R^w$ is alkyl (e.g. $C_1$-$C_6$ alkyl such as, but not limited to, methyl).

In compounds of formula (I), (I-a), (I-b), (I-c), (I-d), (I-e), and (I-f), the variable A is CH or N. In certain embodiments, the variable A is CH. In yet other embodiments, the variable A is N.

In compounds of formula (I), (I-a), (I-b), (I-c), (I-d), (I-e), and (I-f), the variable m has meaning as defined in the Summary and embodiments herein. For example, in certain embodiments, m is 0, 1, or 2.

In compounds of formula (I), (I-a), (I-b), (I-c), (I-d), (I-e), and (I-f), the optional substituents ($R^x$) on any substitutable carbon atom of the ring containing A, if present, are as disclosed in the Summary and embodiments herein. For example, each $R^x$, if present, is independently alkyl (e.g. $C_1$-$C_6$ alkyl such as, but not limited to, methyl, tert-butyl), halogen (e.g. F, Cl, Br), haloalkyl (e.g. trifluoromethyl, fluoromethyl), O(alkyl) (e.g. O(methyl)), or O(haloalkyl) (e.g. O(trifluoromethyl)). In certain embodiments, each $R^x$, if present, is independently alkyl (e.g. tert-butyl), halogen (e.g. F, Cl, Br), haloalkyl (e.g. trifluoromethyl), or O(haloalkyl) (e.g. O(trifluoromethyl)). In certain embodiments, each $R^x$, if present, is halogen (e.g. F, Cl, Br). In certain embodiments, each $R^x$, if present, is independently F or Cl.

In compounds of formula (I), (I-a), (I-b), (I-c), (I-d), (I-e), and (I-f), the variable p has meaning as defined in the Summary and embodiments herein. For example, in certain embodiments, p is 0, 1, or 2. In certain embodiments, p is 0. In certain embodiments, p is 1. In certain embodiments, p is 2.

In the embodiments of compounds of formula (I), (I-a), and (I-b) wherein the variable, n, is 2; $X^1$ is O; and p is 2; and the compounds of formula (I-d), (I-e), and (I-f) wherein p is 2, it is preferred that the two substituents ($R^y$) are on the carbon atom adjacent to the oxygen atom.

In compounds of formula (I), (I-a), (I-b), (I-c), (I-d), (I-e), and (I-f), the optional substituents ($R^y$) on any substitutable carbon atom of the ring containing $X^1$, if present, are as disclosed in the Summary and embodiments herein. For example, each $R^y$, if present, is independently alkyl (e.g. $C_1$-$C_6$ alkyl such as, but not limited to, methyl, ethyl, n-propyl), haloalkyl (e.g. fluoromethyl, difluoromethyl, trifluoromethyl), or —($C_1$-$C_6$ alkylenyl)-O(alkyl) (e.g. —$CH_2$-O (methyl)). In certain embodiments, each $R^y$, if present, is independently alkyl (e.g. $C_1$-$C_6$ alkyl such as, but not limited to, methyl, ethyl, n-propyl) or haloalkyl (e.g. fluoromethyl, difluoromethyl, trifluoromethyl). In certain embodiments, each each $R^y$, if present, is independently alkyl (e.g. $C_1$-$C_6$ alkyl such as, but not limited to, methyl, ethyl, n-propyl). In certain embodiments, each $R^y$, if present, is methyl.

In the embodiments of compounds of formula (I-c) wherein p is 2, examples of the $R^y$ groups are alkyl (e.g. methyl).

In certain embodiments of compounds of formula (I), (I-a), and (I-b) wherein $X^1$ is O or N($R^w$), and compounds of formula (I-d), (I-e), and (I-f), two $R^y$ groups that are attached to the same carbon atom, together with said carbon atom, form a $C_3$-$C_6$ monocyclic cycloalkyl ring as described in the Summary and embodiments herein. In certain embodiments, the monocyclic cycloalkyl ring is cyclobutyl, cyclopentyl, or cyclohexyl, each of which is optionally substituted as described in the Summary and embodiments herein. For example, in certain embodiments, the monocyclic cycloalkyl ring (e.g. cyclobutyl, cyclopentyl, or cyclohexyl) is unsubstituted. In certain embodiments, the monocyclic cycloalkyl is unsubstituted cyclobutyl or unsubstituted cyclopentyl.

In certain embodiments of compounds of formula (I-d), (I-e), and (I-f), Z is O.

In certain embodiments of compounds of formula (I-f), Z is S.

The variable, G, of compounds of formula (I), (I-a), (I-b), (I-c), (I-d), (I-e), and (I-f), is as disclosed in the Summary and embodiments herein. In certain embodiments, G is formula (I) wherein $R^a$, $R^b$, $Y^1$, $Y^2$, and q are as disclosed in the Summary and embodiments herein below.

For example, a group of compounds of formula (I), (I-a), (I-b), (I-c), (I-d), (I-e), and (I-f) is directed to those wherein G is formula (i) wherein $R^a$ is hydrogen, $Y^1$ is $NR^1$ and $Y^2$ is $CH_2$; or $R^a$ is hydrogen, $Y^1$ is $CH_2$, and $Y^2$ is O; or $R^a$ is hydrogen or alkyl (e.g. methyl), $Y^1$ is $CR^{1a}R^{1b}$ wherein $R^{1a}$ and $R^{1b}$ are hydrogen, and $Y^2$ is $CH_2$; or $R^a$ is hydrogen, $Y^1$ is $CR^{1a}R^{1b}$ wherein $R^{1a}$ is hydrogen and $R^{1b}$ is $NR^{1c}R^{1d}$, and $Y^2$ is $CH_2$. $R^1$, $R^{1c}$, and $R^{1d}$ are as disclosed in the Summary and embodiments herein below.

For example, a group of compounds of formula (I), (I-a), (I-b), (I-c), (I-d), (I-e), and (I-f) is directed to those wherein G is formula (i) wherein $R^a$ is hydrogen, $Y^1$ is $NR^1$ and $Y^2$ is $CH_2$. $R^1$ is as disclosed in the Summary. For example, in certain embodiments, $R^1$ is alkyl (e.g. methyl) or —($C_1$-$C_6$ alkylenyl)-OH (e.g. —$CH_2CH_2$—OH). In other embodiments, $R^1$ is alkyl (e.g methyl). In other embodiments, $R^1$ is —($C_1$-$C_6$ alkylenyl)-OH (e.g. —$CH_2CH_2$—OH).

For example, a group of compounds of formula (I), (I-a), (I-b), (I-c), (I-d), (I-e), and (I-f) is directed to those wherein G is formula (i) wherein $R^a$ is hydrogen, $Y^1$ is $CH_2$, and $Y^2$ is O.

For example, a group of compounds of formula (I), (I-a), (I-b), (I-c), (I-d), (I-e), and (I-f) is directed to those wherein G is formula (i) wherein $R^a$ is hydrogen or alkyl (e.g. methyl), $Y^1$ is $CR^{1a}R^{1b}$ wherein $R^{1a}$ and $R^{1b}$ are hydrogen, and $Y^2$ is $CH_2$.

For example, a group of compounds of formula (I), (I-a), (I-b), (I-c), (I-d), (I-e), and (I-f) is directed to those wherein G is formula (i) wherein $R^a$ is hydrogen, $Y^1$ is $CR^{1a}R^{1b}$ wherein $R^{1a}$ is hydrogen and $R^{1b}$ is $NR^{1c}R^{1d}$, and $Y^2$ is $CH_2$. $R^{1c}$ and $R^{1d}$ are as disclosed in the Summary, for example, in certain embodiments, $R^{1c}$ is alkyl (e.g. methyl) and $R^{1d}$ is —$CH_2CH_2OH$ or $CH_2CH_2O$(methyl); or $R^{1c}$ and $R^{1d}$, together with the nitrogen atom, form a monocyclic ring selected from the group consisting of morpholinyl and oxazepanyl. In certain embodiments, $R^{1c}$ is alkyl (e.g. methyl) and $R^{1d}$ is —$CH_2CH_2OH$ or —$CH_2CH_2O$(methyl). In certain embodiments, $R^{1c}$ and $R^{1d}$, together with the nitrogen atom, form a monocyclic ring selected from the group consisting of morpholinyl and oxazepanyl.

In certain embodiments, G is formula (ii) wherein $R^c$, $R^b$, $Y^3$, $Y^4$, and q are as disclosed in the Summary and embodiments herein below.

In certain embodiments, G is formula (ii) wherein $R^c$ is hydrogen, $Y^3$ is $CR^{3a}R^{3b}$, and $Y^4$ is O; or $R^c$ is alkyl (e.g. methyl), $Y^3$ is $CH_2$, and $Y^4$ is $CH_2$; or $R^c$ is alkyl (e.g. methyl, ethyl), $Y^3$ is $NR^3$, and $Y^4$ is $CH_2$. $R^3$, $R^{3a}$, and $R^{3b}$, are as disclosed in the Summary and embodiments herein below.

For example, a group of compounds of formula (I), (I-a), (I-b), (I-c), (I-d), (I-e), and (I-f) is directed to those wherein G is formula (ii) wherein $R^c$ is hydrogen, $Y^3$ is $CR^{3a}R^{3b}$, and $Y^4$ is O. $R^{3a}$ and $R^{3b}$ are as disclosed in the Summary, for example, in certain embodiments, $R^{3a}$ is hydrogen and $R^{3b}$ is alkyl (e.g. methyl).

For example, a group of compounds of formula (I), (I-a), (I-b), (I-c), (I-d), (I-e), and (I-f) is directed to those wherein G is formula (ii) wherein $R^c$ is alkyl (e.g. methyl), $Y^3$ is $CH_2$, and $Y^4$ is $CH_2$.

For example, a group of compounds of formula (I), (I-a), (I-b), (I-c), (I-d), (I-e), and (I-f) is directed to those wherein G is formula (ii) wherein $R^c$ is alkyl (e.g. methyl, ethyl), $Y^3$ is $NR^3$, and $Y^4$ is $CH_2$. $R^3$ is as disclosed in the Summary, for example, in certain embodiments, $R^3$ is hydrogen or methyl. In certain embodiments, $R^3$ is hydrogen. In yet other embodiments, $R^3$ is methyl.

In certain embodiments of a group of compounds of formula (I), (I-a), (I-b), (I-c), (I-d), (I-e), and (I-f), G is formula (iii) wherein $R^d$, $R^b$, and q are as disclosed in the Summary and embodiments herein below.

For example, a group of compounds of formula (I), (I-a), (I-b), (I-c), (I-d), (I-e), and (I-f) is directed to those wherein G is formula (iii) wherein $R^d$ is hydrogen or methyl.

The variable, q, of compounds of formula (I), (I-a), (I-b), (I-c), (I-d), (I-e), and (I-f), are as disclosed in the Summary and embodiments herein. In certain embodiments, q is 0.

It is appreciated that compounds of formula (I), (I-a), (I-b), (I-c), (I-d), (I-e), and (I-f) with combinations of the above embodiments, including particular, more particular and preferred embodiments are contemplated.

Accordingly, one aspect is directed to a group of compounds of formula (I), (I-a), and (I-b) wherein G is formula (I), $X^1$ is $CH_2$, and n is 1.

Another aspect is directed to a group of compounds of formula (I), (I-a), and (I-b) wherein G is formula (i) wherein $R^a$ is hydrogen, $Y^1$ is $NR^1$ and $Y^2$ is $CH_2$; or $R^a$ is hydrogen, $Y^1$ is $CH_2$, and $Y^2$ is O; or $R^a$ is hydrogen or alkyl (e.g. methyl), $Y^1$ is $CR^{1a}R^{1b}$ wherein $R^{1a}$ and $R^{1b}$ are hydrogen, and $Y^2$ is $CH_2$; or $R^a$ is hydrogen, $Y^1$ is $CR^{1a}R^{14}$ wherein $R^{1a}$ is hydrogen and $R^{1b}$ is $NR^{1c}R^{1d}$, and $Y^2$ is $CH_2$; $X^1$ is $CH_2$, and n is 1. $R^1$, $R^{1c}$, and $R^{1d}$ are as disclosed in the Summary and embodiments herein above.

Another aspect is directed to a group of compounds of formula (I), (I-a), and (I-b) wherein G is formula (i) wherein $R^a$ is hydrogen, $Y^1$ is $NR^1$, $Y^2$ is $CH_2$, $X^1$ is $CH_2$, and n is 1. $R^1$ is as disclosed in the Summary. For example, in certain embodiments, $R^1$ is alkyl (e.g. methyl) or —($C_1$-$C_6$ alkylenyl)-OH (e.g. —$CH_2CH_2$—OH). In certain embodiments, $R^1$ is alkyl (e.g. methyl). In certain embodiments, $R^1$ is —($C_1$-$C_6$ alkylenyl)-OH (e.g. —$CH_2CH_2$—OH).

Another aspect is directed to a group of compounds of formula (I), (I-a), and (I-b) wherein G is formula (i) wherein $R^a$ is hydrogen, $Y^1$ is $CH_2$, $Y^2$ is o, $X^1$ is $CH_2$, and n is 1.

Another aspect is directed to a group of compounds of formula (I), (I-a), and (I-b) wherein G is formula (i) wherein $R^a$ is hydrogen or alkyl (e.g. methyl), $Y^1$ is $CR^{1a}R^{1b}$ wherein $R^{1a}$ and $R^{1b}$ are hydrogen, $Y^2$ is $CH_2$, $X^1$ is $CH_2$, and n is 1.

Another aspect is directed to a group of compounds of formula (I), (I-a), and (I-b) wherein G is formula (i) wherein $R^a$ is hydrogen, $Y^1$ is $CR^{1a}R^{1b}$ wherein $R^{1a}$ is hydrogen and $R^{1b}$ is $NR^{1c}R^{1d}$, $Y^2$ is $CH_2$, $X^1$ is $CH_2$, and n is 1. $R^{1c}$ and $R^{1d}$ are as disclosed in the Summary, for example, in certain embodiments, $R^{1c}$ is alkyl (e.g. methyl) and $R^{1d}$ is —$CH_2CH_2OH$ or $CH_2CH_2O$(methyl); or $R^{1c}$ and $R^{1d}$, together with the nitrogen atom, form a monocyclic ring selected from the group consisting of morpholinyl and oxazepanyl. In certain embodiments, $R^{1c}$ is alkyl (e.g. methyl) and $R^{1d}$ is —$CH_2CH_2OH$ or —$CH_2CH_2O$(methyl). In certain embodiments, $R^{1c}$ and $R^{1d}$, together with the nitrogen atom, form a monocyclic ring selected from the group consisting of morpholinyl and oxazepanyl.

Another aspect is directed to a group of compounds of formula (I), (I-a), and (I-b) wherein G is formula (ii), $X^1$ is $CH_2$, and n is 1.

Another aspect is directed to a group of compounds of formula (I), (I-a), and (I-b) wherein G is formula (ii) wherein $R^c$ is hydrogen, $Y^3$ is $CR^{3a}R^{3b}$, and $Y^4$ is O; or $R^c$ is alkyl (e.g. methyl), $Y^3$ is $CH_2$, and $Y^4$ is $CH_2$; or $R^c$ is alkyl (e.g. methyl, ethyl), $Y^3$ is $NR^3$, and $Y^4$ is $CH_2$, $X^1$ is $CH_2$, and n is 1. $R^3$, $R^{3a}$, and $R^{3b}$, are as disclosed in the Summary and embodiments herein above.

Another aspect is directed to a group of compounds of formula (I), (I-a), and (I-b) wherein G is formula (ii) wherein $R^c$ is hydrogen, $Y^3$ is $CR^{3a}R^{3b}$, $Y^4$ is O, $X^1$ is $CH_2$, and n is 1. $R^{3a}$ and $R^{3b}$ are as disclosed in the Summary, for example, in certain embodiments, $R^{3a}$ is hydrogen and $R^{3b}$ is alkyl (e.g. methyl).

Another aspect is directed to a group of compounds of formula (I), (I-a), and (I-b) wherein G is formula (ii) wherein $R^c$ is alkyl (e.g. methyl), $Y^3$ is $CH_2$, $Y^4$ is $CH_2$, $X^1$ is $CH_2$, and n is 1.

Another aspect is directed to a group of compounds of formula (I), (I-a), and (I-b) wherein G is formula (ii) wherein $R^c$ is alkyl (e.g. methyl, ethyl), $Y^3$ is $NR^3$, $Y^4$ is $CH_2$, $X^1$ is $CH_2$, and n is 1. $R^3$ is as disclosed in the Summary, for example, in certain embodiments, $R^3$ is hydrogen or methyl. In certain embodiments, $R^3$ is hydrogen. In yet other embodiments, $R^3$ is methyl.

Another aspect is directed to a group of compounds of formula (I), (I-a), and (I-b) wherein G is formula (iii), $X^1$ is $CH_2$, and n is 1.

Another aspect is directed to a group of compounds of formula (I), (I-a), and (I-b) wherein G is formula (iii) wherein $R^d$ is hydrogen or methyl, $X^1$ is $CH_2$, and n is 1.

Another aspect is directed to a group of compounds of formula (I), (I-a), and (I-b) wherein G is formula (i), $X^1$ is O, and n is 2.

Another aspect is directed to a group of compounds of formula (I), (I-a), and (I-b) wherein G is formula (i) wherein $R^a$ is hydrogen, $Y^1$ is $NR^1$ and $Y^2$ is $CH_2$; or $R^a$ is hydrogen, $Y^1$ is $CH_2$, and $Y^2$ is O; or $R^a$ is hydrogen or alkyl (e.g. methyl), $Y^1$ is $CR^{1a}R^{1b}$ wherein $R^{1a}$ and $R^{1b}$ are hydrogen, and $Y^2$ is $CH_2$; or $R^a$ is hydrogen, $Y^1$ is $CR^{1a}R^{1b}$ wherein $R^{1a}$ is hydrogen and $R^{1b}$ is $NR^{1c}R^{1d}$, and $Y^2$ is $CH_2$; $X^1$ is O, and n is 2. $R^1$, $R^{1c}$, and $R^{1d}$ are as disclosed in the Summary and embodiments herein above.

Another aspect is directed to a group of compounds of formula (I), (I-a), and (I-b) wherein G is formula (i) wherein $R^a$ is hydrogen, $Y^1$ is $NR^1$, $Y^2$ is $CH_2$, $X^1$ is O, and n is 2. $R^1$ is as disclosed in the Summary. For example, in certain embodiments, $R^1$ is alkyl (e.g. methyl) or —($C_1$-$C_6$ alkylenyl)-OH (e.g. —$CH_2CH_2$—OH). In certain embodiments, $R^1$ is alkyl (e.g. methyl). In certain embodiments, $R^1$ is —($C_1$-$C_6$ alkylenyl)-OH (e.g. —$CH_2CH_2$—OH).

Another aspect is directed to a group of compounds of formula (I), (I-a), and (I-b) wherein G is formula (i) wherein $R^a$ is hydrogen, $Y^1$ is $CH_2$, $Y^2$ is O, $X^1$ is O, and n is 2.

Another aspect is directed to a group of compounds of formula (I), (I-a), and (I-b) wherein G is formula (i) wherein $R^a$ is hydrogen or alkyl (e.g. methyl), $Y^1$ is $CR^{1a}R^{1b}$ wherein $R^{1a}$ and $R^{1b}$ are hydrogen, $Y^2$ is $CH_2$, $X^1$ is O, and n is 2.

Another aspect is directed to a group of compounds of formula (I), (I-a), and (I-b) wherein G is formula (i) wherein $R^a$ is hydrogen, $Y^1$ is $CR^{1a}R^{1b}$ wherein $R^{1a}$ is hydrogen and $R^1$ is $NR^{1c}R^{1d}$, $Y^2$ is $CH_2$, $X^1$ is O, and n is 2. $R^{1c}$ and $R^{1d}$ are as disclosed in the Summary, for example, in certain embodiments, $R^{1c}$ is alkyl (e.g. methyl) and $R^{1d}$ is —$CH_2CH_2OH$ or —$CH_2CH_2O$(methyl); or $R^{1c}$ and $R^{1d}$, together with the nitrogen atom, form a monocyclic ring selected from the group consisting of morpholinyl and oxazepanyl. In certain embodiments, $R^{1c}$ is alkyl (e.g. methyl) and $R^{1d}$ is —$CH_2CH_2OH$ or —$CH_2CH_2O$(methyl). In certain embodiments, $R^{1c}$ and $R^{1d}$, together with the nitrogen atom, form a monocyclic ring selected from the group consisting of morpholinyl and oxazepanyl.

Another aspect is directed to a group of compounds of formula (I), (I-a), and (I-b) wherein G is formula (ii), $X^1$ is O, and n is 2.

Another aspect is directed to a group of compounds of formula (I), (I-a), and (I-b) wherein G is formula (ii) wherein $R^c$ is hydrogen, $Y^3$ is $CR^{3a}R^{3b}$, and $Y^4$ is P; or $R^c$ is alkyl (e.g. methyl), $Y^3$ is $CH_2$, and $Y^4$ is $CH_2$; or $R^c$ is alkyl (e.g. methyl, ethyl), $Y^3$ is $NR^3$, and $Y^4$ is $CH_2$, $X^1$ is O, and n is 2. $R^3$, $R^{3a}$, and $R^{3b}$, are as disclosed in the Summary and embodiments herein above.

Another aspect is directed to a group of compounds of formula (I), (I-a), and (I-b) wherein G is formula (ii) wherein $R^c$ is hydrogen, $Y^3$ is $CR^{3a}R^{3b}$, $Y^4$ is O, $X^1$ is O, and n is 2. $R^{3a}$ and $R^{3b}$ are as disclosed in the Summary, for example, in certain embodiments, $R^{3a}$ is hydrogen and $R^{3b}$ is alkyl (e.g. methyl).

Another aspect is directed to a group of compounds of formula (I), (I-a), and (I-b) wherein G is formula (ii) wherein $R^c$ is alkyl (e.g. methyl), $Y^3$ is $CH_2$, $Y^4$ is $CH_2$, $X^1$ is O, and n is 2.

Another aspect is directed to a group of compounds of formula (I), (I-a), and I-b) wherein G is formula (ii) wherein $R^c$ is alkyl (e.g. methyl, ethyl), $Y^3$ is $NR^3$, $Y^4$ is $CH_2$, $X^1$ is O, and n is 2. $R^3$ is as disclosed in the Summary, for example, in certain embodiments, $R^3$ is hydrogen or methyl. In certain embodiments, $R^3$ is hydrogen. In yet other embodiments, $R^3$ is methyl.

Another aspect is directed to a group of compounds of formula (I), (I-a), and (I-b) wherein G is formula (iii), $X^1$ is O, and n is 2.

Another aspect is directed to a group of compounds of formula (I), (I-a), and (I-b) wherein G is formula (iii) wherein $R^d$ is hydrogen or methyl, $X^1$ is O, and n is 2.

Within each group of compounds of formula (I), (I-a), (I-b), (I-c), (I-d), (I-e), and (I-f) herein above, the variables, L, A, and Z, when present, are as disclosed in the Summary and embodiments herein above.

Thus, for example, for each group of (I), (I-a), (I-b), (I-c), (I-d), (I-e), and (I-f) described herein above, examples of a subgroup include those wherein A is CH.

Examples of another subgroup of compounds of formula (I), (I-a), and (I-f) described herein above include those wherein A is N.

Examples of another subgroup of compounds of formula (I), (I-a), (I-b), (I-e), and (I-f) described herein above include those wherein L is a bond.

Examples of another subgroup of compounds of formula (I), (I-a), (I-d), and (I-e), described herein above include those wherein L is $CH_2$.

Examples of another subgroup of compounds of formula (I), (I-d), (I-e), and (I-f) described herein above include those wherein Z is O.

Examples of another subgroup of compounds of formula (I) and (I-f) described herein above include those wherein Z is S.

Examples of another subgroup of compounds of formula (I), (I-d), (I-e), and (I-f) described herein above include those wherein A is CH and Z is O.

Examples of another subgroup of compounds of formula (I) and (I-f) described herein above include those wherein A is N and Z is O.

Examples of another subgroup of compounds of formula (I), (I-a), (I-b), (I-e), and (I-f) described herein above include those wherein A is CH and L is a bond.

Examples of another subgroup of compounds of formula (I), (I-a), and (I-f) described herein above include those wherein A is N and L is a bond.

Examples of another subgroup of compounds of formula (I), (I-a), (I-d), and (I-e), described herein above include those wherein A is CH and L is $CH_2$.

Examples of another subgroup of compounds of formula (I), (I-e), and (I-f) described herein above include those wherein A is CH, Z is O, and L is a bond.

Examples of another subgroup of compounds of formula (I) and (I-f) described herein above include those wherein A is N, Z is O, and L is a bond.

Examples of another subgroup of compounds of formula (I), (I-d), and (I-e), described herein above include those wherein A is CH, Z is O, and L is $CH_2$.

Examples of another subgroup of compounds of formula (I) and (I-f), described herein above include those wherein A is CH, Z is S, and L is a bond.

Within each group and subgroup of compounds of formula (I), (I-a), (I-b), (I-c), (I-d), (I-e), and (I-f) described herein above, the variables, $R^x$, $R^y$, $R^b$, m and p, are as disclosed in the Summary and embodiments herein above.

Exemplary compounds include, but are not limited to,
1-[(4R)-7-fluoro-2,2-dimethyl-3,4-dihydro-2H-chromen-4-yl]-3-(1-methyl-2-oxo-1,2,3,4-tetrahydroquinazolin-5-yl)urea;
1-[(4R)-7-chloro-2,2-bis(fluoromethyl)-3,4-dihydro-2H-chromen-4-yl]-3-(1-methyl-2-oxo-1,2,3,4-tetrahydroquinazolin-5-yl)urea;
1-[(4R)-7-chloro-8-fluoro-2,2-bis(fluoromethyl)-3,4-dihydro-2H-chromen-4-yl]-3-(1-methyl-2-oxo-1,2,3,4-tetrahydroquinazolin-5-yl)urea;
1-[(4R)-2,2-dimethyl-3,4-dihydro-2H-chromen-4-yl]-3-(1-methyl-2-oxo-1,2,3,4-tetrahydroquinazolin-5-yl)urea;
1-[(4R)-8-chloro-7-fluoro-2,2-dimethyl-3,4-dihydro-2H-chromen-4-yl]-3-(1-methyl-2-oxo-1,2,3,4-tetrahydroquinazolin-5-yl)urea;
1-[(4R)-7-chloro-2,2-dimethyl-3,4-dihydro-2H-chromen-4-yl]-3-(1-methyl-2-oxo-1,2,3,4-tetrahydroquinazolin-5-yl)urea;
1-[(2R,4R)-7-chloro-2-(fluoromethyl)-2-methyl-3,4-dihydro-2H-chromen-4-yl]-3-(1-methyl-2-oxo-1,2,3,4-tetrahydroquinazolin-5-yl)urea;
1-[(4R)-2,2-dimethyl-3,4-dihydro-2H-chromen-4-yl]-3-(I-ethyl-2-oxo-1,2,3,4-tetrahydroquinazolin-5-yl)urea;
1-[(4R)-2,2-bis(fluoromethyl)-3,4-dihydro-2H-chromen-4-yl]-3-(1-methyl-2-oxo-1,2,3,4-tetrahydroquinazolin-5-yl)urea;
1-[(2R,4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea;
1-[(2S,4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea;
1-[(2R,4R)-2-(difluoromethyl)-2-methyl-3,4-dihydro-2H-chromen-4-yl]-3-(1-methyl-2-oxo-1,2,3,4-tetrahydroquinazolin-5-yl)urea;
1-[(2S,4R)-2-(difluoromethyl)-2-methyl-3,4-dihydro-2H-chromen-4-yl]-3-(1-methyl-2-oxo-1,2,3,4-tetrahydroquinazolin-5-yl)urea;
1-[(2S,4R)-7-chloro-2-(fluoromethyl)-2-methyl-3,4-dihydro-2H-chromen-4-yl]-3-(1-methyl-2-oxo-1,2,3,4-tetrahydroquinazolin-5-yl)urea;
1-[(4R)-3,4-dihydrospiro[chromene-2,1'-cyclopentan]-4-yl]-3-(1-methyl-2-oxo-1,2,3,4-tetrahydroquinazolin-5-yl)urea;
1-[(4R)-2,2-dimethyl-8-(trifluoromethyl)-3,4-dihydro-2H-chromen-4-yl]-3-(3-methyl-2-oxo-1,2,3,4-tetrahydroquinazolin-7-yl)urea;
1-[(1R)-5-chloro-2,3-dihydro-1H-inden-1-yl]-3-(3-methyl-2-oxo-1,2,3,4-tetrahydroquinazolin-7-yl)urea;
1-(3-methyl-2-oxo-1,2,3,4-tetrahydroquinazolin-7-yl)-3-[(2R,4R)-2-methyl-2-(trifluoromethyl)-3,4-dihydro-2H-chromen-4-yl]urea;
1-[(4R)-7-fluoro-2,2-dimethyl-3,4-dihydro-2H-chromen-4-yl]-3-(1-methyl-2-oxo-1,2-dihydroquinolin-5-yl)urea;
1-[(4R)-7-chloro-2,2-bis(fluoromethyl)-3,4-dihydro-2H-chromen-4-yl]-3-(1-methyl-2-oxo-1,2-dihydroquinolin-5-yl)urea;
1-[(4R)-7-chloro-8-fluoro-2,2-bis(fluoromethyl)-3,4-dihydro-2H-chromen-4-yl]-3-(1-methyl-2-oxo-1,2-dihydroquinolin-5-yl)urea;
1-[(4R)-8-chloro-7-fluoro-2,2-dimethyl-3,4-dihydro-2H-chromen-4-yl]-3-(1-methyl-2-oxo-1,2-dihydroquinolin-5-yl)urea;
1-[(4R)-7-chloro-2,2-dimethyl-3,4-dihydro-2H-chromen-4-yl]-3-(1-methyl-2-oxo-1,2-dihydroquinolin-5-yl)urea;
1-[(4R)-6-fluoro-2,2-dimethyl-3,4-dihydro-2H-chromen-4-yl]-3-(1-methyl-2-oxo-1,2-dihydroquinolin-5-yl)urea;
1-(1-methyl-2-oxo-1,2-dihydroquinolin-5-yl)-3-[(2S,4R)-2-methyl-2-(trifluoromethyl)-3,4-dihydro-2H-chromen-4-yl]urea;
1-[(2S,4R)-2-(difluoromethyl)-2-methyl-3,4-dihydro-2H-chromen-4-yl]-3-(1-methyl-2-oxo-1,2-dihydroquinolin-5-yl)urea;
1-[(4R)-7-fluoro-2,2-bis(fluoromethyl)-3,4-dihydro-2H-chromen-4-yl]-3-(1-methyl-2-oxo-1,2-dihydroquinolin-5-yl)urea;
1-[(2R,4R)-2-(difluoromethyl)-2-methyl-3,4-dihydro-2H-chromen-4-yl]-3-(1-methyl-2-oxo-1,2-dihydroquinolin-5-yl)urea;
1-[(4R)-7-chloro-2,2-bis(fluoromethyl)-3,4-dihydro-2H-chromen-4-yl]-3-(3-oxo-3,4-dihydro-2H-1,4-benzoxazin-6-yl)urea;
1-[(2R,4R)-7-chloro-2-(difluoromethyl)-2-methyl-3,4-dihydro-2H-chromen-4-yl]-3-(2-oxo-1,2,3,4-tetrahydroquinolin-7-yl)urea;

1-[(4R)-7-chloro-2,2-bis(fluoromethyl)-3,4-dihydro-2H-chromen-4-yl]-3-(2-oxo-1,2,3,4-tetrahydroquinolin-7-yl)urea;
1-[(4R)-2,2-dimethyl-7-(trifluoromethyl)-3,4-dihydro-2H-chromen-4-yl]-3-(2-oxo-1,2,3,4-tetrahydroquinolin-7-yl)urea;
1-[(4R)-7,8-difluoro-2,2-dimethyl-3,4-dihydro-2H-chromen-4-yl]-3-(2-oxo-1,2,3,4-tetrahydroquinolin-7-yl)urea;
1-[(2R,4R)-2-methyl-2-(trifluoromethyl)-3,4-dihydro-2H-chromen-4-yl]-3-(2-oxo-1,2,3,4-tetrahydroquinolin-7-yl)urea;
1-(2-oxo-1,2,3,4-tetrahydroquinolin-7-yl)-3-[(1R)-5-(trifluoromethyl)-2,3-dihydro-1H-inden-1-yl]urea;
1-(1-methyl-2-oxo-1,2,3,4-tetrahydroquinolin-7-yl)-3-[(1R)-5-(trifluoromethyl)-2,3-dihydro-1H-inden-1-yl]urea;
1-(1-methyl-2-oxo-1,2,3,4-tetrahydroquinolin-7-yl)-3-[(4R)-7-(trifluoromethyl)-3,4-dihydro-2H-chromen-4-yl]urea;
1-[(4R)-7-fluoro-2,2-dimethyl-3,4-dihydro-2H-chromen-4-yl]-3-(3-oxo-3,4-dihydro-2H-1,4-benzoxazin-6-yl)urea;
1-[(4R)-7-chloro-8-fluoro-2,2-dimethyl-3,4-dihydro-2H-chromen-4-yl]-3-(2-oxo-1,2,3,4-tetrahydroquinolin-7-yl)urea;
1-[(2R,4R)-7-chloro-2-(fluoromethyl)-2-methyl-3,4-dihydro-2H-chromen-4-yl]-3-(1-methyl-2-oxo-1,2-dihydroquinolin-5-yl)urea;
1-[(2S,4R)-7-chloro-2-(fluoromethyl)-2-methyl-3,4-dihydro-2H-chromen-4-yl]-3-(1-methyl-2-oxo-1,2-dihydroquinolin-5-yl)urea;
1-[(4R)-8-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;
1-[(4R)-7-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;
1-[(4R)-2,2-diethyl-8-fluoro-3,4-dihydro-2H-chromen-4-yl]-3-[3-(2-hydroxyethyl)-2-oxo-1,2,3,4-tetrahydroquinazolin-7-yl]urea;
1-[(4R)-2,2-diethyl-3,4-dihydro-2H-chromen-4-yl]-3-[3-(2-hydroxyethyl)-2-oxo-1,2,3,4-tetrahydroquinazolin-7-yl]urea;
1-[(4R)-2,2-diethyl-7-(trifluoromethyl)-3,4-dihydro-2H-chromen-4-yl]-3-[3-(2-hydroxyethyl)-2-oxo-1,2,3,4-tetrahydroquinazolin-7-yl]urea;
1-[(4R)-7-chloro-2,2-diethyl-3,4-dihydro-2H-chromen-4-yl]-3-[3-(2-hydroxyethyl)-2-oxo-1,2,3,4-tetrahydroquinazolin-7-yl]urea;
1-[(4R)-2,2-dimethyl-7-(trifluoromethyl)-3,4-dihydro-2H-chromen-4-yl]-3-[3-(2-hydroxyethyl)-2-oxo-1,2,3,4-tetrahydroquinazolin-7-yl]urea;
1-[(4R)-6-fluoro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea;
1-[(4R)-2,2-diethyl-6-fluoro-3,4-dihydro-2H-chromen-4-yl]-3-[3-(2-hydroxyethyl)-2-oxo-1,2,3,4-tetrahydroquinazolin-7-yl]urea;
1-[(4R)-6-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;
1-[(4R)-6-fluoro-3,4-dihydro-2H-chromen-4-yl]-3-[3-(2-hydroxyethyl)-2-oxo-1,2,3,4-tetrahydroquinazolin-7-yl]urea;
1-[3-(2-hydroxyethyl)-2-oxo-1,2,3,4-tetrahydroquinazolin-7-yl]-3-[(4R)-8-(trifluoromethyl)-3,4-dihydro-2H-chromen-4-yl]urea;
1-[3-(2-hydroxyethyl)-2-oxo-1,2,3,4-tetrahydroquinazolin-7-yl]-3-[(4R)-7-(trifluoromethyl)-3,4-dihydro-2H-chromen-4-yl]urea;
1-[(1R)-5-fluoro-2,3-dihydro-1H-inden-1-yl]-3-[3-(2-hydroxyethyl)-2-oxo-1,2,3,4-tetrahydroquinazolin-7-yl]urea;
1-[(4S)-6-fluoro-3,4-dihydrospiro[chromene-2,1'-cyclobutan]-4-yl]-3-[3-(2-hydroxyethyl)-2-oxo-1,2,3,4-tetrahydroquinazolin-7-yl]urea;
1-[(4S)-6-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;
1-[(2S,4R)-2-(fluoromethyl)-2-methyl-7-(trifluoromethyl)-3,4-dihydro-2H-chromen-4-yl]-3-[3-(2-hydroxyethyl)-2-oxo-1,2,3,4-tetrahydroquinazolin-7-yl]urea;
1-[(2S,4R)-7-chloro-2-(fluoromethyl)-2-methyl-3,4-dihydro-2H-chromen-4-yl]-3-[3-(2-hydroxyethyl)-2-oxo-1,2,3,4-tetrahydroquinazolin-7-yl]urea;
1-[(2R,4R)-2-(difluoromethyl)-2-methyl-3,4-dihydro-2H-chromen-4-yl]-3-[3-(2-hydroxyethyl)-2-oxo-1,2,3,4-tetrahydroquinazolin-7-yl]urea;
1-[(4R)-7-chloro-8-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;
1-[(4R)-2,2-dimethyl-7-(trifluoromethyl)-3,4-dihydro-2H-pyrano[2,3-b]pyridin-4-yl]-3-[3-(2-hydroxyethyl)-2-oxo-1,2,3,4-tetrahydroquinazolin-7-yl]urea;
1-[(4R)-7-bromo-2,2-dimethyl-3,4-dihydro-2H-chromen-4-yl]-3-[3-(2-hydroxyethyl)-2-oxo-1,2,3,4-tetrahydroquinazolin-7-yl]urea;
1-(1-methyl-2-oxo-1,2-dihydroquinolin-5-yl)-3-[(4R)-7-(trifluoromethyl)-3,4-dihydro-2H-chromen-4-yl]urea;
1-[(4R)-3,4-dihydrospiro[chromene-2,1'-cyclopentan]-4-yl]-3-(1-methyl-2-oxo-1,2-dihydroquinolin-5-yl)urea;
1-[(4R)-2,2-diethyl-8-fluoro-3,4-dihydro-2H-chromen-4-yl]-3-(1-methyl-2-oxo-1,2-dihydroquinolin-5-yl)urea;
1-[(4R)-2,2-diethyl-3,4-dihydro-2H-chromen-4-yl]-3-(1-methyl-2-oxo-1,2-dihydroquinolin-5-yl)urea;
1-[(1R)-5-tert-butyl-2,3-dihydro-1H-inden-1-yl]-3-(1-methyl-2-oxo-1,2-dihydroquinolin-5-yl)urea;
1-[(4R)-2,2-diethyl-7-(trifluoromethyl)-3,4-dihydro-2H-chromen-4-yl]-3-(1-methyl-2-oxo-1,2-dihydroquinolin-5-yl)urea;
1-[(4R)-7-chloro-2,2-diethyl-3,4-dihydro-2H-chromen-4-yl]-3-(1-methyl-2-oxo-1,2-dihydroquinolin-5-yl)urea;
1-[(4R)-6-fluoro-2,2-bis(fluoromethyl)-3,4-dihydro-2H-chromen-4-yl]-3-(1-methyl-2-oxo-1,2-dihydroquinolin-5-yl)urea;
1-[(4R)-6,8-difluoro-2,2-bis(fluoromethyl)-3,4-dihydro-2H-chromen-4-yl]-3-(1-methyl-2-oxo-1,2-dihydroquinolin-5-yl)urea;
1-[(4R)-6-fluoro-3,4-dihydrospiro[chromene-2,1'-cyclobutan]-4-yl]-3-(1-methyl-2-oxo-1,2-dihydroquinolin-5-yl)urea;
1-[(4R)-2,2-diethyl-6-fluoro-3,4-dihydro-2H-chromen-4-yl]-3-(1-methyl-2-oxo-1,2-dihydroquinolin-5-yl)urea;
1-[(4R)-8-fluoro-2,2-dipropyl-3,4-dihydro-2H-chromen-4-yl]-3-(1-methyl-2-oxo-1,2-dihydroquinolin-5-yl)urea;
1-[(4R)-2,2-diethyl-7-(trifluoromethoxy)-3,4-dihydro-2H-chromen-4-yl]-3-(1-methyl-2-oxo-1,2-dihydroquinolin-5-yl)urea;
1-[(4R)-2,2-dimethyl-3,4-dihydro-2H-chromen-4-yl]-3-(1-methyl-2-oxo-1,2-dihydroquinolin-5-yl)urea;
1-(1-methyl-2-oxo-1,2-dihydroquinolin-5-yl)-3-[(4S)-7-(trifluoromethoxy)-3,4-dihydro-2H-chromen-4-yl]urea;

1-[(4R)-6-fluoro-2,2-bis(methoxymethyl)-3,4-dihydro-2H-chromen-4-yl]-3-(1-methyl-2-oxo-1,2-dihydroquinolin-5-yl)urea;
1-[(4R)-2,2-bis(fluoromethyl)-3,4-dihydro-2H-chromen-4-yl]-3-(1-methyl-2-oxo-1,2-dihydroquinolin-5-yl)urea;
1-[(4R)-7,8-difluoro-2,2-dimethyl-3,4-dihydro-2H-chromen-4-yl]-3-(1-methyl-2-oxo-1,2-dihydroquinolin-5-yl)urea;
1-[(4R)-6-fluoro-3,4-dihydro-2H-chromen-4-yl]-3-(1-methyl-2-oxo-1,2-dihydroquinolin-5-yl)urea;
1-[(1R)-5-fluoro-2,3-dihydro-1H-inden-1-yl]-3-(1-methyl-2-oxo-1,2-dihydroquinolin-5-yl)urea;
1-[(2S,4R)-2-(fluoromethyl)-2-methyl-7-(trifluoromethyl)-3,4-dihydro-2H-chromen-4-yl]-3-(1-methyl-2-oxo-1,2-dihydroquinolin-5-yl)urea;
1-[(4R)-7-chloro-8-fluoro-2,2-dimethyl-3,4-dihydro-2H-chromen-4-yl]-3-(1-methyl-2-oxo-1,2-dihydroquinolin-5-yl)urea;
1-(1-methyl-2-oxo-1,2-dihydroquinolin-5-yl)-3-[(1R)-5-(trifluoromethyl)-2,3-dihydro-1H-inden-1-yl]urea;
1-(1-methyl-2-oxo-1,2-dihydroquinolin-5-yl)-3-[(4R)-7-(trifluoromethoxy)-3,4-dihydro-2H-chromen-4-yl]urea;
1-[(4S)-6-fluoro-3,4-dihydrospiro[chromene-2,1'-cyclobutan]-4-yl]-3-(1-methyl-2-oxo-1,2-dihydroquinolin-5-yl)urea;
1-[(4R)-7-bromo-2,2-dimethyl-3,4-dihydro-2H-chromen-4-yl]-3-(1-methyl-2-oxo-1,2-dihydroquinolin-5-yl)urea;
1-(1-methyl-2-oxo-1,2-dihydroquinolin-5-yl)-3-[(2R,4R)-2-methyl-2-(trifluoromethyl)-3,4-dihydro-2H-chromen-4-yl]urea;
1-[(4R)-2,2-dimethyl-7-(trifluoromethyl)-3,4-dihydro-2H-chromen-4-yl]-3-(1-methyl-2-oxo-1,2-dihydroquinolin-5-yl)urea;
1-[(4R)-2,2-bis(fluoromethyl)-7-(trifluoromethyl)-3,4-dihydro-2H-chromen-4-yl]-3-(1-methyl-2-oxo-1,2-dihydroquinolin-5-yl)urea;
1-[(4R)-2,2-dimethyl-8-(trifluoromethyl)-3,4-dihydro-2H-chromen-4-yl]-3-(1-methyl-2-oxo-1,2-dihydroquinolin-5-yl)urea;
1-[(4R)-8-fluoro-2,2-dimethyl-3,4-dihydro-2H-chromen-4-yl]-3-(1-methyl-2-oxo-1,2-dihydroquinolin-5-yl)urea;
1-[(4R)-8-fluoro-2,2-bis(fluoromethyl)-3,4-dihydro-2H-chromen-4-yl]-3-(1-methyl-2-oxo-1,2-dihydroquinolin-5-yl)urea;
1-[(1R)-5-chloro-2,3-dihydro-1H-inden-1-yl]-3-(1-methyl-2-oxo-1,2-dihydroquinolin-5-yl)urea;
1-(1-methyl-2-oxo-1,2-dihydroquinolin-5-yl)-3-[(4R)-8-(trifluoromethyl)-3,4-dihydro-2H-chromen-4-yl]urea;
1-[(4S)-6-fluoro-2,2-dimethyl-3,4-dihydro-2H-chromen-4-yl]-3-(1-methyl-2-oxo-1,2-dihydroquinolin-5-yl)urea;
1-[(4R)-7-chloro-2,2-bis(fluoromethyl)-3,4-dihydro-2H-chromen-4-yl]-3-(2-oxo-1,2-dihydroquinolin-5-yl)urea;
1-[(4R)-8-fluoro-2,2-dimethyl-3,4-dihydro-2H-chromen-4-yl]-3-(3-oxo-3,4-dihydro-2H-1,4-benzoxazin-6-yl)urea;
1-[(4R)-2,2-diethyl-8-fluoro-3,4-dihydro-2H-chromen-4-yl]-3-(3-oxo-3,4-dihydro-2H-1,4-benzoxazin-6-yl)urea;
1-[(4R)-2,2-diethyl-3,4-dihydro-2H-chromen-4-yl]-3-(3-oxo-3,4-dihydro-2H-1,4-benzoxazin-6-yl)urea;
1-[(4R)-2,2-diethyl-7-(trifluoromethyl)-3,4-dihydro-2H-chromen-4-yl]-3-(3-oxo-3,4-dihydro-2H-1,4-benzoxazin-6-yl)urea;
1-[(4R)-7-chloro-2,2-diethyl-3,4-dihydro-2H-chromen-4-yl]-3-(3-oxo-3,4-dihydro-2H-1,4-benzoxazin-6-yl)urea;
1-[(4R)-7,8-dichloro-2,2-diethyl-3,4-dihydro-2H-chromen-4-yl]-3-(3-oxo-3,4-dihydro-2H-1,4-benzoxazin-6-yl)urea;
1-[(4R)-2,2-dimethyl-7-(trifluoromethyl)-3,4-dihydro-2H-chromen-4-yl]-3-(3-oxo-3,4-dihydro-2H-1,4-benzoxazin-6-yl)urea;
1-[(4R)-6-fluoro-2,2-dipropyl-3,4-dihydro-2H-chromen-4-yl]-3-(3-oxo-3,4-dihydro-2H-1,4-benzoxazin-6-yl)urea;
1-[(4R)-6-fluoro-3,4-dihydrospiro[chromene-2,1'-cyclobutan]-4-yl]-3-(3-oxo-3,4-dihydro-2H-1,4-benzoxazin-6-yl)urea;
1-[(4R)-2,2-diethyl-6-fluoro-3,4-dihydro-2H-chromen-4-yl]-3-(3-oxo-3,4-dihydro-2H-1,4-benzoxazin-6-yl)urea;
1-[(4R)-8-fluoro-2,2-dipropyl-3,4-dihydro-2H-chromen-4-yl]-3-(3-oxo-3,4-dihydro-2H-1,4-benzoxazin-6-yl)urea;
1-[(4R)-2,2-diethyl-7-(trifluoromethoxy)-3,4-dihydro-2H-chromen-4-yl]-3-(3-oxo-3,4-dihydro-2H-1,4-benzoxazin-6-yl)urea;
1-[(4R)-2,2-dimethyl-3,4-dihydro-2H-chromen-4-yl]-3-(3-oxo-3,4-dihydro-2H-1,4-benzoxazin-6-yl)urea;
1-[(4R)-6-fluoro-2,2-dimethyl-3,4-dihydro-2H-chromen-4-yl]-3-(3-oxo-3,4-dihydro-2H-1,4-benzoxazin-6-yl)urea;
1-[(4R)-7-chloro-2,2-dimethyl-3,4-dihydro-2H-chromen-4-yl]-3-(3-oxo-3,4-dihydro-2H-1,4-benzoxazin-6-yl)urea;
1-(3-oxo-3,4-dihydro-2H-1,4-benzoxazin-6-yl)-3-[(4R)-7-(trifluoromethoxy)-3,4-dihydro-2H-chromen-4-yl]urea;
1-[(4R)-8-fluoro-2,2-bis(fluoromethyl)-3,4-dihydro-2H-chromen-4-yl]-3-(3-oxo-3,4-dihydro-2H-1,4-benzoxazin-6-yl)urea;
1-[(4R)-7,8-difluoro-2,2-dimethyl-3,4-dihydro-2H-chromen-4-yl]-3-(3-oxo-3,4-dihydro-2H-1,4-benzoxazin-6-yl)urea;
1-[(4R)-6-fluoro-3,4-dihydro-2H-chromen-4-yl]-3-(3-oxo-3,4-dihydro-2H-1,4-benzoxazin-6-yl)urea;
1-[(1R)-5-chloro-2,3-dihydro-1H-inden-1-yl]-3-(3-oxo-3,4-dihydro-2H-1,4-benzoxazin-6-yl)urea;
1-(3-oxo-3,4-dihydro-2H-1,4-benzoxazin-6-yl)-3-[(4R)-8-(trifluoromethyl)-3,4-dihydro-2H-chromen-4-yl]urea;
1-(3-oxo-3,4-dihydro-2H-1,4-benzoxazin-6-yl)-3-[(4R)-7-(trifluoromethyl)-3,4-dihydro-2H-chromen-4-yl]urea;
1-[(4S)-6-fluoro-3,4-dihydrospiro[chromene-2,1'-cyclobutan]-4-yl]-3-(3-oxo-3,4-dihydro-2H-1,4-benzoxazin-6-yl)urea;
1-[(4S)-6-fluoro-2,2-dimethyl-3,4-dihydro-2H-chromen-4-yl]-3-(3-oxo-3,4-dihydro-2H-1,4-benzoxazin-6-yl)urea;
1-[(4R)-3,4-dihydrospiro[chromene-2,1'-cyclopentan]-4-yl]-3-(3-oxo-3,4-dihydro-2H-1,4-benzoxazin-6-yl)urea;
1-[(2S,4R)-2-methyl-2-(trifluoromethyl)-3,4-dihydro-2H-chromen-4-yl]-3-(3-oxo-3,4-dihydro-2H-1,4-benzoxazin-6-yl)urea;
1-[(2R,4R)-2-methyl-2-(trifluoromethyl)-3,4-dihydro-2H-chromen-4-yl]-3-(3-oxo-3,4-dihydro-2H-1,4-benzoxazin-6-yl)urea;
1-[(2S,4R)-2-(fluoromethyl)-2-methyl-7-(trifluoromethyl)-3,4-dihydro-2H-chromen-4-yl]-3-(3-oxo-3,4-dihydro-2H-1,4-benzoxazin-6-yl)urea;
1-[(2R,4R)-2-(fluoromethyl)-2-methyl-7-(trifluoromethyl)-3,4-dihydro-2H-chromen-4-yl]-3-(3-oxo-3,4-dihydro-2H-1,4-benzoxazin-6-yl)urea;
1-[(2S,4R)-7-chloro-2-(fluoromethyl)-2-methyl-3,4-dihydro-2H-chromen-4-yl]-3-(3-oxo-3,4-dihydro-2H-1,4-benzoxazin-6-yl)urea;
1-[(2S,4R)-2-(difluoromethyl)-2-methyl-3,4-dihydro-2H-chromen-4-yl]-3-(3-oxo-3,4-dihydro-2H-1,4-benzoxazin-6-yl)urea;
1-[(2R,4R)-2-(difluoromethyl)-2-methyl-3,4-dihydro-2H-chromen-4-yl]-3-(3-oxo-3,4-dihydro-2H-1,4-benzoxazin-6-yl)urea;

1-(3-oxo-3,4-dihydro-2H-1,4-benzoxazin-6-yl)-3-{[7-(trifluoromethyl)-3,4-dihydro-2H-chromen-2-yl]methyl}urea;

1-[(6-fluoro-3,4-dihydro-2H-chromen-3-yl)methyl]-3-(3-oxo-3,4-dihydro-2H-1,4-benzoxazin-6-yl)urea;

1-[(4R)-7-chloro-2,2-bis(fluoromethyl)-3,4-dihydro-2H-chromen-4-yl]-3-[(2R)-2-methyl-3-oxo-3,4-dihydro-2H-1,4-benzoxazin-8-yl]urea;

1-[(4R)-8-fluoro-2,2-dimethyl-3,4-dihydro-2H-chromen-4-yl]-3-(1-methyl-2-oxo-1,2,3,4-tetrahydroquinazolin-5-yl)urea;

1-[(4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea;

1-[(4R)-2,2-dimethyl-7-(trifluoromethoxy)-3,4-dihydro-2H-chromen-4-yl]-3-(1-methyl-2-oxo-1,2,3,4-tetrahydroquinazolin-5-yl)urea;

1-(1-methyl-2-oxo-1,2,3,4-tetrahydroquinazolin-5-yl)-3-[(4R)-8-(trifluoromethoxy)-3,4-dihydro-2H-chromen-4-yl]urea;

1-[(4R)-2,2-diethyl-8-fluoro-3,4-dihydro-2H-chromen-4-yl]-3-(1-methyl-2-oxo-1,2,3,4-tetrahydroquinazolin-5-yl)urea;

1-[(4R)-2,2-diethyl-3,4-dihydro-2H-chromen-4-yl]-3-(1-methyl-2-oxo-1,2,3,4-tetrahydroquinazolin-5-yl)urea;

1-[(1R)-5-tert-butyl-2,3-dihydro-1H-inden-1-yl]-3-(1-methyl-2-oxo-1,2,3,4-tetrahydroquinazolin-5-yl)urea;

1-[(4R)-8-tert-butyl-3,4-dihydro-2H-chromen-4-yl]-3-(1-methyl-2-oxo-1,2,3,4-tetrahydroquinazolin-5-yl)urea;

1-[(4R)-2,2-diethyl-7-fluoro-3,4-dihydro-2H-chromen-4-yl]-3-(1-methyl-2-oxo-1,2,3,4-tetrahydroquinazolin-5-yl)urea;

1-[(4R)-2,2-diethyl-7-(trifluoromethyl)-3,4-dihydro-2H-chromen-4-yl]-3-(1-methyl-2-oxo-1,2,3,4-tetrahydroquinazolin-5-yl)urea;

1-[(4R)-7-chloro-2,2-diethyl-3,4-dihydro-2H-chromen-4-yl]-3-(1-methyl-2-oxo-1,2,3,4-tetrahydroquinazolin-5-yl)urea;

1-[(4R)-2,2-bis(fluoromethyl)-7-(trifluoromethyl)-3,4-dihydro-2H-chromen-4-yl]-3-(1-methyl-2-oxo-1,2,3,4-tetrahydroquinazolin-5-yl)urea;

1-[(4R)-7,8-dichloro-2,2-diethyl-3,4-dihydro-2H-chromen-4-yl]-3-(1-methyl-2-oxo-1,2,3,4-tetrahydroquinazolin-5-yl)urea;

1-[(4R)-8-chloro-2,2-bis(fluoromethyl)-3,4-dihydro-2H-chromen-4-yl]-3-(1-methyl-2-oxo-1,2,3,4-tetrahydroquinazolin-5-yl)urea;

1-[(4R)-2,2-bis(fluoromethyl)-7-(trifluoromethoxy)-3,4-dihydro-2H-chromen-4-yl]-3-(1-methyl-2-oxo-1,2,3,4-tetrahydroquinazolin-5-yl)urea;

1-[(4R)-2,2-dimethyl-7-(trifluoromethyl)-3,4-dihydro-2H-chromen-4-yl]-3-(1-methyl-2-oxo-1,2,3,4-tetrahydroquinazolin-5-yl)urea;

1-[(4R)-6-fluoro-2,2-dipropyl-3,4-dihydro-2H-chromen-4-yl]-3-(1-methyl-2-oxo-1,2,3,4-tetrahydroquinazolin-5-yl)urea;

1-[(4R)-6-fluoro-2,2-bis(fluoromethyl)-3,4-dihydro-2H-chromen-4-yl]-3-(1-methyl-2-oxo-1,2,3,4-tetrahydroquinazolin-5-yl)urea;

1-[(4R)-6,8-difluoro-2,2-bis(fluoromethyl)-3,4-dihydro-2H-chromen-4-yl]-3-(1-methyl-2-oxo-1,2,3,4-tetrahydroquinazolin-5-yl)urea;

1-[(4R)-6-fluoro-3,4-dihydrospiro[chromene-2,1'-cyclobutan]-4-yl]-3-(1-methyl-2-oxo-1,2,3,4-tetrahydroquinazolin-5-yl)urea;

1-[(4R)-2,2-diethyl-6-fluoro-3,4-dihydro-2H-chromen-4-yl]-3-(1-methyl-2-oxo-1,2,3,4-tetrahydroquinazolin-5-yl)urea;

1-[(4R)-8-fluoro-2,2-dipropyl-3,4-dihydro-2H-chromen-4-yl]-3-(1-methyl-2-oxo-1,2,3,4-tetrahydroquinazolin-5-yl)urea;

1-[(4R)-6-fluoro-2,2-dimethyl-3,4-dihydro-2H-chromen-4-yl]-3-(1-methyl-2-oxo-1,2,3,4-tetrahydroquinazolin-5-yl)urea;

1-[(1R)-3,3-dimethyl-2,3-dihydro-1H-inden-1-yl]-3-(1-methyl-2-oxo-1,2,3,4-tetrahydroquinazolin-5-yl)urea;

1-[(4R)-7-fluoro-3,4-dihydro-2H-chromen-4-yl]-3-(1-methyl-2-oxo-1,2,3,4-tetrahydroquinazolin-5-yl)urea;

1-(1-methyl-2-oxo-1,2,3,4-tetrahydroquinazolin-5-yl)-3-[(4R)-7-(trifluoromethyl)-3,4-dihydro-2H-chromen-4-yl]urea;

1-(7-chloro-3,4-dihydro-2H-chromen-3-yl)-3-(1-methyl-2-oxo-1,2,3,4-tetrahydroquinazolin-5-yl)urea;

1-[(4R)-7-chloro-2,2-bis(fluoromethyl)-3,4-dihydro-2H-chromen-4-yl]-3-(1-ethyl-2-oxo-1,2,3,4-tetrahydroquinazolin-5-yl)urea;

1-[(2R,4R)-2-(fluoromethyl)-2-methyl-3,4-dihydro-2H-chromen-4-yl]-3-(1-methyl-2-oxo-1,2,3,4-tetrahydroquinazolin-5-yl)urea;

1-[(2S,4R)-2-(fluoromethyl)-2-methyl-3,4-dihydro-2H-chromen-4-yl]-3-(1-methyl-2-oxo-1,2,3,4-tetrahydroquinazolin-5-yl)urea;

1-(1-methyl-2-oxo-1,2,3,4-tetrahydroquinazolin-5-yl)-3-[(2S,4R)-2-methyl-2-(trifluoromethyl)-3,4-dihydro-2H-chromen-4-yl]urea;

1-(1-methyl-2-oxo-1,2,3,4-tetrahydroquinazolin-5-yl)-3-[(2R,4R)-2-methyl-2-(trifluoromethyl)-3,4-dihydro-2H-chromen-4-yl]urea;

1-[(4R)-7-chloro-2,2-bis(fluoromethyl)-3,4-dihydro-2H-chromen-4-yl]-3-(1,3-dimethyl-2-oxo-1,2,3,4-tetrahydroquinazolin-5-yl)urea;

1-[(4R)-3,4-dihydro-2H-chromen-4-yl]-3-(1-methyl-2-oxo-1,2,3,4-tetrahydroquinazolin-5-yl)urea;

1-(1-methyl-2-oxo-1,2,3,4-tetrahydroquinazolin-5-yl)-3-[(4S)-7-(trifluoromethoxy)-3,4-dihydro-2H-chromen-4-yl]urea;

1-[(4R)-7-chloro-2,2-bis(fluoromethyl)-3,4-dihydro-2H-chromen-4-yl]-3-(3-methyl-2-oxo-1,2,3,4-tetrahydroquinazolin-7-yl)urea;

1-[(2S,4R)-2-(difluoromethyl)-2-methyl-3,4-dihydro-2H-chromen-4-yl]-3-(3-methyl-2-oxo-1,2,3,4-tetrahydroquinazolin-7-yl)urea;

1-[(4R)-8-chloro-7-fluoro-2,2-dimethyl-3,4-dihydro-2H-chromen-4-yl]-3-(3-methyl-2-oxo-1,2,3,4-tetrahydroquinazolin-7-yl)urea;

1-[(4R)-2,2-bis(fluoromethyl)-7-(trifluoromethyl)-3,4-dihydro-2H-chromen-4-yl]-3-(3-methyl-2-oxo-1,2,3,4-tetrahydroquinazolin-7-yl)urea;

1-(3-methyl-2-oxo-1,2,3,4-tetrahydroquinazolin-7-yl)-3-[(1R)-5-(trifluoromethyl)-2,3-dihydro-1H-inden-1-yl]urea;

1-[(4R)-3,4-dihydro-2H-chromen-4-yl]-3-(3-methyl-2-oxo-1,2,3,4-tetrahydroquinazolin-7-yl)urea;

1-[(4R)-7-fluoro-2,2-dimethyl-3,4-dihydro-2H-chromen-4-yl]-3-(3-methyl-2-oxo-1,2,3,4-tetrahydroquinazolin-7-yl)urea;

1-[(4R)-2,2-diethyl-8-fluoro-3,4-dihydro-2H-chromen-4-yl]-3-(3-methyl-2-oxo-1,2,3,4-tetrahydroquinazolin-7-yl)urea;

1-[(4R)-2,2-diethyl-3,4-dihydro-2H-chromen-4-yl]-3-(3-methyl-2-oxo-1,2,3,4-tetrahydroquinazolin-7-yl)urea;

1-[(1R)-5-tert-butyl-2,3-dihydro-1H-inden-1-yl]-3-(3-methyl-2-oxo-1,2,3,4-tetrahydroquinazolin-7-yl)urea;
1-[(4R)-2,2-diethyl-7-(trifluoromethyl)-3,4-dihydro-2H-chromen-4-yl]-3-(3-methyl-2-oxo-1,2,3,4-tetrahydroquinazolin-7-yl)urea;
1-[(4R)-7-chloro-2,2-diethyl-3,4-dihydro-2H-chromen-4-yl]-3-(3-methyl-2-oxo-1,2,3,4-tetrahydroquinazolin-7-yl)urea;
1-[(4R)-7,8-dichloro-2,2-diethyl-3,4-dihydro-2H-chromen-4-yl]-3-(3-methyl-2-oxo-1,2,3,4-tetrahydroquinazolin-7-yl)urea;
1-[(4R)-2,2-bis(fluoromethyl)-7-(trifluoromethoxy)-3,4-dihydro-2H-chromen-4-yl]-3-(3-methyl-2-oxo-1,2,3,4-tetrahydroquinazolin-7-yl)urea;
1-[(4R)-2,2-dimethyl-7-(trifluoromethyl)-3,4-dihydro-2H-chromen-4-yl]-3-(3-methyl-2-oxo-1,2,3,4-tetrahydroquinazolin-7-yl)urea;
1-[(4R)-6-fluoro-2,2-dipropyl-3,4-dihydro-2H-chromen-4-yl]-3-(3-methyl-2-oxo-1,2,3,4-tetrahydroquinazolin-7-yl)urea;
1-[(4R)-6-fluoro-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-6,8-difluoro-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-6-fluoro-3,4-dihydrospiro[chromene-2,1'-cyclobutan]-4-yl]-3-(3-methyl-2-oxo-1,2,3,4-tetrahydroquinazolin-7-yl)urea;
1-[(4R)-2,2-diethyl-6-fluoro-3,4-dihydro-2H-chromen-4-yl]-3-(3-methyl-2-oxo-1,2,3,4-tetrahydroquinazolin-7-yl)urea;
1-[(4R)-8-fluoro-2,2-dipropyl-3,4-dihydro-2H-chromen-4-yl]-3-(3-methyl-2-oxo-1,2,3,4-tetrahydroquinazolin-7-yl)urea;
1-[(4R)-2,2-diethyl-7-(trifluoromethoxy)-3,4-dihydro-2H-chromen-4-yl]-3-(3-methyl-2-oxo-1,2,3,4-tetrahydroquinazolin-7-yl)urea;
1-[(4R)-7-chloro-8-fluoro-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-2,2-dimethyl-3,4-dihydro-2H-chromen-4-yl]-3-(3-methyl-2-oxo-1,2,3,4-tetrahydroquinazolin-7-yl)urea;
1-(3-methyl-2-oxo-1,2,3,4-tetrahydroquinazolin-7-yl)-3-[(4S)-7-(trifluoromethoxy)-3,4-dihydro-2H-chromen-4-yl]urea;
1-(3-methyl-2-oxo-1,2,3,4-tetrahydroquinazolin-7-yl)-3-[(4R)-7-(trifluoromethoxy)-3,4-dihydro-2H-chromen-4-yl]urea;
1-[(4R)-6-fluoro-2,2-bis(methoxymethyl)-3,4-dihydro-2H-chromen-4-yl]-3-(3-methyl-2-oxo-1,2,3,4-tetrahydroquinazolin-7-yl)urea;
1-[(4R)-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-8-fluoro-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-6-fluoro-3,4-dihydro-2H-chromen-4-yl]-3-(3-methyl-2-oxo-1,2,3,4-tetrahydroquinazolin-7-yl)urea;
1-(3-methyl-2-oxo-1,2,3,4-tetrahydroquinazolin-7-yl)-3-[(4R)-8-(trifluoromethyl)-3,4-dihydro-2H-chromen-4-yl]urea;
1-(3-methyl-2-oxo-1,2,3,4-tetrahydroquinazolin-7-yl)-3-[(4R)-7-(trifluoromethyl)-3,4-dihydro-2H-chromen-4-yl]urea;
1-[(1R)-5-fluoro-2,3-dihydro-1H-inden-1-yl]-3-(3-methyl-2-oxo-1,2,3,4-tetrahydroquinazolin-7-yl)urea;
1-[(4S)-6-fluoro-3,4-dihydrospiro[chromene-2,1'-cyclobutan]-4-yl]-3-(3-methyl-2-oxo-1,2,3,4-tetrahydroquinazolin-7-yl)urea;
1-[(4S)-6-fluoro-2,2-dimethyl-3,4-dihydro-2H-chromen-4-yl]-3-(3-methyl-2-oxo-1,2,3,4-tetrahydroquinazolin-7-yl)urea;
1-[(4R)-3,4-dihydrospiro[chromene-2,1'-cyclopentan]-4-yl]-3-(3-methyl-2-oxo-1,2,3,4-tetrahydroquinazolin-7-yl)urea;
1-[(2R,4R)-2-(fluoromethyl)-2-methyl-7-(trifluoromethyl)-3,4-dihydro-2H-chromen-4-yl]-3-(3-methyl-2-oxo-1,2,3,4-tetrahydroquinazolin-7-yl)urea;
1-[(2R,4R)-2-(difluoromethyl)-2-methyl-3,4-dihydro-2H-chromen-4-yl]-3-(3-methyl-2-oxo-1,2,3,4-tetrahydroquinazolin-7-yl)urea;
1-[(4R)-2,2-dimethyl-7-(trifluoromethyl)-3,4-dihydro-2H-pyrano[2,3-b]pyridin-4-yl]-3-(3-methyl-2-oxo-1,2,3,4-tetrahydroquinazolin-7-yl)urea;
1-[(4R)-7-fluoro-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-8-fluoro-2,2-dimethyl-3,4-dihydro-2H-chromen-4-yl]-3-(3-methyl-2-oxo-1,2,3,4-tetrahydroquinazolin-7-yl)urea;
1-[(4R)-2,2-bis(fluoromethyl)-7-(trifluoromethoxy)-3,4-dihydro-2H-chromen-4-yl]-3-(2-oxo-1,2,3,4-tetrahydroquinolin-7-yl)urea;
1-[(2S,4R)-7-chloro-2-(difluoromethyl)-2-methyl-3,4-dihydro-2H-chromen-4-yl]-3-(2-oxo-1,2,3,4-tetrahydroquinolin-7-yl)urea;
1-[(4R)-6-fluoro-2,2-bis(fluoromethyl)-3,4-dihydro-2H-chromen-4-yl]-3-(2-oxo-1,2,3,4-tetrahydroquinolin-7-yl)urea;
1-[(4R)-6,8-difluoro-2,2-bis(fluoromethyl)-3,4-dihydro-2H-chromen-4-yl]-3-(2-oxo-1,2,3,4-tetrahydroquinolin-7-yl)urea;
1-[(4R)-2,2-bis(fluoromethyl)-3,4-dihydro-2H-chromen-4-yl]-3-(2-oxo-1,2,3,4-tetrahydroquinolin-7-yl)urea;
1-[(4R)-8-fluoro-2,2-bis(fluoromethyl)-3,4-dihydro-2H-chromen-4-yl]-3-(2-oxo-1,2,3,4-tetrahydroquinolin-7-yl)urea;
1-[(4S)-7-chloro-2,2-bis(fluoromethyl)-3,4-dihydro-2H-chromen-4-yl]-3-(2-oxo-1,2,3,4-tetrahydroquinolin-7-yl)urea;
1-[(4R)-2,2-dimethyl-8-(trifluoromethyl)-3,4-dihydro-2H-chromen-4-yl]-3-(2-oxo-1,2,3,4-tetrahydroquinolin-7-yl)urea;
1-[(4R)-8-fluoro-2,2-dimethyl-3,4-dihydro-2H-chromen-4-yl]-3-(2-oxo-1,2,3,4-tetrahydroquinolin-7-yl)urea;
1-[(4R)-3,4-dihydro-2H-chromen-4-yl]-3-(2-oxo-1,2,3,4-tetrahydroquinolin-7-yl)urea;
1-[(4R)-7-fluoro-2,2-dimethyl-3,4-dihydro-2H-chromen-4-yl]-3-(2-oxo-1,2,3,4-tetrahydroquinolin-7-yl)urea;
1-[(4R)-2,2-diethyl-8-fluoro-3,4-dihydro-2H-chromen-4-yl]-3-(2-oxo-1,2,3,4-tetrahydroquinolin-7-yl)urea;
1-[(4R)-2,2-diethyl-3,4-dihydro-2H-chromen-4-yl]-3-(2-oxo-1,2,3,4-tetrahydroquinolin-7-yl)urea;
1-[(4R)-2,2-diethyl-7-(trifluoromethyl)-3,4-dihydro-2H-chromen-4-yl]-3-(2-oxo-1,2,3,4-tetrahydroquinolin-7-yl)urea;
1-[(4R)-7-chloro-2,2-diethyl-3,4-dihydro-2H-chromen-4-yl]-3-(2-oxo-1,2,3,4-tetrahydroquinolin-7-yl)urea;
1-[(4R)-7,8-dichloro-2,2-diethyl-3,4-dihydro-2H-chromen-4-yl]-3-(2-oxo-1,2,3,4-tetrahydroquinolin-7-yl)urea;

1-[(4R)-6-fluoro-2,2-dipropyl-3,4-dihydro-2H-chromen-4-yl]-3-(2-oxo-1,2,3,4-tetrahydroquinolin-7-yl)urea;
1-[(4R)-6-fluoro-3,4-dihydrospiro[chromene-2,1'-cyclobutan]-4-yl]-3-(2-oxo-1,2,3,4-tetrahydroquinolin-7-yl)urea;
1-[(4R)-2,2-diethyl-6-fluoro-3,4-dihydro-2H-chromen-4-yl]-3-(2-oxo-1,2,3,4-tetrahydroquinolin-7-yl)urea;
1-[(4R)-8-fluoro-2,2-dipropyl-3,4-dihydro-2H-chromen-4-yl]-3-(2-oxo-1,2,3,4-tetrahydroquinolin-7-yl)urea;
1-[(4R)-7-chloro-8-fluoro-2,2-bis(fluoromethyl)-3,4-dihydro-2H-chromen-4-yl]-3-(2-oxo-1,2,3,4-tetrahydroquinolin-7-yl)urea;
1-[(4R)-6-fluoro-2,2-dimethyl-3,4-dihydro-2H-chromen-4-yl]-3-(2-oxo-1,2,3,4-tetrahydroquinolin-7-yl)urea;
1-[(4R)-8-chloro-7-fluoro-2,2-dimethyl-3,4-dihydro-2H-chromen-4-yl]-3-(2-oxo-1,2,3,4-tetrahydroquinolin-7-yl)urea;
1-(2-oxo-1,2,3,4-tetrahydroquinolin-7-yl)-3-[(4S)-7-(trifluoromethoxy)-3,4-dihydro-2H-chromen-4-yl]urea;
1-[(4R)-7-chloro-2,2-dimethyl-3,4-dihydro-2H-chromen-4-yl]-3-(2-oxo-1,2,3,4-tetrahydroquinolin-7-yl)urea;
1-(2-oxo-1,2,3,4-tetrahydroquinolin-7-yl)-3-[(4R)-7-(trifluoromethoxy)-3,4-dihydro-2H-chromen-4-yl]urea;
1-[(4R)-6-fluoro-2,2-bis(methoxymethyl)-3,4-dihydro-2H-chromen-4-yl]-3-(2-oxo-1,2,3,4-tetrahydroquinolin-7-yl)urea;
1-(2-oxo-1,2,3,4-tetrahydroquinolin-7-yl)-3-[(4R)-8-(trifluoromethyl)-3,4-dihydro-2H-chromen-4-yl]urea;
1-(2-oxo-1,2,3,4-tetrahydroquinolin-7-yl)-3-[(4R)-7-(trifluoromethyl)-3,4-dihydro-2H-chromen-4-yl]urea;
1-[(1R)-5-fluoro-2,3-dihydro-1H-inden-1-yl]-3-(2-oxo-1,2,3,4-tetrahydroquinolin-7-yl)urea;
1-[(2R,4R)-7-chloro-2-(fluoromethyl)-2-methyl-3,4-dihydro-2H-chromen-4-yl]-3-(2-oxo-1,2,3,4-tetrahydroquinolin-7-yl)urea;
1-[(4S)-6-fluoro-3,4-dihydrospiro[chromene-2,1'-cyclobutan]-4-yl]-3-(2-oxo-1,2,3,4-tetrahydroquinolin-7-yl)urea;
1-[(4S)-6-fluoro-2,2-dimethyl-3,4-dihydro-2H-chromen-4-yl]-3-(2-oxo-1,2,3,4-tetrahydroquinolin-7-yl)urea;
1-[(4R)-3,4-dihydrospiro[chromene-2,1'-cyclopentan]-4-yl]-3-(2-oxo-1,2,3,4-tetrahydroquinolin-7-yl)urea;
1-[(2S,4R)-2-methyl-2-(trifluoromethyl)-3,4-dihydro-2H-chromen-4-yl]-3-(2-oxo-1,2,3,4-tetrahydroquinolin-7-yl)urea;
1-[(2S,4R)-7-chloro-2-(fluoromethyl)-2-methyl-3,4-dihydro-2H-chromen-4-yl]-3-(2-oxo-1,2,3,4-tetrahydroquinolin-7-yl)urea;
1-[(4R)-2,2-dimethyl-7-(trifluoromethyl)-3,4-dihydro-2H-pyrano[2,3-b]pyridin-4-yl]-3-(2-oxo-1,2,3,4-tetrahydroquinolin-7-yl)urea;
1-[(2S,4R)-2-(difluoromethyl)-2-methyl-3,4-dihydro-2H-chromen-4-yl]-3-(2-oxo-1,2,3,4-tetrahydroquinolin-7-yl)urea;
1-[(2R,4R)-2-(difluoromethyl)-2-methyl-3,4-dihydro-2H-chromen-4-yl]-3-(2-oxo-1,2,3,4-tetrahydroquinolin-7-yl)urea;
1-[(4R)-7-fluoro-2,2-bis(fluoromethyl)-3,4-dihydro-2H-chromen-4-yl]-3-(2-oxo-1,2,3,4-tetrahydroquinolin-7-yl)urea;
1-[(1R)-5-chloro-2,3-dihydro-1H-inden-1-yl]-3-(2-oxo-1,2,3,4-tetrahydroquinolin-7-yl)urea;
1-[(4R)-7-chloro-2,2-bis(fluoromethyl)-3,4-dihydro-2H-chromen-4-yl]-3-(2-oxo-1,2,3,4-tetrahydroquinolin-7-yl)thiourea;
1-[(4R)-7-fluoro-2,2-dimethyl-3,4-dihydro-2H-chromen-4-yl]-3-(1-methyl-2-oxo-1,2,3,4-tetrahydroquinolin-7-yl)urea;
1-[(4R)-7-chloro-2,2-bis(fluoromethyl)-3,4-dihydro-2H-chromen-4-yl]-3-(1-methyl-2-oxo-1,2,3,4-tetrahydroquinolin-5-yl)urea;
1-[(4R)-7-chloro-2,2-bis(fluoromethyl)-3,4-dihydro-2H-chromen-4-yl]-3-(1-methyl-2-oxo-1,2,3,4-tetrahydroquinolin-7-yl)urea;
1-[(4R)-2,2-dimethyl-8-(trifluoromethyl)-3,4-dihydro-2H-chromen-4-yl]-3-(1-methyl-2-oxo-1,2,3,4-tetrahydroquinolin-7-yl)urea;
1-[(4R)-8-fluoro-2,2-dimethyl-3,4-dihydro-2H-chromen-4-yl]-3-(1-methyl-2-oxo-1,2,3,4-tetrahydroquinolin-7-yl)urea;
1-[(4R)-3,4-dihydro-2H-chromen-4-yl]-3-(1-methyl-2-oxo-1,2,3,4-tetrahydroquinolin-7-yl)urea;
1-[(4R)-2,2-diethyl-8-fluoro-3,4-dihydro-2H-chromen-4-yl]-3-(1-methyl-2-oxo-1,2,3,4-tetrahydroquinolin-7-yl)urea;
1-[(4R)-2,2-diethyl-3,4-dihydro-2H-chromen-4-yl]-3-(1-methyl-2-oxo-1,2,3,4-tetrahydroquinolin-7-yl)urea;
1-[(4R)-2,2-diethyl-7-(trifluoromethyl)-3,4-dihydro-2H-chromen-4-yl]-3-(1-methyl-2-oxo-1,2,3,4-tetrahydroquinolin-7-yl)urea;
1-[(4R)-7-chloro-2,2-diethyl-3,4-dihydro-2H-chromen-4-yl]-3-(1-methyl-2-oxo-1,2,3,4-tetrahydroquinolin-7-yl)urea;
1-[(4R)-2,2-bis(fluoromethyl)-7-(trifluoromethyl)-3,4-dihydro-2H-chromen-4-yl]-3-(1-methyl-2-oxo-1,2,3,4-tetrahydroquinolin-7-yl)urea;
1-[(4R)-7,8-dichloro-2,2-diethyl-3,4-dihydro-2H-chromen-4-yl]-3-(1-methyl-2-oxo-1,2,3,4-tetrahydroquinolin-7-yl)urea;
1-[(4R)-2,2-dimethyl-7-(trifluoromethyl)-3,4-dihydro-2H-chromen-4-yl]-3-(1-methyl-2-oxo-1,2,3,4-tetrahydroquinolin-7-yl)urea;
1-[(4R)-6-fluoro-2,2-dipropyl-3,4-dihydro-2H-chromen-4-yl]-3-(1-methyl-2-oxo-1,2,3,4-tetrahydroquinolin-7-yl)urea;
1-[(4R)-6-fluoro-2,2-bis(fluoromethyl)-3,4-dihydro-2H-chromen-4-yl]-3-(1-methyl-2-oxo-1,2,3,4-tetrahydroquinolin-7-yl)urea;
1-[(4R)-6,8-difluoro-2,2-bis(fluoromethyl)-3,4-dihydro-2H-chromen-4-yl]-3-(1-methyl-2-oxo-1,2,3,4-tetrahydroquinolin-7-yl)urea;
1-[(4R)-6-fluoro-3,4-dihydrospiro[chromene-2,1'-cyclobutan]-4-yl]-3-(1-methyl-2-oxo-1,2,3,4-tetrahydroquinolin-7-yl)urea;
1-[(4R)-2,2-diethyl-6-fluoro-3,4-dihydro-2H-chromen-4-yl]-3-(1-methyl-2-oxo-1,2,3,4-tetrahydroquinolin-7-yl)urea;
1-[(4R)-8-fluoro-2,2-dipropyl-3,4-dihydro-2H-chromen-4-yl]-3-(1-methyl-2-oxo-1,2,3,4-tetrahydroquinolin-7-yl)urea;
1-[(4R)-2,2-diethyl-7-(trifluoromethoxy)-3,4-dihydro-2H-chromen-4-yl]-3-(1-methyl-2-oxo-1,2,3,4-tetrahydroquinolin-7-yl)urea;
1-[(4R)-7-chloro-8-fluoro-2,2-bis(fluoromethyl)-3,4-dihydro-2H-chromen-4-yl]-3-(1-methyl-2-oxo-1,2,3,4-tetrahydroquinolin-7-yl)urea;
1-[(4R)-6-fluoro-2,2-dimethyl-3,4-dihydro-2H-chromen-4-yl]-3-(1-methyl-2-oxo-1,2,3,4-tetrahydroquinolin-7-yl)urea;
1-[(4R)-8-chloro-7-fluoro-2,2-dimethyl-3,4-dihydro-2H-chromen-4-yl]-3-(1-methyl-2-oxo-1,2,3,4-tetrahydroquinolin-7-yl)urea;
1-(1-methyl-2-oxo-1,2,3,4-tetrahydroquinolin-7-yl)-3-[(4S)-7-(trifluoromethoxy)-3,4-dihydro-2H-chromen-4-yl]urea;

1-[(4R)-7-chloro-2,2-dimethyl-3,4-dihydro-2H-chromen-4-yl]-3-(1-methyl-2-oxo-1,2,3,4-tetrahydroquinolin-7-yl)urea;

1-(1-methyl-2-oxo-1,2,3,4-tetrahydroquinolin-7-yl)-3-[(4R)-7-(trifluoromethoxy)-3,4-dihydro-2H-chromen-4-yl]urea;

1-[(4R)-6-fluoro-2,2-bis(methoxymethyl)-3,4-dihydro-2H-chromen-4-yl]-3-(1-methyl-2-oxo-1,2,3,4-tetrahydroquinolin-7-yl)urea;

1-[(4R)-2,2-bis(fluoromethyl)-3,4-dihydro-2H-chromen-4-yl]-3-(1-methyl-2-oxo-1,2,3,4-tetrahydroquinolin-7-yl)urea;

1-[(4R)-8-fluoro-2,2-bis(fluoromethyl)-3,4-dihydro-2H-chromen-4-yl]-3-(1-methyl-2-oxo-1,2,3,4-tetrahydroquinolin-7-yl)urea;

1-[(4R)-6-fluoro-3,4-dihydro-2H-chromen-4-yl]-3-(1-methyl-2-oxo-1,2,3,4-tetrahydroquinolin-7-yl)urea;

1-[(1R)-5-chloro-2,3-dihydro-1H-inden-1-yl]-3-(1-methyl-2-oxo-1,2,3,4-tetrahydroquinolin-7-yl)urea;

1-(1-methyl-2-oxo-1,2,3,4-tetrahydroquinolin-7-yl)-3-[(4R)-8-(trifluoromethyl)-3,4-dihydro-2H-chromen-4-yl]urea;

1-[(1R)-5-fluoro-2,3-dihydro-1H-inden-1-yl]-3-(1-methyl-2-oxo-1,2,3,4-tetrahydroquinolin-7-yl)urea;

1-[(4S)-6-fluoro-3,4-dihydrospiro[chromene-2,1'-cyclobutan]-4-yl]-3-(1-methyl-2-oxo-1,2,3,4-tetrahydroquinolin-7-yl)urea;

1-[(4S)-6-fluoro-2,2-dimethyl-3,4-dihydro-2H-chromen-4-yl]-3-(1-methyl-2-oxo-1,2,3,4-tetrahydroquinolin-7-yl)urea;

1-[(4R)-3,4-dihydrospiro[chromene-2,1'-cyclopentan]-4-yl]-3-(1-methyl-2-oxo-1,2,3,4-tetrahydroquinolin-7-yl)urea;

1-[(2S,4R)-2-(fluoromethyl)-2-methyl-7-(trifluoromethyl)-3,4-dihydro-2H-chromen-4-yl]-3-(1-methyl-2-oxo-1,2,3,4-tetrahydroquinolin-7-yl)urea;

1-[(2R,4R)-2-(fluoromethyl)-2-methyl-7-(trifluoromethyl)-3,4-dihydro-2H-chromen-4-yl]-3-(1-methyl-2-oxo-1,2,3,4-tetrahydroquinolin-7-yl)urea;

1-[(2S,4R)-7-chloro-2-(fluoromethyl)-2-methyl-3,4-dihydro-2H-chromen-4-yl]-3-(1-methyl-2-oxo-1,2,3,4-tetrahydroquinolin-7-yl)urea;

1-[(2S,4R)-2-(difluoromethyl)-2-methyl-3,4-dihydro-2H-chromen-4-yl]-3-(1-methyl-2-oxo-1,2,3,4-tetrahydroquinolin-7-yl)urea;

1-[(2R,4R)-2-(difluoromethyl)-2-methyl-3,4-dihydro-2H-chromen-4-yl]-3-(1-methyl-2-oxo-1,2,3,4-tetrahydroquinolin-7-yl)urea;

1-[(4R)-7-chloro-8-fluoro-2,2-dimethyl-3,4-dihydro-2H-chromen-4-yl]-3-(1-methyl-2-oxo-1,2,3,4-tetrahydroquinolin-7-yl)urea;

1-[(4R)-2,2-dimethyl-7-(trifluoromethyl)-3,4-dihydro-2H-pyrano[2,3-b]pyridin-4-yl]-3-(1-methyl-2-oxo-1,2,3,4-tetrahydroquinolin-7-yl)urea;

1-[(4R)-7-fluoro-2,2-bis(fluoromethyl)-3,4-dihydro-2H-chromen-4-yl]-3-(1-methyl-2-oxo-1,2,3,4-tetrahydroquinolin-7-yl)urea;

1-[(4R)-7-bromo-2,2-dimethyl-3,4-dihydro-2H-chromen-4-yl]-3-(1-methyl-2-oxo-1,2,3,4-tetrahydroquinolin-7-yl)urea;

1-(1-methyl-2-oxo-1,2,3,4-tetrahydroquinolin-7-yl)-3-[(2S,4R)-2-methyl-2-(trifluoromethyl)-3,4-dihydro-2H-chromen-4-yl]urea;

1-[(4R)-7,8-difluoro-2,2-dimethyl-3,4-dihydro-2H-chromen-4-yl]-3-(1-methyl-2-oxo-1,2,3,4-tetrahydroquinolin-7-yl)urea;

1-[(4R)-7-chloro-2,2-bis(fluoromethyl)-3,4-dihydro-2H-chromen-4-yl]-3-[3-(morpholin-4-yl)-2-oxo-1,2,3,4-tetrahydroquinolin-7-yl]urea;

1-[(4R)-7-fluoro-2,2-dimethyl-3,4-dihydro-2H-chromen-4-yl]-3-[3-(morpholin-4-yl)-2-oxo-1,2,3,4-tetrahydroquinolin-7-yl]urea;

1-[(4R)-7-chloro-2,2-bis(fluoromethyl)-3,4-dihydro-2H-chromen-4-yl]-3-[3-(1,4-oxazepan-4-yl)-2-oxo-1,2,3,4-tetrahydroquinolin-7-yl]urea;

1-[(4R)-7-fluoro-2,2-dimethyl-3,4-dihydro-2H-chromen-4-yl]-3-[3-(1,4-oxazepan-4-yl)-2-oxo-1,2,3,4-tetrahydroquinolin-7-yl]urea;

1-[(4R)-7-chloro-2,2-bis(fluoromethyl)-3,4-dihydro-2H-chromen-4-yl]-3-{3-[(2-hydroxyethyl)(methyl)amino]-2-oxo-1,2,3,4-tetrahydroquinolin-7-yl}urea;

1-[(4R)-7-fluoro-2,2-dimethyl-3,4-dihydro-2H-chromen-4-yl]-3-{3-[(2-methoxyethyl)(methyl)amino]-2-oxo-1,2,3,4-tetrahydroquinolin-7-yl}urea;

1-[(4R)-7-chloro-2,2-bis(fluoromethyl)-3,4-dihydro-2H-chromen-4-yl]-3-{3-[(2-methoxyethyl)(methyl)amino]-2-oxo-1,2,3,4-tetrahydroquinolin-7-yl}urea;

1-[(4R)-2,2-dimethyl-8-(trifluoromethyl)-3,4-dihydro-2H-chromen-4-yl]-3-[3-(2-hydroxyethyl)-2-oxo-1,2,3,4-tetrahydroquinazolin-7-yl]urea;

1-[(4R)-3,4-dihydro-2H-chromen-4-yl]-3-[3-(2-hydroxyethyl)-2-oxo-1,2,3,4-tetrahydroquinazolin-7-yl]urea;

1-[(4R)-2,2-bis(fluoromethyl)-7-(trifluoromethyl)-3,4-dihydro-2H-chromen-4-yl]-3-[3-(2-hydroxyethyl)-2-oxo-1,2,3,4-tetrahydroquinazolin-7-yl]urea;

1-[(4R)-6-fluoro-2,2-dipropyl-3,4-dihydro-2H-chromen-4-yl]-3-[3-(2-hydroxyethyl)-2-oxo-1,2,3,4-tetrahydroquinazolin-7-yl]urea;

1-[(4R)-8-fluoro-2,2-dipropyl-3,4-dihydro-2H-chromen-4-yl]-3-[3-(2-hydroxyethyl)-2-oxo-1,2,3,4-tetrahydroquinazolin-7-yl]urea;

1-[(4R)-8-chloro-7-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;

1-[(4R)-7-chloro-2,2-dimethyl-3,4-dihydro-2H-chromen-4-yl]-3-[3-(2-hydroxyethyl)-2-oxo-1,2,3,4-tetrahydroquinazolin-7-yl]urea;

1-[(4R)-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea;

1-[(4R)-8-fluoro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea;

1-[(4R)-7-chloro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea;

1-[(4R)-3,4-dihydrospiro[chromene-2,1'-cyclopentan]-4-yl]-3-[3-(2-hydroxyethyl)-2-oxo-1,2,3,4-tetrahydroquinazolin-7-yl]urea;

1-[(2S,4R)-2-(difluoromethyl)-2-methyl-3,4-dihydro-2H-chromen-4-yl]-3-[3-(2-hydroxyethyl)-2-oxo-1,2,3,4-tetrahydroquinazolin-7-yl]urea; and 1-[(4R)-7-fluoro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea.

Additional exemplary compounds include, but are not limited to,

1-[(4R)-2,2-bis(fluoromethyl)-7-(trifluoromethyl)-3,4-dihydro-2H-chromen-4-yl]-3-(2-oxo-1,2,3,4-tetrahydroquinolin-7-yl)urea;

1-[(2R,4R)-7-chloro-2-(difluoromethyl)-2-methyl-3,4-dihydro-2H-chromen-4-yl]-3-(3-oxo-3,4-dihydro-2H-1,4-benzoxazin-6-yl)urea;

1-[(2S,4R)-7-chloro-2-(difluoromethyl)-2-methyl-3,4-dihydro-2H-chromen-4-yl]-3-(3-oxo-3,4-dihydro-2H-1,4-benzoxazin-6-yl)urea;

1-[(4R)-7-chloro-2,2-bis(fluoromethyl)-3,4-dihydro-2H-chromen-4-yl]-3-(3-oxo-3,4-dihydro-2H-1,4-benzoxazin-8-yl)urea;

1-[(4R)-2,2-bis(fluoromethyl)-7-(trifluoromethyl)-3,4-dihydro-2H-chromen-4-yl]-3-(3-oxo-3,4-dihydro-2H-1,4-benzoxazin-6-yl)urea;

1-[(4R)-7-chloro-8-fluoro-2,2-dimethyl-3,4-dihydro-2H-chromen-4-yl]-3-(3-oxo-3,4-dihydro-2H-1,4-benzoxazin-6-yl)urea;

1-(1-methyl-2-oxo-1,2,3,4-tetrahydroquinolin-7-yl)-3-[(2R,4R)-2-methyl-2-(trifluoromethyl)-3,4-dihydro-2H-chromen-4-yl]urea; and 1-[(2S,4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea.

In one embodiment, the compound of Formula (I) when administered to a human subject produces an increase in average time for hand withdrawal from a temperature-controlled water bath that is less than about 30 seconds relative to a vehicle control. In another embodiment, the compound of Formula (I) when administered to a human subject produces an increase in average time for hand withdrawal from a temperature-controlled water bath that is less than about 10 seconds relative to a vehicle control. In another embodiment, the compound of Formula (I) when administered to a human subject produces an increase in average time for hand withdrawal from a temperature-controlled water bath that is less than about 5 seconds relative to a vehicle control. In still another embodiment, the compound of Formula (I) when administered to a human subject does not significantly change the average time for hand withdrawal from a temperature-controlled water bath relative to a vehicle control. In one embodiment, the water bath is maintained at a constant temperature in the range from about 46° C. to about 52° C. In still another embodiment, the water bath is maintained at a constant temperature of about 49° C.

In one embodiment, the compound of Formula (I), when tested in a rat tail immersion model of noxious thermosensation (such as the model described in the Biological Data section of this application), produces a percent increase in average response latency for tail withdrawal relative to a vehicle control that is less than about 20%. In another embodiment, the compound of Formula (I), when tested in a rat tail immersion model of noxious thermosensation, produces a percent increase in average response latency for tail withdrawal relative to a vehicle control that is less than about 10%. In still another embodiment, the compound of Formula (I), when tested in a rat tail immersion model of noxious thermosensation, produces no statistically significant increase in the average response latency for tail withdrawal relative to a vehicle control.

In one embodiment, the compound of Formula (I), when contacted in vitro at a concentration of about 10 µM with human TRPV1 receptor (such as in the Acid Activation Assay described in the Biological Data section of this application), blocks intracellular calcium flux relative to intracellular calcium flux measured in vitro for human TRPV1 receptor at a pH of about 5.0 in the absence of such compound by less than about 75%.

In one embodiment, the compound of Formula (I), (a) when tested in a rat tail immersion model of noxious thermosensation (such as the model described in the Biological Data section of this application), produces a percent increase in average response latency for tail withdrawal relative to a vehicle control that is less than about 20%; and (b) when contacted in vitro at a concentration of about 10 µM with human TRPV1 receptor (such as in the Acid Activation Assay described in the Biological Data section of this application), blocks intracellular calcium flux relative to intracellular calcium flux measured in vitro for human TRPV1 receptor at a pH of about 5.0 in the absence of such compound by less than about 75%.

In one embodiment, the compound of Formula (I), (a) when tested in a rat tail immersion model of noxious thermosensation (such as the model described in the Biological Data section of this application), produces a percent increase in average response latency for tail withdrawal relative to a vehicle control that is less than about 10%; and (b) when contacted in vitro at a concentration of about 10 µM with human TRPV1 receptor (such as in the Acid Activation Assay described in the Biological Data section of this application), blocks intracellular calcium flux relative to intracellular calcium flux measured in vitro for human TRPV1 receptor at a pH of about 5.0 in the absence of such compound by less than about 75%.

In one embodiment, the compound of Formula (I), (a) when tested in a rat tail immersion model of noxious thermosensation (such as the model described in the Biological Data section of this application), produces no statistically significant increase in the average response latency for tail withdrawal relative to a vehicle control; and (b) when contacted in vitro at a concentration of about 10 µM with human TRPV1 receptor (such as in the Acid Activation Assay described in the Biological Data section of this application), blocks intracellular calcium flux relative to intracellular calcium flux measured in vitro for human TRPV1 receptor at a pH of about 5.0 in the absence of such compound by less than about 75%.

Compounds described herein can exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It can be appreciated two or more asymmetric centers can be present in the present compounds, hence several diastereomers and enantiomers of the exemplified structures can often be possible, and that pure diastereomers and enantiomers represent preferred embodiments. It is intended that pure diasteromers, pure enantiomers, and mixtures thereof, are within the scope of the invention.

Various stereoisomers (including enantiomers and diastereomers) and mixtures thereof (including racemates) are contemplated. Individual stereoisomers of present compounds can be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

For example, compounds of formula (I-f) wherein L is a bond can be isolated as any one of the stereoisomers as shown below, or mixtures of two or more of stereoisomers of various ratios:

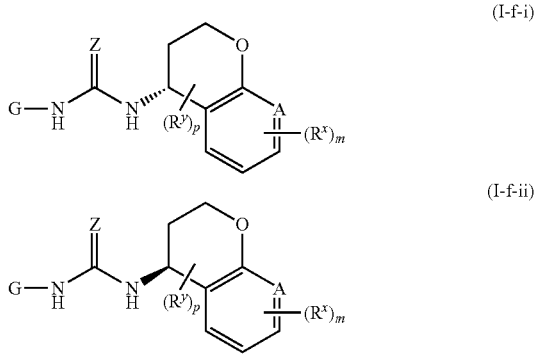

It is to be understood that the substituents and variables, and combinations thereof, in formula (I-f-i) and (I-f-ii) have the same values as those discussed for (I-f) above.

Geometric isomers can exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed herein can exhibit the phenomenon of tautomerism.

Thus, the formula drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formula drawings.

Compounds of the invention can exist in isotope-labeled or isotope-enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds can be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention can be used as standards to determine the effectiveness of TRPV1 ligands in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labeled Comp. Radiopharmaceut., 36(10):927-932 (1995); Kushner et al., Can. J. Physiol. Pharmacol., 77, 79-88 (1999).

In addition, non-radio active isotope containing drugs, such as deuterated drugs called "heavy drugs," can be used for the treatment of diseases and conditions related to TRPV1 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D. M. and Finkel A. J, Ann. N.Y. Acad. Sci. 1960 84: 770; Thomson J. F., Ann. New York Acad. Sci. 1960 84: 736; Czakja D. M. et al., Am. J. Physiol. 1961 201: 357). Acute replacement of as high as 15%-23% in human fluids with deuterium was found not to cause toxicity (Blagojevic N. et al. in "Dosimetry & Treatment Planning for Neutron Capture Therapy", Zamenhof R, Solares G and Harling 0 Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom can be stronger than the same bond between the light isotope and that atom. Accordingly, the incorporation of an isotope at a site of metabolism or enzymatic transformation can slow said reactions, potentially altering the pharmacokinetic profile or efficacy relative to the non-isotopic compound.

C. GENERAL SYNTHESIS

This invention is intended to encompass compounds described herein when prepared by synthetic processes or by metabolic processes. Preparation of the compounds by metabolic processes includes those occurring in the human or animal body (in vivo) or processes occurring in vitro.

The compounds can be prepared by a variety of processes well known for the preparation of compounds of this class. For example, compounds disclosed herein wherein the groups G, $X^1$, L, $R^x$, $R^y$, A, m, n, and p have the meanings as set forth in the summary and detailed description sections unless otherwise noted, can be synthesized as shown in the accompanying Schemes 1-13.

As used in the descriptions of the schemes and the examples, certain abbreviations are intended to have the following meanings: AcOH for acetic acid; AcCl for acetyl chloride; AgOAc for silver acetate; BINAP for 2,2'-bis(diphenylphosphino)-1,1'-binaphthyl; Boc for tert-butoxycarbonyl; (Boc)$_2$O for di-tert-butyl dicarbonate; n-BuLi for n-butyllithium; dba for dibenzylideneacetone; DABCO for 1,4-diazabicyclo[2.2.2]octane; DCE for dichloroethane; DIEA for N,N-diisopropylethylamine; DMF for dimethylformamide; DMSO for dimethyl sulfoxide; DSC for N,N'-disuccinimidyl carbonate; DME for dimethoxyethane; DPPA for diphenylphosphoryl azide; Et$_3$N for triethylamine; EtOAc for ethyl acetate; Et$_2$O for diethyl ether; IPA for isopropanol; KOt-Bu for potassium tert-butoxide; mCPBA for 3-chloroperoxybenzoic acid; MeOH for methanol; MeLi for methyl lithium, Me-THF for 2-methyl tetrahydrofuran; MOM for methoxymethyl; MTBE for methyl tert-butyl ether; Ms$_2$O for methanesulfonic anhydride; NCS for N-chlorosuccinimide; (iPr)$_2$NEt for diisopropylethylamine; i-PrOH for isopropanol; PhCH$_3$ for toluene; pyr for pyridine; Ra—Ni for Raney nickel; THF for tetrahydrofuran; Ti(OEt)$_4$ for titatium(IV) ethoxide; TsOH for p-toluenesulfonic acid; TFA for trifluoroacetic acid; TfOH for triflic acid (trifluoromethansulfonic acid); and HPLC for high performance liquid chromatography.

Ureas of general formula (I-a) can be prepared as described in Scheme 1. Amines of formula (I) are commercially available or known in the art (WO2005/016915, WO2010/0016285) and can be reacted first with N,N'-disuccinimidyl carbonate (DSC) in the presence of a base such as but not limited to pyridine, and in a solvent such as acetonitrile, to provide intermediate (2) that is subsequently with amine nucleophiles of formula (3) in the presence of an amine base such as but not limited to diisopropylethylamine, to provide ureas of general formula (4).

The requisite amines of general formula (3) are commercially available or known in the art (WO2010045401; WO2010045402; Voight, E. A., et al., Tetrahedron Letters, 2010, 51 (45), 5904-5907; US 20080287676; Gomtsyan, A., et al., J. Med. Che., 51, 392-395) or can be prepared by any of several methods and synthetic intermediates selected by one of ordinary skill in the art as described in the schemes described herein below. As shown in Scheme 2, hydroxy benzoic acids of general formula (4) can be reacted with excess methyllithium in a solvent such as diethyl ether at reduced temperatures (less than about 20° C.) to provide methyl ketones of general formula (5). Methyl ketones (5) can be reacted with ketones of general formula (6) to provide chromanones of general formula (7). Non-limiting examples of ketones (6) include acetone and 3-pentanone. The reaction is generally performed in the presence of an amine base such as pyrrolidine, in a protic solvent such as but not limited to methanol. Ketones of general formula (7) can be treated with a variety of chiral hydride sources known to those skilled in the art (Corey, E. J. et al. J. Org. Chem. 1988, 53, 2861; Kawanami, S. et al. Tetrahedron 2003, 59, 8411; Corey, E. J. et al. Tetrahedron Asymm. 2002, 13, 1347) to provide chiral alcohols of general formula (8). Alcohols (8) can be converted to azides of general formula (9) by activation with a sulfonylating agent such as but not limited to methanesulfonic anhydride, followed by displacement with a nucleophile azide source such as but not limited tetrabutylammonium azide (Burgard, A. et al. Tetrahedron 1999, 55, 7555). It is to be noted that the transformation of (8) to (9) proceeds with net overall inversion of absolute stereochemistry. Finally, amines of general formula (10) can be obtained by reduction of azides (9) by treatment with a phosphine agent such as triphenylphosphine (PPh$_3$) under aqueous conditions with an appropriate water-miscible organic co-solvent such as but not limited to THF (Gololobov, Y. G. et al. Tetrahedron 1981, 37, 437). Alternatively, amines of general formula (10) can be obtained by reduction of azides (9) by treatment with hydrogen gas in the presence of a catalyst such as but not limited to Raney nickel (Ra—Ni) in a solvent such as but not limited to methanol. Chiral amines of formula (10) can be converted to compounds of formula (11) using synthetic methods as outlined in Scheme 1.

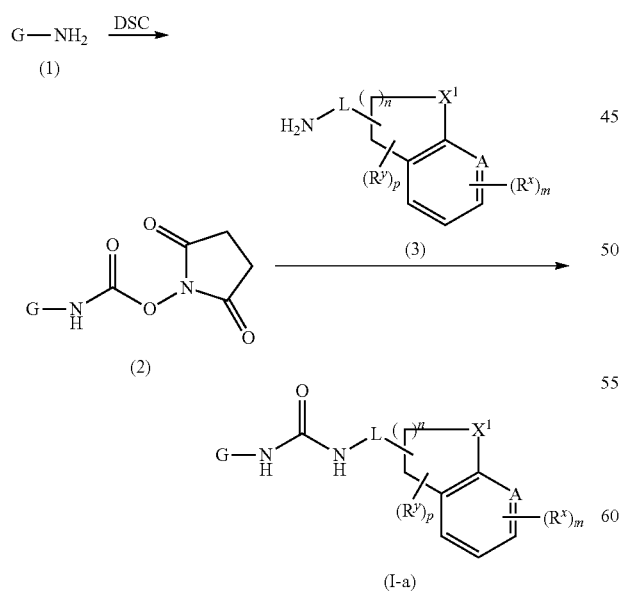

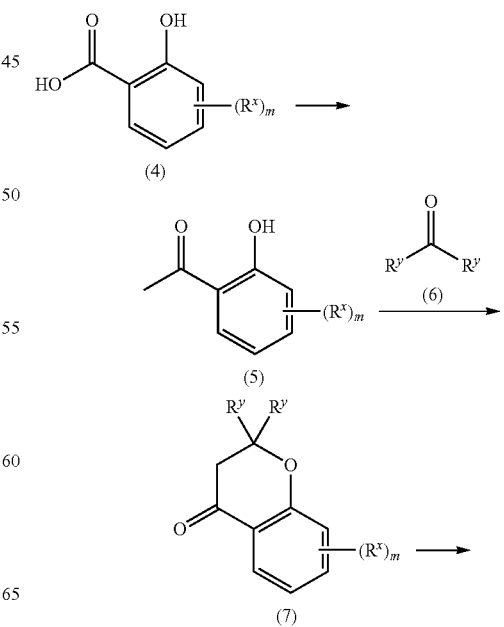

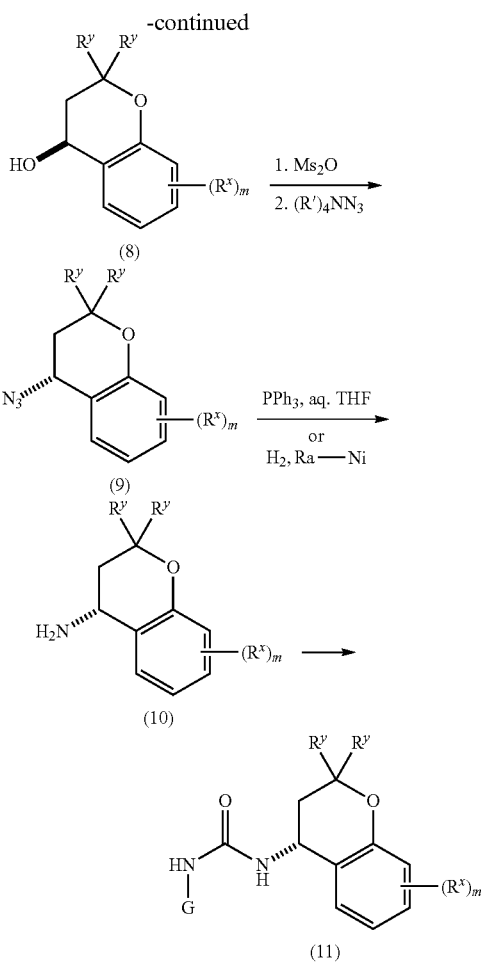

Racemic amines of general formula (3) wherein L is a bond can be prepared from the corresponding ketones (12) as shown in Scheme 3. Ketones (12) can be treated with hydroxyamines or alkoxyamines such as methoxyamine to provide oximes of general formula (13). The oxime group of (13) can be reduced using methodologies known by one skilled in the art, for example, by hydrogenolysis in the presence of a catalyst such as palladium on carbon to provide the amines of general formula (14).

Scheme 3

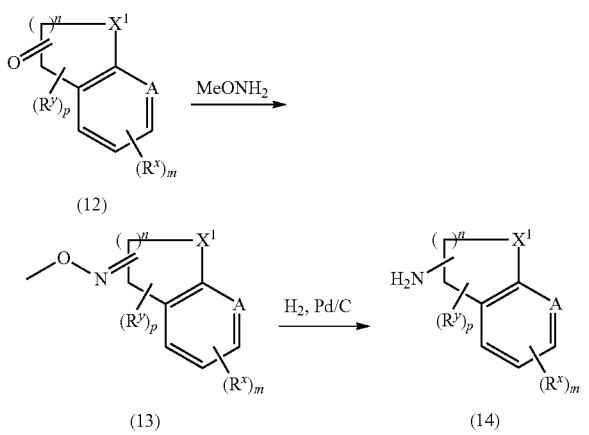

As shown in Scheme 4, amines of general formula (16) can be prepared according to the general procedure described by Ellman and co-workers (Tanuwidjaja, J.; Ellman, J. A. et al. *J. Org. Chem.* 2007, 72, 626). Ketones of general formula (12) can be condensed with a chiral sulfinamide such as tert-butanesulfinamide in the presence of a Lewis acid such as $Ti(OEt)_4$ to provide N-sulfinyl imine intermediates that can undergo a subsequent in situ reduction with reagents such as sodium borohydride to provide sulfinamides of general formula (15). Treatment of sulfinamides of general formula (15) with acetyl chloride and methanol in a solvent such as but not limited to methyl tert-butyl ether provides amine hydrochloride salts of general formula (16).

Scheme 4

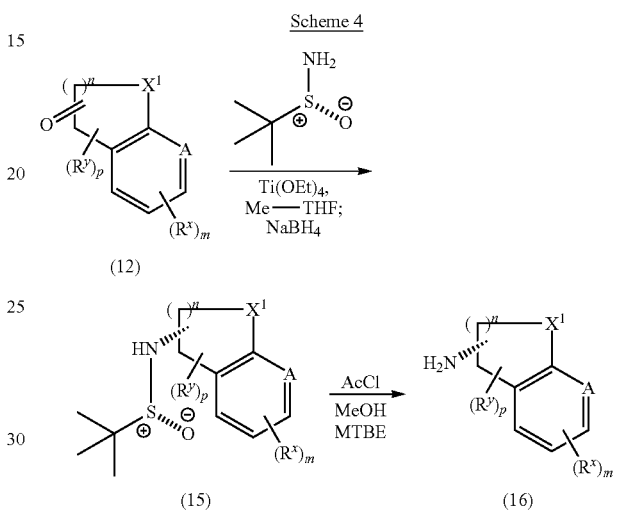

The requisite ketones of general formula (12) wherein A is CH, $X^1$ is O, p is 0, and n is 2 can also be prepared by any of several methods and synthetic intermediates selected by one of ordinary skill in the art as described in Schemes 5-6. As shown in Scheme 5, phenols of general formula (17) can be treated with a propargyl bromide and a base such as but not limited to potassium carbonate in a nonpolar solvent such as but not limited to toluene to provide aryl ethers of general formula (18). Reaction of (18) with NCS in the presence of silver acetate in a solvent such as but not limited to acetone affords chloro alkyne derivatives of general formula (19). Upon heating of chloro alkynes of general formula (19) in a solvent such as but not limited to ethylene glycol, cyclization occurs to give chromanones of general formula (12a).

Scheme 5

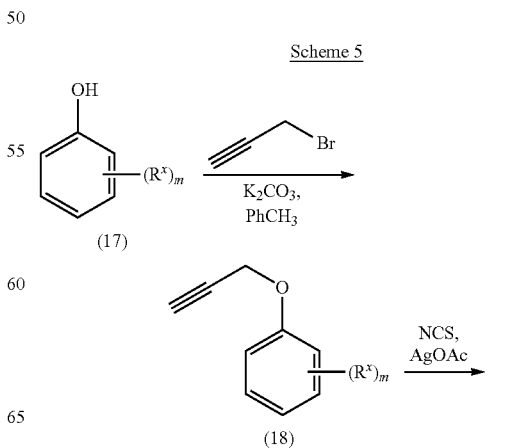

-continued

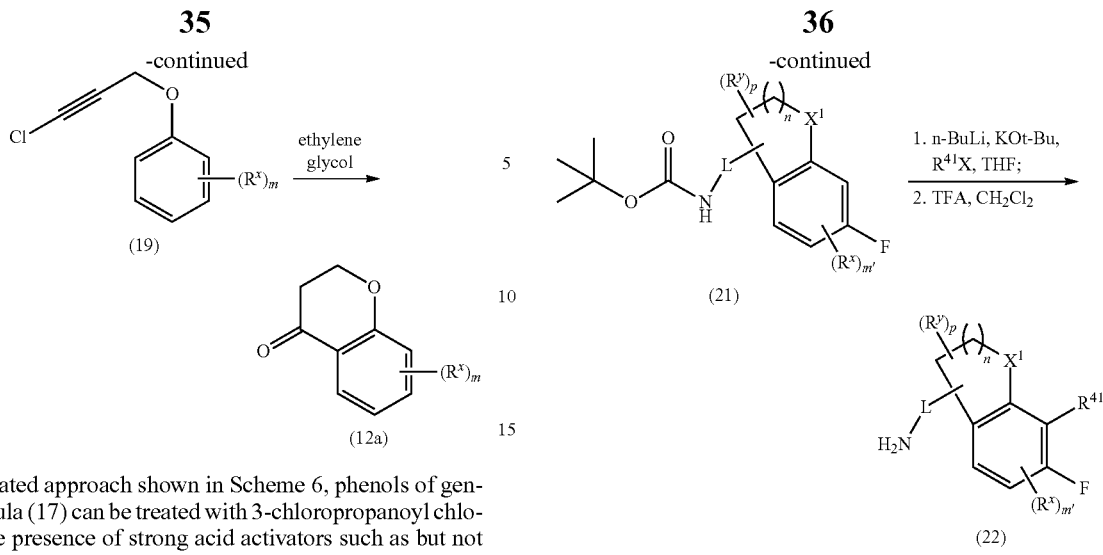

In a related approach shown in Scheme 6, phenols of general formula (17) can be treated with 3-chloropropanoyl chloride in the presence of strong acid activators such as but not limited to TFA and triflic acid to afford directly chromanones of general formula (12a).

Scheme 6

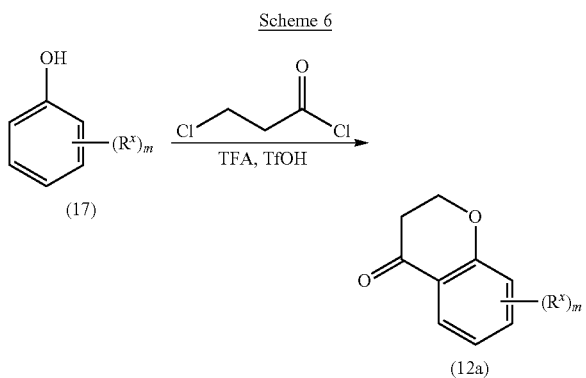

Certain amine intermediates can be further functionalized using the sequence described in Scheme 7. Fluorinated amines of general formula (20) wherein m' is 1 or 2 can be protected as the corresponding tert-butoxy carbamates of general formula (21) using tert-butoxycarbonyl anhydride and an amine base such as but not limited to triethylamine Reaction of (21) with a strong base or combination of strong bases such as but not limited to, n-butyllithium, potassium tert-butoxide, and/or sec-butyllithium, in a solvent such as but not limited to THF effects deprotonation adjacent to the fluorine. It can be appreciated by those skilled in the art that these organometallic intermediates can be reacted with a wide variety of electrophilic reagents ($R^{41}X$) wherein $R^{41}$ is alkyl or haloalkyl and X is Cl, Br, or I. Non limiting examples of $R^{41}X$ include hexachloroethane and methyl iodide. Subsequent removal of the Boc protecting group with a strong acid, such as but not limited to, TFA provides amines of general formula (22).

Scheme 7

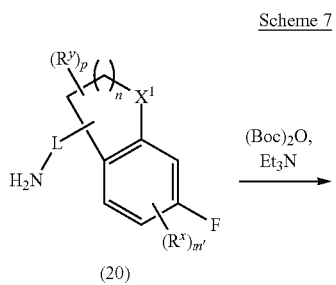

The requisite substituted methyl ketones (6) shown in Scheme 2 can be prepared by the methods described in Schemes 8 and 9. For example, phenols of general formula (17) can be protected and subsequently subjected to direct ortho-metalation as shown in Scheme 9. Treatment of (17) with methoxymethyl chloride in the presence of a non-nucleophilic amine base such as diisopropylethylamine in an aprotic solvent such as dichloromethane provides protected phenols of general formula (23). Other examples of suitable phenol oxygen protecting groups are known in the art. Reaction of (23) with an organolithium base such as n-butyllithium in a solvent at reduced temperature (such as THF at −78° C.) followed by quenching with carbon dioxide and subsequent exposure to mineral acid provides hydroxy benzoic acids of general formula (24). Hydroxy benzoic acids (24) can be transformed to methyl ketones (6) using the chemistry described in Scheme 2.

Scheme 8

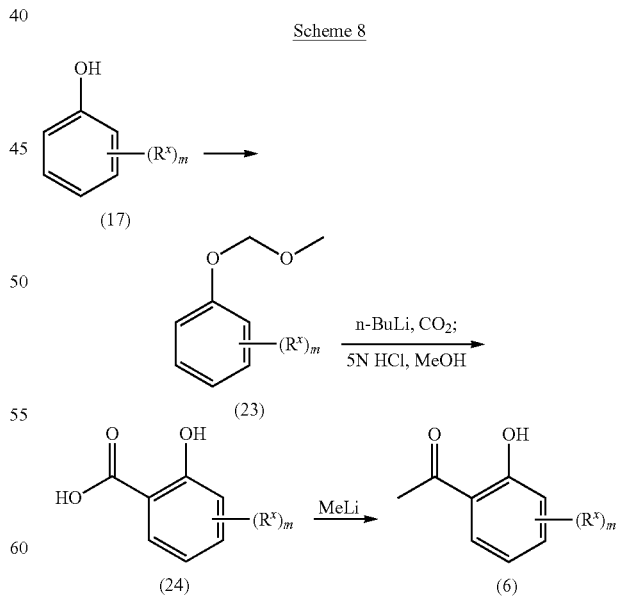

Substituted methyl ketones (6) also can be prepared according to Scheme 9. Phenols of general formula (17) can be treated with an acetylating agent, such as but not limited to, acetyl chloride in the presence of a base, such as but not limited to, pyridine to generate esters of general formula (25). Subjection to a Lewis acid such as but not limited to aluminum trichloride in a solvent such as but not limited to dichloroethane provides methyl ketones of general formula (6).

Scheme 9

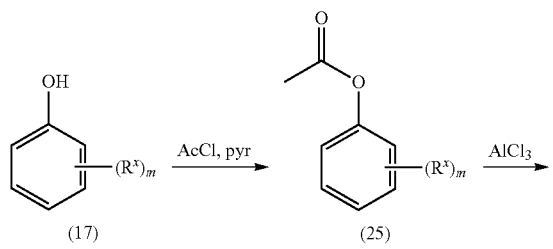

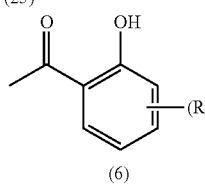

The regiochemistry of attachment of the amino or methylamino substituent on the chroman ring can be varied as described in Schemes 10-11. As shown in Scheme 10, 3-aminomethyl chromans can be prepared via the intermediacy of the nitriles (26). Compounds of general formula (26) upon treatment with hydrogen gas in the presence of a catalyst such as but not limited to Raney nickel provides amines of general formula (27). Aminomethyl chromans (27) can be coupled with amines of general formula (1) using the conditions described in Scheme 1 to provide chromanyl ureas of general formula (28).

Scheme 10

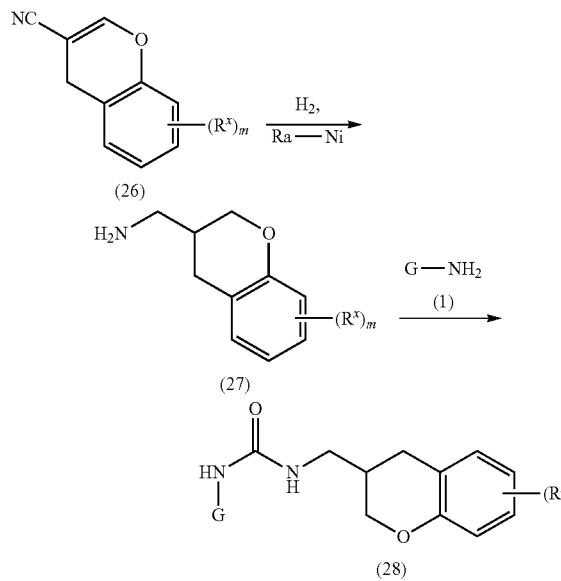

Scheme 11 describes the preparation of 3-amino-substituted chromans. Hydroxy aldehydes of general formula (29), upon heating with acrylonitrile and DABCO, provide chromans of general formula (30). Exposure to aqueous sodium hydroxides affords carboxylic acids of general formula (31). Treatment of (31) with DPPA in the presence of an amine base such as but not limited to triethylamine and heating, followed by exposure to hydrochloric acid provides chromanones of general formula (32). Reaction of (32) with O-methylhydroxyamine in the presence of a base such as but not limited to pyridine provides compounds of general formula (33) which upon treatment with hydrogen gas in the presence of a catalyst such as but not limited to Raney nickel provides amines of general formula (34). Amines (34) can be coupled with activated amines of general formula (2) using the conditions described in Scheme 1 to provide regioisomeric chromanyl ureas of general formula (35).

Scheme 11

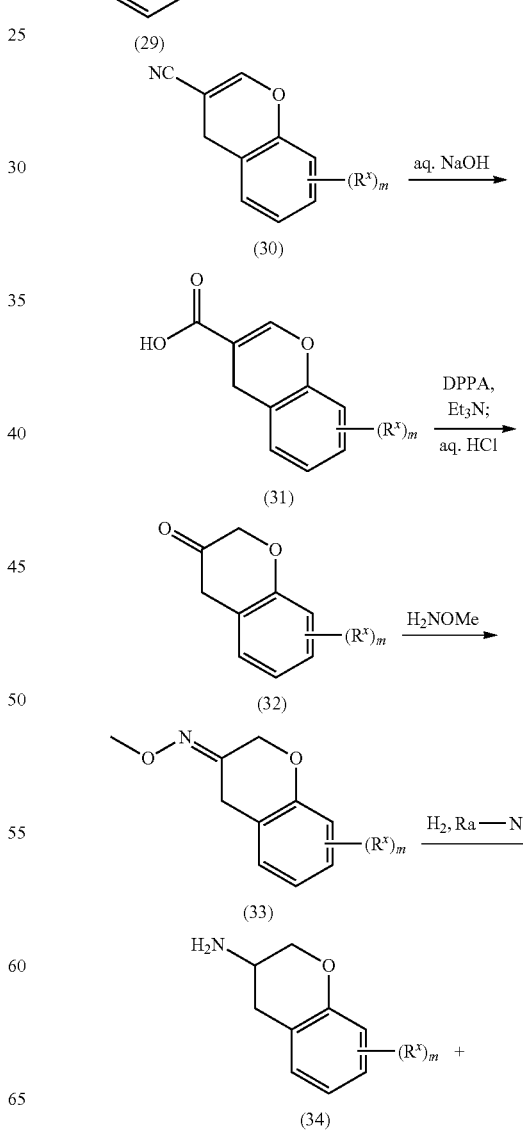

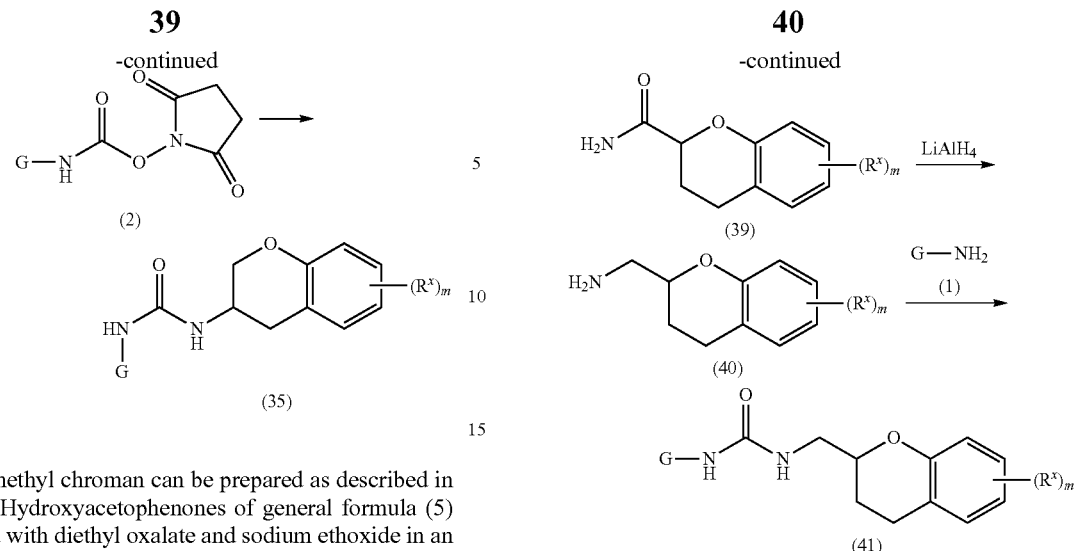

2-Aminomethyl chroman can be prepared as described in Scheme 12. Hydroxyacetophenones of general formula (5) when treated with diethyl oxalate and sodium ethoxide in an alcoholic solvent such as but not limited to ethanol under heated conditions provide compounds of general formula (36). Hydrolysis with hydrochloric acid produces carboxylic acids of general formula (37). Reduction of the carbonyl group in (37) can be accomplished by reaction with hydrogen and 10% palladium on carbon in a solvent such as but not limited to acetic acid to give compounds of general formula (38). Treatment with oxalyl chloride followed by subjection to ammonia gas or concentrated ammonium hydroxide affords primary amides of general formula (39). Compounds of general formula (39) can be reacted with a reducing agent such as but not limited to lithium aluminum hydride to provide 2-aminomethyl chromans of general formula (40) Amines (40) can be coupled with compounds of general formula (1) using the conditions described in Scheme 1 to provide regioisomeric chromanyl ureas of general formula (41).

The preparation of tetrahydroquinoline containing compounds is described in Scheme 13. Commercially available hydroxy quinolines of general formula (42) can be alkylated on nitrogen by treatment with an alkylating agent such as but not limited to methyl iodide in a polar aprotic solvent such as but not limited to DMF in the presence of a base such as but not limited to potassium carbonate to afford compounds of general formula (43). Saponification with sodium hydroxide provides carboxylic acids of general formula (44), which can be treated with a reducing agent such as but not limited to sodium borohydride then decarboxylated with a protic acid such as but not limited to TsOH to afford quinolinones of general formula (45). Carbonyl derivatives of general formula (45) can be converted to amines of general formula (46) using the procedures of Scheme 4, which can be subsequently reacted with indanols of general formula (1) using the conditions described in Scheme 1 to provide tetrahydroquinolines of general formula (47).

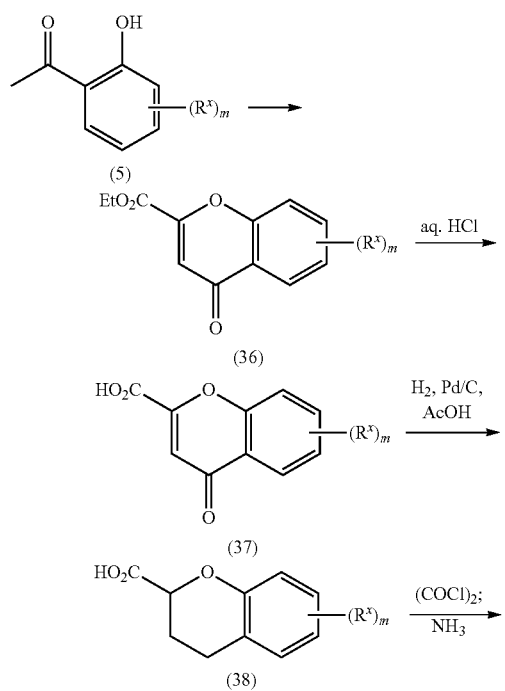

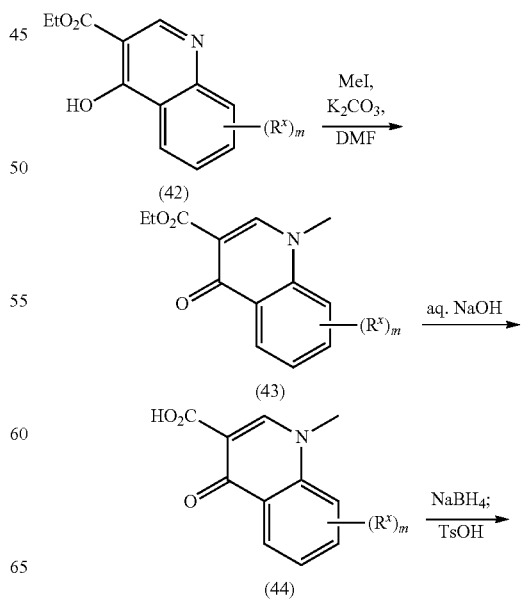

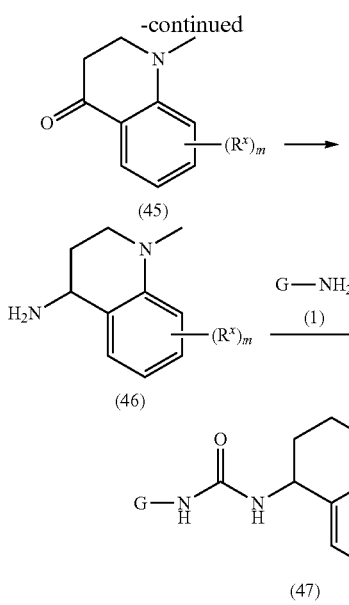

It can be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protecting Groups in Organic Synthesis (3$^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be prepared by carrying out one of the above procedures using a pure geometric isomer as a starting material, or by resolution of a mixture of the geometric isomers of the compound or intermediates using a standard procedure such as chromatographic separation.

Following Examples can be used for illustrative purposes and should not be deemed to narrow the scope of the invention.

D. EXAMPLES

The following descriptions and examples illustrate the preparation of the exemplary compounds of the invention.

Amines of General Formula (1):

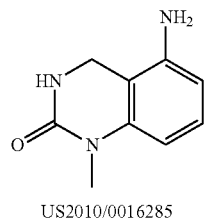

A-1

US2010/0016285

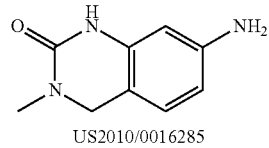

A-2

US2010/0016285

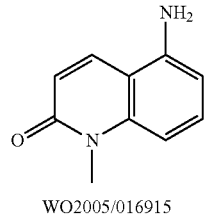

A-3

WO2005/016915

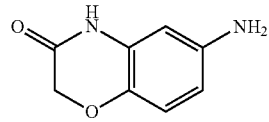

A-4

Commercially available
(Akos Building Blocks)

A-5
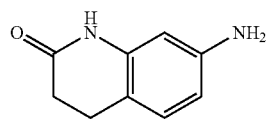
Commercially available
(Asta Tech)
A-6
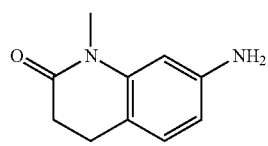
Commercially available
(Aurora Fine Chemicals)
A-7
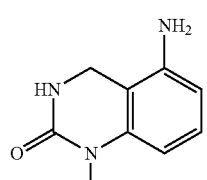
US2010/0016285
A-8
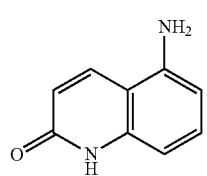
Commercially available
(Aurora Fine Chemicals)
A-9
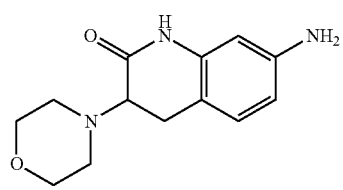
US 2010/0016285
A-10
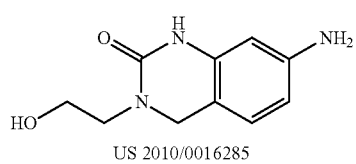
US 2010/0016285
A-11
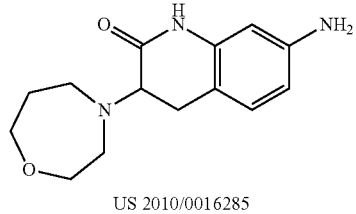
US 2010/0016285
A-12
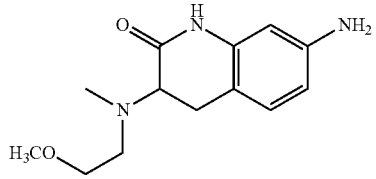
US 2010/0016285
A-13
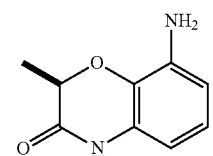
Commercially available
(Xenon Discovery Limited)
A-14
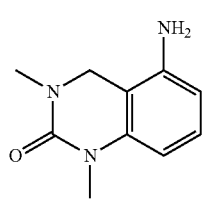
US2010/0016285
A-15
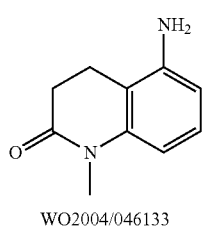
WO2004/046133
A-16
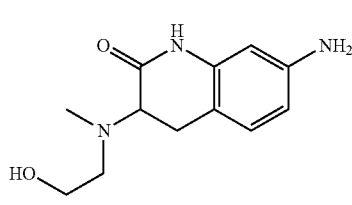
US 2010/0016285
Chromanyl, Indanyl, and Tetrahydroquinolinyl Amines of general formula (3):
B-1
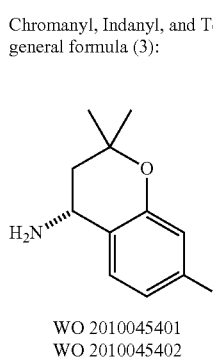
WO 2010045401
WO 2010045402

-continued
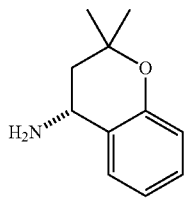
WO 2010045401
WO 2010045402
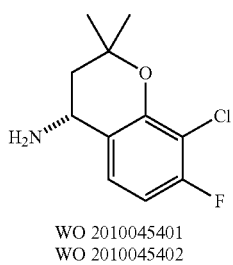
WO 2010045401
WO 2010045402
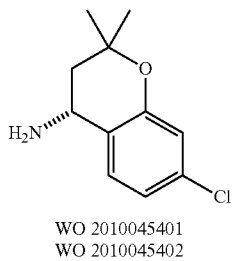
WO 2010045401
WO 2010045402
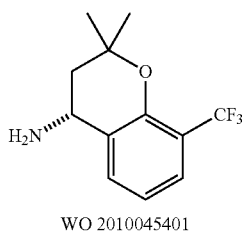
WO 2010045401
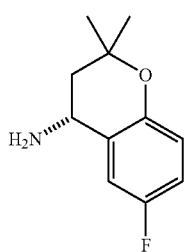
WO 2010045401
WO 2010045402
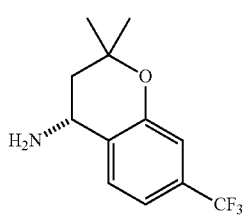
WO 2010045401
WO 2010045402
-continued
B-2
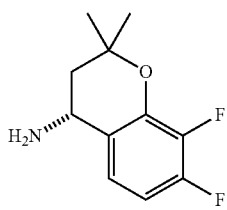
WO 2010045401
WO 2010045402
B-3
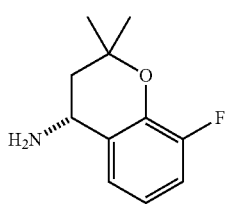
Voight, E.A., *Tet. Letters* (2010), 51(45), 5904-5907
B-4
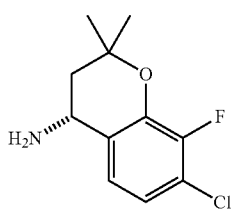
B-5
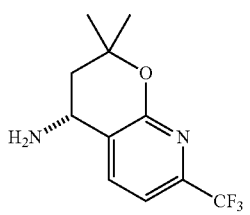
B-6
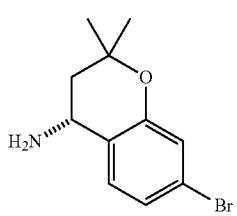
B-7
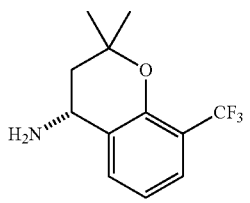
WO 2010045401
WO 2010045402
B-8
B-9
B-10
B-11
B-12
B-13

-continued
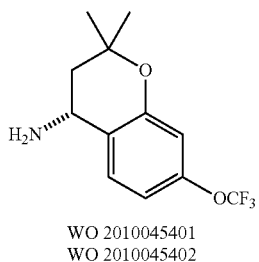
B-13
WO 2010045401
WO 2010045402
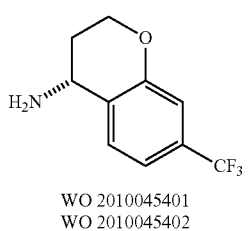
B-14
WO 2010045401
WO 2010045402
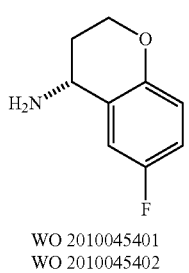
B-15
WO 2010045401
WO 2010045402
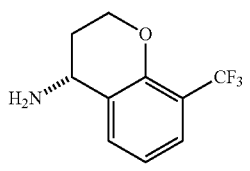
B-16
WO 2010045401
WO 2010045402
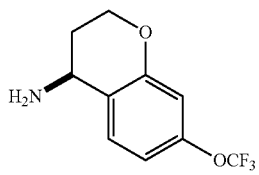
B-17
commercially available
(AlphaChiron Biochemicals)
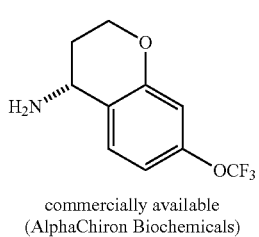
B-18
commercially available
(AlphaChiron Biochemicals)
-continued
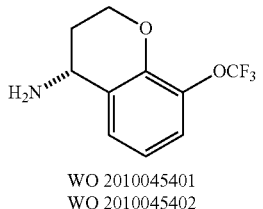
B-19
WO 2010045401
WO 2010045402
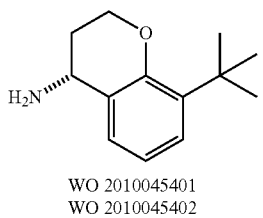
B-20
WO 2010045401
WO 2010045402
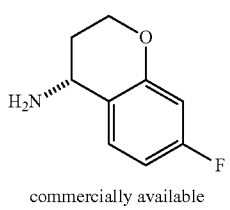
B-21
commercially available
(NetChem Company)
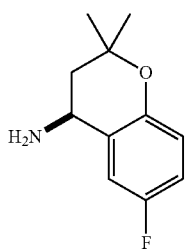
B-22
WO 2010045401
WO 2010045402
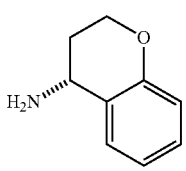
B-23
commercially available
(AlphaChiron Biochemicals)
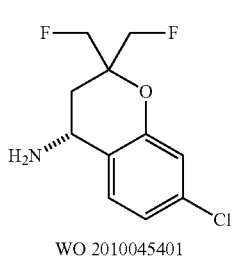
B-24
WO 2010045401

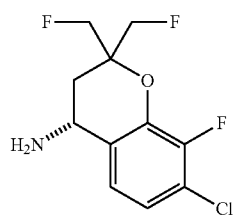
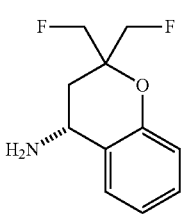
WO 2010045401
WO 2010045402
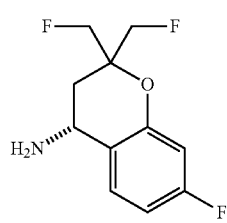
WO 2010045401
WO 2010045402
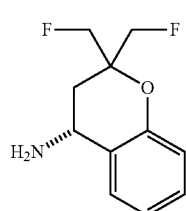
WO 2010045401
WO 2010045402
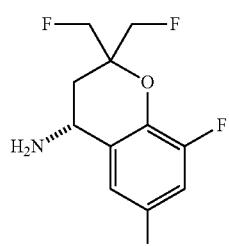
WO 2010045401
WO 2010045402
B-26
B-27
B-28
B-29
B-30
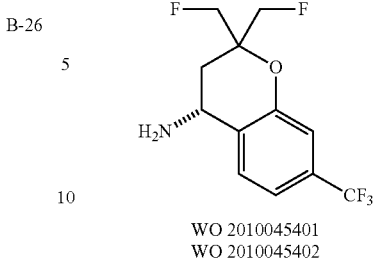
WO 2010045401
WO 2010045402
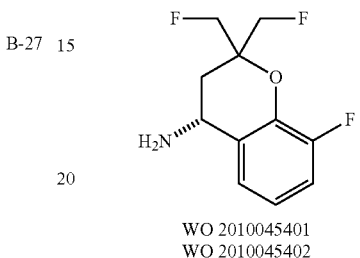
WO 2010045401
WO 2010045402
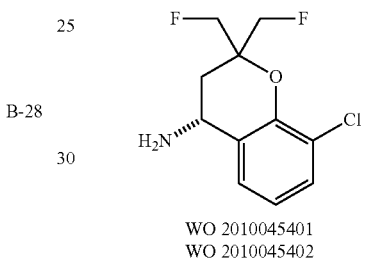
WO 2010045401
WO 2010045402
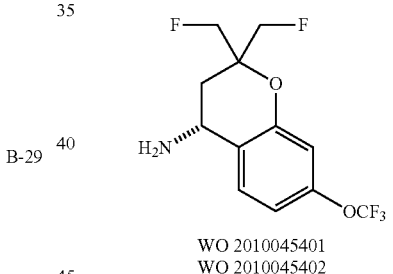
WO 2010045401
WO 2010045402
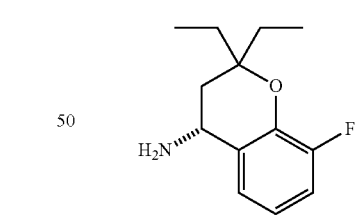
WO 2010045401
WO 2010045402
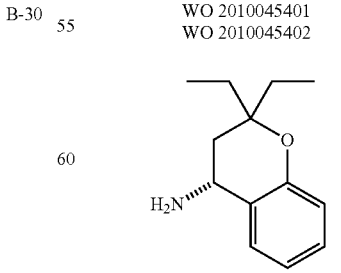
Voight, E.A., *Tet. Letters* (2010), 51(45), 5904-5907
B-31
B-32
B-33
B-34
B-35
B-36

B-37 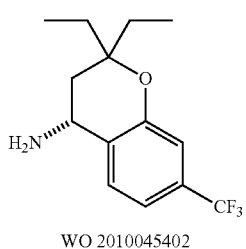
WO 2010045402
B-38 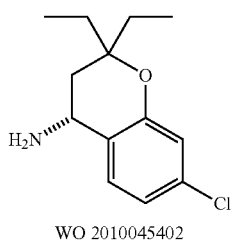
WO 2010045402
B-39 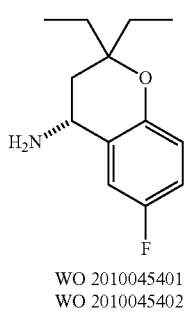
WO 2010045401
WO 2010045402
B-40 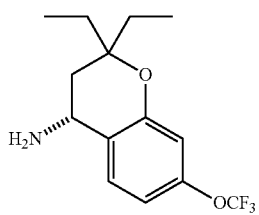
WO 2010045401
WO 2010045402
B-41 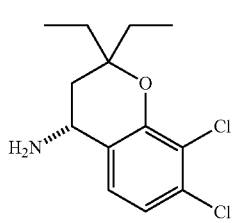
B-42 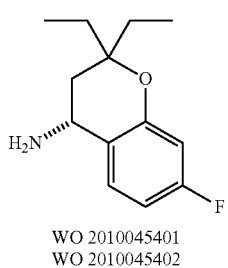
WO 2010045401
WO 2010045402
B-43 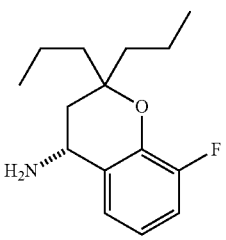
WO 2010045401
WO 2010045402
B-44 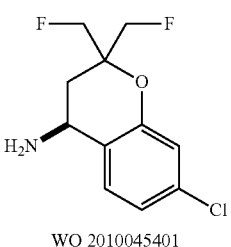
WO 2010045401
B-45 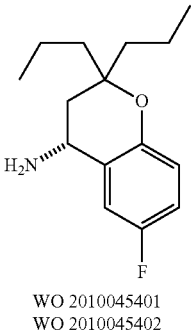
WO 2010045401
WO 2010045402
B-46 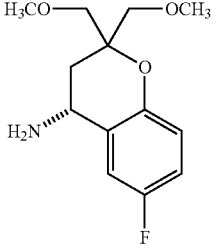
B-47 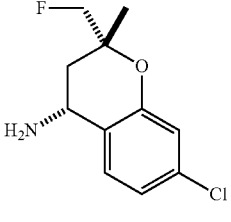
B-48 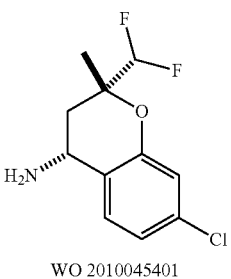
WO 2010045401

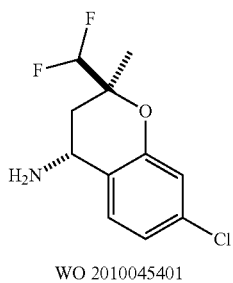
WO 2010045401
B-49
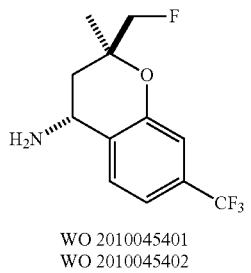
WO 2010045401
WO 2010045402
B-55
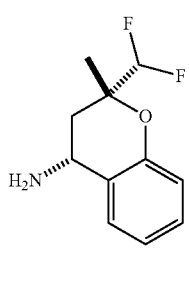
B-50
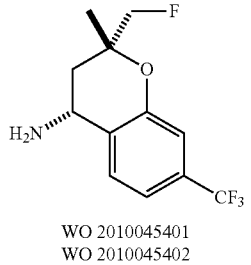
WO 2010045401
WO 2010045402
B-56
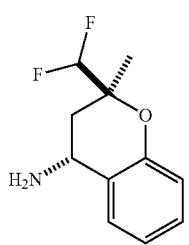
B-51
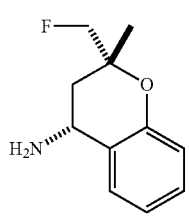
B-57
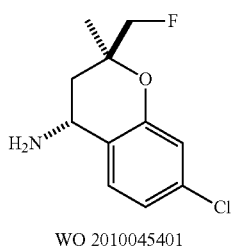
WO 2010045401
WO 2010045402
B-52
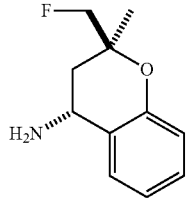
B-58
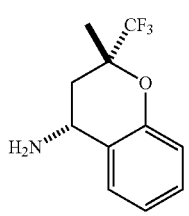
B-53
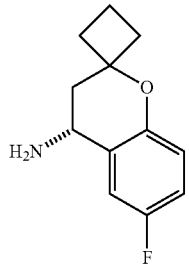
WO 2010045401
WO 2010045402
B-59
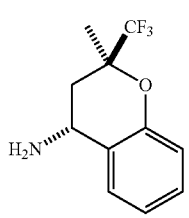
B-54
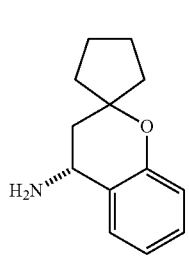
B-60

-continued

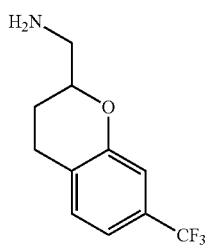

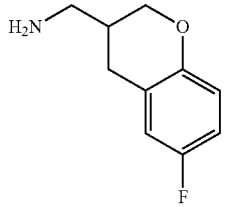

commercially available
(Anichem LLC)

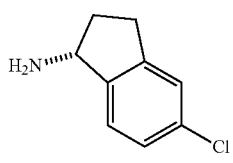

US 20080287676

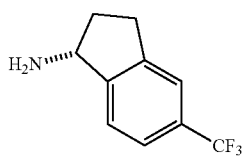

commercially available
(AlphaChiron Biochemicals)

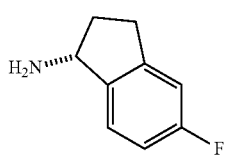

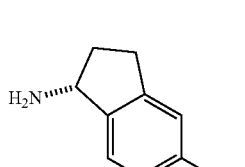

Gomtsyan, *J. Med. Chem.*, 2008, 51, 392-395

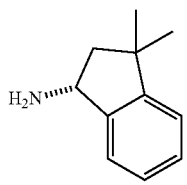

-continued

B-61

B-62

B-63

B-64

B-65

B-66

B-67

B-68

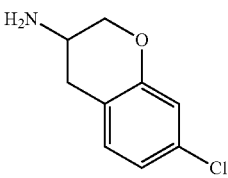

commercially available

B-69

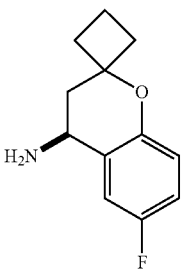

WO 2010045401
WO 2010045402

Examples 1-3, 5-251, and 253-327 were prepared using method similar to that employed in Example 4, by treating an appropriate amine of general formula (1) with a salt or free base of the chromanyl, an indanyl, or a tetrahydroquinolinyl amine of formula (3) listed above. These amines are either commercially available or were prepared using synthetic routes known to one skilled in the art or were prepared using methodologies analogous to those described in the literatures and the schemes depicted herein above.

Example 1

1-[(4R)-7-fluoro-2,2-dimethyl-3,4-dihydro-2H-chromen-4-yl]-3-(1-methyl-2-oxo-1,2,3,4-tetrahydroquinazolin-5-yl)urea $^1$H NMR (300 MHz, DMSO-d$_6$) δ 7.82 (s, 1H), 7.40 (d, J=7.5 Hz, 1H), 7.24-7.33 (m, 1H), 7.10-7.22 (m, 2H), 6.69-6.79 (m, 2H), 6.64 (d, J=7.5 Hz, 1H), 6.59 (dd, J=10.5, 2.6 Hz, 1H), 4.85-4.97 (m, 1H), 4.18 (d, J=1.6 Hz, 2H), 3.14 (s, 3H), 2.13 (dd, J=13.3, 6.1 Hz, 1H), 1.72 (dd, J=13.1, 11.1 Hz, 1H), 1.39 (s, 3H), 1.28 (s, 3H); MS (ESI$^+$) m/z 399 (M+H)$^+$.

Example 2

1-[(4R)-7-chloro-2,2-bis(fluoromethyl)-3,4-dihydro-2H-chromen-4-yl]-3-(1-methyl-2-oxo-1,2,3,4-tetrahydroquinazolin-5-yl)urea $^1$H NMR (300 MHz, DMSO-d$_6$) δ 7.87 (s, 1H), 7.37 (d, J=8.1, 1H), 7.30 (dd, J=8.3, 1.0, 1H), 7.22-7.11 (m, 2H), 7.08-6.94 (m, 2H), 6.82 (d, J=8.1 Hz, 1H), 6.65 (d, J=8.1 Hz, 1H), 5.02-4.90 (m, 1H), 4.74-4.52 (m, 4H), 4.18 (d, J=1.9 Hz, 2H), 3.14 (s, 3H), 2.28 (dd, J=13.7, 6.0 Hz, 1H), 2.03-1.90 (m, 1H); MS (LCMS) m/z 451 (M+H)$^+$.

Example 3

1-[(4R)-7-chloro-8-fluoro-2,2-bis(fluoromethyl)-3,4-dihydro-2H-chromen-4-yl]-3-(1-methyl-2-oxo-1,2,3,4-tetrahydroquinazolin-5-yl)urea $^1$H NMR (300 MHz, DMSO-d$_6$) δ 7.91 (d, J=10.6 Hz, 1H), 7.35 (d, J=8.0 Hz, 1H), 7.25-7.14 (m, 2H), 6.86 (d, J=8.3 Hz, 1H), 6.68 (t, J=13.7 Hz, 1H), 5.01 (dt, J=10.9, 7.3 Hz, 1H), 4.88-4.70 (m, 2H), 4.70-4.45 (m, 2H), 4.18 (d, J=1.3 Hz, 2H), 3.14 (s, 3H), 2.31 (dt, J=12.0, 6.0 Hz, 1H), 2.10-1.93 (m, 1H). MS (ESI$^+$) m/z 468 (M+H)$^+$

Example 4

1-[(4R)-2,2-dimethyl-3,4-dihydro-2H-chromen-4-yl]-3-(1-methyl-2-oxo-1,2,3,4-tetrahydroquinazolin-5-yl)urea A slurry of N,N-disuccinimidyl carbonate (434 mg, 1.69 mmol), acetonitrile (6 mL), pyridine (0.137 mL, 1.69 mmol), and 5-amino-1-methyl-3,4-dihydroquinazolin-2(1H)-one (A-1) (300 mg, 1.69 mmol) was stirred at room temperature. After 45 min, N,N-diisopropylethylamine (0.879 mL, 5.08 mmol) and (R)-2-hydroxy-2-phenylacetate salt of (R)-2,2-dimethylchroman-4-amine (B-2) (558 mg, 1.69 mmol) were added. After 30 minutes, EtOAc (50 mL) and 2N aqueous HCl (20 mL) were added and the layers separated. The organic extract was washed with brine (10 mL), dried (Na$_2$SO$_4$), filtered, and concentrated. The residue was purified by silica gel chromatography (0-10% MeOH/EtOAc gradient) to afford the title compound (565 mg, 1.49 mmol, 88% yield). $^1$H NMR (300 MHz, DMSO-d$_6$) δ 7.80 (s, 1H), 7.42 (d, J=8.1 Hz, 1H), 7.25 (t, J=10.7 Hz, 1H), 7.16 (dd, J=16.6, 8.2 Hz, 3H), 6.89 (t, J=7.0 Hz, 1H), 6.73 (d, J=8.6 Hz, 2H), 6.63 (d, J=8.1 Hz, 1H), 4.94 (dd, J=15.2, 10.0 Hz, 1H), 4.18 (s, 2H), 3.14 (s, 3H), 2.13 (dd, J=13.2, 6.2 Hz, 1H), 1.69 (dd, J=30.9, 18.0 Hz, 1H), 1.39 (s, 3H), 1.27 (s, 3H). MS (ESI$^+$) m/z 449 (M+H)$^+$.

Example 5

1-[(4R)-8-chloro-7-fluoro-2,2-dimethyl-3,4-dihydro-2H-chromen-4-yl]-3-(1-methyl-2-oxo-1,2,3,4-tetrahydroquinazolin-5-yl)urea $^1$H NMR (300 MHz, DMSO-d$_6$) δ 7.88 (s, 1H), 7.38 (d, J=8.1 Hz, 1H), 7.31-7.10 (m, 3H), 6.95 (t, J=8.8 Hz, 1H), 6.77 (d, J=8.5 Hz, 1H), 6.64 (d, J=8.1 Hz, 1H), 5.02-4.89 (m, 1H), 4.18 (d, J=1.9 Hz, 2H), 3.14 (s, 3H), 2.17 (dd, J=13.3, 6.1 Hz, 1H), 1.79 (dd, J=13.3, 11.1 Hz, 1H), 1.46 (s, 3H), 1.31 (s, 3H). MS (ESI$^+$) M/Z 433 (M+H)$^+$.

Example 6

1-[(4R)-7-chloro-2,2-dimethyl-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 7.34-7.18 (m, 3H), 6.97 (dd, J=8.3, 2.2 Hz, 1H), 6.81 (d, J=2.1 Hz, 1H), 6.70 (d, J=8.1 Hz, 1H), 4.92 (dd, J=11.1, 6.1 Hz, 1H), 4.18 (s, 2H), 3.15 (s, 3H), 2.13 (dd, J=13.2, 6.2 Hz, 1H), 1.74 (dd, J=13.2, 11.1 Hz, 1H), 1.40 (s, 3H), 1.27 (s, 3H). MS (ESI$^+$) m/z 425 (M+H)$^+$.

Example 7

1-[(2R,4R)-7-chloro-2-(fluoromethyl)-2-methyl-3,4-dihydro-2H-chromen-4-yl]-3-(1-methyl-2-oxo-1,2,3,4-tetrahydroquinazolin-5-yl)urea $^1$H NMR (300 MHz, DMSO-d$_6$) δ 7.89-7.83 (m, 1H), 7.41-7.26 (m, 2H), 7.22-7.11 (m, 2H), 7.05-6.96 (m, 1H), 6.88 (d, J=2.1 Hz, 1H), 6.81 (d, J=8.4 Hz, 1H), 6.65 (d, J=8.1 Hz, 1H), 5.06-4.93 (m, 1H), 4.56 (s, 1H), 4.40 (s, 1H), 4.18 (d, J=1.9 Hz, 2H), 3.14 (s, 3H), 2.10 (dd, J=13.2, 6.1 Hz, 1H), 1.93-1.78 (m, 1H), 1.27 (d, J=2.2 Hz, 3H). MS (ESI$^+$) M/Z 433 (M+H)$^+$.

Example 8

1-[(4R)-2,2-dimethyl-3,4-dihydro-2H-chromen-4-yl]-3-(l-ethyl-2-oxo-1,2,3,4-tetrahydroquinazolin-5-yl)urea $^1$H NMR (300 MHz, DMSO-d$_6$) δ 7.76 (s, 1H), 7.39 (d, J=8.1, 1H), 7.26 (d, J=7.7, 1H), 7.21-7.09 (m, 2H), 7.04 (bs, 1H), 6.89 (td, J=7.4, 1.2, 1H), 6.78-6.70 (m, 2H), 6.67 (d, J=8.2, 1H), 5.00-4.87 (m, 1H), 4.17 (d, J=1.8, 2H), 3.80 (q, J=6.9, 2H), 2.13 (dd, J=13.2, 6.2, 1H), 1.71 (dd, J=13.2, 10.8, 1H), 1.38 (s, 3H), 1.27 (s, 3H), 1.22-1.08 (m, 3H). MS (DCI$^+$) m/z 395 (M+H)$^+$, 412 (M+NH$_4$)$^+$.

Example 9

1-[(4R)-2,2-bis(fluoromethyl)-3,4-dihydro-2H-chromen-4-yl]-3-(1-methyl-2-oxo-1,2,3,4-tetrahydroquinazolin-5-yl)urea $^1$H NMR (300 MHz, DMSO-d$_6$) δ 7.82 (s, 1H), 7.40 (d, J=8.0, 1H), 7.30 (d, J=7.5 Hz, 1H), 7.25-7.07 (m, 3H), 6.98 (t, J=7.5 Hz, 1H), 6.84 (dd, J=17.0, 8.1 Hz, 2H), 6.64 (d, J=8.0 Hz, 1H), 4.75-4.64 (m, 2H), 4.60-4.48 (m, 2H), 4.18 (d, J=1.5 Hz, 2H), 4.03 (q, J=7.1 Hz, 1H), 3.16 (d, J=10.1 Hz, 1H), 2.04-1.90 (m, 3H), 1.17 (t, J=7.1 Hz, 1H). MS (ESI$^+$) M/Z 417 (M+H)$^+$.

Example 10

1-[(2R,4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea $^1$H NMR (300 MHz, DMSO-d$_6$) δ 7.91 (s, 1H), 7.39-7.28 (m, 2H), 7.23-7.11 (m, 2H), 7.05 (dd, J=8.3, 2.1, 1H), 6.93 (d, J=2.1, 1H), 6.85 (d, J=8.3, 1H), 6.66 (d, J=8.1, 1H), 6.14 (t, J=40, 1H), 5.05-4.92 (m, 1H), 4.18 (d, J=1.9, 2H), 3.14 (s, 3H), 2.14 (dd, J=13.0, 5.9, 1H), 1.95-1.65 (m, 1H), 1.36 (s, 3H). MS (DCI$^+$) m/z 468 (M+NH$_4$)$^+$.

Example 11

1-[(2S,4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea $^1$H NMR (300 MHz, DMSO-d$_6$) δ 7.87 (s, 1H), 7.39 (dd, J=8.2, 0.9, 1H), 7.30 (dd, J=8.3, 1.0, 1H), 7.22-7.10 (m, 2H), 7.03 (dd, J=8.3, 2.1, 1H), 6.95 (d, J=2.1, 1H), 6.78 (d, J=8.2, 1H), 6.65 (d, J=7.6, 1H), 6.20 (t, J=40, 1H), 5.03-4.90 (m, 1H), 4.18 (d, J=1.6, 2H), 3.14 (s, 3H), 2.39 (dd, J=14.1, 6.0, 1H), 1.99 (s, 1H), 1.41 (s, 3H). MS (DCI$^+$) m/z 468 (M+NH$_4$)$^+$.

Example 12

1-[(2R,4R)-2-(difluoromethyl)-2-methyl-3,4-dihydro-2H-chromen-4-yl]-3-(1-methyl-2-oxo-1,2,3,4-tetrahydroquinazolin-5-yl)urea $^1$H NMR (300 MHz, DMSO-d$_6$) δ 7.87 (s, 1H), 7.38 (d, J=7.6, 1H), 7.34-7.27 (m, 1H), 7.25-7.18 (m, 1H), 7.17 (d, J=8.1, 1H), 7.12 (bs, 1H), 6.98 (td, J=7.4, 1.2, 1H), 6.87-6.79 (m, 2H), 6.65 (dd, J=8.2, 1.0, 1H), 6.13 (t, J=54, 1H), 5.07-4.95 (m, 1H), 4.19 (d, J=1.9, 2H), 3.14 (s, 3H), 2.15 (dd, J=12.9, 5.9, 1H), 1.91 (d, J=11.9, 1H), 1.35 (s, 3H). MS (DCI$^+$) m/z 434 (M+NH$_4$)$^+$.

Example 13

1-[(2S,4R)-2-(difluoromethyl)-2-methyl-3,4-dihydro-2H-chromen-4-yl]-3-(1-methyl-2-oxo-1,2,3,4-tetrahydroquinazolin-5-yl)urea $^1$H NMR (300 MHz, DMSO-d$_6$) δ 7.82 (s, 1H), 7.42 (d, J=8.1, 1H), 7.29 (d, J=7.7, 1H), 7.25-7.18 (m, 2H), 7.14 (d, J=6.2, 1H), 6.97 (td, J=7.4, 1.2, 1H), 6.85 (dd, J=8.2, 1.1, 1H), 6.79 (d, J=8.0, 1H), 6.64 (d, J=8.1, 1H), 6.17 (t, J=57, 1H), 5.05-4.92 (m, 1H), 4.18 (d, J=1.9, 2H), 3.14 (s, 3H), 2.37 (dd, J=14.0, 6.0, 1H), 1.98-1.87 (m, 1H), 1.40 (s, 3H). MS (DCI$^+$) m/z 434 (M+NH$_4$)$^+$.

Example 14

1-[(2S,4R)-7-chloro-2-(fluoromethyl)-2-methyl-3,4-dihydro-2H-chromen-4-yl]-3-(1-methyl-2-oxo-1,2,3,4-tetrahydroquinazolin-5-yl)urea $^1$H NMR (300 MHz, DMSO-d$_6$) δ 7.84 (s, 1H), 7.39 (d, J=8.1, 1H), 7.28 (dd, J=8.3, 0.9, 1H), 7.22-7.11 (m, 2H), 6.99 (dd, J=8.3, 2.1, 1H), 6.89 (d, J=2.1, 1H), 6.78 (d, J=8.2, 1H), 6.64 (d, J=8.1, 1H), 4.98-4.85 (m, 1H), 4.61-4.49 (m, 1H), 4.45-4.34 (m, 1H), 4.17 (d, J=1.9, 2H), 3.14 (s, 3H), 2.31 (dd, J=13.9, 6.2, 1H), 1.92-1.81 (m, 1H), 1.38 (d, J=2.0, 3H). MS (DCI$^+$) m/z 450 (M+NH$_4$)$^+$.

Example 15

1-[(4R)-3,4-dihydrospiro[chromene-2,1'-cyclopentan]-4-yl]-3-(1-methyl-2-oxo-1,2,3,4-tetrahydroquinazolin-5-yl)urea $^1$H NMR (300 MHz, DMSO-d$_6$) δ 7.80 (s, 1H), 7.43 (d, J=8.2, 1H), 7.26 (d, J=7.7, 1H), 7.22-7.09 (m, 3H), 6.89 (td, J=7.4, 1.2, 1H), 6.78-6.60 (m, 3H), 5.00-4.87 (m, 1H), 4.18 (d, J=1.9, 1H), 3.14 (s, 2H), 2.15 (dd, J=13.2, 6.0, 1H), 2.01-1.50 (m, 9H), MS (DCI$^+$) m/z 424 (M+NH$_4$)$^+$.

Example 16

1-[(4R)-2,2-dimethyl-8-(trifluoromethyl)-3,4-dihydro-2H-chromen-4-yl]-3-(3-methyl-2-oxo-1,2,3,4-tetrahydroquinazolin-7-yl)urea $^1$H NMR (300 MHz, DMSO-d$_6$) δ 9.14 (s, 1H), 8.53 (s, 1H), 7.54 (d, J=7.8 Hz, 1H), 7.49 (d, J=7.5 Hz, 1H), 7.03 (dd, J=7.6, 7.6 Hz, 1H), 6.94 (s, 3H), 6.48 (d, J=8.5 Hz, 1H), 5.04-4.95 (m, 1H), 4.31 (s, 2H), 2.84 (s, 3H), 2.18 (dd, J=13.4, 6.3 Hz, 1H), 1.84 (dd, J=13.2, 11.2 Hz, 1H), 1.42 (s, 3H), 1.30 (s, 3H); (ESI$^+$) m/z 449 (M+H)$^+$

Example 17

1-[(1R)-5-chloro-2,3-dihydro-1H-inden-1-yl]-3-(3-methyl-2-oxo-1,2,3,4-tetrahydroquinazolin-7-yl)urea $^1$H NMR (300 MHz, DMSO-d$_6$) δ 9.12 (s, 1H), 8.36 (s, 1H), 7.32 (s, 1H), 7.29-7.22 (m, 2H), 6.94-6.91 (m, 3H), 6.43 (d, J=7.9 Hz, 1H), 5.17-5.08 (m, 1H), 4.30 (s, 2H), 2.97-2.86 (m, 1H), 2.84 (s, 3H), 2.84-2.72 (m, 1H), 2.50-2.40 (m, 1H), 1.84-1.71 (m, 1H); (ESI$^+$) m/z 371 (M+H)$^+$

Example 18

1-(3-methyl-2-oxo-1,2,3,4-tetrahydroquinazolin-7-yl)-3-[(2R,4R)-2-methyl-2-(trifluoromethyl)-3,4-dihydro-2H-chromen-4-yl]urea $^1$H NMR (300 MHz, DMSO-d$_6$) δ 9.14 (s, 1H), 8.60 (s, 1H), 7.31 (d, J=7.8 Hz, 1H), 7.25-7.19 (m, 1H), 7.04-6.98 (m, 1H), 6.96 (d, J=1.4 Hz, 1H), 6.94 (br s, 2H), 6.88 (dd, J=8.1, 1.0 Hz, 1H), 6.54 (d, J=8.5 Hz, 1H), 5.11-5.02 (m, 1H), 4.31 (s, 2H), 2.84 (s, 3H), 2.31 (dd, J=12.7, 5.9 Hz, 1H), 2.02 (dd, J=12.4, 12.4 Hz, 1H), 1.52 (s, 3H).

Example 19

1-[(4R)-7-fluoro-2,2-dimethyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 8.05 (t, J=11.7 Hz, 1H), 7.78-7.63 (m, 1H), 7.63-7.50 (m, 1H), 7.39-7.20 (m, 2H), 6.84-6.69 (m, 1H), 6.69-6.53 (m, 2H), 4.95 (dt, J=28.0, 13.9 Hz, 1H), 3.63 (q, J=8.1 Hz, 3H), 2.55 (d, J=14.3 Hz, 1H), 2.15 (dt, J=39.3, 19.6 Hz, 1H), 1.44-1.35 (m, 3H), 1.33-1.24 (m, 3H). MS (ESI$^+$) m/z 395 (M+H)$^+$

Example 20

1-[(4R)-7-chloro-2,2-bis(fluoromethyl)-3,4-dihydro-2H-chromen-4-yl]-3-(1-methyl-2-oxo-1,2-dihydroquinolin-5-yl)urea $^1$H NMR (300 MHz, DMSO-d$_6$) δ 8.65 (s, 1H), 8.04 (d, J=9.8 Hz, 1H), 7.71 (dd, J=8.0, 0.9 Hz, 1H), 7.55 (t, J=8.2 Hz, 1H), 7.35 (dd, J=8.3, 1.0 Hz, 1H), 7.22 (d, J=8.4 Hz, 1H), 7.06 (dd, J=8.3, 2.1 Hz, 1H), 6.98 (d, J=2.2 Hz, 1H), 6.90 (d, J=8.1 Hz, 1H), 6.66 (d, J=9.8 Hz, 1H), 5.08-4.95 (m, 1H), 4.76-4.69 (m, 2H), 4.61-4.54 (m, 2H), 3.62 (s, 3H), 2.33 (dd, J=13.7, 5.9 Hz, 1H), 1.99 (s, 1H). MS (ESI$^+$) M/Z 448 (M+H)$^+$.

Example 21

1-[(4R)-7-chloro-8-fluoro-2,2-bis(fluoromethyl)-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 8.04 (d, J=9.8 Hz, 1H), 7.64 (dd, J=8.0, 1.1 Hz, 1H), 7.59 (t, J=8.2 Hz, 1H), 7.28 (d, J=8.4 Hz, 1H), 7.20-7.15 (m, 2H), 6.67 (d, J=9.8 Hz, 1H), 5.06 (dd, J=10.9, 5.9 Hz, 1H), 4.78-4.60 (m, 4H), 3.64 (s, 3H), 2.36 (dd, J=13.8, 6.0 Hz, 1H), 2.07 (m, J=13.7, 10.9, 2.7 Hz, 1H). MS (ESI$^+$) m/z 466 (M+H)$^+$.

Example 22

1-[(4R)-8-chloro-7-fluoro-2,2-dimethyl-3,4-dihydro-2H-chromen-4-yl]-3-(1-methyl-2-oxo-1,2-dihydroquinolin-5-yl)urea $^1$H NMR (300 MHz, DMSO-d$_6$) δ 8.67 (s, 1H), 8.04 (d, J=9.9 Hz, 1H), 7.72 (d, J=7.6 Hz, 1H), 7.55 (t, J=8.3 Hz, 1H), 7.39-7.27 (m, 1H), 7.21 (d, J=8.5 Hz, 1H), 6.97 (t, J=8.8 Hz, 1H), 6.87 (d, J=8.5 Hz, 1H), 6.65 (d, J=9.9 Hz, 1H), 5.00 (dd, J=16.9, 8.6 Hz, 1H), 3.62 (s, 3H), 2.33-2.12 (m, 1H), 1.91-1.75 (m, 1H), 1.47 (s, 3H), 1.31 (d, J=8.9 Hz, 3H). MS (ESI$^+$) m/z 430 (M+H)$^+$.

Example 23

1-[(4R)-7-chloro-2,2-dimethyl-3,4-dihydro-2H-chromen-4-yl]-3-(1-methyl-2-oxo-1,2-dihydroquinolin-5-yl)urea $^1$H NMR (400 MHz, DMSO-d$_6$) δ 8.65 (s, 1H), 8.04 (d, J=10.0 Hz, 1H), 7.74 (d, J=7.6 Hz, 1H), 7.55 (t, J=8.3 Hz, 1H), 7.32 (dd, J=8.3, 0.9 Hz, 1H), 7.21 (d, J=8.5 Hz, 1H), 6.97 (dd, J=8.3, 2.2 Hz, 1H), 6.84 (dd, J=15.7, 5.3 Hz, 2H), 6.65 (d, J=9.9 Hz, 1H), 4.96 (dd, J=15.9, 9.5 Hz, 1H), 3.62 (s, 3H), 2.17 (dd, J=13.2, 6.2 Hz, 1H), 1.78 (dd, J=13.1, 11.2 Hz, 1H), 1.41 (s, 3H), 1.31-1.17 (m, 3H). MS (ESI$^+$) m/z 412 (M+H)$^+$.

Example 24

1-[(4R)-6-fluoro-2,2-dimethyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 8.06 (d, J=9.8 Hz, 1H), 7.69 (d, J=7.4 Hz, 1H), 7.59 (t, J=8.3 Hz, 1H), 7.27 (d, J=8.6 Hz, 1H), 7.13-6.93 (m, 2H), 6.78 (dd, J=9.0, 4.9 Hz, 1H), 6.66 (d, J=9.8 Hz, 1H), 4.97 (dd, J=11.0, 6.1 Hz, 1H), 3.64 (s, 3H), 2.17 (dd, J=13.2, 6.3 Hz, 1H), 1.85-1.70 (m, 1H), 1.40 (s, 3H), 1.27 (s, 3H). MS (ESI$^+$) m/z 396 (M+H)$^+$.

Example 25

1-(1-methyl-2-oxo-1,2-dihydroquinolin-5-yl)-3-[(2S,4R)-2-methyl-2-(trifluoromethyl)-3,4-dihydro-2H-chromen-4-yl]urea $^1$H NMR (500 MHz, DMSO-d$_6$/D$_2$O) δ 8.05 (d, J=9.9 Hz, 1H), 7.77-7.63 (m, 1H), 7.59 (t, J=8.3 Hz, 1H), 7.36 (d, J=7.6 Hz, 1H), 7.32-7.20 (m, 2H), 7.05 (td, J=7.5, 1.1 Hz, 1H), 6.93 (dd, J=8.2, 1.1 Hz, 1H), 6.67 (d, J=9.9 Hz, 1H), 5.02 (dd, J=9.3, 6.2 Hz, 1H), 3.64 (s, 3H), 2.56 (dd, J=8.3, 5.1 Hz, 1H), 2.24-2.03 (m, 1H), 1.62 (d, J=31.8 Hz, 3H). MS (ESI$^+$) m/z 432 (M+H)$^+$.

Example 26

1-[(2S,4R)-2-(difluoromethyl)-2-methyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 8.05 (d, J=9.9 Hz, 1H), 7.79-7.67 (m, 1H), 7.59 (t, J=8.3 Hz, 1H), 7.33 (d, J=7.6 Hz, 1H), 7.29-7.18 (m, 2H), 7.00 (td, J=7.5, 1.1 Hz, 1H), 6.88 (dd, J=8.2, 1.1 Hz, 1H), 6.66 (d, J=9.9 Hz, 1H), 5.03 (dd, J=9.4, 6.0 Hz, 1H), 3.64 (s, 3H), 2.47-2.33 (m, 1H), 2.11-1.87 (m, 1H), 1.42 (s, 3H). MS (ESI$^+$) m/z 414 (M+H)$^+$.

Example 27

1-[(4R)-7-fluoro-2,2-bis(fluoromethyl)-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 8.04 (d, J=9.9 Hz, 1H), 7.67 (dd, J=8.0, 0.7 Hz, 1H), 7.59 (t, J=8.3 Hz, 1H), 7.42-7.31 (m, 1H), 7.25 (t, J=13.8 Hz, 1H), 6.86 (td, J=8.5, 2.6 Hz, 1H), 6.76 (dd, J=10.3, 2.6 Hz, 1H), 6.66 (d, J=9.8 Hz, 1H), 5.00 (dd, J=10.4, 5.9 Hz, 1H), 4.68 (qd, J=10.2, 5.1 Hz, 2H), 4.64-4.52 (m, 2H), 3.64 (s, 3H), 2.42-2.23 (m, 1H), 2.01 (ddd, J=13.4, 10.5, 2.6 Hz, 1H). MS (ESI$^+$) m/z 432 (M+H)$^+$.

Example 28

1-[(2R,4R)-2-(difluoromethyl)-2-methyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 8.06 (d, J=9.9 Hz, 1H), 7.68 (d, J=7.5 Hz, 1H), 7.59 (t, J=8.3 Hz, 1H), 7.34 (t, J=9.8 Hz, 1H), 7.32-7.16 (m, 2H), 7.01 (td, J=7.6, 1.1 Hz, 1H), 6.85 (dt, J=6.3, 3.1 Hz, 1H), 6.67 (d, J=9.9 Hz, 1H), 5.07 (dd, J=11.4, 5.9 Hz, 1H), 3.64 (s, 3H), 2.19 (dd, J=12.9, 5.9 Hz, 1H), 1.95 (dd, J=21.6, 9.5 Hz, 1H), 1.37 (s, 3H). MS (ESI$^+$) m/z 414 (M+H)$^+$.

Example 29

1-[(4R)-7-chloro-2,2-bis(fluoromethyl)-3,4-dihydro-2H-chromen-4-yl]-3-(3-oxo-3,4-dihydro-2H-1,4-benzoxazin-6-yl)urea $^1$H NMR (300 MHz, DMSO-d$_6$) δ 10.65 (s, 1H), 8.49 (s, 1H), 7.28 (d, J=8.3 Hz, 1H), 7.18 (d, J=2.2 Hz, 1H), 7.03 (dd, J=8.2, 2.1 Hz, 1H), 6.96 (d, J=2.1 Hz, 1H), 6.86 (d, J=2.4 Hz, 1H), 6.48 (d, J=8.3 Hz, 1H), 5.03-4.91 (m, 1H), 4.74-4.65 (m, 2H), 4.56-4.46 (m, 4H), 2.27 (dd, J=13.7, 6.0 Hz, 1H), 2.03-1.90 (m, 2H). MS (ESI$^+$) M/Z 438 (M+H)$^+$.

Example 30

1-[(2R,4R)-7-chloro-2-(difluoromethyl)-2-methyl-3,4-dihydro-2H-chromen-4-yl]-3-(2-oxo-1,2,3,4-tetrahydroquinolin-7-yl)urea $^1$H NMR (300 MHz, DMSO-d$_6$) δ 10.02 (s, 1H), 8.55 (s, 1H), 7.29 (dd, J=8.3, 1.0 Hz, 1H), 7.07-6.98 (m, 3H), 6.99-6.90 (m, 2H), 6.53 (d, J=8.4 Hz, 1H), 5.06-4.93 (m, 1H), 2.78 (d, J=14.9 Hz, 2H), 2.13 (dd, J=13.0, 5.9 Hz, 1H), 1.91 (t, J=12.3 Hz, 1H), 1.37 (s, 3H). MS (ESI$^+$) m/z 486 (M+H)$^+$.

Example 31

1-[(4R)-7-chloro-2,2-bis(fluoromethyl)-3,4-dihydro-2H-chromen-4-yl]-3-(2-oxo-1,2,3,4-tetrahydroquinolin-7-yl)urea $^1$H NMR (500 MHz, DMSO-d$_6$/D$_2$O) δ 7.37 (d, J=8.2 Hz, 1H), 7.20 (dd, J=8.2, 1.9 Hz, 1H), 7.10 (dd, J=8.1, 1.8 Hz, 1H), 7.04-6.99 (m, 2H), 6.98-6.91 (m, 1H), 5.05-4.98 (m, 1H), 4.75-4.60 (m, 4H), 2.79 (t, J=7.4 Hz, 2H), 2.47-2.37 (m, 2H), 2.16 (dd, J=13.2, 6.1 Hz, 1H), 1.80 (dd, J=13.2, 11.3 Hz, 1H); MS (ESI$^+$) m/z 434 (M+H)$^+$.

Example 32

1-[(4R)-2,2-dimethyl-7-(trifluoromethyl)-3,4-dihydro-2H-chromen-4-yl]-3-(2-oxo-1,2,3,4-tetrahydroquinolin-7-yl)urea $^1$H NMR (500 MHz, DMSO-d$_6$/D$_2$O) δ 7.47 (d, J=8.1 Hz, 1H), 7.24 (dd, J=8.1, 1.8 Hz, 1H), 7.10-7.03 (m, 3H), 6.98-6.91 (m, 1H), 5.05-4.98 (m, 1H), 2.80 (t, J=7.4 Hz, 3H), 2.47-2.37 (m, 3H), 2.16 (dd, J=13.2, 6.2 Hz, 1H), 1.80 (dd, J=13.2, 11.3 Hz, 1H), 1.43 (s, 3H), 1.31 (s, 3H). MS (ESI$^+$) m/z 434 (M+H)$^+$.

Example 33

1-[(4R)-7,8-difluoro-2,2-dimethyl-3,4-dihydro-2H-chromen-4-yl]-3-(2-oxo-1,2,3,4-tetrahydroquinolin-7-yl)urea Triphosgene (0.281 g, 0.948 mmol) (Sigma-Aldrich) in THF (5 mL) was added to a to a solution of 7-amino-3,4-dihydroquinolin-2(1H)-one (0.4659 g, 2.87 mmol) (Astatech, Inc) and DIEA (2.01 mL, 11.5 mmol) (Aldrich) in THF (28 mL) at room temperature. After 10 minutes (R)-7,8-difluoro-2,2-dimethylchroman-4-aminium chloride (0.717 g, 2.87 mmol) (B-8; WO2010/04401) was added and the mixture was stirred for an additional 2 hours. The mixture was diluted with saturated aqueous NaHCO$_3$ (30 mL) and extracted with EtOAc (3×30 mL). The combined organic extracts were washed with 1 N aqueous HCl (30 mL) and concentrated. The residue was purified by silica gel chromatography (5% MeOH/CH$_2$Cl$_2$) to afford the title compound (0.970 g, 2.42 mmol, 84% yield). $^1$H NMR (300 MHz, DMSO-d$_6$) δ 10.01 (s, 1H), 8.50 (s, 1H), 7.14-6.84 (m, 5H), 6.44 (d, J=8.6 Hz, 1H), 4.95 (dd, J=15.7, 9.7 Hz, 1H), 2.78 (t, J=7.5 Hz, 2H), 2.41 (dd, J=8.4, 6.5 Hz, 2H), 2.16 (dd, J=13.4, 6.1 Hz, 1H), 1.80 (dd, J=13.2, 11.3 Hz, 1H), 1.45 (s, 3H), 1.32 (s, 3H); MS (ESI+) m/z 402 (M+H)$^+$, 400 (M−H)$^+$.

Example 34

1-[(2R,4R)-2-methyl-2-(trifluoromethyl)-3,4-dihydro-2H-chromen-4-yl]-3-(2-oxo-1,2,3,4-tetrahydroquinolin-7-yl)urea $^1$H NMR (300 MHz, DMSO-d$_6$) δ 10.01 (s, 1H), 8.63 (s, 1H), 7.31 (d, J=7.6 Hz, 1H), 7.27-7.18 (m, 1H), 7.09-6.94 (m, 4H), 6.88 (dd, J=8.2, 1.0 Hz, 1H), 6.58 (d, J=8.5 Hz, 1H), 5.16-4.99 (m, 1H), 2.78 (t, J=7.5 Hz, 2H), 2.41 (dd, J=8.5, 6.5 Hz, 2H), 2.31 (dd, J=12.7, 5.8 Hz, 1H), 2.02 (t, J=12.3 Hz, 1H), 1.52 (s, 3H); MS (ESI$^+$) m/z 420 (M+H)$^+$, 418 (M−H)$^+$.

Example 35

1-(2-oxo-1,2,3,4-tetrahydroquinolin-7-yl)-3-[(1R)-5-(trifluoromethyl)-2,3-dihydro-1H-inden-1-yl]urea $^1$H NMR (300 MHz, DMSO-d$_6$) δ 10.00 (s, 1H), 8.39 (s, 1H), 7.61 (s, 1H), 7.56 (d, J=8.0 Hz, 1H), 7.47 (d, J=7.9 Hz, 1H), 7.04 (d, J=2.0 Hz, 1H), 7.01 (d, J=8.2 Hz, 1H), 6.94 (dd, J=8.1, 2.0 Hz, 1H), 6.51 (d, J=8.1 Hz, 1H), 5.22 (q, J=8.2 Hz, 1H), 3.07-2.81 (m, 2H), 2.78 (t, J=7.5 Hz, 2H), 2.56-2.44 (m, 1H), 2.41 (dd, J=8.5, 6.5 Hz, 2H), 1.83 (dq, J=12.5, 8.8 Hz, 1H); MS (ESI/NH$_3$) m/z: 390.0 (M+H)$^+$.

Example 36

1-(1-methyl-2-oxo-1,2,3,4-tetrahydroquinolin-7-yl)-3-[(1R)-5-(trifluoromethyl)-2,3-dihydro-1H-inden-1-yl]urea $^1$H NMR (400 MHz, DMSO-d$_6$/D$_2$O) δ 7.63-7.54 (m, 2H), 7.48 (dd, J=9.1, 4.9 Hz, 1H), 7.39-7.25 (m, 1H), 7.15-7.05 (m, 1H), 6.99 (dd, J=8.1, 2.0 Hz, 1H), 5.31-5.16 (m, 1H), 3.35-3.17 (m, 3H), 3.09-2.84 (m, 2H), 2.84-2.70 (m, 2H), 2.52-2.43 (m, 2H), 1.99-1.71 (m, 1H).). MS (ESI$^+$) m/z 404 (M+H)$^+$.

Example 37

1-(1-methyl-2-oxo-1,2,3,4-tetrahydroquinolin-7-yl)-3-[(4R)-7-(trifluoromethyl)-3,4-dihydro-2H-chromen-4-yl]urea $^1$H NMR (400 MHz, DMSO-d$_6$/D$_2$O) δ 7.49 (d, J=8.0 Hz, 1H), 7.29 (t, J=7.5 Hz, 1H), 7.25 (dd, J=8.1, 1.3 Hz, 1H), 7.16-7.03 (m, 2H), 6.98 (dd, J=8.0, 2.0 Hz, 1H), 4.99 (q, J=5.6 Hz, 1H), 4.39-4.19 (m, 2H), 3.23 (s, 3H), 2.87-2.68 (m, 2H), 2.26-2.09 (m, 1H), 2.08-1.87 (m, 1H).). MS (ESI$^+$) m/z 420 (M+H)$^+$.

Example 38

1-[(4R)-7-fluoro-2,2-dimethyl-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 7.27 (dd, J=16.0, 8.5 Hz, 1H), 7.22-7.15 (m, 1H), 6.88-6.80 (m, 2H), 6.80-6.67 (m, 1H), 6.57 (dd, J=10.6, 2.6 Hz, 1H), 4.92 (dd, J=11.0, 6.1 Hz, 1H), 4.50 (d, J=4.1 Hz, 2H), 2.11 (dd, J=13.3, 6.2 Hz, 1H), 1.73 (dd, J=13.1, 11.2 Hz, 1H), 1.39 (d, J=7.3 Hz, 3H), 1.33-1.21 (m, 3H). MS (ESI$^+$) m/z 386 (M+H)$^+$.

Example 39

1-[(4R)-7-chloro-8-fluoro-2,2-dimethyl-3,4-dihydro-2H-chromen-4-yl]-3-(2-oxo-1,2,3,4-tetrahydroquinolin-7-yl)urea $^1$H NMR (300 MHz, DMSO-d$_6$) δ 10.02 (s, 1H), 8.53 (s, 1H), 7.15-6.90 (m, 5H), 6.47 (d, J=8.6 Hz, 1H), 5.05-4.88 (m, 1H), 2.78 (t, J=7.5 Hz, 2H), 2.41 (dd, J=8.5, 6.5 Hz, 2H), 2.16 (dd, J=13.3, 6.2 Hz, 1H), 1.81 (dd, J=13.1, 11.4 Hz, 1H), 1.45 (s, 3H), 1.32 (s, 3H); MS (ESI+) m/z 418 (M+H)$^+$, 416 (M−H)$^+$.

Example 40

1-[(2R,4R)-7-chloro-2-(fluoromethyl)-2-methyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 8.05 (d, J=9.8 Hz, 1H), 7.67 (dd, J=13.4, 6.1 Hz, 1H), 7.59 (t, J=8.3 Hz, 1H), 7.34 (dd, J=8.3, 1.0 Hz, 1H), 7.27 (d, J=8.5 Hz, 1H), 7.02 (dd, J=8.3, 2.2 Hz, 1H), 6.89 (d, J=2.1 Hz, 1H), 6.67 (d, J=9.8 Hz, 1H), 5.05 (dd, J=11.4, 6.1 Hz, 1H), 4.59-4.52 (m, 1H), 4.52-4.39 (m, 1H), 3.64 (s, 3H), 2.13 (dd, J=13.1, 6.1 Hz, 1H), 2.03-1.82 (m, 1H), 1.28 (d, J=2.0 Hz, 3H). MS (ESI$^+$) m/z 430 (M+H)$^+$.

Example 41

1-[(2S,4R)-7-chloro-2-(fluoromethyl)-2-methyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 8.04 (d, J=10.0 Hz, 1H), 7.68 (d, J=8.0 Hz, 1H), 7.59 (t, J=8.3 Hz, 1H), 7.41-7.21 (m, 2H), 7.02 (dd, J=8.3, 2.2 Hz, 1H), 6.90 (d, J=2.1 Hz, 1H), 6.66 (d, J=9.8 Hz, 1H), 4.97 (dd, J=9.8, 6.1 Hz, 1H), 4.61-4.50 (m, 1H), 4.44 (dd, J=21.0, 10.0 Hz, 1H), 3.63 (s, 3H), 2.45-2.17 (m, 1H), 2.01-1.75 (m, 1H), 1.36 (t, J=28.2 Hz, 3H). MS (ESI⁺) m/z 430 (M+H)⁺.

Example 42

1-[(4R)-8-fluoro-2,2-dimethyl-3,4-dihydro-2H-chromen-4-yl]-3-[3-(2-hydroxyethyl)-2-oxo-1,2,3,4-tetrahydroquinazolin-7-yl]urea ¹H NMR (500 MHz, DMSO-d₆/D₂O) δ 1.31 (s, 3H), 1.43 (s, 3H), 1.83 (s, 1H), 2.14 (dd, J=13.3, 6.2 Hz, 1H), 3.37 (t, J=5.9 Hz, 2H), 3.57 (t, J=5.9 Hz, 2H), 4.43 (bs, 2H), 4.98 (dd, J=11.1, 6.2 Hz, 1H), 6.87 (td, J=7.9, 4.9 Hz, 2H), 6.90 (dd, J=8.2, 2.1 Hz, 2H), 6.96 (d, J=8.2 Hz, 2H), 6.99 (d, J=2.0 Hz, 1H), 7.04-7.12 (m, 2H). MS (ESI⁺) m/z 429 (M+H)⁺.

Example 43

1-[(4R)-7-fluoro-2,2-dimethyl-3,4-dihydro-2H-chromen-4-yl]-3-[3-(2-hydroxyethyl)-2-oxo-1,2,3,4-tetrahydroquinazolin-7-yl]urea ¹H NMR (500 MHz, DMSO-d₆/D₂O) δ 1.28 (s, 3H), 1.40 (s, 3H), 1.69-1.78 (m, 1H), 1.82 (s, 3H), 2.11 (dd, J=13.2, 6.1 Hz, 1H), 3.37 (t, J=5.9 Hz, 2H), 3.57 (t, J=5.9 Hz, 2H), 4.43 (s, 2H), 4.92 (dd, J=11.0, 6.1 Hz, 1H), 6.57 (dd, J=10.5, 2.6 Hz, 1H), 6.73 (td, J=8.5, 2.6 Hz, 1H), 6.91 (dd, J=8.1, 2.1 Hz, 1H), 6.95 (d, J=8.2 Hz, 1H), 6.99 (d, J=2.0 Hz, 1H), 7.26 (t, J=7.7 Hz, 1H). MS (ESI⁺) m/z 429 (M+H)⁺.

Example 44

1-[(4R)-2,2-diethyl-8-fluoro-3,4-dihydro-2H-chromen-4-yl]-3-[3-(2-hydroxyethyl)-2-oxo-1,2,3,4-tetrahydroquinazolin-7-yl]urea ¹H NMR (500 MHz, DMSO-d₆/D₂O) δ 0.85-0.97 (m, 6H), 1.26-1.37 (m, 2H), 1.52-1.80 (m, 6H), 3.14 (d, J=7.8 Hz, 2H), 3.16 (d, J=5.1 Hz, 1H), 3.37 (t, J=5.9 Hz, 1H), 3.57 (t, J=5.9 Hz, 1H), 4.43 (s, 1H), 6.82-6.98 (m, 2H), 6.99-7.12 (m, 2H). MS ESI⁻ m/z 455 (M−H)⁻.

Example 45

1-[(4R)-2,2-diethyl-3,4-dihydro-2H-chromen-4-yl]-3-[3-(2-hydroxyethyl)-2-oxo-1,2,3,4-tetrahydroquinazolin-7-yl]urea ¹H NMR (500 MHz, DMSO-d₆/D₂O) δ 0.84-0.94 (m, 6H), 1.51-1.72 (m, 5H), 2.11 (dd, J=13.4, 6.1 Hz, 1H), 3.37 (t, J=5.9 Hz, 2H), 3.57 (t, J=5.9 Hz, 2H), 4.43 (s, 2H), 4.89-4.98 (m, 1H), 6.76 (dd, J=8.1, 1.2 Hz, 1H), 6.85-6.92 (m, 2H), 6.96 (d, J=8.2 Hz, 2H), 7.00 (d, J=2.1 Hz, 1H), 7.11-7.18 (m, 1H), 7.24 (d, J=7.7 Hz, 1H). MS (ESI⁺) m/z 439 (M+H)⁺.

Example 46

1-[(4R)-2,2-diethyl-7-(trifluoromethyl)-3,4-dihydro-2H-chromen-4-yl]-3-[3-(2-hydroxyethyl)-2-oxo-1,2,3,4-tetrahydroquinazolin-7-yl]urea ¹H NMR (500 MHz, DMSO-d₆/D₂O) δ 0.83-1.01 (m, 6H), 1.24-1.36 (m, 2H), 1.56 (dt, J=13.4, 6.8 Hz, 3H), 1.62-1.72 (m, 3H), 2.12 (dd, J=13.5, 6.1 Hz, 1H), 3.16 (dd, J=14.8, 6.4 Hz, 2H), 3.37 (t, J=5.9 Hz, 2H), 3.57 (t, J=6.0 Hz, 2H), 4.43 (s, 2H), 4.98 (dd, J=11.4, 6.1 Hz, 1H), 6.92 (dt, J=8.2, 5.2 Hz, 2H), 7.04 (dd, J=9.0, 1.7 Hz, 2H), 7.15-7.24 (m, 1H), 7.46 (d, J=8.1 Hz, 1H). MS ESI⁻ m/z 505.1 (M−H)⁻.

Example 47

1-[(4R)-7-chloro-2,2-diethyl-3,4-dihydro-2H-chromen-4-yl]-3-[3-(2-hydroxyethyl)-2-oxo-1,2,3,4-tetrahydroquinazolin-7-yl]urea ¹H NMR (500 MHz, DMSO-d₆/D₂O) δ 0.84-0.94 (m, 6H), 1.49-1.74 (m, 5H), 2.11 (dd, J=13.5, 6.1 Hz, 1H), 3.36 (t, J=5.9 Hz, 2H), 3.57 (t, J=5.9 Hz, 2H), 4.43 (bs, 2H), 4.90 (dd, J=11.2, 6.1 Hz, 1H), 6.82 (d, J=2.1 Hz, 1H), 6.89 (dd, J=8.1, 2.1 Hz, 1H), 6.91-6.98 (m, 2H), 7.00 (d, J=2.1 Hz, 1H), 7.22-7.28 (m, 1H). MS (ESI⁺) m/z 473 (M+H)⁺.

Example 48

1-[(4R)-2,2-dimethyl-7-(trifluoromethyl)-3,4-dihydro-2H-chromen-4-yl]-3-[3-(2-hydroxyethyl)-2-oxo-1,2,3,4-tetrahydroquinazolin-7-yl]urea ¹H NMR (500 MHz, DMSO-d₆/D₂O) δ 1.31 (s, 3H), 1.42 (s, 3H), 1.76-1.87 (m, 2H), 2.16 (dd, J=13.2, 6.2 Hz, 1H), 3.37 (t, J=5.9 Hz, 2H), 3.58 (t, J=5.9 Hz, 2H), 4.44 (s, 2H), 4.97-5.05 (m, 1H), 6.91 (dd, J=8.1, 2.1 Hz, 1H), 6.96 (d, J=8.2 Hz, 2H), 6.99 (d, J=2.0 Hz, 1H), 7.04 (d, J=1.8 Hz, 1H), 7.24 (dd, J=8.1, 1.8 Hz, 1H), 7.47 (d, J=8.1 Hz, 1H). MS (ESI⁺) m/z 479 (M+H)⁺.

Example 49

1-[(4R)-6-fluoro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea ¹H NMR (500 MHz, DMSO-d₆/D₂O) δ 1.84 (s, 1H), 1.89-1.99 (m, 1H), 2.27 (dd, J=13.7, 6.0 Hz, 1H), 3.18 (s, 1H), 3.37 (t, J=5.9 Hz, 1H), 3.57 (t, J=5.9 Hz, 2H), 4.44 (bs, 1H), 4.52-4.72 (m, 3H), 4.97 (dd, J=10.9, 6.0 Hz, 1H), 6.86-7.10 (m, 6H). MS (ESI⁺) m/z 465 (M+H)⁺.

Example 50

1-[(4R)-2,2-diethyl-6-fluoro-3,4-dihydro-2H-chromen-4-yl]-3-[3-(2-hydroxyethyl)-2-oxo-1,2,3,4-tetrahydroquinazolin-7-yl]urea ¹H NMR (500 MHz, DMSO-d₆/D₂O) δ 0.90 (s, 6H), 1.48-1.72 (m, 5H), 2.10 (dd, J=13.4, 6.1 Hz, 1H), 3.37 (t, J=5.9 Hz, 2H), 3.57 (t, J=5.9 Hz, 2H), 4.44 (s, 2H), 4.90 (dd, J=11.2, 6.1 Hz, 1H), 6.75-6.81 (m, 1H), 6.89 (dd, J=8.1, 2.1 Hz, 1H), 6.93-7.03 (m, 4H). MS (ESI⁺) m/z 457 (M+H)⁺.

Example 51

1-[(4R)-6-fluoro-2,2-dimethyl-3,4-dihydro-2H-chromen-4-yl]-3-[3-(2-hydroxyethyl)-2-oxo-1,2,3,4-tetrahydroquinazolin-7-yl]urea ¹H NMR (500 MHz, DMSO-d₆/D₂O) δ 1.26 (s, 3H), 1.38 (s, 3H), 1.64-1.77 (m, 1H), 1.83 (s, 2H), 2.11 (dd, J=13.2, 6.2 Hz, 1H), 3.37 (t, J=5.9 Hz, 2H), 3.58 (t, J=5.9 Hz, 2H), 4.44 (s, 2H), 4.93 (dd, J=11.1, 6.2 Hz, 1H), 6.72-6.80 (m, 1H), 6.91 (s, 1H), 6.98 (dd, J=18.8, 8.4 Hz, 4H). MS (ESI) m/z 429 (M+H)⁺.

Example 52

1-[(4R)-6-fluoro-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-d$_6$/D$_2$O) δ 0.93 (t, J=7.3 Hz, 1H), 1.15-1.36 (m, 2H), 1.57 (s, 1H), 1.85-2.00 (m, 2H), 2.00-2.20 (m, 2H), 3.36 (t, J=5.9 Hz, 2H), 3.57 (t, J=5.9 Hz, 3H), 4.08-4.20 (m, 2H), 4.23 (ddd, J=10.5, 7.3, 3.0 Hz, 1H), 4.87 (t, J=5.9 Hz, 1H), 6.79 (ddd, J=29.6, 16.8, 6.9 Hz, 1H), 6.88 (dd, J=8.2, 2.1 Hz, 1H), 6.89-7.00 (m, 3H), 7.00-7.08 (m, 2H). MS ESI$^-$ m/z 399 (M−H)$^-$.

Example 53

1-[3-(2-hydroxyethyl)-2-oxo-1,2,3,4-tetrahydroquinazolin-7-yl]-3-[(4R)-8-(trifluoromethyl)-3,4-dihydro-2H-chromen-4-yl]urea $^1$H NMR (500 MHz, DMSO-d$_6$/D$_2$O) δ 1.85-2.07 (m, 1H), 2.15 (dddd, J=13.8, 8.4, 5.2, 3.2 Hz, 1H), 3.36 (t, J=5.9 Hz, 2H), 3.57 (t, J=5.9 Hz, 2H), 4.28 (ddd, J=11.4, 8.2, 3.2 Hz, 1H), 4.43 (s, 3H), 4.91-5.07 (m, 1H), 6.88 (dd, J=8.1, 2.1 Hz, 1H), 6.95 (d, J=8.2 Hz, 1H), 6.97 (d, J=2.1 Hz, 21H), 7.07 (t, J=7.8 Hz, 1H), 7.54 (t, J=8.1 Hz, 2H). MS (ESI) m/z 451 (M+H)$^+$.

Example 54

1-[3-(2-hydroxyethyl)-2-oxo-1,2,3,4-tetrahydroquinazolin-7-yl]-3-[(4R)-7-(trifluoromethyl)-3,4-dihydro-2H-chromen-4-yl]urea $^1$H NMR (500 MHz, DMSO-d$_6$/D$_2$O) δ 2.00 (dtd, J=10.1, 7.2, 3.0 Hz, 1H), 2.14 (tdd, J=8.0, 5.3, 3.2 Hz, 1H), 3.36 (t, J=5.9 Hz, 2H), 3.57 (t, J=5.9 Hz, 2H), 4.24 (ddd, J=11.0, 7.7, 3.0 Hz, 1H), 4.34 (ddd, J=10.7, 7.4, 3.0 Hz, 1H), 4.43 (s, 2H), 4.95 (t, J=5.9 Hz, 1H), 6.88 (dd, J=8.1, 2.0 Hz, 1H), 6.96 (dd, J=8.5, 5.2 Hz, 2H), 7.11 (d, J=1.1 Hz, 1H), 7.24 (d, J=8.2 Hz, 1H), 7.48 (d, J=8.0 Hz, 1H). MS (ESI$^+$) m/z 451 (M+H)$^+$.

Example 55

1-[(1R)-5-fluoro-2,3-dihydro-1H-inden-1-yl]-3-[3-(2-hydroxyethyl)-2-oxo-1,2,3,4-tetrahydroquinazolin-7-yl]urea $^1$H NMR (500 MHz, DMSO-d$_6$/D$_2$O) δ 1.79 (dq, J=12.6, 8.2 Hz, 1H), 2.76-2.87 (m, 1H), 2.94 (ddd, J=16.3, 8.7, 3.7 Hz, 1H), 3.36 (t, J=5.9 Hz, 2H), 3.57 (t, J=5.9 Hz, 2H), 4.43 (s, 2H), 5.11 (t, J=7.6 Hz, 1H), 6.88 (dd, J=8.1, 2.1 Hz, 1H), 6.95 (d, J=8.2 Hz, 2H), 6.96 (d, J=2.1 Hz, 1H), 6.98-7.06 (m, 1H), 7.09 (dd, J=9.2, 2.4 Hz, 1H), 7.28 (dd, J=8.3, 5.3 Hz, 1H). MS (ESI$^+$) m/z 385 (M+H)$^+$.

Example 56

1-[(4S)-6-fluoro-3,4-dihydrospiro[chromene-2,1'-cyclobutan]-4-yl]-3-[3-(2-hydroxyethyl)-2-oxo-1,2,3,4-tetrahydroquinazolin-7-yl]urea $^1$H NMR (500 MHz, DMSO-d$_6$/D$_2$O) δ 1.66-1.79 (m, 1H), 1.84 (bs, 2H), 2.03-2.21 (m, 3H), 2.28 (q, J=10.0 Hz, 1H), 2.36 (dd, J=13.2, 5.9 Hz, 1H), 3.37 (t, J=5.9 Hz, 2H), 3.58 (t, J=5.9 Hz, 2H), 4.44 (bs, 2H), 4.93 (dd, J=10.5, 5.9 Hz, 1H), 6.81 (dd, J=8.8, 4.8 Hz, 1H), 6.90 (dd, J=8.1, 2.1 Hz, 1H), 6.94-7.04 (m, 4H). MS (ESI$^+$) m/z 441 (M+H)$^+$.

Example 57

1-[(4S)-6-fluoro-2,2-dimethyl-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-d$_6$/D$_2$O) δ 1.26 (s, 3H), 1.35-1.41 (m, 3H), 1.72 (dd, J=13.2, 11.2 Hz, 1H), 1.83 (s, 2H), 2.11 (dd, J=13.2, 6.2 Hz, 1H), 3.37 (t, J=5.9 Hz, 2H), 3.57 (t, J=5.9 Hz, 2H), 4.44 (s, 2H), 4.93 (dd, J=11.1, 6.2 Hz, 1H), 6.72-6.80 (m, 1H), 6.90 (dd, J=8.2, 2.1 Hz, 1H), 6.92-7.04 (m, 4H). MS (ESI$^+$) m/z 429 (M+H)$^+$.

Example 58

1-[(2S,4R)-2-(fluoromethyl)-2-methyl-7-(trifluoromethyl)-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-d$_6$/D$_2$O) δ 1.40 (d, J=2.1 Hz, 3H), 1.84-1.97 (m, 1H), 2.35 (dd, J=13.8, 6.2 Hz, 1H), 3.37 (t, J=5.9 Hz, 2H), 3.57 (t, J=5.9 Hz, 2H), 4.42-4.52 (m, 3H), 4.51-4.62 (m, 1H), 4.98-5.06 (m, 1H), 6.91 (dd, J=8.1, 2.1 Hz, 1H), 6.94-7.01 (m, 3H), 7.12 (d, J=1.8 Hz, 1H), 7.27 (dd, J=8.1, 1.8 Hz, 1H), 7.47 (d, J=8.1 Hz, 1H). MS (ESI$^+$) m/z 497 (M+H)$^+$.

Example 59

1-[(2S,4R)-7-chloro-2-(fluoromethyl)-2-methyl-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-d$_6$/D$_2$O) δ 1.37 (d, J=2.0 Hz, 3H), 1.82-1.95 (m, 2H), 2.30 (dd, J=13.8, 6.2 Hz, 1H), 3.36 (t, J=5.9 Hz, 2H), 3.57 (t, J=5.9 Hz, 2H), 4.38-4.48 (m, 3H), 4.48-4.58 (m, 1H), 4.93 (dd, J=10.1, 6.2 Hz, 1H), 6.86-6.93 (m, 2H), 6.93-7.01 (m, 3H), 7.26 (dd, J=8.3, 1.0 Hz, 1H). MS (ESI$^+$) m/z 463 (M+H)$^+$.

Example 60

1-[(2R,4R)-2-(difluoromethyl)-2-methyl-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-d$_6$/D$_2$O) δ 1.40 (s, 3H), 1.81 (s, 2H), 1.87-1.96 (m, 1H), 2.38 (dd, J=14.1, 6.0 Hz, 1H), 3.37 (t, J=5.9 Hz, 2H), 3.57 (t, J=5.9 Hz, 2H), 4.43 (bs, 2H), 5.00 (dd, J=9.7, 6.0 Hz, 1H), 6.85 (dd, J=8.2, 1.1 Hz, 1H), 6.90 (dd, J=8.1, 2.1 Hz, 1H), 6.93-7.01 (m, 3H), 7.20 (td, J=7.7, 1.7 Hz, 1H), 7.26 (d, J=7.7 Hz, 1H). MS (ESI$^+$) m/z 447 (M+H)$^+$.

Example 61

1-[(4R)-7-chloro-8-fluoro-2,2-dimethyl-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-d$_6$/D$_2$O) δ 1.32 (s, 3H), 1.45 (s, 3H), 1.77-1.86 (m, 1H), 2.15 (dd, J=13.3, 6.2 Hz, 1H), 3.36 (t, J=5.9 Hz, 2H), 3.57 (t, J=5.9 Hz, 2H), 4.43 (s, 2H), 4.96

(dd, J=11.1, 6.1 Hz, 1H), 6.90 (dd, J=8.1, 2.1 Hz, 1H), 6.96 (d, J=8.2 Hz, 2H), 6.98 (d, J=2.1 Hz, 1H), 7.01-7.12 (m, 2H). MS (ESI$^+$) m/z 463 (M+H)$^+$.

Example 62

1-[(4R)-2,2-dimethyl-7-(trifluoromethyl)-3,4-dihydro-2H-pyrano[2,3-b]pyridin-4-yl]-3-[3-(2-hydroxyethyl)-2-oxo-1,2,3,4-tetrahydroquinazolin-7-yl]urea Example 62A sodium 3-acetyl-6-(trifluoromethyl)pyridin-2-olate A solution of 4-ethoxy-1,1,1-trifluoro-3-buten-2-one (4.21 g, 22.5 mmol), ethanol (42 mL), acetoacetamide (2.28 g, 22.5 mmol), and sodium ethoxide (21 wt % in ethanol, 8.41 mL, 22.5 mmol) was heated to 75° C. After 12 hours, the mixture was cooled to room temperature over 30 minutes, stirred for 4 hours, then cooled to <5° C. After 10 minutes, the white slurry was filtered, washing with cold ethanol (5 mL). The white solid was dried in a vacuum oven at 60° C. to provide the title compound (4.39 g, 19.3 mmol, 86% yield). MS (DCI) m/z 206 (M+H)$^+$.

Example 62B 2,2-dimethyl-7-(trifluoromethyl)-2H-pyrano[2,3-b]pyridin-4(3H)-one

A mixture of Example 62A (2.62 g, 12.77 mmol), acetone (26 mL), 3 Å molecular sieves (1.55 g), and pyrrolidine (0.211 ml, 2.55 mmol) were stirred at room temperature for 4 days. The mixture was concentrated then purified by flash chromatography (SiO$_2$, 0-50% EtOAc/hexanes gradient) to provide the title compound (1.52 g, 6.20 mmol, 49% yield). MS (DCI$^+$) m/z 246 (M+H)$^+$.

Example 62C

N—((R)-2,2-dimethyl-7-(trifluoromethyl)-3,4-dihydro-2H-pyrano[2,3-b]pyridin-4-yl)-2-methylpropane-2-sulfinamide A solution of Example 62B (1.52 g, 6.20 mmol), (R)-2-methylpropane-2-sulfinamide (1.127 g, 9.30 mmol), 2-methyltetrahydrofuran (20 mL), and tetraethoxytitanium (5.20 mL, 24.8 mmol) was heated to 70° C. After 3 hours the solution was cooled to −10° C. and sodium borohydride (0.469 g, 12.4 mmol) was added. The mixture was warmed to room temperature, stirred for 2 hours then cooled to 0° C. and 10% aqueous citric acid (50 mL) was added. The mixture was stirred vigorously overnight then diluted with methyltetrahydrofuran (300 mL). The layers were separated and the organic extract was washed with water and brine, dried (Na$_2$SO$_4$), filtered, and concentrated. Purification by flash chromatography (SiO$_2$, 20-100% hexane/ethyl acetate gradient) provided the title compound (2.14 g, 6.11 mmol, 99% yield). MS (DCI$^+$) m/z 349 (M+H)$^+$.

Example 62D (R)-2,2-dimethyl-7-(trifluoromethyl)-3,4-dihydro-2H-pyrano[2,3-b]pyridin-4-aminium chloride To a 0° C. solution of methanol (2.22 mL, 55 mmol) was added acetyl chloride (0.868 mL, 12.21 mmol) dropwise. This methanolic HCl solution was added to a room temperature mixture of Example 62C (2.14 g, 6.11 mmol) in methyl tert-butyl ether (20 mL). After 2 hours the solid was collected by filtration (200 mL MTBE wash) and dried at 60° C. overnight in a vacuum oven to provide the title compound (2.14 g, 6.11 mmol). $^1$H NMR (300 MHz, DMSO-d$_6$) δ 8.97 (bs, 2H), 8.43 (d, J=7.8 Hz, 1H), 7.62 (d, J=7.7 Hz, 1H), 4.75-4.66 (m, 1H), 2.51-2.36 (m, 2H), 1.50 (s, 3H), 1.30 (s, 3H). MS (ESI$^+$) m/z 247 (M+H)$^+$.

Example 62E

1-[(4R)-2,2-dimethyl-7-(trifluoromethyl)-3,4-dihydro-2H-pyrano[2,3-b]pyridin-4-yl]-3-[3-(2-hydroxyethyl)-2-oxo-1,2,3,4-tetrahydroquinazolin-7-yl]urea $^1$H NMR (500 MHz, DMSO-d$_6$/D$_2$O) δ 1.35 (s, 3H), 1.48 (s, 3H), 1.84 (s, 2H), 2.18 (dd, J=13.3, 6.1 Hz, 1H), 3.37 (t, J=5.9 Hz, 2H), 3.57 (t, J=5.9 Hz, 2H), 4.43 (bs, 2H), 5.02-5.10 (m, 1H), 6.91 (dd, J=8.1, 2.1 Hz, 1H), 6.96 (d, J=8.2 Hz, 1H), 7.00 (d, J=2.0 Hz, 1H), 7.47 (d, J=7.7 Hz, 1H), 7.91 (d, J=7.7 Hz, 1H). MS (ESI$^+$) m/z 480 (M+H)$^+$.

Example 63

1-[(4R)-7-bromo-2,2-dimethyl-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-d$_6$/D$_2$O) δ 1.28 (s, 3H), 1.39 (s, 3H), 1.69-1.83 (m, 1H), 1.83 (s, 2H), 2.11 (dd, J=13.2, 6.2 Hz, 1H), 3.36 (t, J=5.9 Hz, 2H), 3.57 (t, J=5.9 Hz, 2H), 4.43 (s, 2H), 4.90 (dd, J=11.1, 6.1 Hz, 1H), 6.90 (dd, J=8.1, 2.1 Hz, 2H), 6.91-7.00 (m, 3H), 7.07 (dd, J=8.3, 2.0 Hz, 1H), 7.19 (dd, J=8.2, 1.0 Hz, 1H). MS (ESI$^+$) m/z 489 (M+H)$^+$.

Example 64

1-(1-methyl-2-oxo-1,2-dihydroquinolin-5-yl)-3-[(4R)-7-(trifluoromethyl)-3,4-dihydro-2H-chromen-4-yl]urea $^1$H NMR (500 MHz, DMSO-d$_6$/D$_2$O) δ 1.87-2.00 (m, 1H), 2.00-2.12 (m, 1H), 2.12-2.27 (m, 1H), 3.64 (s, 3H), 4.07 (q, J=7.0 Hz, 1H), 4.20-4.32 (m, 2H), 4.25-4.42 (m, 3H), 4.99 (dd, J=15.3, 9.4 Hz, 1H), 6.66 (d, J=9.8 Hz, 1H), 7.05-7.16 (m, 1H), 7.27 (dt, J=14.4, 5.1 Hz, 2H), 7.53-7.62 (m, 2H), 7.70 (dt, J=7.1, 3.6 Hz, 1H), 8.03 (d, J=10.2 Hz, 1H). MS (ESI$^+$) m/z 418 (M+H)$^+$.

Example 65

1-[(4R)-3,4-dihydrospiro[chromene-2,1'-cyclopentan]-4-yl]-3-(1-methyl-2-oxo-1,2-dihydroquinolin-5-yl)urea $^1$H NMR (500 MHz, DMSO-d$_6$/D$_2$O) δ 1.21 (d, J=7.1 Hz, 1H), 1.68-1.92 (m, 9H), 1.92-2.02 (m, 2H), 2.18 (td, J=13.1, 6.7 Hz, 1H), 3.63 (d, J=10.8 Hz, 3H), 4.09 (dt, J=14.3, 5.3 Hz, 1H), 5.00 (dd, J=9.9, 6.1 Hz, 1H), 6.63-6.78 (m, 3H), 6.84-6.98 (m, 2H), 7.08-7.22 (m, 2H), 7.28 (ddd, J=26.7, 13.7, 8.8 Hz, 2H), 7.51-7.64 (m, 1H), 7.72 (t, J=7.2 Hz, 1H), 8.06 (d, J=9.8 Hz, 1H). MS (ESI$^+$) m/z 404 (M+H)$^+$.

Example 66

1-[(4R)-2,2-diethyl-8-fluoro-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 0.85-0.96 (m, 6H), 1.53-1.84 (m, 5H), 2.19 (dd, J=13.5, 6.1 Hz, 1H), 3.64 (s, 3H), 5.00 (dd, J=11.0, 6.1 Hz, 1H), 6.66 (d, J=9.8 Hz, 1H), 6.89 (td, J=8.0, 4.9 Hz, 1H), 7.06-7.16 (m, 2H), 7.26 (d, J=8.5 Hz, 1H), 7.59 (t, J=8.2 Hz, 1H), 7.67-7.72 (m, 1H), 8.05 (d, J=9.8 Hz, 1H). MS (ESI$^+$) m/z 424 (M+H)$^+$.

Example 67

1-[(4R)-2,2-diethyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 0.84-0.95 (m, 6H), 1.52-1.77 (m, 5H), 2.16 (dd, J=13.4, 6.1 Hz, 1H), 3.64 (s, 3H), 4.97 (dd, J=10.8, 6.1 Hz, 1H), 6.66 (d, J=9.8 Hz, 1H), 6.78 (dd, J=8.1, 1.2 Hz, 1H), 6.92 (td, J=7.4, 1.2 Hz, 1H), 7.14-7.21 (m, 1H), 7.23-7.33 (m, 2H), 7.59 (t, J=8.3 Hz, 1H), 7.72 (d, J=8.0 Hz, 1H), 8.06 (d, J=9.8 Hz, 1H). MS (ESI$^+$) m/z 406 (M+H)$^+$.

Example 68

1-[(1R)-5-tert-butyl-2,3-dihydro-1H-inden-1-yl]-3-(1-methyl-2-oxo-1,2-dihydroquinolin-5-yl)urea $^1$H NMR (500 MHz, DMSO-d$_6$/D$_2$O) δ 0.84-0.97 (m, 9H), 1.88 (dq, J=12.5, 8.6 Hz, 1H), 2.86-2.96 (m, 1H), 3.04 (ddd, J=16.3, 8.7, 3.2 Hz, 1H), 3.63 (s, 3H), 5.23-5.30 (m, 1H), 6.65 (d, J=9.8 Hz, 1H), 7.25 (d, J=8.5 Hz, 1H), 7.53 (d, J=7.9 Hz, 1H), 7.55-7.66 (m, 3H), 7.70 (dd, J=8.0, 0.9 Hz, 1H), 8.04 (d, J=9.8 Hz, 1H). MS (ESI$^+$) m/z 390 (M+H)$^+$.

Example 69

1-[(4R)-2,2-diethyl-7-(trifluoromethyl)-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 0.84-0.97 (m, 6H), 1.53-1.84 (m, 5H), 2.17 (ddd, J=16.7, 13.4, 6.1 Hz, 1H), 3.64 (d, J=1.2 Hz, 3H), 4.90-5.06 (m, 1H), 6.67 (dd, J=9.8, 2.1 Hz, 1H), 7.20-7.35 (m, 2H), 7.51-7.63 (m, 1H), 7.65-7.76 (m, 1H), 8.05 (dd, J=9.8, 3.3 Hz, 1H). MS (ESI$^+$) m/z 474 (M+H)$^+$.

Example 70

1-[(4R)-7-chloro-2,2-diethyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 0.84-0.97 (m, 6H), 1.53-1.82 (m, 5H), 2.17 (ddd, J=16.7, 13.5, 6.1 Hz, 1H), 3.64 (d, J=1.2 Hz, 3H), 4.90-5.06 (m, 1H), 6.67 (d, J=9.8, 1H), 6.82-7.00 (m, 1H), 7.23-7.35 (m, 2H), 7.51-7.63 (m, 1H), 7.65-7.76 (m, 1H), 8.05 (d, J=9.8, 3.2 Hz, 1H). MS (ESI$^+$) m/z 440 (M+H)$^+$.

Example 71

1-[(4R)-6-fluoro-2,2-bis(fluoromethyl)-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 1.47 (d, J=17.7 Hz, 1H), 1.73-1.92 (m, 1H), 1.92-2.24 (m, 2H), 2.24-2.47 (m, 1H), 2.70 (d, J=36.3 Hz, 1H), 3.18 (s, 1H), 3.26 (s, 1H), 3.49 (s, 1H), 3.63 (d, J=4.8 Hz, 3H), 4.12-4.31 (m, 1H), 4.51-4.93 (m, 3H), 4.93-5.10 (m, 1H), 6.60-6.71 (m, 1H), 6.73-7.03 (m, 2H), 7.04-7.34 (m, 3H), 7.41 (d, J=8.5 Hz, 1H), 7.53-7.79 (m, 2H), 7.93 (d, J=9.8 Hz, 1H), 7.98-8.10 (m, 1H). MS (ESI$^-$) m/z 430 (M−H)$^-$.

Example 72

1-[(4R)-6,8-difluoro-2,2-bis(fluoromethyl)-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 2.06 (ddd, J=13.8, 11.0, 2.8 Hz, 1H), 2.36 (dd, J=13.8, 6.0 Hz, 1H), 3.64 (s, 3H), 4.54-4.78 (m, 4H), 5.05 (dd, J=10.9, 5.9 Hz, 1H), 6.66 (d, J=9.8 Hz, 1H), 6.99 (dd, J=9.2, 2.7 Hz, 1H), 7.20-7.31 (m, 2H), 7.59 (t, J=8.2 Hz, 2H), 7.64 (dd, J=8.0, 1.1 Hz, 1H), 8.06 (d, J=9.8 Hz, 1H). MS (ESI$^+$) m/z 450 (M+H)$^+$.

Example 73

1-[(4R)-6-fluoro-3,4-dihydrospiro[chromene-2,1'-cyclobutan]-4-yl]-3-(1-methyl-2-oxo-1,2-dihydroquinolin-5-yl)urea $^1$H NMR (500 MHz, DMSO-d$_6$/D$_2$O) δ 1.67-1.93 (m, 2H), 2.05-2.24 (m, 3H), 2.25-2.35 (m, 1H), 2.41 (dd, J=13.2, 5.9 Hz, 1H), 3.64 (s, 3H), 4.97 (dd, J=10.3, 5.9 Hz, 1H), 6.66 (d, J=9.8 Hz, 1H), 6.83 (dd, J=8.9, 4.8 Hz, 1H), 6.94-7.08 (m, 2H), 7.27 (d, J=8.5 Hz, 1H), 7.59 (t, J=8.2 Hz, 1H), 7.70 (dd, J=8.0, 0.9 Hz, 1H), 8.06 (d, J=9.8 Hz, 1H). MS (ESI$^+$) m/z 408 (M+H)$^+$.

Example 74

1-[(4R)-2,2-diethyl-6-fluoro-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 0.89 (dt, J=22.8, 7.5 Hz, 6H), 1.56-1.72 (m, 4H), 2.15 (dd, J=13.5, 6.2 Hz, 1H), 3.63 (d, J=3.9 Hz, 3H), 4.94 (dd, J=11.1, 6.2 Hz, 1H), 6.64 (d, J=8.7 Hz, 1H), 6.70-6.84 (m, 1H), 6.91-7.01 (m, 1H), 7.07 (dd, J=9.4, 2.6 Hz, 1H), 7.19-7.32 (m, 1H), 7.58 (dd, J=15.8, 7.7 Hz, 1H), 7.63-7.77 (m, 1H), 8.05 (dd, J=18.2, 10.1 Hz, 1H). MS (ESI$^+$) m/z02 424 (M+H)$^+$.

Example 75

1-[(4R)-8-fluoro-2,2-dipropyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 0.74-1.08 (m, 6H), 1.26-1.44 (m, 4H), 1.51-1.85 (m, 5H), 2.18 (dd, J=13.5, 6.0 Hz, 1H), 3.64 (s, 3H), 4.98 (dd, J=11.0, 6.0 Hz, 1H), 6.66 (d, J=9.8 Hz, 1H), 6.89 (td, J=8.0, 4.9 Hz, 1H), 7.06-7.15 (m, 2H), 7.26 (d, J=8.5 Hz, 1H), 7.59 (t, J=8.3 Hz, 1H), 7.69 (d, J=8.0 Hz, 1H), 8.05 (d, J=9.8 Hz, 1H). MS (ESI$^+$) m/z 452 (M+H)$^+$.

Example 76

1-[(4R)-2,2-diethyl-7-(trifluoromethoxy)-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 0.83-0.98 (m, 6H), 1.52-1.81 (m, 5H), 2.17 (dd, J=13.5, 6.1 Hz, 1H), 3.64 (s, 3H), 4.97 (dd, J=11.0, 6.1 Hz, 1H), 6.66 (d, J=9.8 Hz, 1H), 6.75 (d, J=3.0 Hz, 1H), 6.91 (ddd, J=8.5, 2.6, 1.3 Hz, 1H), 7.26 (d, J=8.5 Hz, 1H), 7.42 (dd, J=8.5, 1.0 Hz, 1H), 7.59 (t, J=8.2 Hz, 1H), 7.66-7.71 (m, 1H), 8.05 (d, J=9.8 Hz, 1H). MS (ESI$^+$) m/z 490 (M+H)$^+$.

Example 77

1-[(4R)-2,2-dimethyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 1.29 (s, 3H), 1.41 (s, 3H), 1.72-1.81 (m, 1H), 2.17 (dd, J=13.1, 6.2 Hz, 1H), 3.64 (s, 3H), 4.99 (dd, J=10.8, 6.2 Hz, 1H), 6.66 (d, J=9.8 Hz, 1H), 6.76 (dd, J=8.2, 1.2 Hz, 1H), 6.92 (td, J=7.4, 1.2 Hz, 1H), 7.14-7.21 (m, 1H), 7.26 (d, J=8.5 Hz, 1H), 7.28-7.34 (m, 1H), 7.59 (t, J=8.2 Hz, 1H), 7.69-7.74 (m, 1H), 8.05 (d, J=9.8 Hz, 1H). MS (ESI$^+$) m/z 378 (M+H)$^+$.

Example 78

1-(1-methyl-2-oxo-1,2-dihydroquinolin-5-yl)-3-[(4S)-7-(trifluoromethoxy)-3,4-dihydro-2H-chromen-4-yl]urea $^1$H NMR (500 MHz, DMSO-d$_6$/D$_2$O) δ 1.20-1.47 (m, 1H), 1.95-2.07 (m, 1H), 2.09-2.22 (m, 1H), 3.52-3.65 (m, 3H), 4.22 (ddd, J=11.4, 8.6, 2.9 Hz, 1H), 4.26-4.40 (m, 1H), 4.81-4.98 (m, 1H), 6.65 (t, J=9.8 Hz, 1H), 6.78-7.06 (m, 2H), 7.21-7.31 (m, 1H), 7.50-7.61 (m, 1H), 7.67 (ddd, J=19.8, 6.8, 6.2 Hz, 1H), 8.03 (dd, J=15.3, 9.9 Hz, 1H). MS (ESI$^+$) m/z 434 (M+H)$^+$.

Example 79

1-[(4R)-6-fluoro-2,2-bis(methoxymethyl)-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 1.90 (dd, J=13.4, 11.3 Hz, 1H), 2.18 (dd, J=13.5, 6.0 Hz, 1H), 3.28 (s, 3H), 3.32 (s, 3H), 3.39-3.48 (m, 2H), 3.48 (d, J=10.5 Hz, 2H), 3.64 (s, 3H), 4.97 (dd, J=11.1, 6.0 Hz, 1H), 6.64 (d, J=9.8 Hz, 1H), 6.83 (dd, J=8.9, 4.8 Hz, 1H), 6.95-7.09 (m, 2H), 7.26 (d, J=8.5 Hz, 1H), 7.58 (t, J=8.3 Hz, 1H), 7.67 (dd, J=8.0, 0.7 Hz, 1H), 8.10 (d, J=9.9 Hz, 1H). MS (ESI$^+$) m/z 456 (M+H)$^+$.

Example 80

1-[(4R)-2,2-bis(fluoromethyl)-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 2.00 (ddd, J=13.2, 10.4, 2.5 Hz, 1H), 2.23-2.42 (m, 1H), 3.64 (s, 3H), 4.50-4.64 (m, 2H), 4.62-4.73 (m, 2H), 5.03 (dd, J=10.2, 5.9 Hz, 1H), 6.66 (d, J=9.8 Hz, 1H), 6.82-6.91 (m, 1H), 7.01 (td, J=7.6, 1.1 Hz, 1H), 7.17-7.29 (m, 2H), 7.34 (d, J=7.6 Hz, 1H), 7.59 (t, J=8.3 Hz, 1H), 7.67 (t, J=20.7 Hz, 1H), 8.05 (d, J=9.8 Hz, 1H). MS (ESI$^+$) m/z 414 (M+H)$^+$.

Example 81

1-[(4R)-7,8-difluoro-2,2-dimethyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 1.33 (s, 3H), 1.47 (s, 3H), 1.84 (dd, J=13.3, 11.1 Hz, 1H), 2.20 (dd, J=13.3, 6.1 Hz, 1H), 3.64 (s, 3H), 4.95-5.03 (m, 1H), 6.66 (d, J=9.7 Hz, 1H), 6.95 (td, J=9.4, 7.2 Hz, 1H), 7.10-7.17 (m, 1H), 7.27 (d, J=8.4 Hz, 1H), 7.59 (t, J=8.2 Hz, 1H), 7.64-7.70 (m, 1H), 8.04 (d, J=9.8 Hz, 1H). MS (ESI$^+$) m/z 414 (M+H)$^+$.

Example 82

1-[(4R)-6-fluoro-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 1.92-2.04 (m, 1H), 2.09-2.19 (m, 1H), 3.63 (s, 2H), 4.17 (ddd, J=11.2, 8.2, 3.0 Hz, 1H), 4.20-4.31 (m, 1H), 4.90 (t, J=5.8 Hz, 1H), 6.64 (d, J=9.8 Hz, 1H), 6.84 (dd, J=9.0, 4.8 Hz, 1H), 7.04 (td, J=8.6, 3.2 Hz, 1H), 7.11 (dd, J=9.2, 3.2 Hz, 1H), 7.25 (d, J=8.6 Hz, 1H), 7.58 (t, J=8.2 Hz, 1H), 7.71 (dd, J=8.0, 0.9 Hz, 1H), 8.03 (d, J=9.8 Hz, 1H). MS (ESI$^+$) m/z 368 (M+H)$^+$.

Example 83

1-[(1R)-5-fluoro-2,3-dihydro-1H-inden-1-yl]-3-(1-methyl-2-oxo-1,2-dihydroquinolin-5-yl)urea $^1$H NMR (500 MHz, DMSO-d$_6$/D$_2$O) δ 1.85 (dq, J=12.6, 8.0 Hz, 1H), 2.84 (dt, J=16.3, 8.2 Hz, 1H), 2.97 (ddd, J=16.2, 8.7, 3.8 Hz, 1H), 3.63 (s, 3H), 5.12-5.19 (m, 1H), 6.65 (d, J=9.8 Hz, 1H), 7.01-7.14 (m, 2H), 7.24 (d, J=8.5 Hz, 1H), 7.34 (dd, J=8.3, 5.3 Hz, 1H), 7.58 (t, J=8.2 Hz, 1H), 7.71 (dd, J=8.0, 0.9 Hz, 1H), 8.03 (d, J=9.8 Hz, 1H). MS (ESI$^+$) m/z 352 (M+H)$^+$.

Example 84

1-[(2S,4R)-2-(fluoromethyl)-2-methyl-7-(trifluoromethyl)-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 1.28 (d, J=2.2 Hz, 3H), 1.92 (t, J=12.3 Hz, 1H), 2.13 (dd, J=13.1, 6.0 Hz, 1H), 3.64 (s, 3H), 4.40-4.49 (m, 1H), 4.49-4.58 (m, 1H), 5.05 (dd, J=11.4, 6.0 Hz, 1H), 6.67 (d, J=9.8 Hz, 1H), 6.89 (d, J=2.1 Hz, 1H), 7.02 (dd, J=8.3, 2.1 Hz, 1H), 7.27 (d, J=8.4 Hz, 1H), 7.34 (dd, J=8.3, 1.1 Hz, 1H), 7.59 (t, J=8.2 Hz, 1H), 7.66 (dd, J=8.0, 1.0 Hz, 1H), 8.05 (dd, J=9.8, 0.7 Hz, 1H). MS (ESI$^+$) m/z 430 (M+H)$^+$.

Example 85

1-[(4R)-7-chloro-8-fluoro-2,2-dimethyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 1.33 (s, 3H), 1.44 (d, J=26.4 Hz, 3H), 1.85 (dd, J=13.2, 11.4 Hz, 1H), 2.20 (dd, J=13.4, 6.2 Hz, 1H), 3.63 (s, 3H), 5.00 (dd, J=11.0, 6.2 Hz, 1H), 6.66 (d, J=9.9 Hz, 1H), 7.08 (dd, J=8.6, 6.6 Hz, 1H), 7.16 (d, J=8.7 Hz, 1H), 7.27 (d, J=8.5 Hz, 1H), 7.59 (t, J=8.3 Hz, 1H), 7.66 (d, J=7.6 Hz, 1H), 8.04 (d, J=9.8 Hz, 1H). MS (ESI$^+$) m/z 430 (M+H)$^+$.

Example 86

1-(1-methyl-2-oxo-1,2-dihydroquinolin-5-yl)-3-[(1R)-5-(trifluoromethyl)-2,3-dihydro-1H-inden-1-yl]urea $^1$H NMR (500 MHz, DMSO-d$_6$/D$_2$O) δ 1.88 (dq, J=12.5, 8.6 Hz, 1H), 2.86-2.96 (m, 1H), 3.04 (ddd, J=16.3, 8.7, 3.2 Hz, 1H), 3.63 (s, 3H), 5.23-5.30 (m, 1H), 6.65 (d, J=9.8 Hz, 1H), 7.25 (d, J=8.5 Hz, 1H), 7.53 (d, J=7.9 Hz, 1H), 7.55-7.66 (m, 3H), 7.70 (dd, J=8.0, 0.9 Hz, 1H), 8.04 (d, J=9.8 Hz, 1H). MS (ESI$^+$) m/z 402 (M+H)$^+$.

Example 87

1-(1-methyl-2-oxo-1,2-dihydroquinolin-5-yl)-3-[(4R)-7-(trifluoromethoxy)-3,4-dihydro-2H-chromen-4-yl]urea $^1$H NMR (500 MHz, DMSO-d$_6$/D$_2$O) δ 1.98-2.07 (m, 1H), 2.10-2.20 (m, 1H), 3.63 (s, 3H), 4.22 (ddd, J=11.3, 8.5, 2.9 Hz, 1H), 4.30-4.38 (m, 1H), 4.92 (t, J=5.5 Hz, 1H), 6.65 (d, J=9.8 Hz, 1H), 6.81 (d, J=3.0 Hz, 1H), 6.94 (ddd, J=8.5, 2.5, 1.3 Hz, 1H), 7.25 (d, J=8.5 Hz, 1H), 7.44 (dd, J=8.4, 0.8 Hz, 1H), 7.58 (t, J=8.2 Hz, 1H), 7.71 (dd, J=8.0, 0.9 Hz, 1H), 8.02 (dd, J=9.8, 0.7 Hz, 1H). MS (ESI$^+$) m/z 434 (M+H)$^+$.

Example 88

1-[(4S)-6-fluoro-3,4-dihydrospiro[chromene-2,1'-cyclobutan]-4-yl]-3-(1-methyl-2-oxo-1,2-dihydroquinolin-5-yl)urea $^1$H NMR (500 MHz, DMSO-d$_6$/D$_2$O) δ 1.67-1.80 (m, 1H), 1.79-1.93 (m, 2H), 2.05-2.24 (m, 3H), 2.24-2.35 (m, 1H), 2.40 (dd, J=13.2, 5.8 Hz, 1H), 3.64 (s, 3H), 4.97 (dd, J=10.4, 5.8 Hz, 1H), 6.66 (d, J=9.7 Hz, 1H), 6.83 (dd, J=8.8, 4.8 Hz, 1H), 6.97-7.08 (m, 2H), 7.27 (d, J=8.5 Hz, 1H), 7.60 (t, J=8.2 Hz, 1H), 7.67-7.73 (m, 1H), 8.06 (d, J=9.8 Hz, 1H). MS (ESI$^+$) m/z 408 (M+H)$^+$.

Example 89

1-[(4R)-7-bromo-2,2-dimethyl-3,4-dihydro-2H-chromen-4-yl]-3-(1-methyl-2-oxo-1,2-dihydroquinolin-5-yl)urea $^1$H NMR (500 MHz, DMSO-d$_6$/D$_2$O) δ 1.29 (s, 3H), 1.41 (s, 3H), 1.78 (dd, J=13.2, 11.1 Hz, 1H), 2.17 (dd, J=13.2, 6.2 Hz, 1H), 3.64 (s, 3H), 4.91-4.98 (m, 1H), 6.66 (d, J=9.8 Hz, 1H), 6.95 (d, J=2.0 Hz, 1H), 7.11 (dd, J=8.2, 2.0 Hz, 1H), 7.25 (d, J=1.1 Hz, 2H), 7.27 (d, J=1.2 Hz, 2H), 7.59 (t, J=8.2 Hz, 1H), 7.65-7.71 (m, 1H), 8.04 (d, J=9.8 Hz, 1H). MS (ESI$^+$) m/z 456 (M+H)$^+$.

Example 90

1-(1-methyl-2-oxo-1,2-dihydroquinolin-5-yl)-3-[(2R,4R)-2-methyl-2-(trifluoromethyl)-3,4-dihydro-2H-chromen-4-yl]urea $^1$H NMR (500 MHz, DMSO-d$_6$/D$_2$O) δ 1.53 (s, 3H), 2.05 (t, J=12.2 Hz, 1H), 2.37 (dd, J=12.7, 5.9 Hz, 1H), 3.64 (s, 3H), 5.11 (dd, J=11.7, 5.8 Hz, 1H), 6.67 (d, J=9.8 Hz, 1H), 6.91 (dd, J=8.2, 1.2 Hz, 1H), 7.06 (td, J=7.5, 1.2 Hz, 1H), 7.20-7.31 (m, 2H), 7.38 (dt, J=7.7, 1.3 Hz, 1H), 7.56-7.67 (m, 2H), 8.07 (d, J=9.8 Hz, 1H). MS (ESI$^+$) m/z 432 (M+H)$^+$.

Example 91

1-[(4R)-2,2-dimethyl-7-(trifluoromethyl)-3,4-dihydro-2H-chromen-4-yl]-3-(1-methyl-2-oxo-1,2-dihydroquinolin-5-yl)urea $^1$H NMR (300 MHz, DMSO-d$_6$) δ ppm 1.31 (s, 3H) 1.43 (s, 3H) 1.84 (dd, J=13.09, 11.50 Hz, 1H) 2.21 (dd, J=13.49, 6.35 Hz, 1H) 3.62 (s, 3H) 4.97-5.13 (m, 1H) 6.66 (d, J=9.92 Hz, 1H) 6.92 (d, J=8.73 Hz, 1H) 7.06 (d, J=1.59 Hz, 1H) 7.18-7.30 (m, 2 H) 7.50-7.61 (m, J=8.33, 8.33 Hz, 2H) 7.73 (d, J=7.54 Hz, 1H) 8.04 (d, J=9.92 Hz, 1H) 8.68 (s, 1H); MS (ESI$^+$) m/z 446 (M+H)$^+$.

Example 92

1-[(4R)-2,2-bis(fluoromethyl)-7-(trifluoromethyl)-3,4-dihydro-2H-chromen-4-yl]-3-(1-methyl-2-oxo-1,2-dihydroquinolin-5-yl)urea $^1$H NMR (300 MHz, DMSO-d$_6$) δ ppm 2.05 (dd, 1H) 2.36 (dd, J=13.89, 5.95 Hz, 1H) 3.62 (s, 3H) 4.54-4.66 (m, 2H) 4.69-4.83 (m, 2H) 5.03-5.18 (m, 1H) 6.66 (d, J=9.92 Hz, 1H) 6.97 (d, J=8.33 Hz, 1H) 7.17-7.26 (m, 2H) 7.31-7.38 (m, 1H) 7.51-7.58 (m, 2H) 7.70 (d, J=7.14 Hz, 1H) 8.04 (d, J=9.52 Hz, 1H) 8.70 (s, 1H); MS (ESI$^+$) m/z 482 (M+H)$^+$.

Example 93

1-[(4R)-2,2-dimethyl-8-(trifluoromethyl)-3,4-dihydro-2H-chromen-4-yl]-3-(1-methyl-2-oxo-1,2-dihydroquinolin-5-yl)urea $^1$H NMR (300 MHz, DMSO-d$_6$) δ ppm 1.32 (s, 3H) 1.43 (s, 3H) 1.79-1.96 (m, 1H) 2.23 (dd, J=13.39, 6.27 Hz, 1H) 3.62 (s, 3H) 4.97-5.14 (m, 1H) 6.65 (d, J=9.83 Hz, 1H) 6.90 (d, J=8.48 Hz, 1H) 7.06 (t, J=7.80 Hz, 1H) 7.21 (d, J=8.48 Hz, 1H) 7.56 (d, 3H) 7.72 (d, J=7.46 Hz, 1H) 8.04 (d, J=9.83 Hz, 1H) 8.66 (s, 1H); MS (ESI$^+$) m/z 446 (M+H)$^+$.

Example 94

1-[(4R)-8-fluoro-2,2-dimethyl-3,4-dihydro-2H-chromen-4-yl]-3-(1-methyl-2-oxo-1,2-dihydroquinolin-5-yl)urea $^1$H NMR (300 MHz, DMSO-d$_6$) δ ppm 1.32 (s, 3H) 1.44 (s, 3H) 1.75-1.91 (m, 1H) 2.14-2.26 (m, 1H) 3.62 (s, 3H) 4.94-5.09 (m, 1H) 6.65 (d, J=9.83 Hz, 1H) 6.80-6.94 (m, 2H) 7.03-7.17 (m, 2H) 7.20 (d, J=8.48 Hz, 1H) 7.55 (d, J=16.61 Hz, 1H) 7.74 (d, J=7.46 Hz, 1H) 8.04 (d, J=10.17 Hz, 1H) 8.63 (s, 1H); MS (ESI$^+$) m/z 396 (M+H)$^+$.

Example 95

1-[(4R)-8-fluoro-2,2-bis(fluoromethyl)-3,4-dihydro-2H-chromen-4-yl]-3-(1-methyl-2-oxo-1,2-dihydroquinolin-5-yl)urea $^1$H NMR (300 MHz, DMSO-d$_6$) δ ppm 2.00-2.13 (m, 1H) 2.28-2.42 (m, 1 H) 3.62 (s, 3H) 4.52-4.67 (m, 2H) 4.68-4.84 (m, 2H) 4.99-5.17 (m, 1H) 6.66 (d, J=9.52 Hz, 1H) 6.89-7.06

(m, 2H) 7.08-7.29 (m, J=17.25, 8.13 Hz, 3H) 7.55 (t, J=8.33 Hz, 1H) 7.72 (d, J=7.54 Hz, 1H) 8.04 (d, J=9.91 Hz, 1H) 8.67 (s, 1H); MS (ESI$^+$) m/z 432 (M+H)$^+$.

Example 96

1-[(1R)-5-chloro-2,3-dihydro-1H-inden-1-yl]-3-(1-methyl-2-oxo-1,2-dihydroquinolin-5-yl)urea $^1$H NMR (300 MHz, DMSO-d$_6$) δ ppm $^1$H NMR (300 MHz, DMSO-D6) δ ppm 1.75-1.87 (m, 1H) 2.40-2.58 (m, 1H) 2.76-3.04 (m, 2H) 3.61 (s, 3H) 5.17 (q, J=7.54 Hz, 1H) 6.63 (d, J=9.92 Hz, 1H) 6.91 (d, J=7.93 Hz, 1H) 7.18 (d, J=8.33 Hz, 1H) 7.24-7.39 (m, 3H) 7.54 (t, J=8.33 Hz, 1H) 7.76 (d, J=7.93 Hz, 1H) 8.02 (d, J=9.92 Hz, 1H) 8.55 (s, 1H); MS (ESI$^+$) m/z 368 (M+H)$^+$.

Example 97

1-(1-methyl-2-oxo-1,2-dihydroquinolin-5-yl)-3-[(4R)-8-(trifluoromethyl)-3,4-dihydro-2H-chromen-4-yl]urea $^1$H NMR (300 MHz, DMSO-d$_6$) δ ppm 2.00-2.25 (m, 2H) 3.61 (s, 3H) 4.24-4.36 (m, 1H) 4.37-4.50 (m, 1H) 4.93-5.04 (m, 1H) 6.63 (d, J=9.92 Hz, 1H) 7.02-7.12 (m, 2H) 7.20 (d, J=8.73 Hz, 1H) 7.50-7.58 (m, 2H) 7.61 (d, J=7.14 Hz, 1H) 7.76 (d, J=8.33 Hz, 1H) 8.00 (d, J=9.92 Hz, 1H) 8.50 (s, 1H); MS (ESI$^+$) m/z 418 (M+H)$^+$.

Example 98

1-[(4S)-6-fluoro-2,2-dimethyl-3,4-dihydro-2H-chromen-4-yl]-3-(1-methyl-2-oxo-1,2-dihydroquinolin-5-yl)urea $^1$H NMR (300 MHz, DMSO-d$_6$) δ ppm $^1$H NMR (500 MHz, DMSO-D6) δ ppm 1.27 (s, 3H) 1.40 (s, 3H) 1.71-1.80 (m, J=11.29 Hz, 1H) 2.17 (dd, J=13.27, 6.26 Hz, 1H) 3.62 (s, 3H) 4.92-5.02 (m, 1H) 6.65 (d, J=9.76 Hz, 1H) 6.78 (dd, J=8.85, 4.88 Hz, 1H) 6.90 (d, J=8.24 Hz, 1H) 7.01 (td, J=8.47, 3.20 Hz, 1H) 7.09 (dd, J=9.46, 2.44 Hz, 1H) 7.21 (d, J=8.54 Hz, 1H) 7.55 (t, J=8.24 Hz, 1H) 7.74 (d, J=7.93 Hz, 1H) 8.05 (d, J=10.07 Hz, 1H) 8.65 (s, 1H); MS (ESI$^+$) m/z 396 (M+H)$^+$.

Example 99

1-[(4R)-7-chloro-2,2-bis(fluoromethyl)-3,4-dihydro-2H-chromen-4-yl]-3-(2-oxo-1,2-dihydroquinolin-5-yl)urea $^1$H NMR (300 MHz, DMSO) δ 11.72 (s, 1H), 8.59 (s, 1H), 8.02 (d, J=9.9 Hz, 1H), 7.70-7.57 (m, 1H), 7.45-7.30 (m, 2H), 7.11-6.83 (m, 4H), 6.53 (d, J=9.9 Hz, 1H), 5.00 (dd, J=15.7, 8.6 Hz, 1H), 4.83-4.65 (m, 2H), 4.65-4.48 (m, 2H), 2.32 (dd, J=13.7, 5.9 Hz, 1H), 2.07-1.92 (m, 1H); LCMS m/z 434 (M+H)$^+$.

Example 100

1-[(4R)-8-fluoro-2,2-dimethyl-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 1.31 (s, 3H), 1.43 (s, 3H), 1.79 (dd, J=13.1, 11.3 Hz, 1H), 2.14 (dd, J=13.3, 6.2 Hz, 1H), 4.50 (s, 2H), 4.99 (dd, J=11.1, 6.1 Hz, 1H), 6.83-6.89 (m, 3H), 7.04-7.09 (m, 2H), 7.18-7.21 (m, 1H). MS (ESI$^-$) m/z 384 (M–H)$^-$.

Example 101

1-[(4R)-2,2-diethyl-8-fluoro-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 0.90 (dt, J=16.2, 7.5 Hz, 6H), 1.54-1.65 (m, 4H), 1.67 (dd, J=7.3, 3.7 Hz, 1H), 1.71 (dd, J=7.6, 3.4 Hz, 1H), 1.76 (dd, J=11.9, 9.7 Hz, 1H), 2.13 (dd, J=13.5, 6.1 Hz, 1H), 4.50 (s, 2H), 4.96 (dd, J=11.1, 6.1 Hz, 1H), 6.83-6.89 (m, 3H), 7.08 (dd, J=11.5, 8.0 Hz, 2H), 7.21 (t, J=1.4 Hz, 1H). MS (ESI$^-$) m/z 412 (M–H)$^-$.

Example 102

1-[(4R)-2,2-diethyl-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 0.89 (dt, J=14.8, 7.4 Hz, 6H), 1.55 (dd, J=14.2, 7.4 Hz, 2H), 1.61-1.64 (m, 1H), 1.65 (s, 1H), 1.67-1.72 (m, 1H), 2.10 (dd, J=13.4, 6.1 Hz, 1H), 4.50 (s, 2H), 4.93 (dd, J=11.1, 6.1 Hz, 1H), 6.75 (dd, J=8.2, 1.1 Hz, 1H), 6.86 (d, J=1.4 Hz, 2H), 6.88 (td, J=7.5, 1.2 Hz, 1H), 7.12-7.17 (m, 1H), 7.22 (t, J=1.4 Hz, 1H), 7.24 (d, J=7.6 Hz, 1H). MS (ESI$^-$) m/z 394 (M–H)$^-$.

Example 103

1-[(4R)-2,2-diethyl-7-(trifluoromethyl)-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 0.85-0.96 (m, 6H), 1.57 (dd, J=14.3, 7.4 Hz, 1H), 1.62-1.67 (m, 1H), 1.69 (dd, J=7.4, 3.1 Hz, 1H), 1.77 (dd, J=13.3, 11.6 Hz, 1H), 2.14 (dd, J=13.5, 6.1 Hz, 1H), 4.50 (s, 2H), 4.99 (dd, J=11.4, 6.0 Hz, 1H), 6.86 (d, J=1.4 Hz, 2H), 7.06 (d, J=1.5 Hz, 1H), 7.21-7.24 (m, 2H), 7.46 (d, J=8.1 Hz, 1H). MS (ESI$^-$) m/z 462 (M–H)$^-$.

Example 104

1-[(4R)-7-chloro-2,2-diethyl-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 0.84-0.93 (m, 6H), 1.54 (dd, J=14.3, 7.4 Hz, 1H), 1.59-1.64 (m, 1H), 1.65 (d, J=4.6 Hz, 1H), 1.67-1.75 (m, 2H), 2.10 (dd, J=13.5, 6.1 Hz, 1H), 4.50 (s, 2H), 4.90 (dd, J=11.2, 6.0 Hz, 1H), 6.82 (d, J=2.1 Hz, 1H), 6.86 (d, J=1.4 Hz, 2H), 6.94 (dd, J=8.3, 2.2 Hz, 1H), 7.21 (t, J=1.4 Hz, 1H), 7.25 (dd, J=8.4, 0.7 Hz, 1H). MS (ESI$^+$) m/z 430.0 (M+H)$^+$.

Example 105

1-[(4R)-7,8-dichloro-2,2-diethyl-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 0.88 (t, J=7.4 Hz, 3H), 0.94 (t, J=7.4 Hz, 3H), 1.51-1.68 (m, 2H), 1.72 (dd, J=13.8, 6.3 Hz, 2H), 1.78 (dd, J=12.5, 10.5 Hz, 1H), 2.14 (dd, J=13.6, 6.2 Hz, 1H), 4.50 (s, 2H), 4.96 (dd, J=11.4, 6.0

1H), 6.86 (d, J=1.4 Hz, 2H), 7.13-7.16 (m, 1H), 7.21 (t, J=1.4 Hz, 1H), 7.23 (dd, J=8.4, 0.8 Hz, 1H). MS (ESI⁻) m/z 462 (M–H)⁻.

Example 106

1-[(4R)-2,2-dimethyl-7-(trifluoromethyl)-3,4-dihydro-2H-chromen-4-yl]-3-(3-oxo-3,4-dihydro-2H-1,4-benzoxazin-6-yl)urea ¹H NMR (400 MHz, DMSO-$d_6$/$D_2O$) δ 1.31 (s, 3H), 1.43 (s, 3H), 1.81 (dd, J=12.9, 11.8 Hz, 1H), 2.15 (dd, J=13.3, 6.2 Hz, 1H), 4.50 (s, 2H), 5.02 (dd, J=11.3, 6.2 Hz, 1H), 6.87 (d, J=2.1 Hz, 2H), 7.04 (d, J=1.4 Hz, 1H), 7.20 (dd, J=1.9, 0.6 Hz, 1H), 7.23 (dd, J=8.2, 1.4 Hz, 1H), 7.47 (d, J=8.1 Hz, 1H). MS (ESI⁺) m/z 436 (M+H)⁺.

Example 107

1-[(4R)-6-fluoro-2,2-dipropyl-3,4-dihydro-2H-chromen-4-yl]-3-(3-oxo-3,4-dihydro-2H-1,4-benzoxazin-6-yl)urea ¹H NMR (400 MHz, DMSO-$d_6$/$D_2O$) δ 0.87 (t, J=7.2 Hz, 3H), 0.92 (t, J=7.3 Hz, 3H), 1.28 (dd, J=14.9, 7.7 Hz, 1H), 1.32-1.42 (m, 3H), 1.48-1.54 (m, 2H), 1.57-1.63 (m, 2H), 1.70 (dd, J=13.3, 11.6 Hz, 1H), 2.09 (dd, J=13.4, 6.1 Hz, 1H), 4.50 (s, 2H), 4.90 (dd, J=11.3, 6.0 Hz, 1H), 6.76 (dd, J=9.5, 4.9 Hz, 1H), 6.84-6.87 (m, 2H), 6.95-7.01 (m, 2H), 7.21-7.23 (m, 1H). MS (ESI⁻) m/z 440 (M–H)⁻.

Example 108

1-[(4R)-6-fluoro-3,4-dihydrospiro[chromene-2,1'-cyclobutan]-4-yl]-3-(3-oxo-3,4-dihydro-2H-1,4-benzoxazin-6-yl)urea ¹H NMR (400 MHz, DMSO-$d_6$/$D_2O$) δ 1.72 (dt, J=11.0, 8.8 Hz, 1H), 1.84 (ddd, J=17.1, 9.7, 5.0 Hz, 2H), 2.04-2.21 (m, 4H), 2.27 (t, J=10.6 Hz, 1H), 2.35 (dd, J=13.2, 5.9 Hz, 1H), 4.50 (s, 2H), 4.93 (dd, J=10.5, 5.8 Hz, 1H), 6.81 (dd, J=8.8, 4.8 Hz, 1H), 6.87 (d, J=1.3 Hz, 2H), 6.95-7.03 (m, 2H), 7.21 (t, J=1.4 Hz, 1H). MS (ESI⁻) m/z 396 (M–H)⁻.

Example 109

1-[(4R)-2,2-diethyl-6-fluoro-3,4-dihydro-2H-chromen-4-yl]-3-(3-oxo-3,4-dihydro-2H-1,4-benzoxazin-6-yl)urea ¹H NMR (400 MHz, DMSO-$d_6$/$D_2O$) δ 0.86 (t, J=7.7 Hz, 3H), 0.90 (t, J=7.6 Hz, 3H), 1.50-1.73 (m, 6H), 2.10 (dd, J=13.4, 6.2 Hz, 1H), 4.50 (s, 2H), 4.91 (dd, J=11.2, 6.2 Hz, 1H), 6.75-6.81 (m, 1H), 6.86 (d, J=1.3 Hz, 2H), 6.96-7.01 (m, 2H), 7.22 (t, J=1.4 Hz, 1H). MS (ESI⁻) m/z 412 (M–H)⁻.

Example 110

1-[(4R)-8-fluoro-2,2-dipropyl-3,4-dihydro-2H-chromen-4-yl]-3-(3-oxo-3,4-dihydro-2H-1,4-benzoxazin-6-yl)urea ¹H NMR (400 MHz, DMSO-$d_6$/$D_2O$) δ 0.88 (t, J=7.2 Hz, 3H), 0.93 (t, J=7.3 Hz, 3H), 1.24-1.33 (m, 1H), 1.34-1.44 (m, 3H), 1.52-1.59 (m, 2H), 1.65 (td, J=6.6, 2.3 Hz, 1H), 1.77 (dd, J=13.3, 11.3 Hz, 1H), 2.13 (dd, J=13.5, 6.1 Hz, 1H), 4.50 (s, 2H), 4.95 (dd, J=11.2, 6.0 Hz, 1H), 6.84-6.89 (m, 3H), 7.07 (dd, J=11.6, 8.1 Hz, 2H), 7.20-7.23 (m, 1H). MS (ESI⁺) m/z 442 (M+H)⁺.

Example 111

1-[(4R)-2,2-diethyl-7-(trifluoromethoxy)-3,4-dihydro-2H-chromen-4-yl]-3-(3-oxo-3,4-dihydro-2H-1,4-benzoxazin-6-yl)urea ¹H NMR (400 MHz, DMSO-$d_6$/$D_2O$) δ 0.87 (d, J=7.5 Hz, 3H), 0.91 (t, J=7.2 Hz, 3H), 1.51-1.78 (m, 5H), 2.12 (dd, J=13.5, 6.1 Hz, 1H), 4.50 (s, 2H), 4.94 (dd, J=11.1, 6.1 Hz, 1H), 6.72 (d, J=1.4 Hz, 1H), 6.86 (d, J=1.4 Hz, 2H), 6.86-6.90 (m, 1H), 7.21 (t, J=1.4 Hz, 1H), 7.35 (dd, J=8.6, 0.7 Hz, 1H). MS ESI⁻ m/z 478 (M–H)⁻.

Example 112

1-[(4R)-2,2-dimethyl-3,4-dihydro-2H-chromen-4-yl]-3-(3-oxo-3,4-dihydro-2H-1,4-benzoxazin-6-yl)urea ¹H NMR (400 MHz, DMSO-$d_6$/$D_2O$) δ 1.27 (s, 3H), 1.39 (s, 3H), 1.73 (dd, J=13.0, 11.2 Hz, 1H), 2.11 (dd, J=13.2, 6.2 Hz, 1H), 4.50 (s, 2H), 4.96 (dd, J=11.0, 6.2 Hz, 1H), 6.73 (dt, J=10.9, 5.4 Hz, 1H), 6.86 (d, J=1.6 Hz, 2H), 6.89 (td, J=7.5, 1.2 Hz, 1H), 7.12-7.17 (m, 1H), 7.18-7.21 (m, 1H), 7.24 (d, J=7.6 Hz, 1H). MS ESI⁻ m/z 366 (M–H)⁻.

Example 113

1-[(4R)-6-fluoro-2,2-dimethyl-3,4-dihydro-2H-chromen-4-yl]-3-(3-oxo-3,4-dihydro-2H-1,4-benzoxazin-6-yl)urea ¹H NMR (400 MHz, DMSO-$d_6$/$D_2O$) δ 1.26 (s, 3H), 1.39 (s, 3H), 1.73 (dd, J=13.0, 11.5 Hz, 1H), 2.11 (dd, J=13.2, 6.3 Hz, 1H), 4.50 (s, 2H), 4.93 (dd, J=11.1, 6.2 Hz, 1H), 6.77 (ddd, J=9.4, 4.0, 2.4 Hz, 1H), 6.87 (d, J=1.2 Hz, 2H), 6.99 (ddd, J=7.6, 3.1, 1.8 Hz, 2H), 7.19-7.21 (m, 1H). MS ESI⁻ m/z 384 (M–H)⁻.

Example 114

1-[(4R)-7-chloro-2,2-dimethyl-3,4-dihydro-2H-chromen-4-yl]-3-(3-oxo-3,4-dihydro-2H-1,4-benzoxazin-6-yl)urea ¹H NMR (400 MHz, DMSO-$d_6$/$D_2O$) δ 1.28 (s, 3H), 1.40 (s, 3H), 1.74 (dd, J=13.1, 11.4 Hz, 1H), 2.11 (dd, J=13.3, 6.2 Hz, 1H), 4.50 (s, 2H), 4.93 (dd, J=11.0, 6.2 Hz, 1H), 6.80 (d, J=2.1 Hz, 1H), 6.86 (d, J=1.8 Hz, 2H), 6.95 (dd, J=8.3, 2.2 Hz, 1H), 7.19 (dd, J=1.7, 1.0 Hz, 1H), 7.25 (dd, J=8.4, 0.9 Hz, 1H). MS ESI⁻ m/z 400 (M–H)⁻.

Example 115

1-(3-oxo-3,4-dihydro-2H-1,4-benzoxazin-6-yl)-3-[(4R)-7-(trifluoromethoxy)-3,4-dihydro-2H-chromen-4-yl]urea ¹H NMR (400 MHz, DMSO-$d_6$/$D_2O$) δ 1.97 (dtd, J=9.6, 6.8, 3.0 Hz, 1H), 2.06-2.16 (m, 1H), 4.20 (ddd, J=11.2, 8.2, 3.0 Hz, 1H), 4.31 (ddd, J=10.4, 7.0, 3.1 Hz, 1H), 4.49 (s, 2H), 4.89 (t, J=5.7 Hz, 1H), 6.78 (d, J=1.4 Hz, 1H), 6.84 (d, J=1.8

Hz, 2H), 6.91 (ddd, J=8.5, 2.3, 1.0 Hz, 1H), 7.18 (dd, J=1.8, 0.9 Hz, 1H), 7.37 (d, J=8.9 Hz, 1H). MS ESI⁻ m/z 422 (M−H)⁻.

Example 116

1-[(4R)-8-fluoro-2,2-bis(fluoromethyl)-3,4-dihydro-2H-chromen-4-yl]-3-(3-oxo-3,4-dihydro-2H-1,4-benzoxazin-6-yl)urea ¹H NMR (400 MHz, DMSO-$d_6$/D$_2$O) δ 2.02 (ddd, J=13.7, 10.9, 2.7 Hz, 1H), 2.30 (dd, J=13.8, 6.0 Hz, 1H), 4.50 (s, 2H), 4.55-4.65 (m, 2H), 4.68-4.76 (m, 2H), 5.03 (dd, J=10.8, 5.9 Hz, 1H), 6.86 (d, J=1.3 Hz, 2H), 6.96 (td, J=8.0, 5.0 Hz, 1H), 7.09 (dd, J=7.9, 1.1 Hz, 1H), 7.13-7.18 (m, 1H), 7.19-7.20 (m, 1H). MS ESI⁻ m/z 420 (M−H)⁻.

Example 117

1-[(4R)-7,8-difluoro-2,2-dimethyl-3,4-dihydro-2H-chromen-4-yl]-3-(3-oxo-3,4-dihydro-2H-1,4-benzoxazin-6-yl)urea ¹H NMR (400 MHz, DMSO-$d_6$/D$_2$O) δ 1.32 (s, 3H), 1.45 (s, 3H), 1.80 (dd, J=13.2, 11.4 Hz, 1H), 2.15 (dd, J=13.4, 6.2 Hz, 1H), 4.50 (s, 2H), 4.95 (dd, J=11.2, 6.1 Hz, 1H), 6.85-6.87 (m, 2H), 6.88-6.96 (m, 1H), 7.07 (t, J=6.9 Hz, 1H), 7.19 (dd, J=1.6, 1.2 Hz, 1H). MS ESI⁻ m/z 402 (M−H)⁻.

Example 118

1-[(4R)-6-fluoro-3,4-dihydro-2H-chromen-4-yl]-3-(3-oxo-3,4-dihydro-2H-1,4-benzoxazin-6-yl)urea ¹H NMR (400 MHz, DMSO-$d_6$/D$_2$O) δ 1.94 (dtd, J=10.1, 7.2, 3.1 Hz, 1H), 2.06-2.15 (m, 1H), 4.15 (ddd, J=11.1, 7.7, 3.1 Hz, 1H), 4.24 (ddd, J=10.7, 7.4, 3.1 Hz, 1H), 4.49 (s, 2H), 4.87 (t, J=6.0 Hz, 1H), 6.79-6.84 (m, 1H), 6.85 (d, J=2.0 Hz, 2H), 6.98-7.07 (m, 2H), 7.18 (dd, J=1.9, 0.8 Hz, 1H). MS ESI⁻ m/z 356 (M−H)⁻.

Example 119

1-[(1R)-5-chloro-2,3-dihydro-1H-inden-1-yl]-3-(3-oxo-3,4-dihydro-2H-1,4-benzoxazin-6-yl)urea ¹H NMR (400 MHz, DMSO-$d_6$/D$_2$O) δ 1.79 (dq, J=12.6, 8.7 Hz, 1H), 2.42-2.51 (m, 1H), 2.77-2.86 (m, 1H), 2.94 (ddd, J=16.3, 8.9, 3.6 Hz, 1H), 4.49 (s, 2H), 5.13 (t, J=7.8 Hz, 1H), 6.84 (d, J=1.8 Hz, 2H), 7.18 (dd, J=1.8, 0.9 Hz, 1H), 7.25-7.28 (m, 2H), 7.32 (s, 1H). MS ESI⁻ m/z 356 (M−H)⁻.

Example 120

1-(3-oxo-3,4-dihydro-2H-1,4-benzoxazin-6-yl)-3-[(4R)-8-(trifluoromethyl)-3,4-dihydro-2H-chromen-4-yl]urea ¹H NMR (400 MHz, DMSO-$d_6$/D$_2$O) δ 2.02 (dtd, J=9.8, 6.8, 3.1 Hz, 1H), 2.15 (ddd, J=13.5, 8.3, 3.3 Hz, 1H), 4.28 (ddd, J=11.0, 8.0, 2.9 Hz, 1H), 4.40 (ddd, J=10.5, 6.9, 3.2 Hz, 1H), 4.49 (s, 2H), 4.95 (t, J=5.8 Hz, 1H), 6.85 (d, J=1.9 Hz, 2H), 7.07 (t, J=7.7 Hz, 1H), 7.17-7.20 (m, 1H), 7.54 (t, J=6.6 Hz, 2H). MS ESI⁻ m/z 406 (M−H)⁻.

Example 121

1-(3-oxo-3,4-dihydro-2H-1,4-benzoxazin-6-yl)-3-[(4R)-7-(trifluoromethyl)-3,4-dihydro-2H-chromen-4-yl]urea ¹H NMR (400 MHz, DMSO-$d_6$/D$_2$O) δ 2.00 (dtd, J=10.3, 7.2, 3.1 Hz, 1H), 2.14 (ddt, J=10.6, 5.2, 3.2 Hz, 1H), 4.21-4.29 (m, 1H), 4.33 (td, J=7.8, 3.8 Hz, 1H), 4.49 (s, 2H), 4.96 (t, J=6.0 Hz, 1H), 6.85 (d, J=1.2 Hz, 2H), 7.11 (d, J=1.4 Hz, 1H), 7.16-7.20 (m, 1H), 7.24 (dd, J=8.1, 1.4 Hz, 1H), 7.48 (d, J=8.0 Hz, 1H). MS ESI⁻ m/z 406 (M−H)⁻.

Example 122

1-[(4S)-6-fluoro-3,4-dihydrospiro[chromene-2,1'-cyclobutan]-4-yl]-3-(3-oxo-3,4-dihydro-2H-1,4-benzoxazin-6-yl)urea ¹H NMR (400 MHz, DMSO-$d_6$/D$_2$O) δ 1.66-1.77 (m, 1H), 1.84 (ddd, J=16.8, 9.5, 4.9 Hz, 2H), 2.04-2.21 (m, 3H), 2.27 (t, J=10.6 Hz, 1H), 2.35 (dd, J=13.2, 5.9 Hz, 1H), 4.50 (s, 2H), 4.93 (dd, J=10.5, 5.9 Hz, 1H), 6.81 (dd, J=8.8, 4.8 Hz, 1H), 6.87 (d, J=1.4 Hz, 2H), 6.95-7.03 (m, 2H), 7.21 (t, J=1.4 Hz, 1H). MS ESI⁻ m/z 396 (M−H)⁻.

Example 123

1-[(4S)-6-fluoro-2,2-dimethyl-3,4-dihydro-2H-chromen-4-yl]-3-(3-oxo-3,4-dihydro-2H-1,4-benzoxazin-6-yl)urea ¹H NMR (400 MHz, DMSO-$d_6$/D$_2$O) δ 1.26 (s, 3H), 1.39 (s, 3H), 1.73 (dd, J=13.0, 11.5 Hz, 1H), 2.11 (dd, J=13.2, 6.3 Hz, 1H), 4.50 (s, 2H), 4.93 (dd, J=11.1, 6.2 Hz, 1H), 6.77 (ddd, J=9.4, 4.0, 2.4 Hz, 1H), 6.87 (d, J=1.3 Hz, 2H), 6.96-7.03 (m, 2H), 7.16-7.24 (m, 1H). MS ESI⁻ m/z 384 (M−H)⁻.

Example 124

1-[(4R)-3,4-dihydrospiro[chromene-2,1'-cyclopentan]-4-yl]-3-(3-oxo-3,4-dihydro-2H-1,4-benzoxazin-6-yl)urea ¹H NMR (400 MHz, DMSO-$d_6$/D$_2$O) δ 1.59-1.90 (m, 8H), 1.95 (dd, J=13.2, 10.2 Hz, 1H), 2.12 (dd, J=13.2, 6.1 Hz, 1H), 4.50 (s, 2H), 4.96 (dd, J=10.0, 6.1 Hz, 1H), 6.73 (dd, J=8.2, 1.1 Hz, 1H), 6.86 (d, J=1.4 Hz, 2H), 6.89 (td, J=7.5, 1.2 Hz, 1H), 7.14 (ddd, J=8.3, 7.5, 1.2 Hz, 1H), 7.20 (t, J=1.4 Hz, 1H), 7.24 (d, J=7.6 Hz, 1H). MS ESI⁺ m/z 394 (M+H)⁺.

Example 125

1-[(2S,4R)-2-methyl-2-(trifluoromethyl)-3,4-dihydro-2H-chromen-4-yl]-3-(3-oxo-3,4-dihydro-2H-1,4-benzoxazin-6-yl)urea ¹H NMR (400 MHz, DMSO-$d_6$/D$_2$O) δ 1.56 (s, 3H), 2.09 (dd, J=13.8, 10.4 Hz, 1H), 2.50 (d, J=6.0 Hz, 1H), 4.50 (s, 2H), 4.99 (dd, J=9.7, 6.0 Hz, 1H), 6.86 (d, J=1.4 Hz, 2H), 6.91 (dd, J=8.2, 1.0 Hz, 1H), 7.02 (td, J=7.5, 1.1 Hz, 1H), 7.21 (t, J=1.4 Hz, 1H), 7.23 (dd, J=8.3, 1.3 Hz, 1H), 7.28 (dd, J=12.2, 4.5 Hz, 1H). MS ESI⁻ m/z 420 (M−H)⁻.

Example 126

1-[(2R,4R)-2-methyl-2-(trifluoromethyl)-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 1.53 (s, 3H), 2.04 (t, J=12.3 Hz, 1H), 2.30 (dd, J=12.7, 5.9 Hz, 1H), 4.50 (s, 2H), 5.07 (dd, J=11.8, 5.8 Hz, 1H), 6.86-6.88 (m, 2H), 6.90 (d, J=1.1 Hz, 1H), 7.03 (td, J=7.5, 1.1 Hz, 1H), 7.21 (dd, J=2.1, 0.5 Hz, 1H), 7.24 (ddd, J=8.3, 7.6, 1.1 Hz, 1H), 7.30 (d, J=7.7 Hz, 1H). MS ESI$^-$ m/z 420 (M−H)$^-$.

Example 127

1-[(2S,4R)-2-(fluoromethyl)-2-methyl-7-(trifluoromethyl)-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 1.40 (d, J=2.0 Hz, 3H), 1.88-1.97 (m, 1H), 2.35 (dd, J=13.8, 6.2 Hz, 1H), 4.45 (dd, J=12.8, 7.2 Hz, 1H), 4.50 (s, 2H), 4.58 (dd, J=19.9, 10.0 Hz, 1H), 5.02 (dd, J=10.3, 6.2 Hz, 1H), 6.87 (d, J=1.9 Hz, 2H), 7.12 (d, J=1.4 Hz, 1H), 7.20 (dd, J=1.8, 1.1 Hz, 1H), 7.27 (dd, J=8.0, 1.3 Hz, 1H), 7.47 (d, J=8.1 Hz, 1H). MS ESI$^-$ m/z 452 (M−H)$^-$.

Example 128

1-[(2R,4R)-2-(fluoromethyl)-2-methyl-7-(trifluoromethyl)-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 1.30 (d, J=2.0 Hz, 3H), 1.96 (t, J=12.4 Hz, 1H), 2.11 (dd, J=13.1, 6.1 Hz, 1H), 4.44 (q, J=10.0 Hz, 1H), 4.50 (s, 2H), 4.56 (q, J=10.0 Hz, 1H), 5.10 (dd, J=11.6, 6.1 Hz, 1H), 6.86-6.89 (m, 2H), 7.11 (d, J=1.4 Hz, 1H), 7.21 (dd, J=2.1, 0.5 Hz, 1H), 7.28 (dd, J=8.1, 1.3 Hz, 1H), 7.48 (d, J=8.1 Hz, 1H). MS ESI$^-$ m/z 452 (M−H)$^-$.

Example 129

1-[(2S,4R)-7-chloro-2-(fluoromethyl)-2-methyl-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 1.38 (d, J=1.9 Hz, 3H), 1.83-1.91 (m, 1H), 2.30 (dd, J=13.8, 6.2 Hz, 1H), 4.42 (q, J=9.9 Hz, 1H), 4.50 (s, 2H), 4.54 (dd, J=17.3, 10.0 Hz, 1H), 4.93 (dd, J=10.0, 6.2 Hz, 1H), 6.86 (d, J=1.3 Hz, 2H), 6.88 (d, J=2.1 Hz, 1H), 6.98 (dd, J=8.3, 2.1 Hz, 1H), 7.19 (dd, J=3.8, 2.3 Hz, 1H), 7.26 (dd, J=8.3, 0.8 Hz, 1H). MS ESI$^-$ m/z 418 (M−H)$^-$.

Example 130

1-[(2S,4R)-2-(difluoromethyl)-2-methyl-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 1.40 (s, 3H), 1.92 (dd, J=14.0, 9.8 Hz, 1H), 2.38 (d, J=14.1, 6.1 Hz, 1H), 4.50 (s, 2H), 5.00 (dd, J=9.7, 6.0 Hz, 1H), 6.84-6.87 (m, 3H), 6.97 (td, J=7.5, 1.2 Hz, 1H), 7.17-7.23 (m, 2H), 7.26 (d, J=7.6 Hz, 1H). MS ESI$^-$ m/z 402 (M−H)$^-$.

Example 131

1-[(2R,4R)-2-(difluoromethyl)-2-methyl-3,4-dihydro-2H-chromen-4-yl]-3-(3-oxo-3,4-dihydro-2H-1,4-benzoxazin-6-yl)urea $^1$H NMR (400 MHz, DMSO-d$_6$/D$_2$O) δ 1.36 (s, 3H), 1.87-1.95 (m, 1H), 2.13 (dd, J=12.9, 5.9 Hz, 1H), 4.50 (s, 2H), 5.03 (dd, J=11.5, 5.9 Hz, 1H), 6.84 (dd, J=8.2, 1.0 Hz, 1H), 6.87 (d, J=1.8 Hz, 2H), 6.98 (td, J=7.5, 1.1 Hz, 1H), 7.16-7.24 (m, 2H), 7.28 (d, J=7.7 Hz, 1H). MS ESI$^-$ m/z 402 (M−H)$^-$.

Example 132

1-(3-oxo-3,4-dihydro-2H-1,4-benzoxazin-6-yl)-3-{[7-(trifluoromethyl)-3,4-dihydro-2H-chromen-2-yl]methyl}urea $^1$H NMR (400 MHz, DMSO-d$_6$/D$_2$O) δ 1.63-1.75 (m, 1H), 1.98-2.07 (m, 1H), 2.85 (t, J=14.6 Hz, 2H), 3.40 (ddd, J=20.3, 14.0, 5.4 Hz, 2H), 4.12-4.19 (m, 1H), 4.48 (s, 2H), 6.82-6.85 (m, 2H), 7.05 (d, J=1.4 Hz, 1H), 7.14-7.15 (m, 1H), 7.15-7.19 (m, 1H), 7.32 (d, J=7.9 Hz, 1H). MS ESI$^-$ m/z 420 (M−H)$^-$.

Example 133

1-[(6-fluoro-3,4-dihydro-2H-chromen-3-yl)methyl]-3-(3-oxo-3,4-dihydro-2H-1,4-benzoxazin-6-yl)urea $^1$H NMR (400 MHz, DMSO-d$_6$/D$_2$O) δ 2.13 (d, J=8.2 Hz, 1H), 2.82 (dd, J=16.9, 5.5 Hz, 1H), 3.05-3.18 (m, 2H), 3.81 (dd, J=10.8, 8.2 Hz, 1H), 4.15-4.19 (m, 1H), 4.48 (s, 2H), 6.76 (dd, J=8.8, 5.0 Hz, 1H), 6.82 (d, J=2.3 Hz, 2H), 6.91 (ddd, J=17.2, 8.8, 2.7 Hz, 2H), 7.14 (d, J=1.4 Hz, 1H). MS ESI$^-$ m/z 370 (M−H)$^-$.

Example 134

1-[(4R)-7-chloro-2,2-bis(fluoromethyl)-3,4-dihydro-2H-chromen-4-yl]-3-[(2R)-2-methyl-3-oxo-3,4-dihydro-2H-1,4-benzoxazin-8-yl]urea $^1$H NMR (300 MHz, DMSO) δ 10.61 (s, 1H), 8.01 (s, 1H), 7.80 (dd, J=8.3, 1.4 Hz, 1H), 7.31 (dd, J=12.7, 4.4 Hz, 2H), 7.19 (d, J=8.3 Hz, 1H), 7.12-6.91 (m, 1H), 6.85 (t, J=8.1 Hz, 1H), 6.50 (dd, J=7.9, 1.3 Hz, 1H), 4.97 (dd, J=15.7, 8.5 Hz, 1H), 4.82-4.63 (m, 2H), 4.63-4.46 (m, 1H), 4.08 (q, J=5.2 Hz, 1H), 3.63 (d, J=11.9 Hz, 1H), 3.17 (d, J=5.2 Hz, 1H), 2.32 (dd, J=13.8, 5.9 Hz, 1H), 2.05-1.80 (m, 1H), 1.67 (d, J=6.9 Hz, 1H), 1.44 (t, J=7.0 Hz, 1H), 1.23 (s, 1H). MS (EsI$^+$) M/Z 452 (M+H)$^+$.

Example 135

1-[(4R)-8-fluoro-2,2-dimethyl-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ ppm 1.30 (s, 3H), 1.44 (s, 3H), 1.74-1.83 (m, 1H), 2.16 (dd, J=13.3, 6.1 Hz, 1H), 3.15 (s, 3H), 4.19 (s, 2H), 4.97 (dd, J=11.0, 6.1 Hz, 1H), 6.70

(d, J=8.1 Hz, 1H), 6.89 (td, J=7.9, 4.9 Hz, 1H), 7.06-7.13 (m, 2H), 7.15-7.25 (m, 1H), 7.33 (d, J=8.1 Hz, 1H). MS (ESI$^+$) m/z 399 (M+H)$^+$.

Example 136

1-[(4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 1.38 (dd, J=21.8, 12.6 Hz, 3H), 1.92 (dd, J=24.2, 11.7 Hz, 1H), 2.39 (dd, J=14.1, 6.1 Hz, 1H), 3.16 (t, J=5.9 Hz, 3H), 4.19 (d, J=3.0 Hz, 2H), 4.92-5.05 (m, 1H), 5.98-6.34 (m, 1H), 6.67-6.79 (m, 1H), 6.86-6.97 (m, 1H), 7.05 (ddd, J=17.8, 9.5, 5.8 Hz, 1H), 7.20 (ddd, J=16.2, 11.0, 2.5 Hz, 1H), 7.25-7.36 (m, 2H) MS (ESI$^+$) m/z 451 (M+H)$^+$.

Example 137

1-[(4R)-2,2-dimethyl-7-(trifluoromethoxy)-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 1.18-1.32 (m, 4H), 1.35-1.45 (m, 4H), 1.77 (dd, J=24.4, 11.4 Hz, 1H), 2.15 (dt, J=13.2, 6.4 Hz, 1H), 3.15 (s, 3H), 4.17 (d, J=15.2 Hz, 2H), 4.90-5.10 (m, 1H), 6.70 (d, J=9.0 Hz, 2H), 6.89 (dd, J=11.1, 6.3 Hz, 1H), 7.15-7.26 (m, 1H), 7.30 (dd, J=15.2, 12.0 Hz, 1H), 7.36 (t, J=12.0 Hz, 1H). MS (ESI$^+$) m/z 465 (M+H)$^+$.

Example 138

1-(1-methyl-2-oxo-1,2,3,4-tetrahydroquinazolin-5-yl)-3-[(4R)-8-(trifluoromethoxy)-3,4-dihydro-2H-chromen-4-yl]urea $^1$H NMR (500 MHz, DMSO-d$_6$/D$_2$O) δ 1.20 (dd, J=18.3, 11.2 Hz, 1H), 1.96 (dd, J=10.2, 3.7 Hz, 1H), 2.02-2.25 (m, 1H), 3.16 (d, J=15.3 Hz, 3H), 3.60 (s, 1H), 4.12-4.19 (m, 3H), 4.85 (t, J=5.4 Hz, 1H), 6.67 (d, J=8.1 Hz, 1H), 6.78 (dd, J=24.0, 8.3 Hz, 1H), 6.92 (dd, J=11.7, 4.3 Hz, 1H), 7.13-7.30 (m, 3H), 7.39 (d, J=7.9 Hz, 1H). MS (ESI$^+$) m/z 436 (M+H)$^+$.

Example 139

1-[(4R)-2,2-diethyl-8-fluoro-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 0.83-0.95 (m, 6H), 1.51-1.80 (m, 5H), 2.15 (dd, J=13.5, 6.1 Hz, 1H), 3.15 (s, 3H), 4.19 (bs, 2H), 4.95 (dd, J=11.0, 6.1 Hz, 1H), 6.70 (d, J=8.1 Hz, 1H), 6.88 (td, J=8.0, 4.9 Hz, 1H), 7.05-7.13 (m, 2H), 7.21 (t, J=8.1 Hz, 1H), 7.33 (d, J=8.1 Hz, 1H). MS (ESI$^+$) m/z 427 (M+H)$^+$.

Example 140

1-[(4R)-2,2-diethyl-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 0.83-0.95 (m, 6H), 1.51-1.80 (m, 4H), 2.15 (dd, J=13.5, 6.1 Hz, 1H), 3.15 (s, 3H), 4.19 (bs, 2H), 4.95 (dd, J=11.0, 6.1 Hz, 1H), 6.70 (d, J=8.1 Hz, 1H), 6.88 (td, J=8.0, 4.9 Hz, 1H), 7.05-7.13 (m, 2H), 7.21 (t, J=8.1 Hz, 1H), 7.33 (d, J=8.1 Hz, 1H). MS (ESI$^+$) m/z 409 (M+H)$^+$.

Example 141

1-[(1R)-5-tert-butyl-2,3-dihydro-1H-inden-1-yl]-3-(1-methyl-2-oxo-1,2,3,4-tetrahydroquinazolin-5-yl)urea $^1$H NMR (500 MHz, DMSO-d$_6$/D$_2$O) δ 1.27 (s, 9H), 1.27 (s, 1H), 1.77 (dq, J=12.5, 7.8 Hz, 1H), 2.44 (dtd, J=12.3, 7.8, 4.4 Hz, 1H), 2.79 (dt, J=15.8, 7.9 Hz, 1H), 2.92 (ddd, J=15.8, 8.6, 4.1 Hz, 1H), 3.15 (s, 3H), 4.16 (s, 1H), 5.09 (t, J=7.2 Hz, 1H), 6.67 (d, J=8.1 Hz, 1H), 7.16-7.29 (m, 1H), 7.29 (s, 1H), 7.36 (d, J=8.1 Hz, 1H). MS (ESI$^+$) m/z 393 (M+H)$^+$.

Example 142

1-[(4R)-8-tert-butyl-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 1.20 (dd, J=20.3, 11.3 Hz, 1H), 1.28-1.39 (m, 9H), 1.96 (dtd, J=13.6, 5.5, 2.7 Hz, 1H), 2.02-2.15 (m, 1H), 2.82 (dt, J=23.2, 6.3 Hz, 1H), 3.14 (s, 3H), 4.07-4.21 (m, 3H), 4.27-4.38 (m, 1H), 4.83 (t, J=5.1 Hz, 1H), 6.65 (t, J=9.8 Hz, 1H), 6.80-6.93 (m, 1H), 7.07-7.25 (m, 3H), 7.41 (t, J=7.3 Hz, 1H). MS (ESI$^+$) m/z 409 (M+H)$^+$.

Example 143

1-[(4R)-2,2-diethyl-7-fluoro-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 0.80-0.96 (m, 6H), 1.47-1.74 (m, 4H), 2.11 (dd, J=13.5, 6.1 Hz, 1H), 3.15 (s, 3H), 4.19 (d, J=1.5 Hz, 2H), 4.88 (dd, J=10.9, 6.1 Hz, 1H), 6.60 (dd, J=10.5, 2.6 Hz, 1H), 6.69 (d, J=8.2 Hz, 1H), 6.75 (td, J=8.5, 2.6 Hz, 2H), 7.21 (t, J=8.1 Hz, 1H), 7.28 (t, J=7.6 Hz, 1H), 7.34 (d, J=8.1 Hz, 1H). MS (ESI$^+$) m/z 426 (M+H)$^+$.

Example 144

1-[(4R)-2,2-diethyl-7-(trifluoromethyl)-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 0.84-0.96 (m, 6H), 1.51-1.81 (m, 4H), 2.15 (dd, J=13.5, 6.1 Hz, 1H), 3.16 (s, 3H), 4.20 (d, J=1.7 Hz, 2H), 4.94-5.02 (m, 1H), 6.71 (d, J=8.1 Hz, 1H), 7.06 (d, J=1.8 Hz, 1H), 7.18-7.28 (m, 2H), 7.32 (d, J=8.1 Hz, 1H), 7.48 (d, J=8.1 Hz, 1H). MS (ESI$^+$) m/z 477 (M+H)$^+$.

Example 145

1-[(4R)-7-chloro-2,2-diethyl-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 0.81-0.94 (m, 6H), 1.48-1.76 (m, 4H), 2.11 (dd, J=13.5, 6.1 Hz, 1H), 3.15 (s, 3H), 4.19 (d, J=1.5 Hz, 2H), 4.89 (dd, J=11.1, 6.1 Hz, 1H), 6.70 (d, J=8.1 Hz, 1H), 6.83 (d, J=2.1 Hz, 1H), 6.96 (dd, J=8.3, 2.2 Hz, 1H), 7.21 (t, J=8.1 Hz, 1H), 7.27 (dd, J=8.3, 1.0 Hz, 1H), 7.32 (d, J=8.1 Hz, 1H). MS (ESI+) m/z 477 (M+H)+.

Example 146

1-[(4R)-2,2-bis(fluoromethyl)-7-(trifluoromethyl)-3,4-dihydro-2H-chromen-4-yl]-3-(1-methyl-2-oxo-1,2,3,4-tetrahydroquinazolin-5-yl)urea $^1$H NMR (500 MHz, DMSO-$d_6$/D$_2$O) δ 2.02 (ddd, J=13.8, 11.0, 2.8 Hz, 1H), 2.32 (dd, J=13.7, 6.0 Hz, 1H), 3.16 (s, 2H), 4.20 (s, 2H), 4.58-4.77 (m, 4H), 5.01-5.09 (m, 1H), 6.72 (d, J=8.1 Hz, 1H), 7.20 (d, J=2.0 Hz, 1H), 7.23 (d, J=8.1 Hz, 1H), 7.24-7.38 (m, 2H), 7.51 (d, J=8.1 Hz, 1H). MS (ESI+) m/z 485 (M+H)+.

Example 147

1-[(4R)-7,8-dichloro-2,2-diethyl-3,4-dihydro-2H-chromen-4-yl]-3-(1-methyl-2-oxo-1,2,3,4-tetrahydroquinazolin-5-yl)urea $^1$H NMR (500 MHz, DMSO-$d_6$/D$_2$O) δ 0.82-0.91 (t, 3H), 0.94 (t, J=7.5 Hz, 3H), 1.51-1.81 (m, 5H), 2.16 (dd, J=13.6, 6.2 Hz, 1H), 3.15 (s, 3H), 4.19 (d, J=1.6 Hz, 1H), 4.94 (dd, J=11.2, 6.2 Hz, 1H), 6.70 (d, J=8.1 Hz, 1H), 7.11-7.33 (m, 3H). MS (ESI+) m/z 477 (M+H)+.

Example 148

1-[(4R)-8-chloro-2,2-bis(fluoromethyl)-3,4-dihydro-2H-chromen-4-yl]-3-(1-methyl-2-oxo-1,2,3,4-tetrahydroquinazolin-5-yl)urea $^1$H NMR (500 MHz, DMSO-$d_6$/D$_2$O) δ 2.00 (ddd, J=13.7, 10.6, 3.0 Hz, 1H), 2.30 (dd, J=13.8, 6.0 Hz, 1H), 3.15 (s, 2H), 4.19 (s, 2H), 4.54-4.75 (m, 4H), 4.99 (dd, J=10.7, 5.9 Hz, 1H), 6.71 (d, J=8.1 Hz, 1H), 6.88 (d, J=2.3 Hz, 1H), 6.93-7.03 (m, 1H), 7.22 (t, J=8.1 Hz, 1H), 7.30 (d, J=8.1 Hz, 1H), 7.40 (d, J=8.1 Hz, 1H). MS (ESI+) m/z 451 (M+H)+.

Example 149

1-[(4R)-2,2-bis(fluoromethyl)-7-(trifluoromethoxy)-3,4-dihydro-2H-chromen-4-yl]-3-(1-methyl-2-oxo-1,2,3,4-tetrahydroquinazolin-5-yl)urea $^1$H NMR (500 MHz, DMSO-$d_6$/D$_2$O) δ 2.00 (ddd, J=13.7, 10.6, 3.0 Hz, 1H), 2.30 (dd, J=13.8, 6.0 Hz, 1H), 3.15 (s, 2H), 4.19 (s, 2H), 4.54-4.75 (m, 4H), 4.99 (dd, J=10.7, 5.9 Hz, 1H), 6.71 (d, J=8.1 Hz, 1H), 6.88 (d, J=2.3 Hz, 1H), 6.93-7.03 (m, 1H), 7.22 (t, J=8.1 Hz, 1H), 7.30 (d, J=8.1 Hz, 1H), 7.40 (d, J=8.1 Hz, 1H). MS (ESI+) m/z 501 (M+H)+.

Example 150

1-[(4R)-2,2-dimethyl-7-(trifluoromethyl)-3,4-dihydro-2H-chromen-4-yl]-3-(1-methyl-2-oxo-1,2,3,4-tetrahydroquinazolin-5-yl)urea $^1$H NMR (500 MHz, DMSO-$d_6$/D$_2$O) δ 1.28 (d, J=15.9 Hz, 3H), 1.42 (d, J=10.5 Hz, 3H), 1.72-1.89 (m, 1H), 2.09-2.22 (m, 1H), 3.18 (s, 2H), 4.10-4.26 (m, 2H), 5.00 (dd, J=11.2, 6.2 Hz, 1H), 6.71 (d, J=7.9 Hz, 1H), 7.04 (t, J=6.5 Hz, 1H), 7.17-7.37 (m, 3H), 7.49 (d, J=8.1 Hz, 1H). MS (ESI+) m/z 449 (M+H)+.

Example 151

1-[(4R)-6-fluoro-2,2-dipropyl-3,4-dihydro-2H-chromen-4-yl]-3-(1-methyl-2-oxo-1,2,3,4-tetrahydroquinazolin-5-yl)urea $^1$H NMR (500 MHz, DMSO-$d_6$/D$_2$O) δ 0.81-0.95 (m, 6H), 1.19-1.74 (m, 10H), 2.10 (dd, J=13.4, 6.1 Hz, 1H), 3.15 (s, 3H), 4.19 (d, J=1.8 Hz, 2H), 4.88 (dd, J=11.1, 6.1 Hz, 1H), 6.70 (d, J=8.1 Hz, 1H), 6.71-6.80 (m, 1H), 6.95-7.04 (m, 2H), 7.21 (t, J=8.1 Hz, 1H), 7.34 (d, J=8.1 Hz, 1H). MS (ESI+) m/z 455 (M+H)+.

Example 152

1-[(4R)-6-fluoro-2,2-bis(fluoromethyl)-3,4-dihydro-2H-chromen-4-yl]-3-(1-methyl-2-oxo-1,2,3,4-tetrahydroquinazolin-5-yl)urea $^1$H NMR (500 MHz, DMSO-$d_6$/D$_2$O) δ 2.02 (ddd, J=13.8, 11.0, 2.8 Hz, 1H), 2.32 (dd, J=13.8, 6.0 Hz, 1H), 3.15 (s, 3H), 4.19 (s, 2H), 4.56-4.77 (m, 4H), 5.00 (dd, J=11.0, 5.9 Hz, 1H), 6.71 (d, J=8.1 Hz, 1H), 6.92 (d, J=7.5 Hz, 1H), 7.18-7.32 (m, 3H). MS (ESI+) m/z 435 (M+H)+.

Example 153

1-[(4R)-6,8-difluoro-2,2-bis(fluoromethyl)-3,4-dihydro-2H-chromen-4-yl]-3-(1-methyl-2-oxo-1,2,3,4-tetrahydroquinazolin-5-yl)urea $^1$H NMR (500 MHz, DMSO-$d_6$/D$_2$O) δ 2.02 (ddd, J=13.8, 11.0, 2.8 Hz, 1H), 2.32 (dd, J=13.8, 6.0 Hz, 1H), 3.15 (s, 3H), 4.19 (s, 2H), 4.56-4.77 (m, 4H), 5.00 (dd, J=11.0, 5.9 Hz, 1H), 6.71 (d, J=8.1 Hz, 1H), 6.92 (d, J=7.5 Hz, 1H), 7.18-7.32 (m, 3H). MS (ESI+) m/z 453 (M+H)+.

Example 154

1-[(4R)-6-fluoro-3,4-dihydrospiro[chromene-2,1'-cyclobutan]-4-yl]-3-(1-methyl-2-oxo-1,2,3,4-tetrahydroquinazolin-5-yl)urea $^1$H NMR (500 MHz, DMSO-$d_6$/D$_2$O) δ 1.66-1.92 (m, 4H), 2.03-2.22 (m, 3H), 2.23-2.42 (m, 2H), 3.16 (s, 2H), 4.20 (s, 2H), 4.92 (dd, J=10.4, 5.8 Hz, 1H), 6.70 (d, J=8.1 Hz, 1H), 6.82 (dd, J=8.7, 4.8 Hz, 1H), 6.96-7.05 (m, 2H), 7.22 (t, J=8.1 Hz, 1H), 7.35 (d, J=8.1 Hz, 1H) MS (ESI+) m/z 411 (M+H)+.

Example 155

1-[(4R)-2,2-diethyl-6-fluoro-3,4-dihydro-2H-chromen-4-yl]-3-(1-methyl-2-oxo-1,2,3,4-tetrahydroquinazolin-5-yl)urea $^1$H NMR (500 MHz, DMSO-$d_6$/D$_2$O) δ 0.80-0.94 (m, 6H), 1.49-1.74 (m, 5H), 2.11 (dd, J=13.4, 6.2 Hz, 1H), 3.15 (s, 3H), 4.20 (bs, 2H), 4.90 (dd, J=11.1, 6.2 Hz, 1H), 6.70 (d, J=8.1 Hz, 1H), 6.72-6.82 (m, 1H), 6.93-7.07 (m, 2H), 7.22 (t, J=8.1 Hz, 1H), 7.34 (d, J=8.1 Hz, 1H). MS (ESI+) m/z 427 (M+H)+.

Example 156

1-[(4R)-8-fluoro-2,2-dipropyl-3,4-dihydro-2H-chromen-4-yl]-3-(1-methyl-2-oxo-1,2,3,4-tetrahydroquinazolin-5-yl)urea $^1$H NMR (500 MHz, DMSO-$d_6$/D$_2$O) δ 0.82-0.97 (m, 6H), 1.17-1.45 (m, 4H), 1.47-1.82 (m, 4H), 2.14 (dd, J=13.5, 6.0

Hz, 1H), 3.15 (s, 3H), 4.19 (d, J=1.8 Hz, 2H), 4.94 (dd, J=11.0, 6.0 Hz, 1H), 6.70 (d, J=8.1 Hz, 1H), 6.80-6.99 (m, 1H), 7.05-7.13 (m, 2H), 7.21 (t, J=8.1 Hz, 1H), 7.33 (d, J=8.1 Hz, 1H). MS (ESI$^+$) m/z 455 (M+H)$^+$.

Example 157

1-[(4R)-6-fluoro-2,2-dimethyl-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 1.26 (s, 3H), 1.39 (s, 3H), 1.67-1.76 (m, 1H), 2.12 (dd, J=13.2, 6.2 Hz, 1H), 3.15 (s, 3H), 3.56-3.67 (m, 2H), 4.19 (s, 2H), 4.92 (dd, J=11.1, 6.2 Hz, 1H), 6.70 (d, J=8.1 Hz, 1H), 6.77 (dd, J=8.5, 4.8 Hz, 1H), 6.94-7.05 (m, 2H), 7.22 (t, J=8.1 Hz, 1H), 7.33 (d, J=8.1 Hz, 1H). MS (ESI$^+$) m/z 399 (M+H)$^+$.

Example 158

1-[(1R)-3,3-dimethyl-2,3-dihydro-1H-inden-1-yl]-3-(1-methyl-2-oxo-1,2,3,4-tetrahydroquinazolin-5-yl)urea $^1$H NMR (500 MHz, DMSO-d$_6$/D$_2$O) δ 1.19 (s, 3H), 1.35 (s, 3H), 1.68 (dd, J=12.4, 8.1 Hz, 1H), 2.28-2.40 (m, 1H), 3.15 (s, 3H), 4.17 (s, 2H), 5.20 (t, J=7.7 Hz, 1H), 6.68 (d, J=8.1 Hz, 1H), 7.17-7.30 (m, 5H), 7.36 (d, J=8.1 Hz, 1H). MS (ESI$^+$) m/z 399 (M+H)$^+$.

Example 159

1-[(4R)-7-fluoro-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 1.91-2.01 (m, 1H), 2.04-2.14 (m, 1H), 3.14 (s, 3H), 3.58-3.65 (m, 2H), 4.16 (s, 2H), 4.25-4.33 (m, 1H), 4.80-4.86 (m, 1H), 6.63-6.70 (m, 2H), 6.77 (td, J=8.5, 2.7 Hz, 1H), 7.20 (t, J=8.1 Hz, 1H), 7.26-7.34 (m, 1H), 7.37 (d, J=8.1 Hz, 1H). MS (ESI$^+$) m/z 371 (M+H)$^+$.

Example 160

1-(1-methyl-2-oxo-1,2,3,4-tetrahydroquinazolin-5-yl)-3-[(4R)-7-(trifluoromethyl)-3,4-dihydro-2H-chromen-4-yl]urea $^1$H NMR (500 MHz, DMSO-d$_6$/D$_2$O) δ 2.00 (dd, J=7.0, 3.9 Hz, 1H), 2.08-2.22 (m, 1H), 3.15 (s, 3H), 4.16 (s, 2H), 4.24 (dd, J=9.7, 6.4 Hz, 1H), 4.30-4.41 (m, 1H), 4.94 (t, J=6.1 Hz, 1H), 6.69 (d, J=7.8 Hz, 1H), 7.15 (dd, J=18.4, 5.5 Hz, 1H), 7.14-7.23 (m, 1H), 7.23-7.30 (m, 1H), 7.34 (d, J=7.8 Hz, 1H), 7.49 (d, J=8.1 Hz, 1H). MS (ESI$^+$) m/z 421 (M+H)$^+$.

Example 161

1-(7-chloro-3,4-dihydro-2H-chromen-3-yl)-3-(1-methyl-2-oxo-1,2,3,4-tetrahydroquinazolin-5-yl)urea $^1$H NMR (500 MHz, DMSO-d$_6$/D$_2$O) δ 2.64-2.74 (m, 1H), 3.02-3.12 (m, 1H), 3.13 (s, 3H), 4.04-4.17 (m, 5H), 6.65 (d, J=8.1 Hz, 1H), 6.91 (d, J=2.1 Hz, 1H), 6.92-7.03 (m, 1H), 7.13-7.21 (m, 2H), 7.36 (d, J=7.7 Hz, 1H). MS ESI$^+$ m/z 387(M+H)$^+$.

Example 162

1-[(4R)-7-chloro-2,2-bis(fluoromethyl)-3,4-dihydro-2H-chromen-4-yl]-3-(1-ethyl-2-oxo-1,2,3,4-tetrahydroquinazolin-5-yl)urea $^1$H NMR (300 MHz, DMSO) δ 7.82 (s, 1H), 7.38-7.22 (m, 2H), 7.16 (t, J=8.2 Hz, 1H), 7.04 (dd, J=8.2, 2.1 Hz, 2H), 6.96 (d, J=2.1 Hz, 1H), 6.82 (d, J=8.2 Hz, 1H), 6.69 (d, J=8.0 Hz, 1H), 4.96 (dd, J=14.2, 10.3 Hz, 1H), 4.75-4.64 (m, 2H), 4.60-4.48 (m, 2H), 4.17 (d, J=1.4 Hz, 2H), 3.80 (q, J=6.9 Hz, 2H), 2.28 (dd, J=13.8, 5.9 Hz, 1H), 1.98-1.87 (m, 1H), 1.12 (t, J=6.9 Hz, 3H).); MS (ESI) m/z 465 (M+H)$^+$.

Example 163

1-[(2R,4R)-2-(fluoromethyl)-2-methyl-3,4-dihydro-2H-chromen-4-yl]-3-(1-methyl-2-oxo-1,2,3,4-tetrahydroquinazolin-5-yl)urea $^1$H NMR (300 MHz, DMSO) δ 7.82 (s, 1H), 7.40 (d, J=7.7 Hz, 1H), 7.29 (d, J=7.5 Hz, 1H), 7.16 (dd, J=16.5, 8.4 Hz, 3H), 6.93 (td, J=7.5, 1.1 Hz, 1H), 6.79 (dd, J=8.2, 1.2 Hz, 2H), 6.64 (d, J=7.6 Hz, 1H), 5.01 (dd, J=16.3, 9.2 Hz, 1H), 4.60-4.31 (m, 2H), 4.19 (d, J=1.6 Hz, 2H), 3.14 (s, 3H), 2.10 (dd, J=13.1, 6.1 Hz, 1H), 1.90-1.75 (m, 1H), 1.27 (d, J=2.0 Hz, 3H); MS (DCI) m/z 416 (M+NH$_4$)$^+$.

Example 164

1-[(2S,4R)-2-(fluoromethyl)-2-methyl-3,4-dihydro-2H-chromen-4-yl]-3-(1-methyl-2-oxo-1,2,3,4-tetrahydroquinazolin-5-yl)urea $^1$H NMR (300 MHz, DMSO) δ 7.90 (s, 1H), 7.42 (d, J=7.7 Hz, 1H), 7.34-7.08 (m, 4H), 7.08-6.72 (m, 3H), 6.63 (d, J=7.7 Hz, 1H), 4.92 (dd, J=14.9, 8.9 Hz, 1H), 4.59-4.30 (m, 2H), 4.16 (t, J=7.1 Hz, 2H), 3.14 (s, 3H), 2.29 (dd, J=13.7, 6.2 Hz, 1H), 1.92-1.79 (m, 1H), 1.37 (d, J=1.9 Hz, 3H); MS (DCI) m/z 416 (M+NH$_4$)$^+$.

Example 165

1-(1-methyl-2-oxo-1,2,3,4-tetrahydroquinazolin-5-yl)-3-[(2S,4R)-2-methyl-2-(trifluoromethyl)-3,4-dihydro-2H-chromen-4-yl]urea $^1$H NMR (300 MHz, DMSO) δ 7.97 (s, 1H), 7.38-7.29 (m, 2H), 7.28-7.13 (m, 2H), 7.12 (bs, 2H), 7.03 (td, J=7.5, 1.2 Hz, 2H), 6.92-6.82 (m, 1H), 6.66 (d, J=7.6 Hz, 1H), 5.12-5.00 (m, 1H), 4.20 (d, J=1.9 Hz, 2H), 3.15 (s, 3H), 2.33 (dd, J=12.7, 5.9 Hz, 1H), 2.07-1.94 (m, 1H), 1.52 (s, 3H). MS (ESI$^+$) M/Z 435 (M+H)$^+$.

Example 166

1-(1-methyl-2-oxo-1,2,3,4-tetrahydroquinazolin-5-yl)-3-[(2R,4R)-2-methyl-2-(trifluoromethyl)-3,4-dihydro-2H-chromen-4-yl]urea $^1$H NMR (300 MHz, DMSO) δ 7.97 (s, 1H), 7.38-7.29 (m, 2H), 7.28-7.11 (m, 3H), 7.03 (td, J=7.5, 1.2 Hz, 1H), 6.92-6.82 (m, 1H), 6.66 (d, J=8.1 Hz, 1H), 5.12-5.00 (m, 1H), 4.20 (d, J=1.9 Hz, 2H), 3.15 (s, 3H), 2.33 (dd, J=12.7, 5.9 Hz, 1H), 2.07-1.94 (m, 1H), 1.52 (s, 3H). MS (ESI$^+$) M/Z 452 (M+NH$_4$)$^+$.

Example 167

1-[(4R)-7-chloro-2,2-bis(fluoromethyl)-3,4-dihydro-2H-chromen-4-yl]-3-(1,3-dimethyl-2-oxo-1,2,3,4-tetrahydroquinazolin-5-yl)urea $^1$H NMR (300 MHz, DMSO) δ 7.93 (s, 1H), 7.40-7.29 (m, 2H), 7.19 (t, J=8.1 Hz, 1H), 7.05 (dd, J=8.3, 2.1 Hz, 1H), 6.97 (d, J=2.1 Hz, 2H), 6.85 (d, J=8.1 Hz, 1H), 6.65 (d, J=8.1 Hz, 1H), 5.03-4.91 (m, 1H), 4.65 (dd, J=46.6, 1.9 Hz, 2H), 4.27 (s, 1H), 3.18 (s, 3H), 2.92 (s, 3H), 2.29 (dd, J=13.7, 5.9 Hz, 1H), 2.04-1.89 (m, 1H). MS (ESI$^+$) M/Z 465 (M+H)$^+$.

Example 168

1-[(4R)-3,4-dihydro-2H-chromen-4-yl]-3-(1-methyl-2-oxo-1,2,3,4-tetrahydroquinazolin-5-yl)urea $^1$H NMR (500 MHz, DMSO-d$_6$/D$_2$O) δ 1.99 (s, 1H), 2.11 (s, 1H), 3.14 (s, 3H), 4.12-4.25 (m, 3H), 4.32 (s, 1H), 4.87 (t, J=5.5 Hz, 1H), 6.68 (d, J=8.2 Hz, 1H), 6.80 (s, 1H), 6.92 (d, J=8.1 Hz, 1H), 7.15-7.25 (m, 1H), 7.37 (dd, J=15.0, 8.3 Hz, 2H). MS ESI$^+$ m/z 353(M+H)$^+$.

Example 169

1-(1-methyl-2-oxo-1,2,3,4-tetrahydroquinazolin-5-yl)-3-[(4S)-7-(trifluoromethoxy)-3,4-dihydro-2H-chromen-4-yl]urea $^1$H NMR (500 MHz, DMSO-d$_6$/D$_2$O) δ 1.99 (s, 1H), 2.11 (s, 1H), 3.14 (s, 3H), 4.12-4.25 (m, 3H), 4.32 (s, 1H), 4.87 (t, J=5.5 Hz, 1H), 6.68 (d, J=8.2 Hz, 1H), 6.80 (s, 1H), 6.92 (d, J=8.1 Hz, 1H), 7.15-7.25 (m, 1H), 7.37 (dd, J=15.0, 8.3 Hz, 2H). MS ESI$^+$ m/z 437(M+H)$^+$.

Example 170

1-[(4R)-7-chloro-2,2-bis(fluoromethyl)-3,4-dihydro-2H-chromen-4-yl]-3-(3-methyl-2-oxo-1,2,3,4-tetrahydroquinazolin-7-yl)urea $^1$H NMR (300 MHz, DMSO-d$_6$) δ ppm 1.88-2.01 (ddd, J=13.7, 10.8, 2.7 Hz, 1H), 2.28 (dd, J=13.7, 5.9 Hz, 1H), 2.84 (s, 3H), 4.31 (s, 2H), 4.49-4.78 (m, 4H), 4.90-5.03 (m, 1H), 6.49 (d, J=8.3 Hz, 1H), 6.90-6.98 (m, 4H), 7.03 (dd, J=8.3, 2.1 Hz, 1H), 7.28 (d, J=8.3 Hz, 1H), 8.51 (s, 1H), 9.14 (s, 1H). MS (ESI) 451 (M+H)$^+$.

Example 171

1-[(2S,4R)-2-(difluoromethyl)-2-methyl-3,4-dihydro-2H-chromen-4-yl]-3-(3-methyl-2-oxo-1,2,3,4-tetrahydroquinazolin-7-yl)urea $^1$H NMR (300 MHz, DMSO) δ 9.03 (s, 1H), 8.50 (s, 1H), 7.31-7.13 (m, 2H), 6.96 (d, J=7.5 Hz, 1H), 6.93 (s, 2H), 6.84 (dd, J=8.2, 4.1 Hz, 1H), 6.47-6.30 (m, 1H), 5.06-4.93 (m, 1H), 4.31 (s, 3H), 2.84 (s, 3H), 2.43-2.16 (m, 1H), 1.98-1.85 (m, 1H), 1.46-1.16 (m, 4H). MS (ESI$^+$) M/Z 417 (M+H)$^+$.

Example 172

1-[(4R)-8-chloro-7-fluoro-2,2-dimethyl-3,4-dihydro-2H-chromen-4-yl]-3-(3-methyl-2-oxo-1,2,3,4-tetrahydroquinazolin-7-yl)urea $^1$H NMR (300 MHz, DMSO) δ 9.14 (s, 1H), 8.52 (s, 1H), 7.33-7.13 (m, 1H), 7.03-6.82 (m, 2H), 6.43 (d, J=8.6 Hz, 1H), 4.93 (d, J=9.5 Hz, 1H), 4.31 (s, 1H), 2.84 (s, 2H), 2.73 (d, J=1.8 Hz, 1H), 2.16 (dd, J=13.3, 6.2 Hz, 1H), 1.83 (dd, J=29.1, 17.7 Hz, 1H), 1.45 (s, 3H), 1.58-1.37 (s, 3H), 1.33 (s, 3H).). MS (ESI$^+$) M/Z 433 (M+H)$^+$.

Example 173

1-[(4R)-2,2-bis(fluoromethyl)-7-(trifluoromethyl)-3,4-dihydro-2H-chromen-4-yl]-3-(3-methyl-2-oxo-1,2,3,4-tetrahydroquinazolin-7-yl)urea $^1$H NMR (300 MHz, DMSO) δ 9.05 (s, 1H), 8.55 (s, 1H), 7.49 (d, J=7.8 Hz, 1H), 7.35-7.28 (m, 1H), 7.19 (bs, 1H), 6.97-6.91 (m, 2H), 6.60 (dd, J=18.8, 8.4 Hz, 1H), 5.13-5.00 (m, 1H), 4.82-4.69 (m, 2H), 4.66-4.53 (m, 2H), 4.31 (s, 1H), 2.84 (s, 3H), 2.37-2.23 (m, 2H), 2.11-1.95 (m, 2H). MS (ESI$^+$) M/Z 485 (M+H)$^+$.

Example 174

1-(3-methyl-2-oxo-1,2,3,4-tetrahydroquinazolin-7-yl)-3-[(1R)-5-(trifluoromethyl)-2,3-dihydro-1H-inden-1-yl]urea $^1$H NMR (300 MHz, DMSO) δ 9.20 (s, 1H), 8.40 (s, 1H), 7.64-7.41 (m, 4H), 6.96-6.90 (m, 2H), 5.30-5.17 (m, 1H), 4.30 (s, 3H), 3.05-2.81 (m, 4H), 2.38-1.71 (m, 2H), 1.36 (s, 1H). MS (ESI$^+$) M/Z 405 (M+H)$^+$.

Example 175

1-[(4R)-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 1.95 (dtd, J=9.2, 6.5, 2.8 Hz, 1H), 2.06-2.13 (m, 1H), 2.85 (s, 3H), 4.14 (ddd, J=11.3, 8.6, 2.8 Hz, 1H), 4.25 (ddd, J=10.1, 6.7, 3.1 Hz, 1H), 4.32 (s, 1H), 4.86 (t, J=5.6 Hz, 1H), 6.79 (dd, J=8.2, 1.0 Hz, 1H), 6.88 (dd, J=8.2, 2.1 Hz, 1H), 6.91 (td, J=7.5, 1.2 Hz, 1H), 6.96 (dd, J=5.1, 3.0 Hz, 2H), 7.15-7.20 (m, 1H), 7.25 (d, J=7.7 Hz, 1H). MS ESI$^-$ m/z 351 (M–H)$^-$.

Example 176

1-[(4R)-7-fluoro-2,2-dimethyl-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 1.26 (s, 3H), 1.39 (s, 3H), 1.73 (dd, J=13.1, 11.2 Hz, 1H), 2.12 (dd, J=13.3, 6.2 Hz, 1H), 2.86 (s, 3H), 4.33 (s, 2H), 4.92 (dd, J=10.9, 6.2 Hz, 1H), 6.58 (dd, J=10.6, 2.6 Hz, 1H), 6.74 (td, J=8.5, 2.6 Hz, 1H), 6.90 (dd, J=8.2, 2.1 Hz, 1H), 6.98 (t, J=5.0 Hz, 2H), 7.24-7.28 (m, 1H). MS ESI$^+$ m/z 399 (M+H)$^+$.

Example 177

1-[(4R)-2,2-diethyl-8-fluoro-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 0.89 (dq, J=14.2, 7.4 Hz, 7H), 1.51-1.80 (m, 6H), 1.83 (s, 1H), 2.14 (dd, J=13.5, 6.1 Hz, 1H), 2.86 (s, 3H), 4.33 (s, 2H), 4.96 (dd, J=11.1, 6.1 Hz, 1H), 6.86 (dd, J=8.0, 3.1 Hz, 1H), 6.89 (dd, J=8.2, 2.0 Hz,

Example 178

1-[(4R)-2,2-diethyl-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 0.82-0.94 (m, 7H), 1.52-1.59 (m, 1H), 1.59-1.70 (m, 4H), 2.11 (dd, J=13.4, 6.1 Hz, 1H), 2.86 (s, 3H), 4.33 (s, 2H), 4.93 (dd, J=11.1, 6.2 Hz, 1H), 6.76 (dd, J=8.2, 1.0 Hz, 1H), 6.89 (dd, J=8.2, 1.9 Hz, 2H), 6.97 (d, J=8.3 Hz, 1H), 7.01 (d, J=2.0 Hz, 1H), 7.15 (td, J=8.0, 1.2 Hz, 1H), 7.24 (d, J=7.6 Hz, 1H). MS ESI$^-$ m/z 407 (M−H)$^-$.

Example 179

1-[(1R)-5-tert-butyl-2,3-dihydro-1H-inden-1-yl]-3-(3-methyl-2-oxo-1,2,3,4-tetrahydroquinazolin-7-yl)urea $^1$H NMR (500 MHz, DMSO-d$_6$/D$_2$O) δ 1.27 (s, 9H), 1.75 (tt, J=12.6, 7.8 Hz, 1H), 1.87 (s, 1H), 2.44 (dtd, J=11.8, 7.8, 3.9 Hz, 1H), 2.78 (dd, J=15.8, 7.8 Hz, 1H), 2.85 (s, 3H), 2.88-2.95 (m, 1H), 3.58 (s, 1H), 4.32 (s, 2H), 5.10 (t, J=7.4 Hz, 1H), 6.87 (dd, J=8.2, 2.1 Hz, 1H), 6.93-6.98 (m, 2H), 7.20 (d, J=8.0 Hz, 1H), 7.22-7.26 (m, 1H), 7.28 (s, 1H). MS ESI$^-$ m/z 391 (M−H)$^-$.

Example 180

1-[(4R)-2,2-diethyl-7-(trifluoromethyl)-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 0.84-0.96 (m, 7H), 1.57 (dd, J=14.3, 7.4 Hz, 1H), 1.60-1.72 (m, 1H), 1.76 (dt, J=14.3, 7.2 Hz, 1H), 2.14 (dd, J=13.5, 6.1 Hz, 1H), 2.86 (s, 3H), 4.33 (s, 2H), 4.95-5.03 (m, 1H), 6.90 (dd, J=8.2, 2.1 Hz, 1H), 6.98 (d, J 8.2 Hz, 1H), 7.04 (dd, J=21.9, 1.9 Hz, 2H), 7.23 (dd, J=8.1, 1.8 Hz, 1H), 7.47 (d, J=8.1 Hz, 1H). MS ESI$^-$ m/z 475 (M−H)$^-$.

Example 181

1-[(4R)-7-chloro-2,2-diethyl-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 0.89 (dt, J=16.7, 7.4 Hz, 7H), 1.53-1.58 (m, 1H), 1.60-1.66 (m, 3H), 1.69 (dd, J=10.6, 2.8 Hz, 1H), 2.11 (dd, J=13.5, 6.1 Hz, 1H), 2.85 (s, 3H), 4.33 (s, 2H), 4.90 (dd, J=11.1, 6.1 Hz, 1H), 6.82 (d, J=2.1 Hz, 1H), 6.89 (dd, J=8.2, 2.1 Hz, 1H), 6.94 (dd, J=8.3, 2.1 Hz, 1H), 6.97 (d, J=8.3 Hz, 1H), 7.00 (d, J=2.1 Hz, 1H), 7.25 (dd, J=8.3, 0.8 Hz, 1H). MS ESI$^-$ m/z 441 (M−H)$^-$.

Example 182

1-[(4R)-7,8-dichloro-2,2-diethyl-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 0.88 (t, J=7.4 Hz, 3H), 0.94 (t, J=7.4 Hz, 3H), 1.56 (dt, J=14.3, 7.3 Hz, 1H), 1.65 (td, J=14.8, 7.4 Hz, 1H), 1.72 (dd, J=14.8, 7.3 Hz, 3H), 1.75-1.80 (m, 1H), 2.15 (dd, J=13.6, 6.2 Hz, 1H), 2.86 (s, 3H), 4.33 (s, 2H), 4.95 (dd, J=11.2, 6.2 Hz, 1H), 6.89 (dd, J=8.2, 2.1 Hz, 1H), 6.97 (d, J=8.3 Hz, 1H), 7.00 (d, J=2.1 Hz, 1H), 7.15 (dd, J=8.3, 4.1 Hz, 1H), 7.23 (dd, J=8.5, 0.7 Hz, 1H). MS ESI$^-$ m/z 475 (M−H)$^-$.

Example 183

1-[(4R)-2,2-bis(fluoromethyl)-7-(trifluoromethoxy)-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 1.96-2.03 (m, 1H), 2.29 (dd, J=13.7, 6.0 Hz, 1H), 2.86 (s, 3H), 4.33 (s, 2H), 4.58 (s, 1H), 4.62 (dd, J=14.0, 12.7 Hz, 1H), 4.68 (s, 1H), 4.71 (dd, J=21.7, 5.5 Hz, 1H), 5.01 (dd, J=10.7, 5.9 Hz, 1H), 6.87 (d, J=1.5 Hz, 1H), 6.90 (dd, J=8.2, 2.1 Hz, 1H), 6.96-7.00 (m, 3H), 7.38 (d, J=8.5 Hz, 1H). MS ESI$^-$ m/z 499 (M−H)$^-$.

Example 184

1-[(4R)-2,2-dimethyl-7-(trifluoromethyl)-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 1.31 (s, 3H), 1.42 (s, 3H), 1.80 (dd, J=12.9, 11.8 Hz, 1H), 2.16 (dd, J=13.3, 6.2 Hz, 1H), 2.86 (s, 3H), 4.33 (s, 2H), 5.02 (dd, J=11.2, 6.2 Hz, 1H), 6.91 (dd, J=8.2, 2.1 Hz, 1H), 6.98 (d, J=8.3 Hz, 1H), 7.00 (d, J=2.0 Hz, 1H), 7.04 (d, J=1.3 Hz, 1H), 7.24 (dd, J=8.1, 1.3 Hz, 1H), 7.47 (d, J=8.1 Hz, 1H). MS ESI$^-$ m/z 447 (M−H)$^-$.

Example 185

1-[(4R)-6-fluoro-2,2-dipropyl-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 0.87 (t, J=7.3 Hz, 3H), 0.92 (t, J=7.3 Hz, 3H), 1.28 (dd, J=15.3, 8.0 Hz, 1H), 1.32-1.42 (m, 3H), 1.49-1.54 (m, 2H), 1.60 (dd, J=15.8, 8.5 Hz, 2H), 1.69 (dd, J=13.2, 11.6 Hz, 1H), 2.10 (dd, J=13.4, 6.1 Hz, 1H), 2.86 (s, 3H), 4.33 (s, 2H), 4.89 (dd, J=11.3, 6.1 Hz, 1H), 6.76 (dd, J=9.8, 4.9 Hz, 1H), 6.89 (dd, J=8.2, 2.1 Hz, 1H), 6.96-6.98 (m, 2H), 6.99-7.01 (m, 1H), 7.01 (d, J=2.0 Hz, 1H). MS ESI$^-$ m/z 453 (M−H)$^-$.

Example 186

1-[(4R)-6-fluoro-2,2-bis(fluoromethyl)-3,4-dihydro-2H-chromen-4-yl]-3-(3-methyl-2-oxo-1,2,3,4-tetrahydroquinazolin-7-yl)urea $^1$H NMR (500 MHz, DMSO-d6/D$_2$O) δ 1.94 (ddd, J=13.7, 11.1, 2.8 Hz, 1H), 2.28 (dd, J=13.7, 6.0 Hz, 1H), 2.86 (s, 3H), 4.33 (s, 2H), 4.53-4.55 (m, 1H), 4.56-4.61 (m, 1H), 4.64 (d, J=5.1 Hz, 1H), 4.65-4.70 (m, 1H), 4.98 (dd, J=10.8, 6.0 Hz, 1H), 6.90 (dd, J=6.5, 1.6 Hz, 1H), 6.92 (d, J=5.1 Hz, 1H), 6.98 (d, J=8.3 Hz, 1H), 7.00 (d, J=2.0 Hz, 1H), 7.01-7.05 (m, 1H), 7.07 (dd, J=8.4, 3.2 Hz, 1H). MS ESI$^-$ m/z 433 (M−H)$^-$.

Example 187

1-[(4R)-6,8-difluoro-2,2-bis(fluoromethyl)-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 2.03 (ddd, J=13.8, 11.4, 2.7 Hz, 1H), 2.32 (dd, J=13.7, 6.0 Hz, 1H), 2.86 (s, 3H), 4.33 (s, 2H), 4.59 (s, 1H), 4.60-4.67 (m, 1H), 4.69 (s, 1H), 4.69-4.76 (m, 1H), 5.00 (dd, J=11.0, 6.0 Hz, 1H), 6.90 (dd, J=8.2, 2.0 Hz, 2H), 6.98 (d, J=8.3 Hz, 1H), 7.00 (d, J=2.0 Hz, 1H), 7.22 (ddd, J=11.3, 8.6, 3.0 Hz, 1H). MS ESI⁺ m/z 453 (M+H)⁺.

Example 188

1-[(4R)-6-fluoro-3,4-dihydrospiro[chromene-2,1'-cyclobutan]-4-yl]-3-(3-methyl-2-oxo-1,2,3,4-tetrahydroquinazolin-7-yl)urea ¹H NMR (500 MHz, DMSO-d₆/D₂O) δ 1.72 (dt, J=11.1, 8.7 Hz, 1H), 1.81-1.87 (m, 2H), 2.04-2.10 (m, 1H), 2.15 (ddd, J=12.7, 9.1, 4.4 Hz, 2H), 2.28 (dd, J=20.1, 10.1 Hz, 1H), 2.36 (dd, J=13.2, 5.9 Hz, 1H), 2.86 (s, 3H), 4.33 (s, 2H), 4.93 (dd, J=10.4, 5.9 Hz, 1H), 6.81 (dd, J=8.8, 4.8 Hz, 1H), 6.91 (dd, J=8.2, 2.1 Hz, 1H), 6.97 (dd, J=6.4, 3.4 Hz, 1H), 6.99 (d, J=1.0 Hz, 1H), 7.00 (d, J=2.0 Hz, 1H). MS ESI⁻ m/z 409 (M−H)⁻.

Example 189

1-[(4R)-2,2-diethyl-6-fluoro-3,4-dihydro-2H-chromen-4-yl]-3-(3-methyl-2-oxo-1,2,3,4-tetrahydroquinazolin-7-yl)urea ¹H NMR (500 MHz, DMSO-d₆/D₂O) δ 0.88 (dt, J=19.4, 7.4 Hz, 6H), 1.51-1.57 (m, 1H), 1.58-1.62 (m, 1H), 1.63-1.67 (m, 2H), 1.69 (dd, J=10.3, 3.0 Hz, 1H), 2.10 (dd, J=13.4, 6.2 Hz, 1H), 2.86 (s, 3H), 4.33 (s, 2H), 4.90 (dd, J=11.2, 6.2 Hz, 1H), 6.78 (dd, J=9.6, 4.9 Hz, 1H), 6.89 (dd, J=8.2, 2.1 Hz, 1H), 6.97 (d, J=5.2 Hz, 1H), 6.98-7.00 (m, 2H), 7.01 (d, J=2.1 Hz, 1H). MS ESI⁻ m/z 425 (M−H)⁻.

Example 190

1-[(4R)-8-fluoro-2,2-dipropyl-3,4-dihydro-2H-chromen-4-yl]-3-(3-methyl-2-oxo-1,2,3,4-tetrahydroquinazolin-7-yl)urea ¹H NMR (500 MHz, DMSO-d₆/D₂O) δ 0.86-0.90 (m, 3H), 0.93 (t, J=7.3 Hz, 3H), 1.27-1.33 (m, 1H), 1.35 (dd, J=7.6, 2.8 Hz, 1H), 1.36-1.43 (m, 3H), 1.53-1.58 (m, 2H), 1.62-1.68 (m, 2H), 1.72-1.81 (m, 1H), 2.13 (dd, J=13.5, 6.1 Hz, 1H), 2.85 (s, 3H), 4.33 (s, 2H), 4.95 (dd, J=11.1, 6.1 Hz, 1H), 6.73 (d, J=1.4 Hz, 1H), 6.89 (ddd, J=8.6, 4.2, 1.7 Hz, 2H), 6.97 (d, J=8.3 Hz, 1H), 7.00 (d, J=2.0 Hz, 1H), 7.35 (d, J=8.6 Hz, 1H). MS ESI⁻ m/z 453 (M−H)⁻.

Example 191

1-[(4R)-2,2-diethyl-7-(trifluoromethoxy)-3,4-dihydro-2H-chromen-4-yl]-3-(3-methyl-2-oxo-1,2,3,4-tetrahydroquinazolin-7-yl)urea ¹H NMR (500 MHz, DMSO-d₆/D₂O) δ 0.89 (dt, J=17.4, 7.4 Hz, 6H), 1.53-1.59 (m, 1H), 1.67 (ddd, J=21.9, 10.6, 5.0 Hz, 3H), 1.71-1.74 (m, 1H), 2.12 (dd, J=13.5, 6.1 Hz, 1H), 2.86 (s, 3H), 4.33 (s, 2H), 4.93 (dd, J=11.1, 6.1 Hz, 1H), 6.73 (d, J=1.4 Hz, 1H), 6.89 (ddd, J=8.6, 4.2, 1.7 Hz, 2H), 6.97 (d, J=8.3 Hz, 1H), 7.00 (d, J=2.0 Hz, 1H), 7.35 (d, J=8.6 Hz, 1H). MS ESI⁻ m/z 491 (M−H)⁻.

Example 192

1-[(4R)-7-chloro-8-fluoro-2,2-bis(fluoromethyl)-3,4-dihydro-2H-chromen-4-yl]-3-(3-methyl-2-oxo-1,2,3,4-tetrahydroquinazolin-7-yl)urea ¹H NMR (500 MHz, DMSO-d₆/D₂O) δ 2.00-2.06 (m, 1H), 2.32 (dd, J=13.8, 6.0 Hz, 1H), 2.85 (s, 3H), 4.33 (s, 2H), 4.61 (d, J=5.5 Hz, 1H), 4.62-4.68 (m, 1H), 4.70 (d, J=5.9 Hz, 1H), 4.71-4.78 (m, 1H), 5.02 (dd, J=11.0, 6.0 Hz, 1H), 6.90 (dd, J=8.2, 2.1 Hz, 1H), 6.98 (t, J=5.3 Hz, 2H), 7.10 (d, J=8.7 Hz, 1H), 7.15 (dd, J=8.6, 6.3 Hz, 1H). MS ESI⁻ m/z 467 (M−H)⁻.

Example 193

1-[(4R)-2,2-dimethyl-3,4-dihydro-2H-chromen-4-yl]-3-(3-methyl-2-oxo-1,2,3,4-tetrahydroquinazolin-7-yl)urea ¹H NMR (500 MHz, DMSO-d₆/D₂O) δ 1.28 (s, 3H), 1.39 (s, 3H), 1.72 (dd, J=13.0, 11.2 Hz, 1H), 2.12 (dd, J=13.2, 6.2 Hz, 1H), 2.86 (s, 3H), 4.33 (s, 2H), 4.96 (dd, J=10.9, 6.2 Hz, 1H), 6.74 (dd, J=8.2, 0.9 Hz, 1H), 6.89-6.92 (m, 2H), 6.98 (dd, J=7.1, 5.2 Hz, 2H), 7.12-7.18 (m, 1H), 7.24 (d, J=7.7 Hz, 1H). MS ESI⁺ m/z 381 (M+H)⁺.

Example 194

1-(3-methyl-2-oxo-1,2,3,4-tetrahydroquinazolin-7-yl)-3-[(4S)-7-(trifluoromethoxy)-3,4-dihydro-2H-chromen-4-yl]urea ¹H NMR (500 MHz, DMSO-d₆/D₂O) δ 1.94-2.00 (m, 1H), 2.07-2.14 (m, 1H), 2.85 (s, 3H), 4.20 (ddd, J=11.2, 8.3, 2.9 Hz, 1H), 4.28-4.31 (m, 1H), 4.32 (s, 2H), 4.89 (t, J=5.7 Hz, 1H), 6.79 (d, J=1.5 Hz, 1H), 6.88 (dd, J=8.2, 2.1 Hz, 1H), 6.91 (dd, J=8.6, 1.3 Hz, 1H), 6.96 (dd, J=5.1, 3.0 Hz, 2H), 7.38 (d, J=8.8 Hz, 1H). MS (ESI⁻) m/z 435 (M−H)⁻.

Example 195

1-(3-methyl-2-oxo-1,2,3,4-tetrahydroquinazolin-7-yl)-3-[(4R)-7-(trifluoromethoxy)-3,4-dihydro-2H-chromen-4-yl]urea ¹H NMR (500 MHz, DMSO-d₆/D₂O) δ 1.94-2.00 (m, 1H), 2.08-2.15 (m, 1H), 2.85 (s, 3H), 4.20 (ddd, J=11.2, 8.3, 2.9 Hz, 1H), 4.30 (dd, J=7.2, 3.4 Hz, 1H), 4.32 (s, 2H), 4.89 (t, J=5.7 Hz, 1H), 6.79 (d, J=1.5 Hz, 1H), 6.88 (dd, J=8.2, 2.1 Hz, 1H), 6.89-6.92 (m, 1H), 6.96 (dd, J=5.1, 3.0 Hz, 2H), 7.38 (d, J=8.7 Hz, 1H). MS ESI⁻ m/z 435 (M−H)⁻.

Example 196

1-[(4R)-6-fluoro-2,2-bis(methoxymethyl)-3,4-dihydro-2H-chromen-4-yl]-3-(3-methyl-2-oxo-1,2,3,4-tetrahydroquinazolin-7-yl)urea ¹H NMR (500 MHz, DMSO-d₆/D₂O) δ 1.85 (dd, J=13.4, 11.4 Hz, 1H), 2.15 (dd, J=13.4, 6.0 Hz, 1H), 2.86 (s, 3H), 3.28 (s, 3H), 3.32 (s, 3H), 3.43 (dd, J=22.4, 10.1 Hz, 2H), 3.48 (s, 2H), 4.33 (s, 2H), 4.93 (dd, J=11.2, 6.0 Hz, 1H), 6.82 (dd, J=8.9, 4.8 Hz, 1H), 6.89 (dd, J=8.2, 2.1 Hz, 1H), 6.97 (s, 1H), 6.98-7.01 (m, 2H). MS ESI⁻ m/z 457 (M–H)⁻.

Example 197

1-[(4R)-2,2-bis(fluoromethyl)-3,4-dihydro-2H-chromen-4-yl]-3-(3-methyl-2-oxo-1,2,3,4-tetrahydroquinazolin-7-yl)urea ¹H NMR (500 MHz, DMSO-d₆/D₂O) δ 1.95 (ddd, J=13.5, 10.7, 2.7 Hz, 1H), 2.27 (dd, J=13.7, 5.9 Hz, 1H), 2.86 (s, 3H), 4.33 (s, 2H), 4.53-4.61 (m, 2H), 4.63-4.70 (m, 2H), 4.99 (dd, J=10.5, 6.0 Hz, 1H), 6.87 (dd, J=8.2, 1.0 Hz, 1H), 6.90 (dd, J=8.2, 2.1 Hz, 1H), 6.97 (s, 1H), 6.99 (dd, J=4.2, 2.1 Hz, 2H), 7.22 (td, J=8.0, 1.3 Hz, 1H), 7.27 (d, J=7.7 Hz, 1H). MS ESI⁻ m/z 415 (M–H)⁻.

Example 198

1-[(4R)-8-fluoro-2,2-bis(fluoromethyl)-3,4-dihydro-2H-chromen-4-yl]-3-(3-methyl-2-oxo-1,2,3,4-tetrahydroquinazolin-7-yl)urea ¹H NMR (500 MHz, DMSO-d₆/D₂O) δ 2.01 (ddd, J=13.6, 11.0, 2.6 Hz, 1H), 2.31 (dd, J=13.7, 5.9 Hz, 1H), 2.86 (s, 3H), 4.33 (s, 2H), 4.58-4.66 (m, 2H), 4.67-4.77 (m, 2H), 5.03 (dd, J=10.7, 5.9 Hz, 1H), 6.90 (dd, J=8.2, 2.1 Hz, 1H), 6.96 (dt, J=8.0, 3.8 Hz, 2H), 6.98-7.00 (m, 1H), 7.09 (d, J=7.9 Hz, 1H), 7.13-7.18 (m, 1H), 13.29-13.44 (m, 1H). MS ESI⁻ m/z 433 (M–H)⁻.

Example 199

1-[(4R)-6-fluoro-3,4-dihydro-2H-chromen-4-yl]-3-(3-methyl-2-oxo-1,2,3,4-tetrahydroquinazolin-7-yl)urea ¹H NMR (500 MHz, DMSO-d₆/D₂O) δ 1.94 (dtd, J=9.9, 7.1, 3.0 Hz, 1H), 2.11 (dddd, J=10.9, 8.1, 5.3, 3.1 Hz, 1H), 2.86 (s, 3H), 4.15 (ddd, J=11.1, 7.9, 3.0 Hz, 1H), 4.24 (ddd, J=10.6, 7.3, 3.0 Hz, 1H), 4.33 (s, 2H), 4.87 (t, J=5.9 Hz, 1H), 6.82 (dd, J=8.9, 4.8 Hz, 1H), 6.88 (dd, J=8.2, 2.1 Hz, 1H), 6.96 (s, 1H), 6.98 (d, J=1.8 Hz, 1H), 7.01 (dd, J=8.4, 3.2 Hz, 1H), 7.04 (dd, J=9.5, 3.0 Hz, 1H). MS ESI⁻ m/z 369 (M–H)⁻.

Example 200

1-(3-methyl-2-oxo-1,2,3,4-tetrahydroquinazolin-7-yl)-3-[(4R)-8-(trifluoromethyl)-3,4-dihydro-2H-chromen-4-yl]urea ¹H NMR (500 MHz, DMSO-d₆/D₂O) δ 2.02 (dtd, J=9.7, 6.8, 3.1 Hz, 1H), 2.12-2.19 (m, 1H), 2.86 (d, J=4.6 Hz, 3H), 4.28 (ddd, J=11.2, 8.3, 3.0 Hz, 1H), 4.32 (s, 2H), 4.37-4.42 (m, 1H), 4.94 (t, J=5.7 Hz, 1H), 6.88 (dd, J=8.2, 2.1 Hz, 1H), 6.97 (dd, J=6.9, 4.7 Hz, 2H), 7.07 (t, J=7.7 Hz, 1H), 7.53 (d, J=6.4 Hz, 2H). MS ESI⁻ m/z 419 (M–H)⁻.

Example 201

1-(3-methyl-2-oxo-1,2,3,4-tetrahydroquinazolin-7-yl)-3-[(4R)-7-(trifluoromethyl)-3,4-dihydro-2H-chromen-4-yl]urea ¹H NMR (500 MHz, DMSO-d₆/D₂O) δ 1.87 (s, 1H), 2.00 (dtd, J=10.1, 7.2, 3.0 Hz, 1H), 2.14 (tdd, J=10.7, 5.2, 3.1 Hz, 1H), 2.85 (s, 3H), 4.24 (ddd, J=11.0, 7.7, 3.0 Hz, 1H), 4.33 (s, 2H), 4.33-4.36 (m, 1H), 4.95 (t, J=5.9 Hz, 1H), 6.89 (dd, J=8.2, 2.1 Hz, 1H), 6.97 (t, J=5.2 Hz, 2H), 7.11 (d, J=1.2 Hz, 1H), 7.24 (dd, J=8.1, 1.4 Hz, 1H), 7.48 (d, J=8.0 Hz, 1H). MS ESI⁻ m/z 419 (M–H)⁻.

Example 202

1-[(1R)-5-fluoro-2,3-dihydro-1H-inden-1-yl]-3-(3-methyl-2-oxo-1,2,3,4-tetrahydroquinazolin-7-yl)urea ¹H NMR (500 MHz, DMSO-d₆/D₂O) δ 1.80 (dq, J=12.6, 8.5 Hz, 1H), 2.44-2.51 (m, 1H), 2.80 (dd, J=16.2, 8.3 Hz, 1H), 2.85 (s, 3H), 2.94 (ddd, J=16.1, 8.7, 3.6 Hz, 1H), 4.32 (s, 2H), 5.11 (t, J=7.5 Hz, 1H), 6.88 (dd, J=8.2, 2.1 Hz, 1H), 6.94-6.97 (m, 2H), 6.99-7.04 (m, 1H), 7.09 (dd, J=9.2, 2.2 Hz, 1H), 7.28 (dd, J=8.2, 5.4 Hz, 1H). MS ESI⁻ m/z 353 (M–H)⁻.

Example 203

1-[(4S)-6-fluoro-3,4-dihydrospiro[chromene-2,1'-cyclobutan]-4-yl]-3-(3-methyl-2-oxo-1,2,3,4-tetrahydroquinazolin-7-yl)urea ¹H NMR (500 MHz, DMSO-d₆/D₂O) δ 1.69-1.76 (m, 1H), 1.80-1.87 (m, 2H), 2.05-2.20 (m, 3H), 2.28 (dd, J=20.2, 9.9 Hz, 1H), 2.36 (dd, J=13.2, 5.9 Hz, 1H), 2.86 (s, 3H), 4.33 (s, 2H), 4.93 (dd, J=10.4, 5.9 Hz, 1H), 6.81 (dd, J=8.9, 4.8 Hz, 1H), 6.91 (dd, J=8.2, 2.1 Hz, 1H), 6.97 (ddd, J=6.2, 3.2, 1.8 Hz, 2H), 7.00 (d, J=2.2 Hz, 1H). MS ESI⁻ m/z 409 (M–H)⁻.

Example 204

1-[(4S)-6-fluoro-2,2-dimethyl-3,4-dihydro-2H-chromen-4-yl]-3-(3-methyl-2-oxo-1,2,3,4-tetrahydroquinazolin-7-yl)urea ¹H NMR (500 MHz, DMSO-d₆/D₂O) δ 1.27 (s, 3H), 1.39 (s, 3H), 1.72 (dd, J=13.0, 11.5 Hz, 1H), 2.11 (dd, J=13.2, 6.3 Hz, 1H), 2.86 (s, 3H), 4.33 (s, 2H), 4.93 (dd, J=11.1, 6.3 Hz, 1H), 6.74-6.78 (m, 1H), 6.91 (dt, J=8.2, 2.2 Hz, 1H), 6.96-7.01 (m, 4H). MS ESI⁻ m/z 397 (M–H)⁻.

Example 205

1-[(4R)-3,4-dihydrospiro[chromene-2,1'-cyclopentan]-4-yl]-3-(3-methyl-2-oxo-1,2,3,4-tetrahydroquinazolin-7-yl)urea ¹H NMR (500 MHz, DMSO-d₆/D₂O) δ 1.58-1.84 (m, 7H), 1.88 (dd, J=5.5, 2.9 Hz, 1H), 1.90-1.97 (m, 1H), 2.13 (dd, J=13.2, 6.1 Hz, 1H), 2.86 (s, 3H), 4.33 (s, 2H), 4.96 (dd, J=9.9, 6.1 Hz, 1H), 6.73 (dd, J=8.2, 1.0 Hz, 1H), 6.86-6.92 (m, 2H), 6.97 (t, J=5.1 Hz, 2H), 7.12-7.17 (m, 1H), 7.24 (d, J=7.6 Hz, 1H). MS ESI⁻ m/z 405 (M–H)⁻.

Example 206

1-[(2R,4R)-2-(fluoromethyl)-2-methyl-7-(trifluoromethyl)-3,4-dihydro-2H-chromen-4-yl]-3-(3-methyl-2-oxo-1,2,3,4-tetrahydroquinazolin-7-yl)urea ¹H NMR (500 MHz, DMSO-d₆/D₂O) δ 1.30 (d, J=1.9 Hz, 3H), 1.85 (s, 2H), 1.96 (t, J=12.4 Hz, 1H), 2.11 (dd, J=13.1, 6.1 Hz, 1H), 2.86 (s, 3H), 4.33 (s, 2H), 4.45 (dd, J=19.1, 10.0 Hz, 1H), 4.55 (dd, J=19.6, 10.1 Hz, 1H), 5.10 (dd, J=11.6, 6.0 Hz, 1H), 6.92 (dd, J=8.2, 2.1 Hz, 1H), 6.98 (d, J=8.3 Hz, 1H), 7.01 (d, J=2.0 Hz, 1H), 7.11 (d, J=1.3 Hz, 1H), 7.28 (dd, J=8.2, 1.3 Hz, 1H), 7.48 (d, J=8.1 Hz, 1H). MS ESI⁻ m/z 465 (M−H)⁻.

Example 207

1-[(2R,4R)-2-(difluoromethyl)-2-methyl-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 1.36 (s, 3H), 1.89 (t, J=12.2 Hz, 1H), 2.13 (dd, J=12.9, 5.9 Hz, 1H), 2.86 (s, 3H), 4.33 (s, 2H), 5.03 (dd, J=11.5, 5.9 Hz, 1H), 6.10 (s, 1H), 6.84 (dd, J=8.2, 1.0 Hz, 1H), 6.91 (dd, J=8.2, 2.1 Hz, 1H), 6.97 (d, J=2.5 Hz, 1H), 6.98-7.00 (m, 2H), 7.21 (t, J=7.1 Hz, 1H), 7.28 (d, J=7.7 Hz, 1H). MS ESI⁻ m/z 415 (M−H)⁻.

Example 208

1-[(4R)-2,2-dimethyl-7-(trifluoromethyl)-3,4-dihydro-2H-pyrano[2,3-b]pyridin-4-yl]-3-(3-methyl-2-oxo-1,2,3,4-tetrahydroquinazolin-7-yl)urea $^1$H NMR (500 MHz, DMSO-d$_6$/D$_2$O) δ 1.35 (s, 3H), 1.48 (s, 3H), 1.84 (s, 2H), 1.89 (d, J=12.6 Hz, 1H), 2.18 (dd, J=13.3, 6.1 Hz, 1H), 2.85 (s, 3H), 4.33 (s, 2H), 5.06 (dd, J=11.7, 6.2 Hz, 1H), 6.91 (dd, J=8.2, 2.1 Hz, 1H), 6.98 (dd, J=8.7, 5.2 Hz, 2H), 7.47 (d, J=7.7 Hz, 1H), 7.91 (d, J=7.7 Hz, 1H). MS ESI⁻ m/z 448 (M−H)⁻.

Example 209

1-[(4R)-7-fluoro-2,2-bis(fluoromethyl)-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 1.96 (ddd, J=13.5, 10.7, 2.6 Hz, 1H), 2.27 (dd, J=13.7, 5.9 Hz, 1H), 2.85 (s, 3H), 4.33 (s, 2H), 4.54-4.62 (m, 2H), 4.63-4.72 (m, 2H), 4.96 (dd, J=10.4, 6.0 Hz, 1H), 6.74 (dd, J=10.3, 2.6 Hz, 1H), 6.83 (td, J=8.5, 2.6 Hz, 1H), 6.90 (dd, J=8.2, 2.1 Hz, 1H), 6.98 (t, J=5.2 Hz, 2H), 7.27-7.32 (m, 1H). MS ESI⁻ m/z 433 (M−H)⁻.

Example 210

1-[(4R)-8-fluoro-2,2-dimethyl-3,4-dihydro-2H-chromen-4-yl]-3-(3-methyl-2-oxo-1,2,3,4-tetrahydroquinazolin-7-yl)urea $^1$H NMR (500 MHz, DMSO-d$_6$/D$_2$O) δ 1.31 (s, 3H), 1.43 (s, 3H), 1.75-1.84 (m, 1H), 2.15 (dd, J=13.3, 6.2 Hz, 1H), 2.86 (s, 3H), 4.33 (s, 2H), 4.98 (dd, J=11.0, 6.2 Hz, 1H), 6.87 (dd, J=8.0, 3.0 Hz, 1H), 6.90 (dd, J=8.2, 2.1 Hz, 1H), 6.97 (s, 1H), 6.99 (d, J=2.2 Hz, 1H), 7.05-7.11 (m, 2H). MS ESI⁺ m/z 397 (M+H)⁺.

Example 211

1-[(4R)-2,2-bis(fluoromethyl)-7-(trifluoromethoxy)-3,4-dihydro-2H-chromen-4-yl]-3-(2-oxo-1,2,3,4-tetrahydroquinolin-7-yl)urea $^1$H NMR (500 MHz, DMSO-d$_6$/D$_2$O) δ 2.00 (ddd, J=13.7, 10.8, 2.9 Hz, 1H), 2.29 (dd, J=13.7, 6.0 Hz, 1H), 2.40-2.47 (m, 2H), 2.80 (t, J=7.5 Hz, 2H), 4.56-4.76 (m, 4H), 5.01 (dd, J=10.9, 6.0 Hz, 1H), 6.87 (d, J=2.3 Hz, 1H), 6.90-7.10 (m, 4H), 7.38 (d, J=8.6 Hz, 1H). MS ESI⁺ m/z 486 (M+H)⁺.

Example 212

1-[(2S,4R)-7-chloro-2-(difluoromethyl)-2-methyl-3,4-dihydro-2H-chromen-4-yl]-3-(2-oxo-1,2,3,4-tetrahydroquinolin-7-yl)urea $^1$H NMR (500 MHz, DMSO-d$_6$/D$_2$O) δ 1.21 (dd, J=13.9, 6.9 Hz, 1H), 1.40 (d, J=11.7 Hz, 4H), 1.87-1.99 (m, 1H), 2.39 (ddd, J=31.1, 20.0, 7.9 Hz, 3H), 2.80 (t, J=7.5 Hz, 2H), 3.61 (d, J=48.1 Hz, 1H), 4.97 (dd, J=10.2, 6.1 Hz, 1H), 6.16 (t, J=54.8 Hz, 1H), 6.88-6.99 (m, 2H), 7.00-7.13 (m, 3H), 7.27 (d, J=8.4 Hz, 1H). MS ESI⁺ m/z 436 (M+H)⁺.

Example 213

1-[(4R)-6-fluoro-2,2-bis(fluoromethyl)-3,4-dihydro-2H-chromen-4-yl]-3-(2-oxo-1,2,3,4-tetrahydroquinolin-7-yl)urea $^1$H NMR (500 MHz, DMSO-d$_6$/D$_2$O) δ 1.22 (t, J=7.1 Hz, 1H), 1.86-2.04 (m, 1H), 2.19 (dd, J=13.9, 6.1 Hz, 1H), 2.26 (dt, J=24.6, 12.4 Hz, 1H), 2.41-2.47 (m, 2H), 2.80 (t, J=7.5 Hz, 2H), 4.09 (q, J=7.0 Hz, 1H), 4.47-4.61 (m, 2H), 4.61-4.73 (m, 2H), 4.80 (dd, J=11.0, 5.5 Hz, 1H), 4.98 (dd, J=10.8, 5.9 Hz, 1H), 6.83-6.98 (m, 3H), 7.00-7.12 (m, 4H). MS ESI⁺ m/z 420 (M+H)⁺.

Example 214

1-[(4R)-6,8-difluoro-2,2-bis(fluoromethyl)-3,4-dihydro-2H-chromen-4-yl]-3-(2-oxo-1,2,3,4-tetrahydroquinolin-7-yl)urea $^1$H NMR (500 MHz, DMSO-d$_6$/D$_2$O) δ 1.97-2.07 (m, 1H), 2.32 (dd, J=13.8, 6.0 Hz, 1H), 2.43 (d, J=15.0 Hz, 2H), 2.80 (t, J=7.5 Hz, 2H), 4.55-4.77 (m, 4H), 4.95-5.06 (m, 1H), 6.87-6.96 (m, 2H), 7.06 (d, J=8.2 Hz, 2H), 7.08 (d, J=2.1 Hz, 1H), 7.22 (ddd, J=11.1, 8.4, 2.8 Hz, 1H). MS ESI⁺ m/z 438 (M+H)⁺.

Example 215

1-[(4R)-2,2-bis(fluoromethyl)-3,4-dihydro-2H-chromen-4-yl]-3-(2-oxo-1,2,3,4-tetrahydroquinolin-7-yl)urea $^1$H NMR (500 MHz, DMSO-d$_6$/D$_2$O) δ 1.95 (ddd, J=13.6, 10.6, 2.9 Hz, 1H), 2.27 (dd, J=13.7, 6.0 Hz, 1H), 2.40-2.47 (m, 2H), 2.80 (t, J=7.5 Hz, 2H), 4.51-4.63 (m, 2H), 4.60-4.72 (m, 2H), 5.00 (dd, J=10.5, 5.9 Hz, 1H), 6.88 (dd, J=8.2, 1.1 Hz, 1H), 6.93 (dd, J=8.1, 2.2 Hz, 1H), 6.98 (td, J=7.5, 1.2 Hz, 1H), 7.06 (d, J=8.2 Hz, 2H), 7.08 (d, J=2.1 Hz, 1H), 7.19-7.26 (m, 1H), 7.27 (d, J=7.8 Hz, 1H). MS ESI⁺ m/z 402 (M+H)⁺.

Example 216

1-[(4R)-8-fluoro-2,2-bis(fluoromethyl)-3,4-dihydro-2H-chromen-4-yl]-3-(2-oxo-1,2,3,4-tetrahydroquinolin-7-yl)urea $^1$H NMR (500 MHz, DMSO-d$_6$/D$_2$O) δ 1.21 (t, J=7.0 Hz, 2H), 1.97-2.07 (m, 1H), 2.37-2.49 (m, 1H), 2.80 (t, J=7.5 Hz, 1H), 4.08 (q, J=7.0 Hz, 1H), 4.54-4.77 (m, 4H), 6.90-7.20 (m, 6H). MS ESI⁺ m/z 420 (M+H)⁺.

Example 217

1-[(4S)-7-chloro-2,2-bis(fluoromethyl)-3,4-dihydro-2H-chromen-4-yl]-3-(2-oxo-1,2,3,4-tetrahydroquinolin-7-yl)urea ¹H NMR (500 MHz, DMSO-$d_6$/$D_2O$) δ 1.96 (ddd, J=13.7, 10.8, 2.8 Hz, 1H), 2.28 (dd, J=13.7, 6.0 Hz, 1H), 2.39-2.46 (m, 2H), 2.79 (t, J=7.5 Hz, 2H), 4.53-4.74 (m, 4H), 4.98 (dd, J=10.8, 5.9 Hz, 1H), 6.90-6.98 (m, 2H), 7.01-7.09 (m, 3H), 7.28 (dd, J=8.3, 1.0 Hz, 1H). MS ESI⁺ m/z 436 (M+H)⁺.

Example 218

1-[(4R)-2,2-dimethyl-8-(trifluoromethyl)-3,4-dihydro-2H-chromen-4-yl]-3-(2-oxo-1,2,3,4-tetrahydroquinolin-7-yl)urea ¹H NMR (500 MHz, DMSO-$d_6$/$D_2O$) δ 1.31 (s, 3H), 1.42 (s, 3H), 1.84 (dd, J=13.2, 11.3 Hz, 1H), 2.18 (dd, J=13.3, 6.3 Hz, 1H), 2.43 (dd, J=8.4, 6.8 Hz, 2H), 2.80 (t, J=7.5 Hz, 2H), 5.01 (dd, J=11.1, 6.3 Hz, 1H), 6.95 (dd, J=8.1, 2.1 Hz, 1H), 7.05 (dd, J=7.8, 6.3 Hz, 2H), 7.09 (d, J=2.1 Hz, 1H), 7.52 (dd, J=12.4, 7.7 Hz, 2H). MS ESI⁻ m/z 432 (M−H)⁻.

Example 219

1-[(4R)-8-fluoro-2,2-dimethyl-3,4-dihydro-2H-chromen-4-yl]-3-(2-oxo-1,2,3,4-tetrahydroquinolin-7-yl)urea ¹H NMR (500 MHz, DMSO-$d_6$/$D_2O$) δ 1.31 (s, 3H), 1.43 (d, J=8.8 Hz, 3H), 1.79 (dd, J=13.2, 11.3 Hz, 1H), 2.15 (dd, J=13.3, 6.2 Hz, 1H), 2.43 (dd, J=8.4, 6.7 Hz, 2H), 2.80 (t, J=7.5 Hz, 2H), 4.99 (dd, J=11.0, 6.2 Hz, 1H), 6.87 (td, J=8.0, 5.0 Hz, 1H), 6.94 (dd, J=8.1, 2.2 Hz, 1H), 7.02-7.12 (m, 4H). MS ESI⁻ m/z 382 (M−H)⁻.

Example 220

1-[(4R)-3,4-dihydro-2H-chromen-4-yl]-3-(2-oxo-1,2,3,4-tetrahydroquinolin-7-yl)urea ¹H NMR (500 MHz, DMSO-$d_6$/$D_2O$) δ 1.95 (dtd, J=9.2, 6.5, 2.9 Hz, 1H), 2.05-2.14 (m, 1H), 2.43 (dd, J=8.3, 6.8 Hz, 2H), 2.79 (t, J=7.5 Hz, 2H), 4.14 (ddd, J=11.3, 8.6, 2.8 Hz, 1H), 4.25 (ddd, J=10.1, 6.7, 3.1 Hz, 1H), 4.86 (t, J=5.6 Hz, 1H), 6.79 (dd, J=8.2, 1.1 Hz, 1H), 6.88-6.93 (m, 2H), 7.04 (t, J=5.0 Hz, 2H), 7.15-7.20 (m, 1H), 7.23-7.27 (m, 1H). MS ESI⁻ m/z 336 (M−H)⁻.

Example 221

1-[(4R)-7-fluoro-2,2-dimethyl-3,4-dihydro-2H-chromen-4-yl]-3-(2-oxo-1,2,3,4-tetrahydroquinolin-7-yl)urea ¹H NMR (500 MHz, DMSO-$d_6$/$D_2O$) δ 1.29 (s, 3H), 1.40 (s, 3H), 1.73 (dd, J=13.1, 11.2 Hz, 1H), 2.12 (dd, J=13.3, 6.2 Hz, 1H), 2.43 (dd, J=8.3, 6.8 Hz, 2H), 2.80 (t, J=7.5 Hz, 2H), 4.93 (dd, J=11.0, 6.2 Hz, 1H), 6.58 (dd, J=10.6, 2.6 Hz, 1H), 6.74 (td, J=8.5, 2.6 Hz, 1H), 6.94 (dd, J=8.1, 2.2 Hz, 1H), 7.05 (d, J=8.1 Hz, 1H), 7.07 (d, J=2.1 Hz, 1H), 7.24-7.29 (m, 1H). MS ESI⁻ m/z 382 (M−H)⁻.

Example 222

1-[(4R)-2,2-diethyl-8-fluoro-3,4-dihydro-2H-chromen-4-yl]-3-(2-oxo-1,2,3,4-tetrahydroquinolin-7-yl)urea ¹H NMR (500 MHz, DMSO-$d_6$/$D_2O$) δ 0.88 (t, J=7.5 Hz, 3H), 0.92 (t, J=7.5 Hz, 3H), 1.54-1.79 (m, 5H), 2.14 (dd, J=13.6, 6.1 Hz, 1H), 2.43 (dd, J=8.4, 6.7 Hz, 2H), 2.80 (t, J=7.5 Hz, 2H), 4.96 (dd, J=11.1, 6.1 Hz, 1H), 6.86 (td, J=8.0, 5.0 Hz, 1H), 6.92 (dd, J=8.1, 2.2 Hz, 1H), 7.03-7.11 (m, 4H). MS ESI⁻ m/z 410 (M−H)⁻.

Example 223

1-[(4R)-2,2-diethyl-3,4-dihydro-2H-chromen-4-yl]-3-(2-oxo-1,2,3,4-tetrahydroquinolin-7-yl)urea ¹H NMR (500 MHz, DMSO-$d_6$/$D_2O$) δ 0.87 (t, J=7.5 Hz, 3H), 0.91 (t, J=7.5 Hz, 3H), 1.49-1.72 (m, 5H), 2.11 (dd, J=13.4, 6.1 Hz, 1H), 2.41-2.45 (m, 2H), 2.80 (t, J=7.5 Hz, 2H), 4.93 (dd, J=11.1, 6.1 Hz, 1H), 6.76 (dd, J=8.2, 1.1 Hz, 1H), 6.88 (td, J=7.5, 1.2 Hz, 1H), 6.92 (dd, J=8.1, 2.2 Hz, 1H), 7.05 (d, J=8.2 Hz, 1H), 7.09 (d, J=2.1 Hz, 1H), 7.12-7.17 (m, 1H), 7.21-7.25 (m, 1H). MS ESI⁻ m/z 392 (M−H)⁻.

Example 224

1-[(4R)-2,2-diethyl-7-(trifluoromethyl)-3,4-dihydro-2H-chromen-4-yl]-3-(2-oxo-1,2,3,4-tetrahydroquinolin-7-yl)urea ¹H NMR (500 MHz, DMSO-$d_6$/$D_2O$) δ 0.88 (t, J=7.4 Hz, 3H), 0.92 (t, J=7.5 Hz, 3H), 1.53-1.80 (m, 6H), 2.14 (dd, J=13.5, 6.1 Hz, 1H), 2.40-2.46 (m, 3H), 2.76-2.83 (m, 3H), 4.99 (dd, J=11.4, 6.0 Hz, 1H), 6.93 (dd, J=8.1, 2.1 Hz, 1H), 7.06 (dd, J=9.5, 5.2 Hz, 3H), 7.10 (d, J=2.1 Hz, 1H), 7.23 (dd, J=8.1, 1.3 Hz, 1H), 7.46 (d, J=8.1 Hz, 1H). MS ESI⁻ m/z 460 (M−H)⁻.

Example 225

1-[(4R)-7-chloro-2,2-diethyl-3,4-dihydro-2H-chromen-4-yl]-3-(2-oxo-1,2,3,4-tetrahydroquinolin-7-yl)urea ¹H NMR (500 MHz, DMSO-$d_6$/$D_2O$) δ 0.87 (t, J=7.5 Hz, 3H), 0.90 (t, J=7.5 Hz, 3H), 1.49-1.59 (m, 1H), 1.60-1.74 (m, 4H), 2.11 (dd, J=13.5, 6.1 Hz, 1H), 2.40-2.45 (m, 3H), 2.78-2.81 (m, 2H), 4.90 (dd, J=11.1, 6.2 Hz, 1H), 6.82 (d, J=2.1 Hz, 1H), 6.91-6.95 (m, 2H), 7.02-7.07 (m, 1H), 7.09 (d, J=2.2 Hz, 1H), 7.25 (dd, J=8.4, 0.8 Hz, 1H). MS ESI⁻ m/z 426 (M−H)⁻.

Example 226

1-[(4R)-7,8-dichloro-2,2-diethyl-3,4-dihydro-2H-chromen-4-yl]-3-(2-oxo-1,2,3,4-tetrahydroquinolin-7-yl)urea ¹H NMR (500 MHz, DMSO-$d_6$/$D_2O$) δ 0.88 (t, J=7.5 Hz, 3H), 0.94 (t, J=7.5 Hz, 3H), 1.56 (dd, J=14.3, 7.4 Hz, 1H), 1.65 (dd, J=14.3, 7.4 Hz, 1H), 1.72 (dd, J=15.1, 7.6 Hz, 2H), 1.76-1.81 (m, 1H), 2.15 (dd, J=13.6, 6.2 Hz, 1H), 2.43 (dd, J=8.3, 6.8 Hz, 2H), 2.76-2.82 (m, 2H), 4.96 (dd, J=11.0, 6.3 Hz, 1H), 6.92 (dd, J=8.1, 2.2 Hz, 1H), 7.05 (d, J=8.1 Hz, 1H), 7.09 (d, J=2.1 Hz, 1H), 7.15 (d, J=8.4 Hz, 1H), 7.23 (dd, J=8.5, 1.0 Hz, 1H). MS ESI⁻ m/z 460 (M−H)⁻.

Example 227

1-[(4R)-6-fluoro-2,2-dipropyl-3,4-dihydro-2H-chromen-4-yl]-3-(2-oxo-1,2,3,4-tetrahydroquinolin-7-yl)urea ¹H NMR (500 MHz, DMSO-d₆/D₂O) δ 0.87 (t, J=7.3 Hz, 3H), 0.92 (t, J=7.3 Hz, 3H), 1.25-1.32 (m, 1H), 1.33-1.43 (m, 3H), 1.48-1.54 (m, 2H), 1.57-1.63 (m, 2H), 1.69 (dd, J=13.3, 11.5 Hz, 1H), 2.10 (dd, J=13.4, 6.1 Hz, 1H), 2.43 (dd, J=8.4, 6.7 Hz, 2H), 2.80 (t, J=7.5 Hz, 2H), 4.90 (dd, J=11.3, 6.1 Hz, 1H), 6.76 (dd, J=9.5, 4.9 Hz, 1H), 6.92 (dd, J=8.1, 2.2 Hz, 1H), 6.97-7.00 (m, 2H), 7.05 (d, J=8.1 Hz, 1H), 7.10 (d, J=2.1 Hz, 1H). MS ESI⁻ m/z 438 (M−H)⁻.

Example 228

1-[(4R)-6-fluoro-3,4-dihydrospiro[chromene-2,1'-cyclobutan]-4-yl]-3-(2-oxo-1,2,3,4-tetrahydroquinolin-7-yl)urea ¹H NMR (500 MHz, DMSO-d₆/D₂O) δ 1.69-1.77 (m, 1H), 1.81-1.87 (m, 2H), 2.05-2.20 (m, 3H), 2.29 (dd, J=20.2, 9.9 Hz, 1H), 2.36 (dd, J=13.2, 5.9 Hz, 1H), 2.43 (dd, J=8.3, 6.8 Hz, 2H), 2.80 (t, J=7.5 Hz, 2H), 4.94 (dd, J=10.4, 5.9 Hz, 1H), 6.81 (dd, J=8.9, 4.8 Hz, 1H), 6.94 (dd, J=8.1, 2.2 Hz, 1H), 6.96-6.99 (m, 1H), 6.99-7.02 (m, 1H), 7.06 (d, J=8.2 Hz, 1H), 7.09 (d, J=2.1 Hz, 1H). MS ESI⁻ m/z 394 (M−H)⁻.

Example 229

1-[(4R)-2,2-diethyl-6-fluoro-3,4-dihydro-2H-chromen-4-yl]-3-(2-oxo-1,2,3,4-tetrahydroquinolin-7-yl)urea ¹H NMR (500 MHz, DMSO-d₆/D₂O) δ 0.86 (t, J=7.5 Hz, 3H), 0.90 (t, J=7.5 Hz, 3H), 1.50-1.71 (m, 5H), 2.10 (dd, J=13.4, 6.2 Hz, 1H), 2.43 (dd, J=8.3, 6.7 Hz, 2H), 2.80 (t, J=7.5 Hz, 2H), 4.91 (dd, J=11.2, 6.2 Hz, 1H), 6.75-6.80 (m, 1H), 6.92 (dd, J=8.1, 2.2 Hz, 1H), 6.97-7.01 (m, 2H), 7.05 (d, J=8.2 Hz, 1H), 7.10 (d, J=2.1 Hz, 1H). MS ESI⁻ m/z 410 (M−H)⁻.

Example 230

1-[(4R)-8-fluoro-2,2-dipropyl-3,4-dihydro-2H-chromen-4-yl]-3-(2-oxo-1,2,3,4-tetrahydroquinolin-7-yl)urea ¹H NMR (500 MHz, DMSO-d₆/D₂O) δ 0.85-0.90 (m, 3H), 0.93 (t, J=7.3 Hz, 3H), 1.25-1.44 (m, 4H), 1.52-1.58 (m, 2H), 1.62-1.69 (m, 2H), 1.76 (dd, J=13.5, 11.4 Hz, 1H), 2.13 (dd, J=13.5, 6.1 Hz, 1H), 2.41-2.46 (m, 2H), 2.80 (dd, J=13.6, 6.8 Hz, 2H), 4.95 (dd, J=11.2, 6.0 Hz, 1H), 6.87 (dd, J=8.0, 5.0 Hz, 1H), 6.92 (dd, J=8.1, 2.2 Hz, 1H), 7.03-7.10 (m, 4H). MS ESI⁻ m/z 438 (M−H)⁻.

Example 231

1-[(4R)-7-chloro-8-fluoro-2,2-bis(fluoromethyl)-3,4-dihydro-2H-chromen-4-yl]-3-(2-oxo-1,2,3,4-tetrahydroquinolin-7-yl)urea ¹H NMR (500 MHz, DMSO-d₆/D₂O) δ 2.00-2.07 (m, 1H), 2.32 (dd, J=13.7, 6.0 Hz, 1H), 2.43 (dd, J=8.3, 6.7 Hz, 2H), 2.80 (t, J=7.5 Hz, 2H), 4.60-4.68 (m, 2H), 4.70-4.78 (m, 2H), 5.02 (dd, J=11.0, 6.0 Hz, 1H), 6.93 (dd, J=8.1, 2.2 Hz, 1H), 7.05 (d, J=8.1 Hz, 1H), 7.07 (d, J=2.1 Hz, 1H), 7.10 (d, J=8.7 Hz, 1H), 7.15 (dd, J=8.6, 6.3 Hz, 1H). MS ESI⁻ m/z 452 (M−H)⁻.

Example 232

1-[(4R)-6-fluoro-2,2-dimethyl-3,4-dihydro-2H-chromen-4-yl]-3-(2-oxo-1,2,3,4-tetrahydroquinolin-7-yl)urea ¹H NMR (500 MHz, DMSO-d₆/D₂O) δ 1.27 (s, 3H), 1.39 (s, 3H), 1.72 (dd, J=13.0, 11.4 Hz, 1H), 2.11 (dd, J=13.2, 6.3 Hz, 1H), 2.43 (dd, J=8.3, 6.7 Hz, 2H), 2.80 (t, J=7.5 Hz, 2H), 4.94 (dd, J=11.0, 6.3 Hz, 1H), 6.77 (ddd, J=9.5, 4.0, 2.3 Hz, 1H), 6.94 (dd, J=8.1, 2.1 Hz, 1H), 6.98-7.01 (m, 2H), 7.05 (d, J=8.2 Hz, 1H), 7.08 (d, J=2.1 Hz, 1H). MS ESI⁻ m/z 382 (M−H)⁻.

Example 233

1-[(4R)-8-chloro-7-fluoro-2,2-dimethyl-3,4-dihydro-2H-chromen-4-yl]-3-(2-oxo-1,2,3,4-tetrahydroquinolin-7-yl)urea ¹H NMR (500 MHz, DMSO-d₆/D₂O) δ 1.31 (s, 3H), 1.46 (s, 3H), 1.80 (dd, J=13.2, 11.4 Hz, 1H), 2.16 (dd, J=13.3, 6.2 Hz, 1H), 2.43 (dd, J=8.4, 6.8 Hz, 2H), 2.80 (t, J=7.5 Hz, 2H), 4.97 (dd, J=11.1, 6.2 Hz, 1H), 6.92-6.96 (m, 2H), 7.05 (d, J=8.2 Hz, 1H), 7.07 (d, J=2.1 Hz, 1H), 7.25 (ddd, J=8.7, 6.4, 0.9 Hz, 1H). MS ESI⁻ m/z 416 (M−H)⁻.

Example 234

1-(2-oxo-1,2,3,4-tetrahydroquinolin-7-yl)-3-[(4S)-7-(trifluoromethoxy)-3,4-dihydro-2H-chromen-4-yl]urea ¹H NMR (500 MHz, DMSO-d₆/D₂O) δ 1.93-2.01 (m, 1H), 2.08-2.15 (m, 1H), 2.43 (dd, J=8.3, 6.7 Hz, 2H), 2.79 (t, J=7.5 Hz, 2H), 4.20 (ddd, J=11.2, 8.3, 2.9 Hz, 1H), 4.31 (ddd, J=10.4, 7.0, 3.1 Hz, 1H), 4.89 (t, J=5.7 Hz, 1H), 6.79 (d, J=1.5 Hz, 1H), 6.90-6.92 (m, 2H), 7.05 (t, J=5.5 Hz, 2H), 7.38 (dd, J=8.6, 0.5 Hz, 1H). MS ESI⁻ m/z 420 (M−H)⁻.

Example 235

1-[(4R)-7-chloro-2,2-dimethyl-3,4-dihydro-2H-chromen-4-yl]-3-(2-oxo-1,2,3,4-tetrahydroquinolin-7-yl)urea ¹H NMR (500 MHz, DMSO-d₆/D₂O) δ 1.28 (s, 3H), 1.40 (s, 3H), 1.74 (dd, J=13.1, 11.4 Hz, 1H), 2.12 (dd, J=13.2, 6.2 Hz, 1H), 2.43 (dd, J=8.3, 6.7 Hz, 2H), 2.77-2.82 (m, 2H), 4.93 (dd, J=10.7, 6.3 Hz, 1H), 6.80 (d, J=2.2 Hz, 1H), 6.92-6.96 (m, 2H), 7.05 (d, J=8.2 Hz, 1H), 7.07 (d, J=2.2 Hz, 1H), 7.25 (dd, J=8.3, 1.0 Hz, 1H). MS ESI⁻ m/z 398 (M−H)⁻.

Example 236

1-(2-oxo-1,2,3,4-tetrahydroquinolin-7-yl)-3-[(4R)-7-(trifluoromethoxy)-3,4-dihydro-2H-chromen-4-yl]urea ¹H NMR (500 MHz, DMSO-d₆/D₂O) δ 1.94-2.01 (m, 1H), 2.08-2.15 (m, 1H), 2.43 (dd, J=8.3, 6.7 Hz, 2H), 2.79 (t, J=7.5

Hz, 2H), 4.20 (ddd, J=11.2, 8.3, 2.9 Hz, 1H), 4.31 (ddd, J=10.4, 6.9, 3.1 Hz, 1H), 4.89 (t, J=5.7 Hz, 1H), 6.79 (d, J=1.4 Hz, 1H), 6.91 (ddd, J=8.5, 3.6, 1.6 Hz, 2H), 7.05 (dd, J=6.6, 5.2 Hz, 2H), 7.38 (dd, J=8.6, 0.4 Hz, 1H). MS ESI⁻ m/z 420 (M−H)⁻.

Example 237

1-[(4R)-6-fluoro-2,2-bis(methoxymethyl)-3,4-dihydro-2H-chromen-4-yl]-3-(2-oxo-1,2,3,4-tetrahydroquinolin-7-yl)urea ¹H NMR (500 MHz, DMSO-d₆/D₂O) δ 1.85 (dd, J=13.4, 11.4 Hz, 1H), 2.15 (dd, J=13.4, 6.0 Hz, 1H), 2.41-2.45 (m, 2H), 2.80 (t, J=7.5 Hz, 2H), 3.28 (s, 3H), 3.32 (s, 3H), 3.43 (dd, J=22.2, 10.1 Hz, 2H), 3.48 (s, 2H), 4.94 (dd, J=11.2, 6.0 Hz, 1H), 6.82 (dd, J=8.9, 4.8 Hz, 1H), 6.92 (dd, J=8.1, 2.2 Hz, 1H), 6.95-7.03 (m, 2H), 7.06 (dd, J=8.5, 5.2 Hz, 1H), 7.10 (d, J=2.1 Hz, 1H). MS ESI⁻ m/z 442 (M−H)⁻.

Example 238

1-(2-oxo-1,2,3,4-tetrahydroquinolin-7-yl)-3-[(4R)-8-(trifluoromethyl)-3,4-dihydro-2H-chromen-4-yl]urea ¹H NMR (500 MHz, DMSO-d₆/D₂O) δ 1.98-2.05 (m, 1H), 2.12-2.19 (m, 1H), 2.40-2.45 (m, 3H), 2.77-2.81 (m, 2H), 4.28 (ddd, J=11.1, 8.3, 3.0 Hz, 1H), 4.40 (ddd, J=10.5, 7.0, 3.2 Hz, 1H), 4.95 (t, J=5.8 Hz, 1H), 6.91 (dd, J=8.1, 2.2 Hz, 1H), 7.03-7.09 (m, 3H), 7.54 (t, J=7.1 Hz, 2H). MS ESI⁻ m/z 404 (M−H)⁻.

Example 239

1-(2-oxo-1,2,3,4-tetrahydroquinolin-7-yl)-3-[(4R)-7-(trifluoromethyl)-3,4-dihydro-2H-chromen-4-yl]urea ¹H NMR (500 MHz, DMSO-d₆/D₂O) δ 1.96-2.03 (m, 1H), 2.11-2.19 (m, 1H), 2.43 (dd, J=8.3, 6.8 Hz, 2H), 2.77-2.82 (m, 2H), 4.24 (ddd, J=11.1, 7.7, 3.0 Hz, 1H), 4.34 (ddd, J=10.8, 7.5, 3.0 Hz, 1H), 4.96 (t, J=6.0 Hz, 1H), 6.92 (dd, J=8.1, 2.2 Hz, 1H), 7.02-7.09 (m, 2H), 7.11 (d, J=1.5 Hz, 1H), 7.25 (dd, J=8.0, 1.3 Hz, 1H), 7.48 (d, J=8.0 Hz, 1H). MS ESI⁻ m/z 404 (M−H)⁻.

Example 240

1-[(1R)-5-fluoro-2,3-dihydro-1H-inden-1-yl]-3-(2-oxo-1,2,3,4-tetrahydroquinolin-7-yl)urea ¹H NMR (500 MHz, DMSO-d₆/D₂O) δ 1.80 (dq, J=12.6, 8.5 Hz, 1H), 2.43 (dd, J=8.3, 6.7 Hz, 2H), 2.45-2.50 (m, 1H), 2.79 (t, J=7.4 Hz, 2H), 2.91-2.97 (m, 1H), 5.12 (t, J=7.6 Hz, 1H), 6.91 (dd, J=8.1, 2.2 Hz, 1H), 7.01 (dd, J=8.6, 2.4 Hz, 1H), 7.02-7.05 (m, 1H), 7.06 (dd, J=6.2, 2.1 Hz, 1H), 7.09 (dd, J=9.1, 2.4 Hz, 1H), 7.28 (dd, J=8.2, 5.5 Hz, 1H). MS ESI⁻ m/z 338 (M−H)⁻.

Example 241

1-[(2R,4R)-7-chloro-2-(fluoromethyl)-2-methyl-3,4-dihydro-2H-chromen-4-yl]-3-(2-oxo-1,2,3,4-tetrahydroquinolin-7-yl)urea ¹H NMR (500 MHz, DMSO-d₆/D₂O) δ 1.28 (d, J=2.0 Hz, 3H), 1.88 (t, J=12.3 Hz, 1H), 2.08 (dd, J=13.1, 6.1 Hz, 1H), 2.43 (dd, J=8.3, 6.7 Hz, 2H), 2.80 (t, J=7.5 Hz, 2H), 4.43 (q, J=10.0 Hz, 1H), 4.52 (q, J=10.0 Hz, 1H), 5.02 (dd, J=11.5, 6.1 Hz, 1H), 6.87 (d, J=2.1 Hz, 1H), 6.94 (dd, J=8.1, 2.2 Hz, 1H), 6.99 (dd, J=8.3, 2.1 Hz, 1H), 7.05 (d, J=8.1 Hz, 1H), 7.08 (d, J=2.1 Hz, 1H), 7.27 (dd, J=8.3, 0.9 Hz, 1H). MS ESI⁻ m/z 416 (M−H)⁻.

Example 242

1-[(4S)-6-fluoro-3,4-dihydrospiro[chromene-2,1'-cyclobutan]-4-yl]-3-(2-oxo-1,2,3,4-tetrahydroquinolin-7-yl)urea ¹H NMR (500 MHz, DMSO-d₆/D₂O) δ 1.69-1.77 (m, 1H), 1.81-1.87 (m, 2H), 2.05-2.20 (m, 3H), 2.29 (dd, J=20.2, 9.9 Hz, 1H), 2.36 (dd, J=13.2, 5.9 Hz, 1H), 2.43 (dd, J=8.1, 6.6 Hz, 2H), 2.80 (t, J=7.5 Hz, 2H), 4.93 (dd, J=10.4, 5.9 Hz, 1H), 6.81 (dd, J=8.9, 4.8 Hz, 1H), 6.94 (dd, J=8.1, 2.2 Hz, 1H), 6.97 (dd, J=9.3, 2.2 Hz, 1H), 7.01 (dd, J=8.3, 3.1 Hz, 1H), 7.06 (d, J=8.2 Hz, 1H), 7.09 (d, J=2.1 Hz, 1H). MS ESI⁻ m/z 394 (M−H)⁻.

Example 243

1-[(4S)-6-fluoro-2,2-dimethyl-3,4-dihydro-2H-chromen-4-yl]-3-(2-oxo-1,2,3,4-tetrahydroquinolin-7-yl)urea ¹H NMR (500 MHz, DMSO-d₆/D₂O) δ 1.27 (s, 3H), 1.39 (s, 3H), 1.72 (dd, J=13.0, 11.4 Hz, 1H), 2.11 (dd, J=13.2, 6.3 Hz, 1H), 2.43 (dd, J=8.3, 6.8 Hz, 2H), 2.80 (t, J=7.5 Hz, 2H), 4.93 (dd, J=11.0, 6.3 Hz, 1H), 6.75-6.78 (m, 1H), 6.94 (dd, J=8.1, 2.2 Hz, 1H), 6.98-7.01 (m, 2H), 7.05 (d, J=8.1 Hz, 1H), 7.08 (d, J=2.1 Hz, 1H). MS ESI⁻ m/z 382 (M−H)⁻.

Example 244

1-[(4R)-3,4-dihydrospiro[chromene-2,1'-cyclopentan]-4-yl]-3-(2-oxo-1,2,3,4-tetrahydroquinolin-7-yl)urea ¹H NMR (500 MHz, DMSO-d₆/D₂O) δ 1.60-1.85 (m, 8H), 1.86-1.91 (m, 1H), 1.95 (dd, J=13.2, 10.1 Hz, 1H), 2.13 (dd, J=13.2, 6.1 Hz, 1H), 2.43 (dd, J=8.4, 6.7 Hz, 2H), 2.77-2.82 (m, 2H), 4.96 (dd, J=10.0, 6.1 Hz, 1H), 6.73 (dd, J=8.2, 1.1 Hz, 1H), 6.89 (td, J=7.6, 1.2 Hz, 1H), 6.93 (dd, J=8.0, 2.0 Hz, 1H), 7.05 (d, J=8.2 Hz, 1H), 7.07 (d, J=2.2 Hz, 1H), 7.12-7.17 (m, 1H), 7.22-7.25 (m, 1H). MS ESI⁻ m/z 390 (M−H)⁻.

Example 245

1-[(2S,4R)-2-methyl-2-(trifluoromethyl)-3,4-dihydro-2H-chromen-4-yl]-3-(2-oxo-1,2,3,4-tetrahydroquinolin-7-yl)urea ¹H NMR (500 MHz, DMSO-d₆/D₂O) δ 1.56 (s, 3H), 2.08 (dd, J=13.9, 10.2 Hz, 1H), 2.41-2.45 (m, 2H), 2.80 (t, J=7.5 Hz, 2H), 4.99 (dd, J=9.7, 6.1 Hz, 1H), 6.90-6.95 (m, 2H), 7.02 (td, J=7.5, 1.1 Hz, 1H), 7.06 (dd, J=8.6, 5.2 Hz, 1H), 7.09 (d, J=2.2 Hz, 1H), 7.22-7.26 (m, 1H), 7.28-7.30 (m, 1H). MS ESI⁻ m/z 418 (M−H)⁻.

Example 246

1-[(2S,4R)-7-chloro-2-(fluoromethyl)-2-methyl-3,4-dihydro-2H-chromen-4-yl]-3-(2-oxo-1,2,3,4-tetrahydroquinolin-7-yl)urea ¹H NMR (500 MHz, DMSO-d₆/D₂O) δ 1.37 (d, J=1.9 Hz, 3H), 1.83-1.90 (m, 1H), 2.31 (dd, J=13.8, 6.2 Hz, 1H), 2.40-

2.46 (m, 3H), 2.77-2.81 (m, 2H), 4.43 (q, J=20.5, 10.0 Hz, 1H), 4.53 (q, J=20.6, 9.9 Hz, 1H), 4.93 (dd, J=9.9, 6.3 Hz, 1H), 6.89 (d, J=2.1 Hz, 1H), 6.93 (dd, J=8.1, 2.1 Hz, 1H), 6.99 (dd, J=8.3, 2.1 Hz, 1H), 7.03-7.08 (m, 2H), 7.26 (dd, J=8.3, 0.9 Hz, 1H). MS ESI⁻ m/z 416 (M−H)⁻.

Example 247

1-[(4R)-2,2-dimethyl-7-(trifluoromethyl)-3,4-dihydro-2H-pyrano[2,3-b]pyridin-4-yl]-3-(2-oxo-1,2,3,4-tetrahydroquinolin-7-yl)urea $^1$H NMR (500 MHz, DMSO-d$_6$/D$_2$O) δ 1.35 (s, 3H), 1.48 (s, 3H), 1.84-1.91 (m, 1H), 2.18 (dd, J=13.3, 6.1 Hz, 1H), 2.43 (dd, J=8.4, 6.7 Hz, 2H), 2.80 (t, J=7.5 Hz, 2H), 5.06 (dd, J=11.7, 6.1 Hz, 1H), 6.94 (dd, J=8.1, 2.2 Hz, 1H), 7.05 (d, J=8.2 Hz, 1H), 7.07 (dd, J=5.1, 2.2 Hz, 1H), 7.47 (d, J=7.7 Hz, 1H), 7.91 (d, J=7.8 Hz, 1H). MS ESI⁻ m/z 433 (M−H)⁻.

Example 248

1-[(2S,4R)-2-(difluoromethyl)-2-methyl-3,4-dihydro-2H-chromen-4-yl]-3-(2-oxo-1,2,3,4-tetrahydroquinolin-7-yl)urea $^1$H NMR (500 MHz, DMSO-d$_6$/D$_2$O) δ 1.40 (s, 3H), 1.92 (dd, J=14.0, 9.9 Hz, 1H), 2.39 (dd, J=14.1, 6.1 Hz, 1H), 2.43 (dd, J=8.4, 6.7 Hz, 2H), 2.80 (t, J=7.5 Hz, 2H), 5.00 (dd, J=9.6, 6.1 Hz, 1H), 6.86 (dd, J=8.2, 1.1 Hz, 1H), 6.93 (dd, J=8.1, 2.2 Hz, 1H), 6.97 (td, J=7.5, 1.1 Hz, 1H), 7.05 (d, J=8.2 Hz, 1H), 7.08 (d, J=2.1 Hz, 1H), 7.19-7.23 (m, 1H), 7.26-7.28 (m, 1H). MS ESI⁻ m/z 400 (M−H)⁻.

Example 249

1-[(2R,4R)-2-(difluoromethyl)-2-methyl-3,4-dihydro-2H-chromen-4-yl]-3-(2-oxo-1,2,3,4-tetrahydroquinolin-7-yl)urea $^1$H NMR (500 MHz, DMSO-d$_6$/D$_2$O) δ 1.36 (s, 3H), 1.90 (t, J=12.3 Hz, 1H), 2.13 (dd, J=12.9, 5.9 Hz, 1H), 2.43 (dd, J=8.3, 6.8 Hz, 2H), 2.80 (t, J=7.5 Hz, 2H), 5.03 (dd, J=11.5, 5.9 Hz, 1H), 6.84 (dd, J=8.2, 1.1 Hz, 1H), 6.94 (dd, J=8.1, 2.2 Hz, 1H), 6.98 (td, J=7.6, 1.2 Hz, 1H), 7.06 (dd, J=7.1, 5.2 Hz, 1H), 7.09 (d, J=2.1 Hz, 1H), 7.20-7.24 (m, 1H), 7.28 (d, J=7.7 Hz, 1H). MS ESI⁻ m/z 400 (M−H)⁻.

Example 250

1-[(4R)-7-fluoro-2,2-bis(fluoromethyl)-3,4-dihydro-2H-chromen-4-yl]-3-(2-oxo-1,2,3,4-tetrahydroquinolin-7-yl)urea $^1$H NMR (500 MHz, DMSO-d$_6$/D$_2$O) δ 1.96 (ddd, J=13.5, 10.7, 2.7 Hz, 1H), 2.27 (dd, J=13.7, 5.9 Hz, 1H), 2.43 (dd, J=8.4, 6.7 Hz, 3H), 2.80 (t, J=7.4 Hz, 3H), 4.53-4.62 (m, 2H), 4.63-4.72 (m, 2H), 4.97 (dd, J=10.4, 6.0 Hz, 1H), 6.74 (dd, J=10.3, 2.6 Hz, 1H), 6.83 (td, J=8.5, 2.6 Hz, 1H), 6.93 (dd, J=8.0, 2.2 Hz, 1H), 7.05 (d, J=8.1 Hz, 1H), 7.06-7.08 (m, 1H), 7.27-7.32 (m, 1H). MS ESI⁻ m/z 418 (M−H)⁻.

Example 251

1-[(1R)-5-chloro-2,3-dihydro-1H-inden-1-yl]-3-(2-oxo-1,2,3,4-tetrahydroquinolin-7-yl)urea $^1$H NMR (300 MHz, DMSO-d$_6$) δ ppm 1.78 (dq, J=12.5, 8.7 Hz, 1H), 2.36-2.48 (m, 3H), 2.71-2.99 (m, 4H), 5.12 (q, J=7.8 Hz, 1H), 6.43 (d, J=8.0 Hz, 1H), 6.93 (dd, J=8.1, 2.0 Hz, 1H), 7.00 (d, J=8.2 Hz, 1H), 7.03 (d, J=2.0 Hz, 1H), 7.20-7.34 (m, 3H), 8.35 (s, 1H), 9.99 (s, 1H); MS (ESI) m/z 356 (M+H)⁺.

Example 252

1-[(4R)-7-chloro-2,2-bis(fluoromethyl)-3,4-dihydro-2H-chromen-4-yl]-3-(2-oxo-1,2,3,4-tetrahydroquinolin-7-yl)thiourea

Example 252A 7-isothiocyanato-3,4-dihydroquinolin-2(1H)-one

A solution of 7-amino-3,4-dihydroquinolin-2(1H)-one (0.20 g, 1.2 mmol) in DMF (5.2 mL) was added dropwise to a solution of 1,1'-thiocarbonyldiimidazole (0.22 g, 1.2 mmol) in DMF (2.1 mL) at room temperature over 1 hour. The mixture was stirred for 30 minutes and then water was slowly added. The resulting precipitate was collected by filtration (rinsed with water) and dried under vacuum to afford the title compound (0.21 g, 83% yield), which was used without purification.

Example 252B

1-[(4R)-7-chloro-2,2-bis(fluoromethyl)-3,4-dihydro-2H-chromen-4-yl]-3-(2-oxo-1,2,3,4-tetrahydroquinolin-7-yl)thiourea To a slurry of (R)-7-chloro-2,2-bis(fluoromethyl)chroman-4-aminium (2S,3S)-3-carboxy-2,3-dihydroxypropanoate (0.20 g, 0.51 mmol) in CH$_2$Cl$_2$ (1.3 mL) was added the product of Example 252A (0.10 g, 0.51 mmol) and diisopropylethyl amine (0.088 mL, 0.51 mmol). The mixture was stirred at ambient temperature overnight then placed directly onto a silica gel column. Elution with a 20-60% EtOAc/hexane gradient afforded the title compound (0.18 g, 76% yield). $^1$H NMR (300 MHz, DMSO-d$_6$) δ ppm 10.12 (s, 1H), 9.63 (s, 1H), 7.98 (d, J=8.1 Hz, 1H), 7.28 (d, J=8.3 Hz, 1H), 7.11 (d, J=8.1 Hz, 1H), 7.03 (dd, J=8.3, 2.1 Hz, 1H), 6.99-6.92 (m, 2H), 6.90 (d, J=1.9 Hz, 1H), 5.84-5.73 (m, 1H), 4.77-4.62 (m, 2H), 4.58-4.50 (m, 2H), 2.83 (dd, J=8.4, 6.6 Hz, 2H), 2.43 (dd, J=8.4, 6.7 Hz, 2H), 2.34 (dd, J=13.5, 5.8 Hz, 1H), 2.12-2.00 (m, 1H); MS (ESI) m/z: 451.9 (M+H)⁺.

Example 253

1-[(4R)-7-fluoro-2,2-dimethyl-3,4-dihydro-2H-chromen-4-yl]-3-(1-methyl-2-oxo-1,2,3,4-tetrahydroquinolin-7-yl)urea $^1$H NMR (300 MHz, DMSO) δ 8.54 (s, 1H), 7.34 (d, J=1.9 Hz, 1H), 7.32-7.23 (m, 1H), 7.07 (d, J=8.1 Hz, 1H), 6.97 (dd, J=8.0, 1.9 Hz, 1H), 6.73 (td, J=8.5, 2.6 Hz, 1H), 6.58 (dd, J=10.6, 2.6 Hz, 1H), 6.49 (d, J=8.6 Hz, 1H), 5.01-4.88 (m, 1H), 4.13-3.97 (m, 1H), 3.22 (s, 3H), 3.20-3.14 (m, 1H), 2.78 (d, J=14.4 Hz, 1H), 1.74 (dd, J=13.2, 11.0 Hz, 1H), 1.40 (s, 3H), 1.28 (s, 3H). MS (ESI⁺) M/Z 398 (M+H)⁺.

Example 254

1-[(4R)-7-chloro-2,2-bis(fluoromethyl)-3,4-dihydro-2H-chromen-4-yl]-3-(1-methyl-2-oxo-1,2,3,4-tetrahydroquinolin-5-yl)urea $^1$H NMR (300 MHz, DMSO) δ 7.99 (s, 1H), 7.54-7.40 (m, 1H), 7.31 (dd, J=8.3, 0.8 Hz, 1H), 7.19 (t, J=8.2 Hz, 1H), 7.05

(dd, J=8.3, 2.1 Hz, 1H), 6.97 (d, J=2.1 Hz, 1H), 6.84 (t, J=7.1 Hz, 2H), 4.97 (dd, J=16.2, 8.6 Hz, 1H), 4.81-4.49 (m, 4H), 3.25 (s, 3H), 2.75 (dd, J=8.5, 6.1 Hz, 2H), 2.61-2.52 (m, 2H), 2.29 (dd, J=13.8, 5.8 Hz, 1H), 1.94 (dd, J=13.6, 2.7 Hz, 1H); MS (ESI) m/z 450 (M+H)$^+$.

Example 255

1-[(4R)-7-chloro-2,2-bis(fluoromethyl)-3,4-dihydro-2H-chromen-4-yl]-3-(1-methyl-2-oxo-1,2,3,4-tetrahydroquinolin-7-yl)urea $^1$H NMR (500 MHz, DMSO-d$_6$) δ ppm 1.27 (s, 3H) 1.40 (s, 3H) 1.71-1.80 (m, J=11.29 Hz, 1H) 2.17 (dd, J=13.27, 6.26 Hz, 1H) 3.62 (s, 3H) 4.92-5.02 (m, 1H) 6.65 (d, J=9.76 Hz, 1H) 6.78 (dd, J=8.85, 4.88 Hz, 1H) 6.90 (d, J=8.24 Hz, 1H) 7.01 (td, J=8.47, 3.20 Hz, 1H) 7.09 (dd, J=9.46, 2.44 Hz, 1H) 7.21 (d, J=8.54 Hz, 1H) 7.55 (t, J=8.24 Hz, 1H) 7.74 (d, J=7.93 Hz, 1H) 8.05 (d, J=10.07 Hz, 1H) 8.65 (s, 1H); MS (ESI) m/z: 450 (M+H)$^+$.

Example 256

1-[(4R)-2,2-dimethyl-8-(trifluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ ppm 1.31 (s, 3H), 1.43 (s, 3H), 1.80-1.89 (m, 1H), 2.18 (dd, J=13.3, 6.3 Hz, 1H), 2.75-2.82 (m, 2H), 3.23 (s, 3H), 3.73 (s, 2H), 4.99-5.07 (m, 1H), 7.00 (dd, J=8.0, 2.0 Hz, 1H), 7.05 (t, J=7.7 Hz, 1H), 7.10 (d, J=8.1 Hz, 1H), 7.34 (d, J=2.0 Hz, 1H), 7.52 (t, J=8.5 Hz, 2H). MS ESI$^-$ m/z 446.1 (M−H)$^-$.

Example 257

1-[(4R)-8-fluoro-2,2-dimethyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.31 (s, 3H), 1.44 (s, 3H), 1.81 (dd, J=13.0, 11.5 Hz, 1H), 2.15 (dd, J=13.3, 6.2 Hz, 1H), 2.50 (s, 1H), 2.76-2.81 (m, 2H), 3.23 (s, 3H), 5.01 (dd, J=11.1, 6.2 Hz, 1H), 6.87 (td, J=8.0, 5.0 Hz, 1H), 6.99 (dd, J=8.1, 2.0 Hz, 1H), 7.09 (dd, J=10.6, 8.2 Hz, 3H), 7.34 (d, J=1.9 Hz, 1H). MS ESI$^-$ m/z 396.1 (M−H)$^-$.

Example 258

1-[(4R)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.96 (dtd, J=9.3, 6.5, 2.9 Hz, 1H), 2.10 (ddd, J=13.6, 9.4, 4.2 Hz, 1H), 2.50 (s, 1H), 2.75-2.81 (m, 2H), 3.23 (s, 3H), 4.15 (ddd, J=11.2, 8.4, 2.9 Hz, 1H), 4.26 (ddd, J=10.1, 6.7, 3.2 Hz, 1H), 4.89 (t, J=5.6 Hz, 1H), 6.80 (dd, J=8.2, 0.9 Hz, 1H), 6.91 (td, J=7.5, 1.1 Hz, 1H), 6.96 (dd, J=8.0, 2.0 Hz, 1H), 7.09 (d, J=8.1 Hz, 1H), 7.15-7.21 (m, 1H), 7.25 (d, J=7.7 Hz, 1H), 7.31 (d, J=2.0 Hz, 1H). MS ESI$^-$ m/z 350.0 (M−H)$^-$.

Example 259

1-[(4R)-2,2-diethyl-8-fluoro-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.89-2.00 (m, 1H), 2.11 (ddd, J=13.6, 8.3, 3.2 Hz, 1H), 2.50 (s, 1H), 2.75-2.81 (m, 2H), 3.23 (s, 3H), 4.01-4.09 (m, 1H), 4.12-4.20 (m, 2H), 4.25 (ddd, J=10.1, 6.7, 3.1 Hz, 1H), 4.89 (t, J=5.6 Hz, 1H), 6.80 (dd, J=8.2, 1.0 Hz, 1H), 6.91 (td, J=7.5, 1.1 Hz, 1H), 6.96 (dd, J=8.0, 2.0 Hz, 1H), 7.09 (d, J=8.1 Hz, 1H), 7.15-7.21 (m, 2H), 7.25 (d, J=7.7 Hz, 1H), 7.31 (d, J=2.0 Hz, 1H). MS ESI$^+$ m/z 426.0 (M+H)$^+$.

Example 260

1-[(4R)-2,2-diethyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 0.90 (dt, J=16.6, 7.5 Hz, 6H), 1.51-1.65 (m, 2H), 1.66-1.72 (m, 2H), 1.74-1.81 (m, 1H), 2.14 (dd, J=13.5, 6.2 Hz, 1H), 2.50 (s, 1H), 2.74-2.82 (m, 2H), 3.23 (s, 3H), 4.99 (dd, J=11.2, 6.1 Hz, 1H), 6.86 (td, J=8.0, 5.0 Hz, 1H), 6.99 (dd, J=8.0, 2.0 Hz, 1H), 7.08 (dd, J=12.8, 8.1 Hz, 3H), 7.32 (d, J=2.0 Hz, 1H). MS ESI$^+$ m/z 408.1 (M+H)$^+$.

Example 261

1-[(4R)-2,2-diethyl-7-(trifluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 0.86-0.95 (m, 6H), 1.53-1.61 (m, 1H), 1.61-1.67 (m, 1H), 1.69 (dd, J=7.4, 3.1 Hz, 2H), 1.78 (dd, J=13.2, 11.8 Hz, 1H), 2.09-2.17 (m, 1H), 2.50 (s, 2H), 2.79 (t, J=7.3 Hz, 2H), 3.23 (s, 3H), 4.98-5.05 (m, 1H), 7.01 (dd, J=8.1, 1.9 Hz, 1H), 7.06 (d, J=1.1 Hz, 1H), 7.10 (d, J=8.1 Hz, 1H), 7.23 (dd, J=7.9, 1.0 Hz, 1H), 7.33 (d, J=1.9 Hz, 1H), 7.46 (d, J=8.1 Hz, 1H). MS ESI$^-$ m/z 474.1 (M−H)$^-$.

Example 262

1-[(4R)-7-chloro-2,2-diethyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 0.89 (dt, J=14.6, 7.4 Hz, 6H), 1.55 (dd, J=14.3, 7.4 Hz, 1H), 1.60-1.66 (m, 1H), 1.68 (dd, J=7.6, 2.7 Hz, 1H), 1.71-1.77 (m, 1H), 2.11 (dd, J=13.5, 6.2 Hz, 1H), 2.50 (s, 1H), 2.75-2.82 (m, 2H), 3.23 (s, 3H), 4.93 (dd, J=11.4, 6.1 Hz, 1H), 6.82 (d, J=2.1 Hz, 1H), 6.91-6.96 (m, 1H), 6.99 (dd, J=8.0, 2.0 Hz, 1H), 7.10 (d, J=8.1 Hz, 1H), 7.25 (dd, J=8.4, 0.6 Hz, 1H), 7.32 (d, J=2.0 Hz, 1H). MS ESI$^+$ m/z 442.0 (M+H)$^+$.

Example 263

1-[(4R)-2,2-bis(fluoromethyl)-7-(trifluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 2.00-2.08 (m, 1H), 2.33 (dd, J=13.7, 6.0 Hz, 1H), 2.50 (s, 1H), 2.76-2.81 (m, 2H), 3.23 (s, 3H), 4.58 (s, 1H), 4.60-4.66 (m, 1H), 4.70 (s, 1H), 4.72-4.78 (m, 1H), 5.09 (dd, J=11.1, 5.9 Hz, 1H), 7.01 (dd, J=8.1, 2.0 Hz, 1H), 7.11 (d, J=8.1 Hz, 1H), 7.20 (d, J=1.1 Hz, 1H), 7.33 (dd, J=4.9, 1.6 Hz, 2H), 7.50 (d, J=8.1 Hz, 1H). MS ESI$^-$ m/z 482.1 (M−H)$^-$.

Example 264

1-[(4R)-7,8-dichloro-2,2-diethyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 0.88 (t, J=7.4 Hz, 3H), 0.95 (t, J=7.4 Hz, 3H), 1.51-1.68 (m, 2H), 1.69-1.76 (m, 2H), 1.78-1.84 (m, 1H), 2.15 (dd, J=13.6, 6.2 Hz, 1H), 2.50 (s, 1H), 2.75-2.81 (m, 2H), 3.23 (s, 3H), 4.98 (dd, J=11.2, 6.2 Hz, 1H), 7.00 (dd, J=8.1, 2.0 Hz, 1H), 7.10 (d, J=8.1 Hz, 1H), 7.15 (d, J=8.5 Hz, 1H), 7.23 (dd, J=8.4, 0.8 Hz, 1H), 7.32 (d, J=1.9 Hz, 1H). MS ESI$^+$ m/z 475.9 (M+H)$^+$.

Example 265

1-[(4R)-2,2-dimethyl-7-(trifluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.31 (s, 3H), 1.43 (s, 3H), 1.77-1.85 (m, 1H), 2.16 (dd, J=13.3, 6.2 Hz, 1H), 2.50 (s, 1H), 2.76-2.82 (m, 2H), 3.23 (s, 3H), 5.04 (dd, J=11.3, 6.1 Hz, 1H), 7.00 (dd, J=8.1, 2.0 Hz, 1H), 7.04 (d, J=1.3 Hz, 1H), 7.10 (d, J=8.1 Hz, 1H), 7.24 (dd, J=8.1, 1.2 Hz, 1H), 7.34 (d, J=2.0 Hz, 1H), 7.47 (d, J=8.1 Hz, 1H). MS ESI$^+$ m/z 448.0 (M+H)$^+$.

Example 266

1-[(4R)-6-fluoro-2,2-dipropyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 0.87 (t, J=7.2 Hz, 3H), 0.92 (t, J=7.3 Hz, 3H), 1.24-1.43 (m, 4H), 1.49-1.55 (m, 2H), 1.57-1.64 (m, 2H), 1.72 (dd, J=13.2, 11.6 Hz, 1H), 2.10 (dd, J=13.4, 6.1 Hz, 1H), 2.50 (s, 1H), 2.76-2.82 (m, 2H), 3.23 (s, 3H), 4.92 (dd, J=11.3, 6.1 Hz, 1H), 6.76 (dd, J=9.6, 4.8 Hz, 1H), 6.96-7.02 (m, 3H), 7.10 (d, J=8.1 Hz, 1H), 7.32 (d, J=1.9 Hz, 1H). MS ESI$^+$ m/z 454.1 (M+H)$^+$.

Example 267

1-[(4R)-6-fluoro-2,2-bis(fluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.88-2.01 (m, 1H), 2.28 (dd, J=13.7, 6.0 Hz, 1H), 2.50 (s, 1H), 2.75-2.82 (m, 2H), 3.23 (s, 3H), 4.52-4.61 (m, 2H), 4.64-4.73 (m, 2H), 5.01 (dd, J=11.0, 6.0 Hz, 1H), 6.91 (dd, J=8.8, 4.8 Hz, 1H), 7.04 (dtd, J=10.0, 8.2, 2.5 Hz, 3H), 7.11 (d, J=8.2 Hz, 1H), 7.33 (d, J=1.9 Hz, 1H). MS ESI$^+$ m/z 434.0 M+H)$^+$.

Example 268

1-[(4R)-6,8-difluoro-2,2-bis(fluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 2.04 (ddd, J=13.8, 11.4, 2.7 Hz, 1H), 2.32 (dd, J=13.7, 6.0 Hz, 1H), 2.49 (d, J=8.4 Hz, 1H), 2.75-2.82 (m, 2H), 3.23 (s, 3H), 4.58 (s, 1H), 4.59-4.66 (m, 1H), 4.70 (s, 1H), 4.71-4.78 (m, 1H), 5.03 (dd, J=11.1, 5.9 Hz, 1H), 6.87-6.93 (m, 1H), 7.01 (d, J=8.1, 2.0 Hz, 1H), 7.11 (d, J=8.1 Hz, 1H), 7.22 (ddd, J=11.3, 8.6, 3.0 Hz, 1H), 7.32 (d, J=1.9 Hz, 1H). MS ESI$^+$ m/z 452.0 (M+H)$^+$.

Example 269

1-[(4R)-6-fluoro-3,4-dihydrospiro[chromene-2,1'-cyclobutan]-4-yl]-3-(1-methyl-2-oxo-1,2,3,4-tetrahydroquinolin-7-yl)urea $^1$H NMR (400 MHz, DMSO-d$_6$/D$_2$O) δ 1.73 (dt, J=11.1, 8.7 Hz, 1H), 1.85 (dd, J=16.9, 6.9 Hz, 2H), 2.04-2.21 (m, 3H), 2.28 (dd, J=15.4, 5.9 Hz, 1H), 2.37 (dd, J=13.2, 5.9 Hz, 1H), 2.51 (s, 1H), 2.76-2.82 (m, 2H), 3.23 (s, 3H), 4.96 (dd, J=10.7, 5.9 Hz, 1H), 6.79-6.83 (m, 1H), 6.95-7.03 (m, 3H), 7.11 (d, J=8.1 Hz, 1H), 7.33 (d, J=1.9 Hz, 1H). MS ESI$^-$ m/z 408.1 (M−H)$^-$.

Example 270

1-[(4R)-2,2-diethyl-6-fluoro-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 0.89 (dt, J=15.4, 7.4 Hz, 6H), 1.47-1.74 (m, 5H), 2.10 (dd, J=13.4, 6.2 Hz, 1H), 2.50 (s, 1H), 2.75-2.82 (m, 2H), 3.23 (s, 3H), 4.93 (dd, J=11.2, 6.1 Hz, 1H), 6.78 (dd, J=9.7, 4.8 Hz, 1H), 6.99 (ddd, J=8.2, 5.2, 1.4 Hz, 3H), 7.10 (d, J=8.1 Hz, 1H), 7.32 (d, J=2.0 Hz, 1H). MS ESI$^-$ m/z 424.1 (M−H)$^-$.

Example 271

1-[(4R)-8-fluoro-2,2-dipropyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 0.88 (t, J=7.2 Hz, 3H), 0.93 (t, J=7.3 Hz, 3H), 1.27-1.45 (m, 4H), 1.52-1.59 (m, 2H), 1.66 (td, J=6.6, 2.5 Hz, 2H), 1.79 (dd, J=13.4, 11.4 Hz, 1H), 2.13 (dd, J=13.5, 6.1 Hz, 1H), 2.50 (s, 1H), 2.76-2.82 (m, 2H), 3.23 (s, 3H), 4.98 (dd, J=11.2, 6.1 Hz, 1H), 6.86 (td, J=8.0, 5.0 Hz, 1H), 6.99 (dd, J=8.1, 2.0 Hz, 1H), 7.08 (dd, J=13.6, 8.1 Hz, 3H), 7.32 (d, J=2.0 Hz, 1H). MS ESI$^-$ m/z 452.1 (M−H)$^-$.

Example 272

1-[(4R)-2,2-diethyl-7-(trifluoromethoxy)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 0.90 (dt, J=14.9, 7.4 Hz, 6H), 1.52-1.79 (m, 5H), 2.12 (dd, J=13.5, 6.1 Hz, 1H), 2.50 (s, 1H), 2.75-2.82 (m, 2H), 3.23 (s, 3H), 4.96 (dd, J=11.2, 6.1 Hz, 1H), 6.73 (d, J=1.3 Hz, 1H), 6.88 (dd, J=8.6, 1.3 Hz, 1H), 7.00 (dd, J=8.1, 2.0 Hz, 1H), 7.10 (d, J=8.1 Hz, 1H), 7.33 (d, J=1.9 Hz, 1H), 7.36 (d, J=8.5 Hz, 1H). MS ESI$^-$ m/z 490.2 (M−H)$^-$.

Example 273

1-[(4R)-7-chloro-8-fluoro-2,2-bis(fluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 2.05 (ddd, J=13.8, 11.4, 2.6 Hz, 1H), 2.32 (dd, J=13.7, 6.0 Hz, 1H), 2.50 (s, 1H), 2.75-2.82 (m, 2H), 3.22 (s, 3H), 4.58-4.68 (m, 2H), 4.70-4.80 (m, 2H), 5.05 (dd, J=11.1, 6.0 Hz, 1H), 7.00 (dd, J=8.1, 2.0 Hz, 1H), 7.08-7.17 (m, 3H), 7.32 (d, J=2.0 Hz, 1H). MS ESI⁻ m/z 466.1 (M−H)⁻.

Example 274

1-[(4R)-6-fluoro-2,2-dimethyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.27 (s, 3H), 1.39 (s, 3H), 1.68-1.79 (m, 1H), 2.12 (dd, J=13.2, 6.3 Hz, 1H), 2.51 (s, 1H), 2.75-2.82 (m, 2H), 3.23 (s, 3H), 4.96 (dd, J=11.1, 6.2 Hz, 1H), 6.72-6.80 (m, 1H), 6.96-7.02 (m, 3H), 7.10 (d, J=8.1 Hz, 1H), 7.34 (d, J=2.0 Hz, 1H). MS ESI⁺ m/z 398.0 (M+H)⁺.

Example 275

1-[(4R)-8-chloro-7-fluoro-2,2-dimethyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.30 (d, J=10.2 Hz, 3H), 1.47 (s, 3H), 1.81 (dd, J=13.1, 11.6 Hz, 1H), 2.16 (dd, J=13.4, 6.2 Hz, 1H), 2.50 (s, 1H), 2.76-2.81 (m, 2H), 3.23 (s, 3H), 4.99 (dd, J=11.2, 6.1 Hz, 1H), 6.95 (t, J=8.8 Hz, 1H), 6.99 (dd, J=8.0, 2.0 Hz, 1H), 7.10 (d, J=8.1 Hz, 1H), 7.25 (ddd, J=8.5, 6.4, 0.7 Hz, 1H), 7.33 (d, J=2.0 Hz, 1H). MS ESI⁻ m/z 430.1 (M−H)⁻.

Example 276

1-(1-methyl-2-oxo-1,2,3,4-tetrahydroquinolin-7-yl)-3-[(4S)-7-(trifluoromethoxy)-3,4-dihydro-2H-chromen-4-yl]urea $^1$H NMR (400 MHz, DMSO-d$_6$/D$_2$O) δ 1.93-2.02 (m, 1H), 2.08-2.17 (m, 1H), 2.50 (s, 1H), 2.75-2.81 (m, 2H), 3.22 (s, 3H), 4.21 (ddd, J=11.2, 8.1, 3.0 Hz, 1H), 4.31 (ddd, J=10.4, 6.9, 3.1 Hz, 1H), 4.91 (t, J=5.7 Hz, 1H), 6.79 (d, J=1.4 Hz, 1H), 6.91 (ddd, J=8.5, 2.3, 1.0 Hz, 1H), 6.97 (dd, J=8.1, 2.0 Hz, 1H), 7.09 (d, J=8.1 Hz, 1H), 7.30 (d, J=2.0 Hz, 1H), 7.38 (d, J=8.7 Hz, 1H). MS ESI⁺ m/z 436.0 (M+H)⁺.

Example 277

1-[(4R)-7-chloro-2,2-dimethyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.28 (s, 3H), 1.40 (s, 3H), 1.69-1.81 (m, 1H), 2.12 (dd, J=13.3, 6.2 Hz, 1H), 2.50 (s, 1H), 2.79 (t, J=7.3 Hz, 2H), 3.23 (s, 3H), 4.96 (dd, J=11.1, 6.2 Hz, 1H), 6.80 (d, J=2.1 Hz, 1H), 6.97 (ddd, J=14.6, 8.2, 2.0 Hz, 2H), 7.10 (d, J=8.1 Hz, 1H), 7.26 (d, J=8.4 Hz, 1H), 7.34 (d, J=1.8 Hz, 1H). MS ESI⁻ m/z 412.1 (M−H)⁻.

Example 278

1-(1-methyl-2-oxo-1,2,3,4-tetrahydroquinolin-7-yl)-3-[(4R)-7-(trifluoromethoxy)-3,4-dihydro-2H-chromen-4-yl]urea $^1$H NMR (400 MHz, DMSO-d$_6$/D$_2$O) δ 1.98 (dtd, J=9.5, 6.8, 3.0 Hz, 1H), 2.07-2.18 (m, 1H), 2.50 (s, 1H), 2.73-2.83 (m, 2H), 3.22 (s, 3H), 4.21 (ddd, J=11.2, 8.2, 3.0 Hz, 1H), 4.31 (ddd, J=10.4, 6.9, 3.1 Hz, 1H), 4.91 (t, J=5.7 Hz, 1H), 6.79 (d, J=1.4 Hz, 1H), 6.91 (ddd, J=8.5, 2.3, 1.0 Hz, 1H), 6.97 (dd, J=8.0, 2.0 Hz, 1H), 7.09 (d, J=8.1 Hz, 1H), 7.30 (d, J=2.0 Hz, 1H), 7.38 (d, J=8.6 Hz, 1H). MS ESI⁺ m/z 436.0 (M+H)⁺.

Example 279

1-[(4R)-6-fluoro-2,2-bis(methoxymethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.88 (dd, J=13.4, 11.4 Hz, 1H), 2.15 (dd, J=13.5, 6.1 Hz, 1H), 2.50 (s, 1H), 2.75-2.82 (m, 2H), 3.23 (s, 3H), 3.28 (s, 3H), 3.32 (s, 3H), 3.43 (q, J=10.1 Hz, 2H), 3.48 (s, 2H), 4.96 (dd, J=11.2, 6.0 Hz, 1H), 6.82 (dd, J=8.8, 4.8 Hz, 1H), 6.95-7.04 (m, 3H), 7.10 (d, J=8.1 Hz, 1H), 7.32 (d, J=2.0 Hz, 1H). MS ESI⁻ m/z 456.1 (M−H)⁻.

Example 280

1-[(4R)-2,2-bis(fluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.97 (ddd, J=13.6, 10.8, 2.8 Hz, 1H), 2.28 (dd, J=13.7, 5.9 Hz, 1H), 2.50 (s, 1H), 2.75-2.84 (m, 2H), 3.23 (s, 3H), 4.50-4.60 (m, 2H), 4.63-4.72 (m, 2H), 5.02 (dd, J=10.6, 6.0 Hz, 1H), 6.88 (dd, J=8.2, 0.9 Hz, 1H), 6.95-7.02 (m, 2H), 7.10 (d, J=8.1 Hz, 1H), 7.19-7.24 (m, 1H), 7.28 (d, J=7.6 Hz, 1H), 7.34 (d, J=2.0 Hz, 1H). MS ESI⁺ m/z 416.0 (M+H)⁺.

Example 281

1-[(4R)-8-fluoro-2,2-bis(fluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 2.04 (ddd, J=13.7, 11.1, 2.7 Hz, 1H), 2.32 (dd, J=13.8, 6.0 Hz, 1H), 2.50 (s, 1H), 2.75-2.84 (m, 2H), 3.23 (s, 3H), 4.56-4.66 (m, 2H), 4.68-4.78 (m, 2H), 5.06 (dd, J=10.8, 5.9 Hz, 1H), 6.96 (dd, J=8.0, 3.0 Hz, 1H), 7.00 (dd, J=8.0, 1.8 Hz, 1H), 7.08-7.12 (m, 2H), 7.16 (dd, J=11.0, 8.2 Hz, 1H), 7.33 (d, J=2.0 Hz, 1H). MS ESI⁻ m/z 432.1 (M−H)⁻.

Example 282

1-[(4R)-6-fluoro-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.95 (dtd, J=9.8, 7.0, 2.9 Hz, 1H), 2.07-2.16 (m, 1H), 2.50 (s, 1H), 2.75-2.81 (m, 2H), 3.23 (s, 3H), 4.12-4.19 (m, 1H), 4.24 (ddd, J=10.6, 7.2, 3.0 Hz, 1H), 4.89 (t, J=6.0 Hz, 1H), 6.79-6.85 (m, 1H), 6.98 (dd, J=8.1, 2.0 Hz, 1H), 7.01-7.06 (m, 2H), 7.10 (d, J=8.1 Hz, 1H), 7.30 (d, J=1.9 Hz, 1H). MS ESI⁻ m/z 368.0 (M−H)⁻.

Example 283

1-[(1R)-5-chloro-2,3-dihydro-1H-inden-1-yl]-3-(1-methyl-2-oxo-1,2,3,4-tetrahydroquinolin-7-yl)urea $^1$H NMR (400 MHz, DMSO-d$_6$/D$_2$O) δ 1.80 (dq, J=12.6, 8.6 Hz, 1H), 2.41-2.52 (m, 2H), 2.74-2.80 (m, 2H), 2.84 (t, J=8.3 Hz, 1H), 2.88-2.98 (m, 1H), 3.23 (s, 3H), 5.15 (t, J=7.8 Hz, 1H), 6.97 (dd, J=8.1, 2.0 Hz, 1H), 7.09 (d, J=8.1 Hz, 1H), 7.25-7.28 (m, 2H), 7.30 (d, J=2.0 Hz, 1H), 7.32 (s, 1H). MS ESI⁻ m/z 368.1 (M−H)⁻.

Example 284

1-(1-methyl-2-oxo-1,2,3,4-tetrahydroquinolin-7-yl)-3-[(4R)-8-(trifluoromethyl)-3,4-dihydro-2H-chromen-4-yl]urea $^1$H NMR (400 MHz, DMSO-d$_6$/D$_2$O) δ 2.03 (dtd, J=9.7, 6.8, 3.1 Hz, 1H), 2.16 (dddd, J=11.3, 8.2, 5.0, 3.3 Hz, 1H), 2.50 (s, 1H), 2.75-2.82 (m, 2H), 3.23 (s, 3H), 4.29 (ddd, J=11.2, 8.1, 3.0 Hz, 1H), 4.35-4.44 (m, 1H), 4.97 (t, J=5.8 Hz, 1H), 6.98 (dd, J=8.1, 2.0 Hz, 1H), 7.08 (dd, J=13.4, 7.9 Hz, 2H), 7.30 (d, J=1.9 Hz, 1H), 7.54 (t, J=7.3 Hz, 2H). MS ESI⁻ m/z 420.0 (M−H)⁻.

Example 285

1-[(1R)-5-fluoro-2,3-dihydro-1H-inden-1-yl]-3-(1-methyl-2-oxo-1,2,3,4-tetrahydroquinolin-7-yl)urea $^1$H NMR (400 MHz, DMSO-d$_6$/D$_2$O) δ 1.82 (dq, J=12.6, 8.5 Hz, 1H), 2.43-2.52 (m, 2H), 2.75-2.80 (m, 2H), 2.84 (t, J=8.3 Hz, 1H), 2.95 (ddd, J=16.2, 8.7, 3.6 Hz, 1H), 3.23 (s, 3H), 5.14 (t, J=7.6 Hz, 1H), 6.97 (dd, J=8.0, 2.0 Hz, 1H), 6.99-7.05 (m, 1H), 7.09 (d, J=8.1 Hz, 2H), 7.26-7.29 (m, 1H), 7.30 (d, J=2.0 Hz, 1H). MS ESI⁻ m/z 352.1 (M−H)⁻.

Example 286

1-[(4S)-6-fluoro-3,4-dihydrospiro[chromene-2,1'-cyclobutan]-4-yl]-3-(1-methyl-2-oxo-1,2,3,4-tetrahydroquinolin-7-yl)urea $^1$H NMR (400 MHz, DMSO-d$_6$/D$_2$O) δ 1.68-1.77 (m, 1H), 1.85 (dd, J=16.9, 6.9 Hz, 2H), 2.04-2.11 (m, 1H), 2.12-2.21 (m, 2H), 2.28 (dd, J=15.3, 5.8 Hz, 1H), 2.37 (dd, J=13.2, 5.9 Hz, 1H), 2.51 (s, 1H), 2.76-2.82 (m, 2H), 3.23 (s, 3H), 4.96 (dd, J=10.6, 6.0 Hz, 1H), 6.82 (dd, J=8.8, 4.8 Hz, 1H), 6.95-7.03 (m, 3H), 7.11 (d, J=8.1 Hz, 1H), 7.33 (d, J=1.9 Hz, 1H). MS ESI⁻ m/z 408.1 (M−H)⁻.

Example 287

1-[(4S)-6-fluoro-2,2-dimethyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.27 (s, 3H), 1.39 (s, 3H), 1.74 (dd, J=12.9, 11.6 Hz, 1H), 2.12 (dd, J=13.2, 6.3 Hz, 1H), 2.51 (s, 1H), 2.75-2.82 (m, 2H), 3.23 (s, 3H), 4.96 (dd, J=11.1, 6.2 Hz, 1H), 6.74-6.79 (m, 1H), 6.96-7.02 (m, 3H), 7.10 (d, J=8.1 Hz, 1H), 7.34 (d, J=2.0 Hz, 1H). MS ESI⁺ m/z 398.0 (M+H)⁺.

Example 288

1-[(4R)-3,4-dihydrospiro[chromene-2,1'-cyclopentan]-4-yl]-3-(1-methyl-2-oxo-1,2,3,4-tetrahydroquinolin-7-yl)urea $^1$H NMR (400 MHz, DMSO-d$_6$/D$_2$O) δ 1.59-1.86 (m, 7H), 1.86-2.01 (m, 2H), 2.13 (dd, J=13.2, 6.1 Hz, 1H), 2.50 (s, 1H), 2.76-2.81 (m, 2H), 3.23 (s, 3H), 4.98 (dd, J=10.1, 6.1 Hz, 1H), 6.73 (dd, J=8.2, 0.8 Hz, 1H), 6.89 (td, J=7.5, 1.0 Hz, 1H), 6.98 (dd, J=8.0, 2.0 Hz, 1H), 7.10 (d, J=8.1 Hz, 1H), 7.11-7.17 (m, 1H), 7.24 (d, J=7.6 Hz, 1H), 7.34 (d, J=1.9 Hz, 1H). MS ESI⁻ m/z 404.1 (M−H)⁻.

Example 289

1-[(2S,4R)-2-(fluoromethyl)-2-methyl-7-(trifluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.40 (d, J=1.8 Hz, 3H), 1.94 (ddd, J=13.4, 10.8, 2.3 Hz, 1H), 2.36 (dd, J=13.8, 6.2 Hz, 1H), 2.50 (s, 1H), 2.76-2.82 (m, 2H), 3.23 (s, 3H), 4.46 (dd, J=20.6, 10.0 Hz, 1H), 4.58 (dd, J=20.6, 10.0 Hz, 1H), 5.05 (dd, J=10.4, 6.3 Hz, 1H), 7.00 (dd, J=8.1, 2.0 Hz, 1H), 7.11 (dd, J=7.5, 4.7 Hz, 2H), 7.27 (dd, J=8.2, 1.1 Hz, 1H), 7.33 (d, J=1.9 Hz, 1H), 7.48 (d, J=8.1 Hz, 1H). MS ESI⁻ m/z 464.0 (M−H)⁻.

Example 290

1-[(2R,4R)-2-(fluoromethyl)-2-methyl-7-(trifluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.31 (d, J=1.9 Hz, 3H), 1.97 (t, J=12.4 Hz, 1H), 2.12 (dd, J=13.1, 6.1 Hz, 1H), 2.51 (s, 1H), 2.74-2.82 (m, 2H), 3.23 (s, 3H), 4.45 (q, J=10.0 Hz, 1H), 4.57 (q, J=10.1 Hz, 1H), 5.13 (dd, J=11.6, 6.1 Hz, 1H), 7.01 (dd, J=8.1, 2.0 Hz, 1H), 7.11 (dd, J=4.7, 3.2 Hz, 2H), 7.28 (dd, J=8.1, 1.2 Hz, 1H), 7.34 (d, J=1.9 Hz, 1H), 7.49 (d, J=8.1 Hz, 1H). MS ESI⁺ m/z 466.0 (M+H)⁺.

Example 291

1-[(2S,4R)-7-chloro-2-(fluoromethyl)-2-methyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.38 (d, J=1.8 Hz, 3H), 1.84-1.93 (m, 1H), 2.31 (dd, J=13.8, 6.2 Hz, 1H), 2.50 (s, 1H), 2.75-2.82 (m, 2H), 3.23 (s, 3H), 4.43 (q, J=10.0 Hz, 1H), 4.54 (q, J=10.0 Hz, 1H), 4.96 (dd, J=10.1, 6.2 Hz, 1H), 6.88 (d, J=2.1 Hz, 1H), 6.99 (dt, J=8.1, 1.9 Hz, 2H), 7.10 (d, J=8.1 Hz, 1H), 7.26 (dd, J=8.3, 0.6 Hz, 1H), 7.33 (d, J=2.0 Hz, 1H). MS ESI⁻ m/z 430.1 (M−H)⁻.

Example 292

1-[(2S,4R)-2-(difluoromethyl)-2-methyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.41 (s, 3H), 1.93 (dd, J=13.9, 10.1 Hz, 1H), 2.40 (dd, J=14.1, 6.0 Hz, 1H), 2.50 (s, 1H), 2.74-2.83 (m, 2H), 3.23 (s, 3H), 5.03 (dd, J=9.7, 6.1 Hz, 1H), 6.14 (s, 1H), 6.86 (dd, J=8.2, 0.8 Hz, 1H), 6.97 (td, J=8.2, 1.6 Hz, 2H), 7.10 (d, J=8.1 Hz, 1H), 7.17-7.24 (m, 1H), 7.27 (d, J=7.6 Hz, 1H), 7.34 (d, J=1.9 Hz, 1H). MS ESI⁻ m/z 414.0 (M−H)⁻.

Example 293

1-[(2R,4R)-2-(difluoromethyl)-2-methyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.37 (s, 3H), 1.92 (t, J=12.3 Hz, 1H), 2.14 (dd, J=12.9, 5.9 Hz, 1H), 2.51 (s, 1H), 2.75-2.84 (m, 2H), 3.23 (s, 3H), 5.06 (dd, J=11.5, 5.9 Hz, 1H), 6.10 (s, 1H), 6.84 (dd, J=8.1, 0.8 Hz, 1H), 6.95-7.03 (m, 2H), 7.11 (d, J=8.1 Hz, 1H), 7.18-7.24 (m, 1H), 7.29 (d, J=7.7 Hz, 1H), 7.34 (d, J=1.9 Hz, 1H). MS ESI$^+$ m/z 416.0 (M+H)$^+$.

Example 294

1-[(4R)-7-chloro-8-fluoro-2,2-dimethyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.32 (s, 3H), 1.46 (s, 3H), 1.83 (dd, J=13.1, 11.6 Hz, 1H), 2.16 (dd, J=13.4, 6.2 Hz, 1H), 2.50 (s, 1H), 2.76-2.82 (m, 2H), 3.23 (s, 3H), 4.99 (dd, J=11.2, 6.2 Hz, 1H), 6.99 (dd, J=8.1, 2.0 Hz, 1H), 7.07 (ddd, J=14.8, 8.8, 7.1 Hz, 3H), 7.33 (d, J=1.9 Hz, 1H). MS ESI$^-$ m/z 430.1 (M−H)$^-$.

Example 295

1-[(4R)-2,2-dimethyl-7-(trifluoromethyl)-3,4-dihydro-2H-pyrano[2,3-b]pyridin-4-yl]-3-(1-methyl-2-oxo-1,2,3,4-tetrahydroquinolin-7-yl)urea $^1$H NMR (400 MHz, DMSO-d$_6$/D$_2$O) δ 1.36 (s, 3H), 1.48 (s, 3H), 1.89 (t, J=12.6 Hz, 1H), 2.19 (dd, J=13.3, 6.1 Hz, 1H), 2.50 (s, 1H), 2.76-2.82 (m, 2H), 3.23 (s, 3H), 5.09 (dd, J=11.8, 6.1 Hz, 1H), 7.01 (dd, J=8.1, 2.0 Hz, 1H), 7.11 (d, J=8.1 Hz, 1H), 7.33 (d, J=1.9 Hz, 1H), 7.47 (d, J=7.7 Hz, 1H), 7.92 (d, J=7.7 Hz, 1H). MS ESI$^+$ m/z 449.0 (M+H)$^+$.

Example 296

1-[(4R)-7-fluoro-2,2-bis(fluoromethyl)-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.98 (ddd, J=13.6, 10.9, 2.7 Hz, 1H), 2.28 (dd, J=13.7, 6.0 Hz, 1H), 2.50 (s, 1H), 2.75-2.81 (m, 2H), 3.23 (s, 3H), 4.53-4.62 (m, 2H), 4.65-4.74 (m, 2H), 4.99 (dd, J=10.6, 5.9 Hz, 1H), 6.74 (dd, J=10.3, 2.6 Hz, 1H), 6.83 (td, J=8.5, 2.6 Hz, 1H), 6.99 (dd, J=8.1, 2.0 Hz, 1H), 7.10 (d, J=8.1 Hz, 1H), 7.27-7.32 (m, 1H), 7.33 (d, J=1.9 Hz, 1H). MS ESI$^+$ m/z 434.0 (M+H)$^+$.

Example 297

1-[(4R)-7-bromo-2,2-dimethyl-3,4-dihydro-2H-chromen-4-yl]-3-(1-methyl-2-oxo-1,2,3,4-tetrahydroquinolin-7-yl)urea $^1$H NMR (400 MHz, DMSO-d$_6$/D$_2$O) δ 1.28 (s, 3H), 1.40 (s, 3H), 1.75 (dd, J=12.9, 11.6 Hz, 1H), 2.12 (dd, J=13.2, 6.2 Hz, 1H), 2.50 (s, 1H), 2.75-2.83 (m, 2H), 3.23 (s, 3H), 4.93 (dd, J=11.1, 6.2 Hz, 1H), 6.94 (d, J=2.0 Hz, 1H), 6.98 (dd, J=8.1, 2.0 Hz, 1H), 7.05-7.11 (m, 2H), 7.20 (dd, J=8.3, 0.8 Hz, 1H), 7.33 (d, J=1.9 Hz, 1H). MS ESI$^+$ m/z 458.0 (M+H)$^+$.

Example 298

1-(1-methyl-2-oxo-1,2,3,4-tetrahydroquinolin-7-yl)-3-[(2S,4R)-2-methyl-2-(trifluoromethyl)-3,4-dihydro-2H-chromen-4-yl]urea $^1$H NMR (300 MHz, DMSO-d$_6$) δ ppm 56 (s, 3H) 2.08-2.19 (m, 1H) 2.50-2.58 (m, 3H) 2.74-2.82 (m, 2H) 3.22 (s, 3H) 4.94-5.07 (m, 1H) 6.58 (d, J=8.14 Hz, 1H) 6.91 (dd, J=8.14, 1.02 Hz, 1H) 6.95-7.04 (m, 2H) 7.04-7.12 (m, 1H) 7.17-7.27 (m, 1H) 7.27-7.36 (m, 2H) 8.61 (s, 1H)); MS (ESI$^+$) m/z 434 (M+H)$^+$.

Example 299

1-[(4R)-7,8-difluoro-2,2-dimethyl-3,4-dihydro-2H-chromen-4-yl]-3-(1-methyl-2-oxo-1,2,3,4-tetrahydroquinolin-7-yl)urea $^1$H NMR (300 MHz, CDCl$_3$) δ 7.22 (d, J=1.9 Hz, 1H), 7.07 (d, J=8.0 Hz, 1H), 7.05-6.99 (m, 1H), 6.80 (dd, J=8.0, 2.0 Hz, 1H), 6.66 (td, J=9.2, 7.0 Hz, 1H), 6.53 (s, 1H), 5.20 (dd, J=16.3, 9.7 Hz, 1H), 4.89 (d, J=8.9 Hz, 1H), 3.33 (s, 3H), 2.90-2.80 (m, 2H), 2.67-2.56 (m, 2H), 2.27 (dd, J=13.4, 6.3 Hz, 1H), 1.70 (dd, J=13.2, 11.2 Hz, 1H), 1.48 (s, 3H), 1.37 (s, 3H). MS (ESI$^+$) m/z 416 (M+H)$^+$, 414 (M−H$^+$).

Example 300

1-[(4R)-7-chloro-2,2-bis(fluoromethyl)-3,4-dihydro-2H-chromen-4-yl]-3-[3-(morpholin-4-yl)-2-oxo-1,2,3,4-tetrahydroquinolin-7-yl]urea $^1$H NMR (400 MHz, PYRIDINE-d$_5$) δ ppm 2.15 (ddd, J=13.7, 10.8, 3.0 Hz, 1H), 2.55 (dd, J=13.7, 5.9 Hz, 1H), 2.88-3.08 (m, 5H), 3.13 (dd, J=15.8, 9.2 Hz, 1H), 3.47 (ddd, J=9.1, 5.8, 1.9 Hz, 1H), 3.68-3.76 (m, 4H), 4.52-4.80 (m, 4H), 5.53-5.63 (m, 1H), 6.93-6.99 (m, 2H), 7.16 (d, J=8.1 Hz, 1H), 7.50 (td, J=7.9, 2.1 Hz, 1H), 8.17 (dd, J=10.3, 2.0 Hz, 1H), 10.19 (s, 1H), 11.58 (d, J=3.2 Hz, 1H); MS (ESI) m/z 521 (M+H)$^+$.

Example 301

1-[(4R)-7-fluoro-2,2-dimethyl-3,4-dihydro-2H-chromen-4-yl]-3-[3-(morpholin-4-yl)-2-oxo-1,2,3,4-tetrahydroquinolin-7-yl]urea $^1$H NMR (400 MHz, PYRIDINE-d$_5$) δ ppm 1.18 (s, 3H), 1.27 (s, 3H), 1.83 (t, J=12.2 Hz, 1H), 2.20 (ddd, J=13.2, 6.1, 1.9 Hz, 1H), 2.85-3.08 (m, 5H), 3.14 (dd, J=15.7, 9.1 Hz, 1H), 3.43-3.51 (m, 1H), 3.67-3.78 (m, 4H), 5.46-5.57 (m, 1H), 6.64-6.74 (m, 2H), 7.17 (d, J=8.1 Hz, 1H), 7.32 (d, J=8.7 Hz, 1H), 7.45-7.54 (m, 1H), 7.63-7.70 (m, 1H), 8.20 (dd, J=12.4, 2.0 Hz, 1H), 10.04 (s, 1H), 11.60 (d, J=2.8 Hz, 1H); MS (ESI) m/z 469 (M+H)$^+$.

Example 302

1-[(4R)-7-chloro-2,2-bis(fluoromethyl)-3,4-dihydro-2H-chromen-4-yl]-3-[3-(1,4-oxazepan-4-yl)-2-oxo-1,2,3,4-tetrahydroquinolin-7-yl]urea $^1$H NMR (400 MHz, PYRIDINE-d$_5$) δ ppm 1.83-2.10 (m, 2H), 2.16 (ddd, J=13.7, 11.1, 2.8 Hz, 1H), 2.56 (dd, J=13.7, 5.9 Hz, 1H), 3.10-3.17 (m, 2H), 3.24-3.34 (m, 2H), 3.34-3.48 (m, 2H), 3.79-3.99 (m, 5H), 4.53-4.79 (m, 4H), 5.52-5.63 (m, 1H), 6.93-6.99 (m, 2H), 7.15 (d, J=8.2 Hz, 1H), 7.48-7.54 (m, 1H), 7.58-7.62 (m, 1H), 7.66 (d, J=8.4 Hz, 1H), 8.18 (dd, J=7.6, 2.0 Hz, 1H), 10.29 (d, J=1.5 Hz, 1H), 11.60 (d, J=2.6 Hz, 1H); MS (ESI) m/z 535 (M+H)$^+$.

Example 303

1-[(4R)-7-fluoro-2,2-dimethyl-3,4-dihydro-2H-chromen-4-yl]-3-[3-(1,4-oxazepan-4-yl)-2-oxo-1,2,3,4-tetrahydroquinolin-7-yl]urea $^1$H NMR (400 MHz, PYRIDINE-$d_5$) δ ppm 1.18 (s, 3H), 1.27 (s, 3H), 1.77-1.88 (m, 1H), 1.90-1.98 (m, 1H), 1.98-2.10 (m, 1H), 2.20 (dd, J=13.2, 6.1 Hz, 1H), 3.14 (d, J=9.5 Hz, 2H), 3.21-3.33 (m, 2H), 3.35-3.48 (m, 2H), 3.79-3.99 (m, 5H), 5.45-5.58 (m, 1H), 6.64-6.74 (m, 2H), 7.17 (d, J=8.2 Hz, 1H), 7.38 (d, J=8.7 Hz, 1H), 7.46-7.55 (m, 1H), 7.67 (t, J=7.5 Hz, 1H), 8.21 (dd, J=11.8, 2.0 Hz, 1H), 10.13 (d, J=2.2 Hz, 1H), 11.61 (d, J=2.2 Hz, 1H); MS (ESI) m/z 483 (M+H)$^+$.

Example 304

1-[(4R)-7-chloro-2,2-bis(fluoromethyl)-3,4-dihydro-2H-chromen-4-yl]-3-{3-[(2-hydroxyethyl)(methyl)amino]-2-oxo-1,2,3,4-tetrahydroquinolin-7-yl}urea $^1$H NMR (400 MHz, PYRIDINE-$d_5$) δ ppm 2.11-2.21 (m, 1H), 2.55 (dd, J=13.7, 6.0 Hz, 1H), 2.99 (s, 3H), 3.18-3.33 (m, 2H), 3.40 (dt, J=13.0, 5.0 Hz, 1H), 3.48-3.58 (m, 1H), 4.12 (t, J=5.2 Hz, 2H), 4.30 (ddd, J=13.1, 6.6, 3.0 Hz, 1H), 4.50-4.80 (m, 4H), 5.51-5.63 (m, 1H), 6.93-6.98 (m, 2H), 7.11 (d, J=8.2 Hz, 1H), 7.56-7.59 (m, 1H), 7.62 (d, J=8.7 Hz, 1H), 7.84 (d, J=8.3 Hz, 1H), 8.18 (dd, J=7.3, 2.0 Hz, 1H), 10.56 (d, J=3.3 Hz, 1H), 11.94 (bs, 1H); MS (ESI) m/z 509 (M+H)$^+$.

Example 305

1-[(4R)-7-fluoro-2,2-dimethyl-3,4-dihydro-2H-chromen-4-yl]-3-{3-[(2-methoxyethyl)(methyl)amino]-2-oxo-1,2,3,4-tetrahydroquinolin-7-yl}urea $^1$H NMR (400 MHz, PYRIDINE-$d_5$) δ ppm 1.18 (s, 3H), 1.27 (s, 3H), 1.85 (t, J=12.2 Hz, 1H), 2.19 (dd, J=13.2, 6.1 Hz, 1H), 2.88 (s, 3H), 3.14-3.24 (m, 2H), 3.26 (s, 3H), 3.30-3.48 (m, 2H), 3.69 (t, J=5.7 Hz, 2H), 3.99-4.09 (m, 1H), 5.46-5.54 (m, 1H), 6.64-6.74 (m, 2H), 7.13 (d, J=8.1 Hz, 1H), 7.47 (d, J=8.5 Hz, 1H), 7.50-7.56 (m, 1H), 7.68 (t, J=7.5 Hz, 1H), 8.19 (d, J=11.2 Hz, 1H), 10.25 (bs, 1H), 11.73 (bs, 1H); MS (ESI) m/z 471 (M+H)$^+$.

Example 306

1-[(4R)-7-chloro-2,2-bis(fluoromethyl)-3,4-dihydro-2H-chromen-4-yl]-3-{3-[(2-methoxyethyl)(methyl)amino]-2-oxo-1,2,3,4-tetrahydroquinolin-7-yl}urea $^1$H NMR (400 MHz, PYRIDINE-$d_5$) δ ppm 2.10-2.20 (m, 1H), 2.56 (dd, J=13.7, 5.9 Hz, 1H), 2.85 (s, 3H), 3.06-3.24 (m, 2H), 3.26 (s, 3H), 3.29-3.44 (m, 2H), 3.66 (t, J=5.7 Hz, 2H), 3.95-4.04 (m, 1H), 4.53-4.78 (m, 4H), 6.93-6.99 (m, 2H), 7.12 (d, J=8.2 Hz, 1H), 7.51 (td, J=7.9, 1.5 Hz, 1H), 7.58-7.61 (m, 1H), 7.65 (d, J=8.4 Hz, 1H), 8.16 (dd, J=8.2, 2.0 Hz, 1H), 10.29 (bs, 1H), 11.68 (bs, 1H); MS (ESI) m/z 523 (M+H)$^+$.

Example 307

1-[(4R)-2,2-dimethyl-8-(trifluoromethyl)-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 1.31 (s, 3H), 1.43 (s, 3H), 1.83 (s, 1H), 2.14 (dd, J=13.3, 6.2 Hz, 1H), 3.37 (t, J=5.9 Hz, 2H), 3.57 (t, J=5.9 Hz, 2H), 4.43 (bs, 2H), 4.98 (dd, J=11.1, 6.2 Hz, 1H), 6.87 (td, J=7.9, 4.9 Hz, 2H), 6.90 (dd, J=8.2, 2.1 Hz, 2H), 6.96 (d, J=8.2 Hz, 2H), 6.99 (d, J=2.0 Hz, 1H), 7.04-7.12 (m, 2H). MS ESI$^-$ m/z 477 (M−H)$^-$.

Example 308

1-[(4R)-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 1.81-1.99 (m, 1H), 2.05-2.15 (m, 1H), 3.36 (t, J=5.9 Hz, 2H), 3.57 (t, J=5.9 Hz, 2H), 4.14 (ddd, J=11.3, 8.5, 2.8 Hz, 1H), 4.21-4.29 (m, 1H), 4.43 (s, 2H), 4.82-4.93 (m, 1H), 6.79 (dd, J=8.2, 1.2 Hz, 1H), 6.85-6.98 (m, 3H), 7.14-7.21 (m, 1H), 7.25 (d, J=7.7 Hz, 1H). MS ESI$^-$ m/z 383 (M+H)$^+$.

Example 309

1-[(4R)-2,2-bis(fluoromethyl)-7-(trifluoromethyl)-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 1.98-2.07 (m, 1H), 2.32 (dd, J=13.7, 6.0 Hz, 1H), 3.37 (t, J=5.9 Hz, 2H), 3.57 (t, J=5.9 Hz, 2H), 4.44 (bs, 2H), 4.57-4.78 (m, 4H), 5.03-5.10 (m, 1H), 6.91 (dd, J=8.1, 2.1 Hz, 1H), 6.97 (d, J=8.2 Hz, 1H), 7.00 (d, J=2.1 Hz, 1H), 7.19 (d, J=1.7 Hz, 1H), 7.33 (dd, J=8.1, 1.8 Hz, 1H), 7.49 (d, J=8.0 Hz, 1H) MS ESI$^-$ m/z 513 (M−H)$^-$.

Example 310

1-[(4R)-6-fluoro-2,2-dipropyl-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 0.77-1.00 (m, 6H), 1.18-1.47 (m, 4H), 1.49-1.69 (m, 4H), 1.75 (s, 1H), 3.12-3.19 (m, 2H), 3.36 (t, J=5.9 Hz, 2H), 3.57 (t, J=5.9 Hz, 2H), 4.43 (s, 2H), 6.82-6.91 (m, 2H), 6.99-7.11 (m, 4H). MS (ESI$^-$) m/z 483 (M−H)$^-$.

Example 311

1-[(4R)-8-fluoro-2,2-dipropyl-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 0.77-1.00 (m, 6H), 1.18-1.47 (m, 4H), 1.49-1.69 (m, 4H), 1.75 (s, 1H), 3.12-3.19 (m, 1H), 3.36 (t, J=5.9 Hz, 2H), 3.57 (t, J=5.9 Hz, 1H), 4.43 (s, 1H), 6.82-6.91 (m, 1H), 6.99-7.11 (m, 2H). MS ESI$^-$ m/z 483 (M−H)$^-$.

Example 312

1-[(4R)-8-chloro-7-fluoro-2,2-dimethyl-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 1.31 (s, 3H), 1.46 (s, 3H), 1.75-1.96 (m, 1H), 2.16 (dd, J=13.3, 6.2 Hz, 1H), 3.37 (t, J=5.9 Hz, 2H), 3.57 (t, J=5.9 Hz, 2H), 4.43 (bs, 2H), 4.93-5.00 (m, 1H), 6.87-7.00 (m, 4H), 7.21-7.28 (m, 1H). MS ESI$^-$ m/z 461 (M−H)$^-$.

Example 313

1-[(4R)-7-chloro-2,2-dimethyl-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 1.28 (s, 3H), 1.40 (s, 3H), 1.69-1.78 (m, 1H), 1.84 (s, 1H), 2.12 (dd, J=13.2, 6.2 Hz, 1H), 3.37 (t, J=5.9 Hz, 2H), 3.57 (t, J=5.9 Hz, 2H), 4.43 (bs, 2H), 4.93 (dd, J=11.1, 6.2 Hz, 1H), 6.80 (d, J=2.1 Hz, 1H), 6.85-7.02 (m, 4H), 7.25 (d, J=7.8 Hz, 1H). MS ESI$^-$ m/z 443 (M−H)$^-$.

Example 314

1-[(4R)-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 1.90-1.99 (m, 1H), 2.27 (dd, J=13.7, 5.9 Hz, 1H), 3.37 (t, J=5.9 Hz, 2H), 3.57 (t, J=5.9 Hz, 2H), 4.43 (s, 2H), 4.52-4.62 (m, 2H), 4.61-4.73 (m, 2H), 4.99 (dd, J=10.5, 5.9 Hz, 1H), 6.87 (dd, J=8.2, 1.1 Hz, 1H), 6.90 (dd, J=8.1, 2.1 Hz, 1H), 6.93-7.02 (m, 3H), 7.18-7.30 (m, 2H). MS ESI$^-$ m/z 445 (M−H)$^-$.

Example 315

1-[(4R)-8-fluoro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 1.80 (s, 1H), 2.01 (ddd, J=13.7, 10.8, 2.9 Hz, 1H), 2.31 (dd, J=13.7, 5.9 Hz, 1H), 3.36 (t, J=5.9 Hz, 2H), 3.57 (t, J=5.9 Hz, 2H), 4.43 (s, 2H), 4.56-4.77 (m, 4H), 5.03 (dd, J=10.8, 5.9 Hz, 1H), 6.90 (dd, J=8.1, 2.1 Hz, 1H), 6.92-7.01 (m, 3H), 7.09 (dd, J=7.8, 1.4 Hz, 1H), 7.12-7.19 (m, 1H). MS ESI$^-$ m/z 463 (M−H)$^-$.

Example 316

1-[(4R)-7-chloro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 0.94 (t, J=7.3 Hz, 1H), 1.32 (h, J=7.3 Hz, 1H), 1.51-1.62 (m, 1H), 1.96 (ddd, J=13.6, 10.9, 2.8 Hz, 1H), 2.28 (dd, J=13.7, 6.0 Hz, 1H), 3.12-3.19 (m, 1H), 3.36 (t, J=5.9 Hz, 2H), 3.57 (t, J=5.9 Hz, 1H), 4.43 (s, 1H), 4.54-4.73 (m, 2H), 4.97 (dd, J=10.8, 5.9 Hz, 1H), 6.90 (dd, J=8.1, 2.1 Hz, 1H), 6.93-7.01 (m, 1H), 7.04 (dd, J=8.3, 2.1 Hz, 1H), 7.28 (dd, J=8.3, 1.0 Hz, 1H). MS ESI$^-$ m/z 479 (M−H)$^-$.

Example 317

1-[(4R)-3,4-dihydrospiro[chromene-2,1'-cyclopentan]-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 1.65-1.84 (m, 6H), 1.85-1.99 (m, 2H), 2.12 (dd, J=13.2, 6.0 Hz, 1H), 3.37 (t, J=5.9 Hz, 2H), 3.57 (t, J=5.9 Hz, 2H), 4.43 (bs, 2H), 4.95 (dd, J=10.0, 6.0 Hz, 1H), 6.73 (d, J=8.1 Hz, 1H), 6.85-6.93 (m, 2H), 6.95 (d, J=8.2 Hz, 2H), 6.98 (d, J=2.0 Hz, 1H), 7.11-7.18 (m, 1H), 7.24 (d, J=7.7 Hz, 1H). MS ESI$^-$ m/z 435 (M−H)$^-$.

Example 318

1-[(2S,4R)-2-(difluoromethyl)-2-methyl-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 1.40 (s, 3H), 1.81 (s, 2H), 1.87-1.96 (m, 1H), 2.38 (dd, J=14.1, 6.0 Hz, 1H), 3.37 (t, J=5.9 Hz, 2H), 3.57 (t, J=5.9 Hz, 2H), 4.43 (bs, 2H), 5.00 (dd, J=9.7, 6.0 Hz, 1H), 6.85 (dd, J=8.2, 1.1 Hz, 1H), 6.90 (dd, J=8.1, 2.1 Hz, 1H), 6.93-7.01 (m, 3H), 7.20 (td, J=7.7, 1.7 Hz, 1H), 7.26 (d, J=7.7 Hz, 1H). MS ESI$^-$ m/z 445 (M−H)$^-$.

Example 319

1-[(4R)-7-fluoro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea $^1$H NMR (500 MHz, DMSO-$d_6$/D$_2$O) δ 1.85-2.00 (m, 2H), 2.27 (dd, J=13.8, 5.9 Hz, 1H), 3.36 (t, J=5.9 Hz, 2H), 3.57 (t, J=5.9 Hz, 3H), 4.43 (bs, 2H), 4.53-4.64 (m, 3H), 4.63-4.73 (m, 3H), 4.93-5.00 (m, 1H), 6.68-6.77 (m, 1H), 6.83 (td, J=8.5, 2.6 Hz, 1H), 6.90 (dd, J=8.2, 2.1 Hz, 1H), 6.96 (d, J=8.2 Hz, 2H), 6.98 (d, J=2.1 Hz, 1H), 7.29 (t, J=7.6 Hz, 1H). MS ESI$^-$ m/z 463 (M−H)$^-$.

Example 320

1-[(4R)-2,2-bis(fluoromethyl)-7-(trifluoromethyl)-3,4-dihydro-2H-chromen-4-yl]-3-(2-oxo-1,2,3,4-tetrahydroquinolin-7-yl)urea $^1$H NMR (500 MHz, DMSO-$d_6$) δ 10.03 (s, 1H), 8.58 (s, 1H), 7.49 (d, J=8.1 Hz, 1H), 7.32 (d, J=8.2 Hz, 1H), 7.19 (s, 1H), 7.05 (d, J=1.9 Hz, 1H), 7.02 (d, J=8.2 Hz, 1H), 6.96 (dd, J=8.1, 2.0 Hz, 1H), 6.58 (d, J=8.4 Hz, 1H), 5.06 (dt, J=9.6, 7.8 Hz, 1H), 4.68 (ddd, J=38.5, 26.0, 11.8 Hz, 4H), 2.78 (t, J=7.5 Hz, 2H), 2.46-2.38 (m, 2H), 2.32 (dd, J=13.6, 6.0 Hz, 1H), 2.08-1.95 (m, 1H). MS (ESI$^+$) m/z 470 (M+H)$^+$.

Example 321

1-[(2R,4R)-7-chloro-2-(difluoromethyl)-2-methyl-3,4-dihydro-2H-chromen-4-yl]-3-(3-oxo-3,4-dihydro-2H-1,4-benzoxazin-6-yl)urea $^1$H NMR (300 MHz, DMSO-$d_6$) δ 10.64 (s, 1H), 8.53 (s, 1H), 7.29 (dd, J=8.3, 1.0 Hz, 1H), 7.19 (d, J=2.3 Hz, 1H), 7.03 (dd, J=8.3, 2.1 Hz, 1H), 6.95-6.85 (m, 2H), 6.82 (d, J=8.6 Hz, 1H), 6.52 (d, J=8.5 Hz, 1H), 5.06-4.93 (m, 2H), 4.49 (s, 2H), 2.12 (dd, J=12.9, 6.0 Hz, 1H), 1.95 (d, J=12.1 Hz, 1H), 1.37 (s, 3H). MS (ESI$^+$) M/Z 438 (M+H)$^+$.

Example 322

1-[(2S,4R)-7-chloro-2-(difluoromethyl)-2-methyl-3,4-dihydro-2H-chromen-4-yl]-3-(3-oxo-3,4-dihydro-2H-1,4-benzoxazin-6-yl)urea $^1$H NMR (300 MHz, DMSO-$d_6$) δ 10.65 (d, J=8.9 Hz, 1H), 9.52 (s, 1H), 8.49 (d, J=3.2 Hz, 1H), 7.50-7.38 (m, 1H), 7.28 (d, J=8.5 Hz, 1H), 7.20 (t, J=6.7 Hz, 1H), 7.18 (d, J=2.0 Hz, 1H), 6.42 (d, J=8.3 Hz, 1H), 6.49-6.33 (m, 1H), 4.98 (dd, J=15.2, 9.3 Hz, 1H), 3.62 (d, J=10.4 Hz, 1H), 3.23-2.68 (m, 1H), 2.41-2.28 (m, 1H), 2.15 (s, 3H), 2.01-1.88 (m, 1H), 1.32-1.09 (m, 1H). MS (ESI$^+$) M/Z 438 (M+H)$^+$.

Example 323

1-[(4R)-7-chloro-2,2-bis(fluoromethyl)-3,4-dihydro-2H-chromen-4-yl]-3-(3-oxo-3,4-dihydro-2H-1,4-benzoxazin-8-yl)urea $^1$H NMR (300 MHz, DMSO-d$_6$) δ 10.66 (s, 1H), 8.10 (s, 1H), 7.79 (dd, J=8.4, 1.3 Hz, 1H), 7.27 (t, J=7.7 Hz, 2H), 7.04 (dd, J=8.3, 2.1 Hz, 1H), 6.97 (d, J=2.1 Hz, 1H), 6.84 (t, J=8.1 Hz, 1H), 6.50 (dd, J=8.0, 1.4 Hz, 1H), 4.96 (dd, J=15.7, 8.6 Hz, 1H), 4.81-4.40 (m, 6H), 2.31 (dd, J=13.8, 5.9 Hz, 1H), 1.99-1.75 (m, 1H). LCMS (M+H)$^+$ 438.

Example 324

1-[(4R)-2,2-bis(fluoromethyl)-7-(trifluoromethyl)-3,4-dihydro-2H-chromen-4-yl]-3-(3-oxo-3,4-dihydro-2H-1,4-benzoxazin-6-yl)urea $^1$H NMR (300 MHz, DMSO-d$_6$) δ 10.65 (s, 1H), 8.57 (s, 1H), 7.49 (d, J=8.1 Hz, 1H), 7.32 (d, J=7.0 Hz, 1H), 7.22-7.17 (m, 2H), 6.88 (dd, J=8.6, 2.3 Hz, 1H), 6.83 (d, J=8.6 Hz, 1H), 6.57 (d, J=8.3 Hz, 1H), 5.13-5.00 (m, 1H), 4.82-4.69 (m, 2H), 4.66-4.53 (m, 2H), 4.49 (s, 2H), 2.31 (dd, J=13.6, 5.9 Hz, 1H), 2.09-1.96 (m, 1H). MS (ESI$^+$) M/Z 472 (M+H)$^+$.

Example 325

1-[(4R)-7-chloro-8-fluoro-2,2-dimethyl-3,4-dihydro-2H-chromen-4-yl]-3-(3-oxo-3,4-dihydro-2H-1,4-benzoxazin-6-yl)urea $^1$H NMR (300 MHz, DMSO-d$_6$) δ 10.65 (s, 1H), 8.51 (s, 1H), 7.18 (d, J=2.3 Hz, 1H), 7.13-6.96 (m, 2H), 6.92-6.74 (m, 2H), 6.44 (d, J=8.6 Hz, 1H), 5.03-4.90 (m, 1H), 4.49 (s, 2H), 2.15 (dd, J=13.3, 6.1 Hz, 1H), 1.88-1.76 (m, 1H), 1.45 (s, 3H), 1.32 (s, 3H). MS (ESI$^+$) M/Z 420 (M+H)$^+$.

Example 326

1-(1-methyl-2-oxo-1,2,3,4-tetrahydroquinolin-7-yl)-3-[(2R,4R)-2-methyl-2-(trifluoromethyl)-3,4-dihydro-2H-chromen-4-yl]urea $^1$H NMR (300 MHz, CDCl$_3$) δ 7.33 (d, J=7.7 Hz, 1H), 7.24-7.16 (m, 2H), 7.08 (d, J=7.9 Hz, 1H), 7.00-6.86 (m, 2H), 6.82 (dd, J=7.9, 2.0 Hz, 1H), 6.55 (s, 1H), 5.36-5.23 (m, 1H), 4.97 (d, J=8.9 Hz, 1H), 3.33 (s, 3H), 2.89-2.80 (m, 2H), 2.67-2.58 (m, 2H), 2.43 (dd, J=13.1, 6.2 Hz, 1H), 1.96 (dd, J=12.8, 11.2 Hz, 1H), 1.53 (s, 3H). MS (ESI$^+$) m/z 434 (M+H)$^+$ 432 (M−H)$^+$.

Example 327

1-[(2S,4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea $^1$H NMR (300 MHz, DMSO) δ 7.87 (s, 1H), 7.39 (dd, J=8.2, 0.9 Hz, 2H), 7.30 (dd, J=8.3, 1.0 Hz, 2H), 7.22-7.10 (m, 2H), 7.03 (dd, J=8.3, 2.1 Hz, 1H), 6.95 (d, J=2.1 Hz, 1H), 6.78 (d, J=8.2 Hz, 1H), 6.65 (d, J=7.6 Hz, 1H), 5.03-4.90 (m, 1H), 4.18 (d, J=1.6 Hz, 1H), 3.14 (s, 3H), 2.39 (dd, J=14.1, 6.0 Hz, 1H), 1.99 (s, 1H), 1.41 (s, 3H). MS (DCI$^+$) m/z 468 (M+NH$_4$)$^+$.

E. BIOLOGICAL DATA (i) Capsaicin Activation Assay

Dulbecco's modified Eagle medium (DMEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/l Na pyruvate, without phenol red), L-glutamine, hygromycin B, and Lipofectamine® were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)-methoxy]-2,7-difluoro-3-oxo-3H-xanthen-9-yl]-2-[2-[2-[bis[2-[(acetyloxy)methoxy]-2-oxyethyl]amino]-5-methylphenoxy]ethoxy]phenyl]-N-[2-[(acetyloxy)methoxy]-2-oxyethyl]-glycine, (acetyloxy) methyl ester) was purchased from Molecular Probes (Eugene, Oreg.).

The cDNA for human TRPV1 (hTRPV1) was isolated by reverse transcriptase-polymerase chain reaction (RT-PCR) from human small intestine poly A+ RNA supplied by Clontech (Palo Alto, Calif.) using primers designed surrounding the initiation and termination codons identical to the published sequences (Hayes et al. Pain 2000, 88, 205-215). The resulting cDNA PCR products were subcloned into pCIneo mammalian expression vector (Promega) and fully sequenced using fluorescent dye-terminator reagents (Prism, PerkinElmer Applied Biosystems Division) and a PerkinElmer Applied Biosystems Model 373 DNA sequencer or Model 310 genetic analyzer. Expression plasmids encoding the hTRPV1 cDNA were transfected into HEK293 cells using Lipofectamine®. Forty-eight hours after transfection, the neomycin-resistant cells were selected with growth medium containing 800 μg/mL Geneticin (Life Technologies, formerly Gibco BRL). Surviving individual colonies were isolated and screened for TRPV1 activity. Cells expressing recombinant TRPV1 were maintained at 37° C. in DMEM containing 4 mM L-glutamine, 300 μg/mL G418 (Calbiochem) and 10% fetal bovine serum under a humidified 5% CO$_2$ atmosphere.

The functional activity of compounds at the TRPV1 receptor was determined by measurement of intracellular Ca$^{2+}$ levels ([Ca$^{2+}$]$_i$) using the Fluorescence Imaging Plate Reader (FLIPR)TETRA®. All compounds were tested over a 12-point one-third-log concentration range. Compound stocks, 10 mM, were prepared in DMSO, and diluted serially across a 384-well plate using a Bravo BenchCel workstation (Agilent Technologies, Santa Clara, Calif.). A stock concentration of capsaicin (10 mM) was made in DMSO, and diluted in D-PBS to a final concentration of 200 nM (4×). On the day prior to the experiment, the recombinant HEK293 cells expressing human TRPV1 (hTRPV1) were removed from tissue culture flasks and plated in growth medium into black-walled clear-bottom 384-well Biocoat™ poly-D-lysine assay plates (BD Biosciences, Bedford, Mass.) using a Multidrop® dispenser (ThermoScientific, Waltham, Mass.). On the day of the experiment, growth medium was removed, and the no-wash FLIPR® Calcium-4 dye ($\lambda_{EX}$=470-495 nm, $\lambda_{EM}$=515-575 nm; Molecular Devices, Sunnyvale, Calif.) was added to each well using the Multidrop® dispenser. The plated cells were incubated for 90-120 minutes in the dark at room temperature and then test compound was added to each well.

Three minutes later, 200 nM capsaicin (4×) solution was added to each well in an amount sufficient to provide a final assay volume of 80 µL and capsaicin concentration of 50 nM. Fluorescence readings were made at 1 to 5 second intervals over the course of the experimental run. The peak increase in relative fluorescence units (minus baseline) was calculated, and expressed as a percentage of the 50 nM capsaicin (control) response. Curve-fits of the data were solved using a four-parameter logistic Hill equation in GraphPad Prism® (GraphPad Software, Inc., San Diego, Calif.), and $IC_{50}$ values (concentration of the test compounds that inhibits 50% of the intracellular $Ca^{2+}$ concentration increase induced by capsaicin) were calculated.

Selected compounds also were tested in 1321N1 cells expressing recombinant human TRPV1 as a confirmation of potency in a cell line of neuronal lineage. The cDNA for human TRPV1 (hTRPV1) was isolated and the resulting cDNA PCR products were subcloned into pCIneo mammalian expression vector (Promega) as discussed above. Expression plasmids encoding the hTRPV1 cDNA were transfected into 1321N1 human astrocytoma cells using Lipofectamine®. Forty-eight hours after transfection, the neomycin-resistant cells were selected with growth medium containing 800 µg/mL Geneticin (Life Technologies, formerly Gibco BRL). Surviving individual colonies were isolated and screened for TRPV1 activity. Cells expressing recombinant TRPV1 were maintained at 37° C. in DMEM containing 4 mM L-glutamine, 300 µg/mL G418 (Calbiochem) and 10% fetal bovine serum under a humidified 5% $CO_2$ atmosphere.

Table 1 reports the $IC_{50}$ values calculated for the compounds tested in the recombinant HEK293 cell assay. Many of the compounds exhibited an $IC_{50}$ (cap) value less than about 1000 nM, for example, in the range of about 500 nM to about 1000 nM, or in the range of about 100 to about 500 nM, or in the range of about less than 100 nM. As illustrated by the data in Table 1, the claimed compounds are TRPV1 antagonists that inhibit an increase in cellular calcium in response to capsaicin (50 nM) addition.

(ii) Acid Activation Assay

Dulbecco's modified Eagle's medium (DMEM) with 4.5 m g/mL D-glucose, fetal bovine serum, L-glutamine, and 2-morpholinoethanesulfonic acid (MES) were purchased from Sigma-Aldrich Co. (St. Louis, Mo.). Dulbecco's phosphate-buffered saline (DPBS) with $Ca^{2+}$, $Mg^{2+}$, and 1 mg/mL D-glucose (pH 7.4), Geneticin®, 0.25% trypsin-1 mM EDTA, and penicillin-streptomycin were purchased from Invitrogen Corp. (Carlsbad, Calif.). The FLIPR® Calcium 4 assay kit was purchased from Molecular Devices (Sunnyvale, Calif.).

The cDNA for human TRPV1 (hTRPV1) was isolated by reverse transcriptase-polymerase chain reaction (RT-PCR) from human small intestine poly A+ RNA supplied by Clontech (Palo Alto, Calif.) using primers designed surrounding the initiation and termination codons identical to the published sequences (Hayes et al. Pain 2000, 88, 205-215). The resulting cDNA PCR products were subcloned into pCIneo mammalian expression vector (Promega) and fully sequenced using fluorescent dye-terminator reagents (Prism, PerkinElmer Applied Biosystems Division) and a PerkinElmer Applied Biosystems Model 373 DNA sequencer or Model 310 genetic analyzer. Expression plasmids encoding the hTRPV1 cDNA were transfected into HEK293 cells using Lipofectamine®. Forty-eight hours after transfection, the neomycin-resistant cells were selected with growth medium containing 800 µg/mL Geneticin (Life Technologies, formerly Gibco BRL). Surviving individual colonies were isolated and screened for TRPV1 activity. Cells expressing recombinant TRPV1 were maintained at 37° C. in DMEM containing 4 mM L-glutamine, 300 µg/mL G418 (Calbiochem) and 10% fetal bovine serum under a humidified 5% $CO_2$ atmosphere.

The functional activity of compounds at the TRPV1 receptor was determined by measurement of intracellular $Ca^{2+}$ levels ($[Ca^{2+}]_i$) using the Fluorescence Imaging Plate Reader (FLIPR)TETRA®. All compounds were tested over a 12-point one-half-log concentration range with 37.5 µM being the maximum concentration tested. Compound stocks, 10 mM, were prepared in DMSO, and diluted serially across a 384-well plate using a Bravo BenchCel workstation (Agilent Technologies, Santa Clara, Calif.). On the day prior to the experiment, the recombinant HEK293 cells expressing human TRPV1 (hTRPV1) were removed from tissue culture flasks and plated in growth medium into black-walled clear-bottom 384-well Biocoat™ poly-D-lysine assay plates (BD Biosciences, Bedford, Mass.) using a Multidrop® dispenser (ThermoScientific, Waltham, Mass.). On the day of the experiment growth medium was removed, and the no-wash FLIPR® Calcium-4 dye ($\lambda_{EX}$=470-495 nm, $\lambda_{EM}$=515-575 nm) was added to each well using the Multidrop® dispenser. The plated cells were incubated for 90-120 min in the dark at 25° C. The test compounds dissolved in DMSO were then added to the plates using an Agilent Bravo workstation (Agilent Technologies Inc., Santa Clara, Calif.). Three minutes later, a pH 5.0 solution was added to each well. Reagents were delivered at a rate of 40 µL/sec, and the final assay volume was 80 µL. Acidic pH solutions were prepared by titration of DPBS/MES with 1 N HCl. The intensity of the fluorescence was captured and digitally transferred to an interfaced PC. The maximum peak measured for the concentration range tested was used to calculate the corresponding peak increase in fluorescence over baseline (relative fluorescence units) which was expressed as the percentage (max % remain) of the maximal pH 5.0-induced response.

Table 1 reports the percentage (max % remain) of the maximal pH 5.0-induced response measured for the compounds tested in the recombinant HEK293 cell assay. Most of the compounds tested inhibited calcium flux only partially following TRPV1 activation by the pH 5.0 solution. For example, the maximum % remaining for many of the compounds tested was at least 25% (i.e., the compounds blocked the pH 5.0 induced activation of TRPV1 by no more than 75%).

(iii) Rat Tail Immersion Protocol:

Compounds were tested for their effects on noxious thermosensation using the tail immersion assay. Testing was performed one hour following oral administration of 100 µmol/kg of the compound in 10% ethanol/20% Tween-80/70% PEG-400 (2 mL/kg). Mophine (6 mg/kg) was administered interperitoneally (i.p.) using saline (2 mL/kg) as the vehicle. For testing, a circulating water bath was heated to 55° C. Thirty to sixty minutes post dosing, the rats were handled for a few seconds to calm them down and then cupped with their back against the testers hand at a slight angle with head facing away from tester. With rat in one hand and a 0.01 second stopwatch in the other hand, the tail was quickly immersed 6-8 cm in water bath or to a distance leaving 2-3 cm of tail out of water. The timer was started simultaneously. When the rat flinched or attempted withdrawal, timer was immediately stopped and the rat's tail was quickly removed from water bath. This response latency (in seconds) was recorded. Process was repeated 3 times with 3-4 minutes between readings for a final average.

For a given compound, a percent increase in the average response latency (in seconds) for tail withdrawal relative to a vehicle control was determined $$\% \text{ increase} = [(t_c - t_v)/t_v] \times 100\%$$

$t_c$=response time (in seconds) with oral dosing of compounds $t_v$=response time (in seconds) with oral dosing of vehicle The % increases in tail withdrawal latency relative to vehicle control were divided into the following categories:

+++ is greater than or equal to 25% increase

++ is greater than or equal to 10% but less than 25% increase

+ is less than 10% increase

− is no statistically significant increase relative to vehicle control

Table 1 reports the % increase in tail withdrawal latency measured for the compounds tested. Specifically, Examples 1-39, Examples A-E (shown below), and morphine were tested in the rat tail immersion assay at one hour post dosing (100 µmol/kg). Many of the compounds tested imparted little or no impairment of the subject's ability to sense noxious temperature. For example, many of the compounds tested showed less than a 10% increase in tail withdrawal latency in rats when administered orally, relative to those that were dosed with vehicle.

Example A

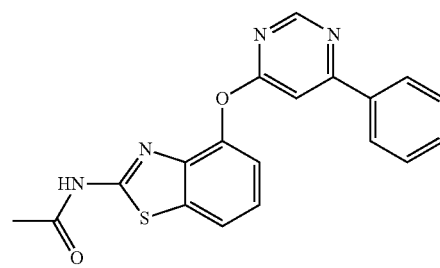

Example B

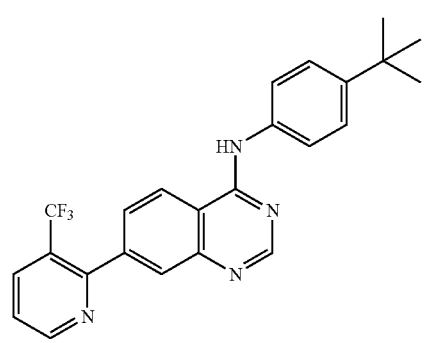

Example C

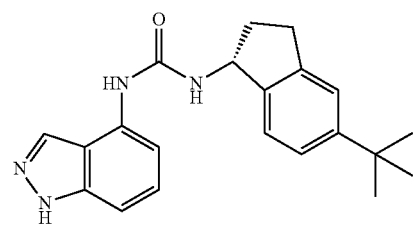

Example D

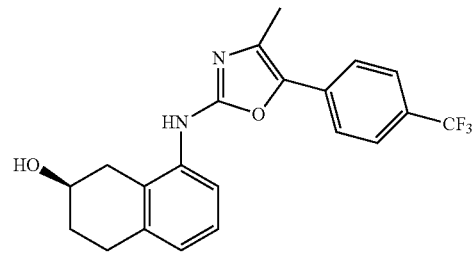

Example E

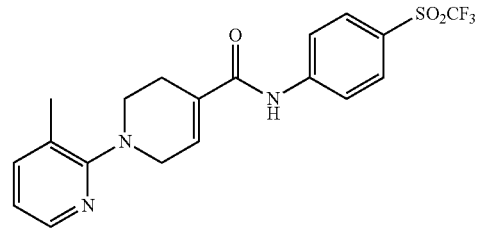

TABLE 1

| Example | human TRPV1 capsaicin IC$_{50}$ (nM) | human TRPV1 H$^+$ (max % remain) | % Increase in tail withdrawal latency |
|---|---|---|---|
| A | 20 | 10 | +++ |
| B | 55 | 1 | +++ |
| C | 35 | 1 | +++ |
| D | 180 | 3 | +++ |
| E | 100 | 2 | +++ |
| Morphine | | | +++ |
| 1 | 10 | 25 | − |
| 2 | 36 | 21 | ++ |
| 3 | 25 | 19 | − |
| 4 | 37 | 35 | − |
| 5 | 17 | 24 | ++ |
| 6 | 42 | 30 | − |
| 7 | 51 | 27 | ++ |
| 8 | 94 | 1 | +++ |
| 9 | 300 | 30 | − |
| 10 | 17 | 19 | ++ |
| 11 | 21 | 32 | ++ |
| 12 | 32 | 28 | +++ |
| 13 | 53 | 41 | − |
| 14 | 63 | 23 | +++ |
| 15 | 21 | 40 | − |
| 16 | 100 | 53 | − |
| 17 | 70 | 54 | − |
| 18 | 48 | 51 | − |
| 19 | 10 | 38 | +++ |
| 20 | 58 | 34 | ++ |
| 21 | 26 | 48 | ++ |
| 22 | 15 | 47 | +++ |
| 23 | 16 | 50 | +++ |
| 24 | 21 | 60 | − |
| 25 | 18 | 65 | − |
| 26 | 25 | 54 | − |
| 27 | 21 | 42 | +++ |
| 28 | 12 | 53 | − |
| 29 | 100 | 93 | − |
| 30 | 4 | 31 | − |
| 31 | 35 | 36 | − |
| 32 | 36 | 37 | − |
| 33 | 20 | 42 | − |
| 34 | 7 | 34 | − |
| 35 | 4 | 38 | − |
| 36 | 34 | 66 | − |
| 37 | 50 | 60 | − |
| 38 | 56 | 92 | − |
| 39 | 14 | 34 | − |

TABLE 1-continued

| Example | human TRPV1 capsaicin $IC_{50}$ (nM) | human TRPV1 $H^+$ (max % remain) | % Increase in tail withdrawal latency |
|---|---|---|---|
| 40 | 22 | 38 | |
| 41 | 12 | 74 | |
| 42 | 510 | 8 | |
| 43 | 94 | 8 | |
| 44 | 65 | 3 | |
| 45 | 43 | 4 | |
| 46 | 367 | 0 | |
| 47 | 169 | 0 | |
| 48 | 21 | 1 | |
| 49 | 6100 | 8 | |
| 50 | 45 | 0 | |
| 51 | 330 | 10 | |
| 52 | 950 | 32 | |
| 53 | 1800 | 1 | |
| 54 | 260 | 1 | |
| 55 | 7300 | 36 | |
| 56 | 700 | 67 | |
| 57 | 380 | 43 | |
| 58 | 63 | 2 | |
| 59 | 1500 | 2 | |
| 60 | 1300 | 9 | |
| 61 | 1200 | 2 | |
| 62 | 1500 | 9 | |
| 63 | 97 | 3 | |
| 64 | 14 | 26 | |
| 65 | 28 | 37 | |
| 66 | 15 | 42 | |
| 67 | 17 | 41 | |
| 68 | 20 | 34 | |
| 69 | 55 | 13 | |
| 70 | 29 | 17 | |
| 71 | 29 | 46 | |
| 72 | 54 | 36 | |
| 73 | 19 | 32 | |
| 74 | 19 | 28 | |
| 75 | 24 | 50 | |
| 76 | 32 | 17 | |
| 77 | 41 | 58 | |
| 78 | 91 | 46 | |
| 79 | 260 | 46 | |
| 80 | 63 | 45 | |
| 81 | 53 | 39 | |
| 82 | 250 | 56 | |
| 83 | 19 | 36 | |
| 84 | 23 | 40 | |
| 85 | 23 | 39 | |
| 86 | 10 | 23 | |
| 87 | 28 | 57 | |
| 88 | 2500 | 51 | |
| 89 | 31 | 53 | |
| 90 | 11 | 45 | |
| 91 | 15 | 50 | |
| 92 | 19 | 43 | |
| 93 | 39 | 47 | |
| 94 | 19 | 53 | |
| 95 | 63 | 54 | |
| 96 | 8 | 37 | |
| 97 | 17 | 26 | |
| 98 | 3700 | 58 | |
| 99 | 91 | 0 | |
| 100 | 310 | 95 | |
| 101 | 95 | 105 | |
| 102 | 44 | 99 | |
| 103 | 110 | 75 | |
| 104 | 200 | 80 | |
| 105 | 460 | 79 | |
| 106 | 94 | 98 | |
| 107 | 400 | 113 | |
| 108 | 240 | 104 | |
| 109 | 130 | 92 | |
| 110 | 150 | 111 | |
| 111 | 190 | 71 | |
| 112 | 440 | 101 | |
| 113 | 770 | 102 | |
| 114 | 56 | 99 | |
| 115 | >38000 | 91 | |
| 116 | 2000 | 99 | |
| 117 | 120 | 99 | |
| 118 | >38000 | 101 | |
| 119 | 170 | 110 | |
| 120 | 200 | 103 | |
| 121 | >38000 | 107 | |
| 122 | >38000 | 104 | |
| 123 | >38000 | 94 | |
| 124 | 1600 | 97 | |
| 125 | 330 | 96 | |
| 126 | 58 | 87 | |
| 127 | 67 | 100 | |
| 128 | 34 | 99 | |
| 129 | 120 | 97 | |
| 130 | 1000 | 98 | |
| 131 | 360 | 89 | |
| 132 | 31000 | 98 | |
| 133 | 2500 | 100 | |
| 134 | 8 | 0 | |
| 135 | 31 | 32 | |
| 136 | 23 | 26 | |
| 137 | 38 | 17 | |
| 138 | 38 | 19 | |
| 139 | 12 | 27 | |
| 140 | 11 | 27 | |
| 141 | 28 | 8 | |
| 142 | 110 | 18 | |
| 143 | 24 | 19 | |
| 144 | 130 | 5 | |
| 145 | 160 | 7 | |
| 146 | 38 | 15 | |
| 147 | 600 | 15 | |
| 148 | 100 | 33 | |
| 149 | 120 | 16 | |
| 150 | 16 | 20 | |
| 151 | 170 | 53 | |
| 152 | 470 | 22 | |
| 153 | 170 | 23 | |
| 154 | 15 | 20 | |
| 155 | 16 | 20 | |
| 156 | 190 | 67 | |
| 157 | 47 | 36 | |
| 158 | 29 | 35 | |
| 159 | 600 | 21 | |
| 160 | 42 | 23 | |
| 161 | 95 | 9 | |
| 162 | 130 | 0 | |
| 163 | 220 | 33 | |
| 164 | 120 | 35 | |
| 165 | 3 | 18 | |
| 166 | 1 | 10 | |
| 167 | 5 | 5 | |
| 168 | 1200 | 28 | |
| 169 | >38000 | 96 | |
| 170 | 130 | 16 | |
| 171 | 1300 | 63 | |
| 172 | 210 | 51 | |
| 173 | 100 | 54 | |
| 174 | 130 | 52 | |
| 175 | 4100 | 62 | |
| 176 | 120 | 50 | |
| 177 | 91 | 59 | |
| 178 | 72 | 52 | |
| 179 | 190 | 37 | |
| 180 | 230 | 12 | |
| 181 | 210 | 28 | |
| 182 | 380 | 29 | |
| 183 | 120 | 42 | |
| 184 | 86 | 44 | |
| 185 | 210 | 61 | |
| 186 | 1500 | 58 | |
| 187 | 760 | 50 | |
| 188 | 290 | 46 | |
| 189 | 200 | 40 | |
| 190 | 450 | 79 | |
| 191 | 450 | 19 | |

TABLE 1-continued

| Example | human TRPV1 capsaicin IC$_{50}$ (nM) | human TRPV1 H$^+$ (max % remain) | % Increase in tail withdrawal latency |
|---|---|---|---|
| 192 | 280 | 53 | |
| 193 | 270 | 56 | |
| 194 | 1800 | 52 | |
| 195 | 280 | 49 | |
| 196 | 2700 | 53 | |
| 197 | 1100 | 57 | |
| 198 | 350 | 55 | |
| 199 | 6700 | 58 | |
| 200 | 90 | 21 | |
| 201 | 130 | 45 | |
| 202 | 220 | 50 | |
| 203 | 28000 | 64 | |
| 204 | 1600 | 55 | |
| 205 | 400 | 56 | |
| 206 | 240 | 43 | |
| 207 | 330 | 57 | |
| 208 | 1300 | 55 | |
| 209 | 290 | 57 | |
| 210 | 820 | 60 | |
| 211 | 20 | 55 | |
| 212 | 61 | 34 | |
| 213 | 170 | 42 | |
| 214 | 180 | 40 | |
| 215 | 60 | 49 | |
| 216 | 220 | 50 | |
| 217 | 430 | 50 | |
| 218 | 3600 | 101 | |
| 219 | 56 | 29 | |
| 220 | 190 | 41 | |
| 221 | 1600 | 39 | |
| 222 | 32 | 30 | |
| 223 | 37 | 44 | |
| 224 | 35 | 44 | |
| 225 | 130 | 12 | |
| 226 | 100 | 12 | |
| 227 | 220 | 19 | |
| 228 | 120 | 57 | |
| 229 | 74 | 36 | |
| 230 | 38 | 24 | |
| 231 | 76 | 55 | |
| 232 | 140 | 32 | |
| 233 | 350 | 37 | |
| 234 | 90 | 27 | |
| 235 | 1300 | 29 | |
| 236 | 32 | 27 | |
| 237 | 150 | 52 | |
| 238 | 510 | 47 | |
| 239 | 47 | 26 | |
| 240 | 37 | 25 | |
| 241 | 130 | 54 | |
| 242 | 86 | 30 | |
| 243 | 4900 | 45 | |
| 244 | 7100 | 41 | |
| 245 | 280 | 28 | |
| 246 | 130 | 33 | |
| 247 | 38 | 18 | |
| 248 | 160 | 24 | |
| 249 | 110 | 28 | |
| 250 | 53 | 23 | |
| 251 | 78 | 26 | |
| 252 | 13 | 48 | |
| 253 | 110 | 31 | |
| 254 | 130 | 73 | |
| 255 | 20 | 5 | |
| 256 | 390 | 89 | |
| 257 | 21 | 72 | |
| 258 | 170 | 72 | |
| 259 | 4700 | 89 | |
| 260 | 130 | 61 | |
| 261 | 220 | 70 | |
| 262 | 460 | 37 | |
| 263 | 500 | 51 | |
| 264 | 170 | 82 | |
| 265 | 660 | 53 | |
| 266 | 65 | 54 | |
| 267 | 380 | 63 | |
| 268 | 1200 | 66 | |
| 269 | 540 | 70 | |
| 270 | 220 | 86 | |
| 271 | 170 | 69 | |
| 272 | 180 | 101 | |
| 273 | 210 | 55 | |
| 274 | 53 | 81 | |
| 275 | 920 | 83 | |
| 276 | 44 | 77 | |
| 277 | 4200 | 33 | |
| 278 | 77 | 68 | |
| 279 | 510 | 50 | |
| 280 | 960 | 68 | |
| 281 | 820 | 86 | |
| 282 | 410 | 81 | |
| 283 | 4800 | 84 | |
| 284 | 94 | 79 | |
| 285 | 55 | 27 | |
| 286 | 260 | 68 | |
| 287 | 13000 | 92 | |
| 288 | 10000 | 75 | |
| 289 | 230 | 68 | |
| 290 | 15 | 68 | |
| 291 | 26 | 71 | |
| 292 | 26 | 68 | |
| 293 | 270 | 72 | |
| 294 | 120 | 71 | |
| 295 | 99 | 67 | |
| 296 | 130 | 68 | |
| 297 | 130 | 67 | |
| 298 | 67 | 69 | |
| 299 | 54 | 84 | |
| 300 | 62 | 75 | |
| 301 | 1300 | 60 | |
| 302 | 200 | 36 | |
| 303 | 610 | 2 | |
| 304 | 230 | 0 | |
| 305 | 2000 | 26 | |
| 306 | 440 | 31 | |
| 307 | 1300 | 37 | |
| 308 | 68 | 3 | |
| 309 | 18000 | 36 | |
| 310 | 190 | 2 | |
| 311 | 150 | 14 | |
| 312 | 200 | 36 | |
| 313 | 76 | 4 | |
| 314 | 57 | 0 | |
| 315 | 830 | 18 | |
| 316 | 1900 | 20 | |
| 317 | 600 | 17 | |
| 318 | 590 | 14 | |
| 319 | 5000 | 21 | |
| 320 | 12 | 80 | |
| 321 | 21 | 87 | |
| 322 | 46 | 76 | |
| 323 | 4.5 | 0 | |
| 324 | 19 | 96 | |
| 325 | 21 | 83 | |
| 326 | 32 | 80 | |
| 327 | 21 | 32 | |

There are numerous recognized animal models for studying pain. Generally, these pain models mimic one of the mechanisms of pain (e.g. nociceptive, inflammatory, or neuropathic), rather than the pain associated with any one disease or injury. Such models provide evidence of whether a drug or therapy would be effective in treating any of a number of injuries, diseases, or conditions that generate pain via a particular mechanism. Exemplary animal models of pain include, but are not limited to, the rat acute capsaicin-induced flinching behavior and sodium iodoacetate-induced knee joint osteoarthritic pain model discussed below.

Rat Acute Capsaicin-Induced Flinching Behavior:

Rats were placed in individual observation cages. Following an acclimation period of 30 minutes, selected compounds were administered orally at a dose of 100 nmol/kg in a vehicle (10% ethanol/20% Tween 80/70% polyethylene glycol-400) at a volume of 2 mL/kg. One hour after administration of the compound, 2.5 µg of capsaicin in a 10 µL solution of 10% ethanol/90% hydroxypropyl-β-cyclodextrin was injected subcutaneously into the dorsal aspect of the right hind paw. The observation cage was then suspended above mirrors in order to facilitate observation. Rats were observed for a continuous period of five minutes. The number of flinching behaviors of the injured paw was recorded during the five minute observation period (Gilchrist, H. D.; Allard, B. L.; Simone, D. A.; Enhanced withdrawal responses to heat and mechanical stimuli following intraplantar injection of capsaicin in rats. *Pain,* 1996, 67, 179-188). The percent reduction in the number of flinching behaviors produced from oral administration of the test compounds relative to control-treated animals (% effect) is reported in Table 2.

TABLE 2

| Example | % effect |
|---|---|
| 17 | 83 |
| 18 | 64 |
| 19 | 90 |
| 24 | 58 |
| 27 | 33 |
| 28 | 81 |
| 33 | 59 |
| 36 | 60 |
| 37 | 78 |
| 38 | 69 |
| 221 | 53 |
| 241 | 53 |

(iv) Sodium Iodoacetate-Induced Knee Joint Osteoarthritic Pain Model

Unilateral knee joint osteoarthritis was induced in the rats by a single intra-articular (i.a.) injection of sodium iodoacetate (3 mg in 0.05 mL sterile isotonic saline) into the right knee joint cavity under light isoflurane anesthesia using a 26 G needle. The dose of the sodium iodoacetate (3 mg/i.a.injection) was selected based on results obtained from preliminary studies wherein an optimal pain behavior was observed at this dose. Pain behavioral assessment of hind limb grip force was conducted by recording the maximum compressive force exerted on the hind limb strain gauge setup, in a commercially available grip force measurement system (Columbus Instruments, Columbus, Ohio). The grip force data was converted to a maximum hindlimb cumulative compressive force (CFmax) (gram force)/kg body weight for each animal. The analgesic effects of test compounds were determined 20 days following the i.a. injection of sodium iodoacetate. The vehicle control group for each compound being tested was assigned 0% whereas the age matched naïve group was assigned as being 100% (normal). The % effect for each dose group was then expressed as % return to normalcy compared to the naïve group. Test compounds were administered orally in 10% ethanol/20% Tween 80/70% polyethylene glycol-400 vehicle at a volume of 2 mL/kg. The assessment of the analgesic effects of test compounds was made 1 hour following oral administration. The assessment of the analgesic effects of test compounds can be made following a single dose or following repeated administration wherein the frequency of dosing is 1 to 2 times daily. The duration of such repeated daily dosing may last for any time greater than one day. A typical duration of repeated daily dosing is about 5 days to about 12 days. Table 3 illustrates that representative compounds tested showed a statistically significant change in hind limb grip force strength versus a vehicle-dosed control after administration of a single acute oral dose.

TABLE 3

| Example | Dose (mg/kg, po) | % effect |
|---|---|---|
| 2 | 14 | 36 |
| 13 | 12 | 63 |
| 18 | 13 | 62 |
| 31 | 10 | 24 |
| 32 | 10 | 22 |
| 33 | 10 | 37 |
| 34 | 10 | 46 |
| 35 | 10 | 42 |
| 37 | 13 | 43 |
| 38 | 10 | 63 |
| 39 | 10 | 50 |
| 222 | 10 | 26 |
| 251 | 10 | 38 |
| 321 | 10 | 31 |
| 324 | 10 | 67 |

(v) Drug-Induced Thermosensory Impairment in Human Subjects (Water Bath Test)

Compounds can be tested for drug-induced thermosensory impairment in human subjects using a temperature-controlled water bath. Specifically, a temperature-controlled water bath is maintained at a constant temperature of 49° C. The subject immerses his or her hand (dominant hand preferred) in the water bath up to the distal wrist crease with the palm side down and withdraws the hand from the water upon first experiencing discomfort. The time taken by the subject to withdraw his or her hand from the water bath is recorded. The water bath test is performed once on the day prior to initial dosing of test compound and again on the morning of initial dosing but prior to administration of the test compound. Test compound is administered daily and the water bath test is performed at a time that corresponds to maximal exposure of the test compound.

The data in Tables 1, 2, and 3 demonstrate that the present compounds are TRPV1 antagonists and are expected to have promising effect of treating or preventing the various diseases and conditions described herein.

One embodiment provides a method for treating a disorder that can be ameliorated by suppressing activation of the vanilloid receptor subtype 1 (TRPV1) receptor in a host mammal in need of such treatment. The method comprises administering therapeutically effective amounts of a compound described herein or a pharmaceutically acceptable salt, prodrug, solvate, salt of a solvate, or solvate of a salt thereof, with or without a pharmaceutically acceptable carrier, and alone, or in combination with an analgesic (e.g. acetaminophen, opioids such as morphine), or an NSAIDs, or combinations thereof Another embodiment provides a method for treating pain in a mammal in need of such treatment. The method comprises administering therapeutically effective amount of a compound described herein or a pharmaceutically acceptable salt, prodrug, or solvate thereof, with or without a pharmaceutically acceptable carrier, and alone, or in combination with an analgesic (e.g. acetaminophen, opioids), or with an NSAID, or a combination thereof Yet another embodiment provides a method for treating pain including, but not limited to, chronic pain, neuropathic pain, nociceptive pain, allodynia, inflammatory pain, inflammatory hyperalgesia, post herpetic neuralgia, post operative pain, post stroke pain, neuropathies, neuralgia, diabetic neuropathy, HIV-related neuropathy, nerve injury, rheumatoid arthritic pain, osteoarthritic pain, burns, back pain, eye pain, visceral pain, cancer pain (e.g. bone cancer pain), dental pain, headache, migraine, carpal tunnel syndrome, fibromyalgia, neuritis, sciatica, pelvic hypersensitivity, pelvic pain, menstrual pain, bladder disease, such as incontinence and bladder overactivity, micturition disorder, renal colic; and cystitis; inflammation such as burns, rheumatoid arthritis and osteoarthritis; neurodegenerative disease such as stroke and multiple sclerosis; pulmonary disease such as asthma, cough, chronic obstructive pulmonary disease (COPD) and bronchoconstriction; gastrointestinal disease such as gastro esophageal reflux disease (GERD), dysphagia, ulcer, irritable bowel syndrome (IBS), inflammatory bowel disease (IBD), colitis and Crohn's disease; ischemia such as cerebrovascular ischemia, acute cerebral ischemia; emesis such as cancer chemotherapy-induced emesis, and obesity, in mammals, especially humans. For example, the present compounds are useful for the treatment of pain, particularly osteoarthritic pain. The method comprises administering therapeutically effective amount of a compound described herein or a pharmaceutically acceptable salt, prodrug, or solvates thereof, with or without a pharmaceutically acceptable carrier, and alone, or in combination with an analgesic (e.g. acetaminophen, opioid), or with an NSAID, or a combination thereof The present compounds can be used to treat pain as reported in Nolano, M. et al., *Pain*, 1999, 81, 135-145; Caterina, M. J. and Julius, D., *Annu. Rev. Neurosci.*, 2001, 24, 487-517; Caterina, M. J. et al., *Science*, 2000, 288, 306-313; Caterina, M. J. et al., *Nature*, 1997, 389, 816-824.

Physiological pain is an important protective mechanism designed to warn of danger from potentially injurious stimuli from the external environment. The system operates through a specific set of primary sensory neurons and is activated by noxious stimuli via peripheral transducing mechanisms (see Millan in *Prog. Neurobiol.*, 1999, 57, 1-164 for a review). These sensory fibers are known as nociceptors and are characteristically small-diameter axons with slow conduction velocities. Nociceptors encode the intensity, duration and quality of noxious stimulus and by virtue of their topographically organized projection to the spinal cord, the location of the stimulus. The nociceptors are found on nociceptive nerve fibers of which there are two main types, A-delta fibers (myelinated) and C fibers (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain can generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitization in the periphery, locally around the injury and centrally where the nociceptors terminate. These effects lead to a heightened sensation of pain. In acute pain, these mechanisms can be useful in promoting protective behaviors that can better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibers associated with maladaptation and aberrant activity (Woolf & Salter, Science, 2000, 288, 1765-1768).

Clinical pain is present when discomfort and abnormal sensitivity feature among the patient's symptoms. Patients tend to be quite heterogeneous and can present with various pain symptoms. Such symptoms include: 1) spontaneous pain which can be dull, burning, or stabbing; 2) exaggerated pain responses to noxious stimuli (hyperalgesia); and 3) pain produced by normally innocuous stimuli (allodynia: Meyer et al. Textbook of Pain, 13-44 (1994)). Although patients suffering from various forms of acute and chronic pain can have similar symptoms, the underlying mechanisms can be different and can, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury.

Pain afferents are activated by transduction of stimuli by nociceptors at the site of injury and activate neurons in the spinal cord at the level of their termination. This is then relayed up the spinal tracts to the brain where pain is perceived (Meyer et al., Textbook of Pain, 13-44 (1994). The activation of nociceptors activates two types of afferent nerve fibers. Myelinated A-delta fibers transmit rapidly and are responsible for sharp and stabbing pain sensations, whilst unmyelinated C fibers transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain can be chronic pain such as tumor related pain (e.g. bone pain, headache, facial pain or visceral pain) or pain associated with cancer therapy (e.g. post-chemotherapy syndrome, chronic postsurgical pain syndrome or post radiation syndrome). Cancer pain can also occur in response to chemotherapy, immunotherapy, hormonal therapy or radiotherapy. Back pain can be due to herniated or ruptured intervertebral discs or abnormalities of the lumber facet joints, sacroiliac joints, paraspinal muscles or the posterior longitudinal ligament. Back pain can resolve naturally but in some patients, where it lasts over 12 weeks, it becomes a chronic condition, which can be particularly debilitating.

Neuropathic pain is currently defined as pain initiated or caused by a primary lesion or dysfunction in the nervous system. Nerve damage can be caused by trauma and disease and thus the term neuropathic pain' encompasses many disorders with diverse etiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological, as it has no protective role. It is often present well after the original cause has dissipated, commonly lasting for years, significantly decreasing a patient's quality of life (Woolf and Mannion *Lancet* 1999, 353, 1959-1964). The symptoms of neuropathic pain are difficult to treat, as they are often heterogeneous even between patients with the same disease (Woolf and Decosterd *Pain Supp.* 1999, 6, S141-S147; Woolf and Mannion *Lancet* 1999, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, Textbook of Pain, 45-56 (1994)). Arthritic pain is the most common inflammatory pain.

Rheumatoid disease is one of the commonest chronic inflammatory conditions in developed countries and rheumatoid arthritis is a common cause of disability. The exact etiology of rheumatoid arthritis is unknown, but current hypotheses suggest that both genetic and microbiological factors can be important (Grennan & Jayson, Textbook of Pain, 397-407 (1994)). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder *Ann. Pharmacother.* 2002, 36, 679-686; McCarthy et al., Textbook of Pain, 387-395 (1994)). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs. Fernihough, J. et al. describe in *Neurosci. Lett.* 2005, 75-80 a potential role for TRPV1 in the manifestation of pain behavior accompanied by osteoarthritis changes in the knee.

Compounds described herein are TRPV1 antagonists and thus are useful in ameliorating acute and chronic inflammatory pain and postoperative pain as demonstrated in Honore, P. et al., *J. Pharmacol. Exp. Ther.* 2005, 410-421.

Another type of inflammatory pain is visceral pain, which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain.

Commonly encountered gastrointestinal (GI) disorders that cause pain include functional bowel disorder (FBD) and inflammatory bowel disease (IBD). These GI disorders include a wide range of disease states that are currently only moderately controlled, including, with respect to FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Elevated TRPV1 immunoreactivity has been observed in colonic sensory nerve fibers in patients with IBD (Szallasi, A. et al., *Nature Rev.*, 2007, 6, 357-373).

Other types of visceral pain include the pain associated with dysmenorrheal, cystitis and pancreatitis and pelvic pain.

It should be noted that some types of pain have multiple etiologies and thus can be classified in more than one area, e.g. back pain and cancer pain have both nociceptive and neuropathic components.

Other types of pain include: pain resulting from muscular-skeletal disorders, including myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardial infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, optic pain, burning mouth syndrome and temporomandibular myofascial pain. It has been shown that CGRP-receptor antagonists block the vasodilatation effects of CGRP and exhibits efficacy in patients with migraine and cluster headaches. CGRP is strongly co-expressed in many TRPV1 expressing nerve fibers, it is plausible that activation of TRPV1 could partially underlie a neurogenic-mediated component of headache.

Another type of pain is ocular pain (eye pain), which includes pain associated with dry eye syndrome, increased intraocular pressure, glaucoma, accidental trauma, and surgical procedures. intraocular pressure. Activation of TRPV1 induces inflammatory cytokine release in corneal epithelium in the eye (Zhang, F. et al., *J. Cell. Physiol.*, 2007, 213, 730; Murata, Y. et al., *Brain Res.*, 2006, 1085, 87). Retinal ganglion cell apoptosis induced by elevated hydrostatic pressure arises substantially through TRPV1, likely through the influx of extracellular $Ca^{2+}$ (Sappington, R. M. et al., *Invest. Ophth. Vis. Sci.*, 2009, 50, 717). TRPV1 antagonists can effectively reduce symptoms of dry eye without causing anesthesia effects on the ocular surface (US2009/0131449). Silencing of TRPV1 by administration of siRNA can be a useful therapy in the treatment of ocular pain associated with dry eye syndrome and could reduce side effects associated with medications currently used to treat patients suffering from this pathology. Investigators at Sylentis have reported data indicating that an siRNA targeting TRPV1 could be used to decrease the behavioral response of guinea pigs to ocular surface irritation (Association for Research in Vision and Ophthalmology Meeting, 2008). Administration of the TRPV1 agonist capsaicin resulted in a significant increase in irritation parameters compared with saline and that topical administration of TRPV1 siRNA twice a day for three days resulted in reduced scratching and wiping movements for up to nine days in the treated eyes. The reported analgesic effect was greater than that observed using the reference standard capsazepine.

It is known that capsaicin, a TRPV1 agonist, induces cough and reduced airway conductance in human clinical trials. TRPV1 antagonists such as capsazepine have been shown to block capsaicin and citric acid-induced cough responses in guinea pigs as demonstrated by Geppetti P. et al., *Eur. J. Pharmacol.*, 2006, 533, 207-214. Thus, TRPV1 antagonists demonstrate potential in the treatment of asthma, cough, chronic obstructive pulmonary disease (COPD) and bronchoconstriction as demonstrated by Watanabe N. et al., *Pulmonary Pharmacol. Ther.*, 2005, 18, 187-197; and Jia Y. et al., *Br. J. Pharmacol.*, 2002, 137, 831-836.

Present compounds can be used to treat bladder overactivity and/or urinary incontinence as demonstrated by Fowler, C., *Urology*, 2005, 65, 400-405.

Present compounds can be used to treat inflammatory thermal hyperalgesia as demonstrated by Davis, J. et al., Nature, 2000, 405, 183-187.

Present compounds can be used for the treatment of anxiety-related disorders as demonstrated by Marsch, R. et al., *J. Neurosci.*, 2007, 27, 832-839.

Present compounds can be used for the treatment of disorders associated with hyperdopaminergia such as psychosis, attention deficit hyperactivity disorder and schizophrenia as demonstrated by Tzavara, E. et al., *Biol. Psych.*, 2006, 59, 508-515.

Present compounds can be used for the treatment of diabetes and obesity as demonstrated by Suni, A. and Sallazi, A., *Trends Pharmacol. Sci.*, 2008, 29, 29-36.

Ischemia (e.g. cerebral ischemia) is the shortage or inadequate of oxygenated blood flow to body parts and organs, and often results in dysfunction or damage of tissue. The neuroprotective efficacy of induced hypothermia following or during cerebral ischemia is evident in experimental anima models of stroke (Barone, F. C. et al., *Neurosci. Biobehav. Rev.*, 1997; 2(1), 31-44; Onesti, S. T. et al., *Neurosurgery*, 1991, 29, 369; Coimbra, C. et al., *Acta Neuropathol. (Berl)*, 1994; 87, 325; Zhang, Y. et al., *Acta Anaesthesiol. Sin.*, 2001, 39, 65; Yamashita, K. et al., Stroke, 1991, 22, 1574; Ooboshi, H. et al., *Brain Res.*, 2000, 884, 23; Colbourne, F. et al., *J. Cereb. Blood Flow Metab.*, 2000, 20(1-2), 1702; Kawai, N. et al., *Stroke*, 2000, 3, 1982; Maier, C. M. et al., *J. Neurosurg.*, 2001, 94, 90; Maier, C. M. et al., *Stroke*, 1998, 29, 2171). Two trials conducted in cardiac arrest patients have demonstrated improved neurological outcome of inducing hypothermia (Mild therapeutic hypothermia to improve the neurologic outcome after cardiac arrest: Bernard, S. A. et al., *N. Engl. J. Med.*, 2002, 346, 549; and *N. Engl. J. Med.*, 2002, 346, 557). Induction of hypothermia by lowering of the core temperature has been attempted by mechanical devices such as surface cooling using catheters placed in a large vessel. However, such mechanical devices have been shown to have considerable side effects, including shivering, serious infections, and lung puncture. Regulation of the core body temperature by pharmaceutical compositions comprising TRPV1 agonists as a safer and less expensive alternative to the mechanical method was discussed in WO2008/040360 and WO2008/040361. Such treatments can have unintended side effects such as the sensation of burning pain, known to be elicited by TRPV1 agonists. TRPV1 antagonists that are capable of inducing hypothermia can be used for the treatment of ischemia without the pungent effects.

Present compounds can be administered alone, or in combination with one or more other compounds described herein, or in combination (i.e. co-administered) with one or more additional pharmaceutical agents. For example, a compound of the present invention, or a pharmaceutically acceptable salt, prodrug, or solvate thereof, can be administered in combination with an analgesic (e.g. acetaminophen, or an opioid such as morphine), or with a nonsteroidal anti-inflammatory drug (NSAID) such as, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac; or administered with a combination of an analgesic (e.g. acetaminophen, opioids) and an NSAID. In certain embodiments, the nonsteroidal anti-inflammatory drug (NSAID) is ibuprofen. In certain embodiments, the analgesic is acetaminophen. Combination therapy includes administration of a single pharmaceutical dosage formulation containing one or more of the compounds described herein and one or more additional pharmaceutical agents, as well as administration of the compounds of the invention and each additional pharmaceutical agent, in its own separate pharmaceutical dosage formulation. For example, a compound of formula (I) and one or more additional pharmaceutical agent(s) can be administered to the patient together, in a single oral dosage composition having a fixed ratio of each active ingredient, such as a tablet or capsule; or each agent can be administered in separate oral dosage formulations.

Where separate dosage formulations are used, the present compounds and one or more additional pharmaceutical agents can be administered at essentially the same time (e.g., concurrently) or at separately staggered times (e.g., sequentially).

Actual dosage levels of active ingredients in the pharmaceutical compositions can be varied so as to obtain an amount of the active compound that is effective to achieve the desired therapeutic response for a particular patient, compositions and mode of administration. The selected dosage level can depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds can be employed in pure form or, where such forms exist, in pharmaceutically acceptable salts thereof. The present compounds can also be administered as a pharmaceutical composition comprising the compound of interest in combination with a pharmaceutically acceptable carrier. The phrase "therapeutically effective amount" of the compound of the invention means a sufficient amount of the compound to treat disorders, at a reasonable benefit/risk ratio applicable to any medical treatment. It can be understood, however, that the total daily usage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds administered to a human or lower animal range from about 0.10 µg/kg body weight to about 25 mg/kg body weight. More preferable doses can be in the range of from about 0.10 µg/kg body weight to about 1 mg/kg body weight. If desired, the effective daily dose can be divided into multiple doses for purposes of administration. Consequently, single dose compositions can contain such amounts or submultiples thereof to make up the daily dose.

F. PHARMACEUTICAL COMPOSITIONS

Described herein are also pharmaceutical compositions comprising of a compound described herein, or a pharmaceutically acceptable salt, prodrug, or solvate thereof, formulated together with a pharmaceutically acceptable carrier. The pharmaceutical compositions can be formulated for oral administration in solid or liquid form, for parenteral injection or for rectal administration.

The compounds identified by the methods described herein can be administered as the sole pharmaceutical agent or in combination with one or more other pharmaceutical agents. For example, the compounds or salts or solvate thereof can be combined with an analgesic, or with a nonsteroidal anti-inflammatory drug (NSAID, or with a combination of an analgesic and an NSAID. Thus, the present invention also includes pharmaceutical compositions which are comprised of therapeutically effective amount of a compound identified by the methods described herein, or pharmaceutically acceptable salt, prodrug, or solvate thereof, a pharmaceutical agent as disclosed hereinabove, and a pharmaceutically acceptable carrier.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition can be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, can depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof If desired, and for more effective distribution, the compounds can be incorporated into slow-release or targeted-delivery systems such as polymer matrices, liposomes, and microspheres. They can be sterilized, for example, by filtration through a bacteria-retaining filter or by incorporation of sterilizing agents in the form of sterile solid compositions, which can be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, and perfuming agents.

Dosage forms for topical or transdermal administration include ointments, pastes, creams, lotions, gels, powders, solutions, sprays, inhalants or patches. A desired compound of the invention is admixed under sterile conditions with a pharmaceutically acceptable carrier and any needed preservatives or buffers as can be required. Ophthalmic formulation, eardrops, eye ointments, powders and solutions are also contemplated as being within the scope of this invention.

The ointments, pastes, creams and gels can contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof Powders and sprays can contain, in addition to the compounds of interest, lactose, talc, silicic acid, aluminum hydroxide, calcium silicates and polyamide powder, or mixtures of these substances. Sprays can additionally contain customary propellants such as chlorofluorohydrocarbons.

The present compounds can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of interest, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., p 33 et seq (1976).

Dosage forms for topical administration include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds can be used in the form of pharmaceutically acceptable salts derived from inorganic or organic acids. The term "pharmaceutically acceptable salts" as used herein, include salts and zwitterions of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds or separately by mixing together solutions of the compounds of invention and a suitable acid or base. The salt can precipitate from the solution and be collected by filtration or can be recovered by evaporation of the solvent. The degree of ionization in the salt can vary from completely ionized to almost non-ionized.

Suitable acid addition salts are formed from acids which form non-toxic salts.

Representative acid addition salts include, but are not limited to acetate, adipate, alginate, citrate, aspartate, benzoate, benzenesulfonate, bisulfate, bicarbonate, butyrate, camphorate, camphorsulfonate, carbonate, citrate, digluconate, glycerophosphate, hemisulfate, heptanoate, hexanoate, formate, fumarate, gluconate, glucuronate, glutamate, hydrochloride, hydrobromide, hydroiodide, 2-hydroxyethansulfonate (isethionate), lactate, maleate, malate, malonate, methanesulfonate, nicotinate, 2-naphthalenesulfonate, nicotinate nitrate, orotate, oxalate, palmitate, pamoate, pectinate, persulfate, 3-phenylpropionate, picrate, pivalate, propionate, saccharate, stearate, succinate, sulfate, tartrate, thiocyanate, phosphate, hydrogenphosphate, dihydrogen phosphate, p-toluenesulfonate, trifluoroacetate, and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds by reacting a carboxylic acid-containing moiety with a suitable base such as the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as lithium, sodium, potassium, calcium, magnesium, zinc, and aluminum salts, and the like, and nontoxic quaternary ammonia and amine cations including ammonium, tetramethylammonium, tetraethylammonium, methylamine, dimethylamine, trimethylamine, triethylamine, diethylamine, and ethylamine. Other representative organic amines useful for the formation of base addition salts include ethylenediamine, ethanolamine, diethanolamine, piperidine, and piperazine.

The term "pharmaceutically acceptable prodrug" or "prodrug" as used herein, represents those prodrugs of the compounds of the invention which are, within the scope of sound medical judgment, suitable for use in contact with the tissues of humans and animals without undue toxicity, irritation, allergic response, and the like, commensurate with a reasonable benefit/risk ratio, and effective for their intended use. Prodrugs of the invention can be rapidly transformed in vivo to a parent compound of formula (I), for example, by hydrolysis in blood. A thorough discussion is provided in T. Higuchi and V. Stella, Prodrugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention also contemplates pharmaceutically acceptable compounds that when administered to a patient in need thereof can be converted through in vivo biotransformation into compounds of the invention.

The compounds of the invention can exist in both unsolvated and solvated forms. The term "solvate" is used herein to describe a molecular complex comprising the compound of the invention and one or more pharmaceutically acceptable solvent molecules, for example, ethanol. The term "hydrate" is employed when said solvent is water.

It is understood that the foregoing detailed description and accompanying examples are merely illustrative and are not to be taken as limitations upon the scope of the invention, which is defined solely by the appended claims and their equivalents. Various changes and modifications to the disclosed embodiments can be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

We claim:

1. A compound of formula (I-f):

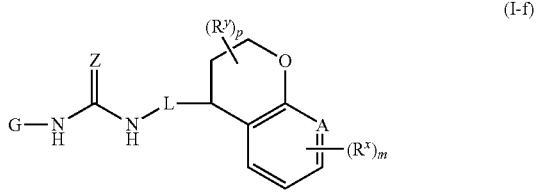

(I-f)

or a salt thereof, wherein:
G is formula (i), (ii), or (iii):

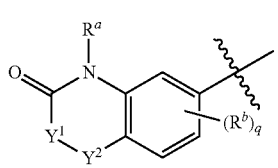

(i)

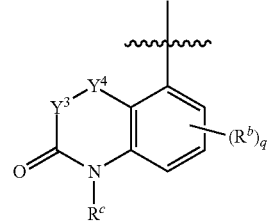

(ii)

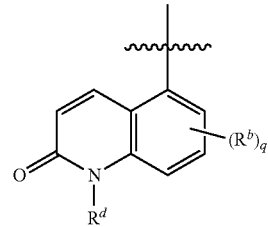

(iii)

$R^a$ is hydrogen or methyl;
$Y^1$ is $CH_2$ and $Y^2$ is O; or
$Y^1$ is $CR^{1a}R^{1b}$, and $Y^2$ is $CH_2$; wherein $R^{1a}$ is hydrogen, and $R^{1b}$ is hydrogen or $NR^{1c}R^{1d}$ wherein $R^{1c}$ is hydrogen or methyl, and $R^{1d}$ is —($C_1$-$C_2$ alkylenyl)-OH or —($C_1$-$C_2$ alkylenyl)-O(methyl), or $R^{1c}$ and $R^{1d}$, together with the nitrogen atom to which they are attached form a monocyclic ring selected from the group consisting of morpholinyl and oxazepanyl; or
$Y^1$ is $NR^1$ and $Y^2$ is $CH_2$; wherein $R^1$ is hydrogen, methyl, or —($C_1$-$C_2$ alkylenyl)-OH;
$R^c$ is hydrogen, methyl, or ethyl;
$Y^3$ is $CR^{3a}R^{3b}$, and $Y^4$ is O; wherein $R^{3a}$ and $R^{3b}$ are each independently hydrogen or methyl; or
$Y^3$ and $Y^4$ are $CH_2$; or
$Y^3$ is $NR^3$ and $Y^4$ is $CH_2$; wherein $R^3$ is hydrogen or methyl;
$R^d$ is hydrogen or methyl;
$R^b$, at each occurrence, represents an optional substituent on the benzo moiety of the bicyclic rings of formula (i), (ii), and (iii), and is independently alkyl, halogen, or haloalkyl
q is 0;
Z is O or S;
A is CH or N;
L is a bond or $CH_2$;
m is 0, 1, 2, 3, or 4;
$R^x$, at each occurrence, represents an optional substituent on any substitutable carbon atom of the ring containing A, and each $R^x$ is independently $C_{1-6}$-alkyl, halogen, halomethyl, OH, O(methyl), or O(halomethyl);
p is 0, 1, or 2; and
$R^y$, at each occurrence, represents an optional substituent on any substitutable carbon atom of the ring containing O, and each $R^y$ is independently $C_{1-6}$-alkyl, halomethyl, or —$CH_2$-O(methyl);
two $R^y$ groups that are attached to the same carbon atom, together with said carbon atom to which they are attached, optionally form an unsubstituted cyclobutyl or cyclopentyl ring.

2. The compound or salt according to claim 1, wherein A is CH, Z is O, and L is a bond.

3. The compound or salt according to claim 1, wherein A is CH, Z is S, and L is a bond.

4. The compound or salt according to claim 1, wherein A is N, Z is O, and L is a bond.

5. The compound or salt according to claim 1, wherein A is CH, Z is O, and L is $CH_2$.

6. The compound or salt according to claim 1, wherein G is formula (i).

7. The compound or salt according to claim 1, wherein G is formula (ii).

8. The compound or salt according to claim 1, wherein G is formula (iii).

9. The compound or salt according to claim 1, wherein A is CH.

10. The compound or salt according to claim 1, wherein A is N.

11. The compound or salt according to claim 1, wherein A is CH and Z is O.

12. The compound or salt according to claim 1, wherein A is N and Z is O.

13. The compound or salt according to claim 1, wherein:
G is formula (i);
A is CH;
L is a bond; and
Z is O.

14. The compound or salt according to claim 13, wherein:
$R^a$ is hydrogen,
$Y^1$ is $CH_2$, and
$Y^2$ is O.

15. The compound or salt according to claim 13, wherein:
$R^a$ is hydrogen or methyl,
$Y^1$ is $cR^{1a}R^{1b}$,
$R^{1a}$ is hydrogen,
$R^{1b}$ is hydrogen, and
$Y^2$ is $CH_2$.

16. The compound or salt according to claim 1, wherein:
G is formula (ii);
A is CH;
L is a bond; and
Z is O.

17. The compound or salt according to claim 1, wherein:
G is formula (iii);
A is CH;
L is a bond; and
Z is O.

18. The compound or salt according to claim 1, wherein:
G is formula (i);
A is N;
L is a bond; and
Z is O.

19. The compound or salt according to claim 1, wherein:
G is formula (i);
A is CH;
L is a bond; and
Z is S.

20. The compound or salt according to claim 1, wherein the compound is selected from the group consisting of:
1-[(4R)-7-fluoro-2,2-dimethyl-3,4-dihydro-2H-chromen-4-yl]-3-(1-methyl-2-oxo-1,2,3,4-tetrahydroquinazolin-5-yl)urea;
1-[(4R)-7-chloro-8-fluoro-2,2-bis(fluoromethyl)-3,4-dihydro-2H-chromen-4-yl]-3-(1-methyl-2-oxo-1,2,3,4-tetrahydroquinazolin-5-yl)urea;
1-[(4R)-2,2-dimethyl-3,4-dihydro-2H-chromen-4-yl]-3-(1-methyl-2-oxo-1,2,3,4-tetrahydroquinazolin-5-yl)urea;
1-[(4R)-7-chloro-2,2-dimethyl-3,4-dihydro-2H-chromen-4-yl]-3-(1-methyl-2-oxo-1,2,3,4-tetrahydroquinazolin-5-yl)urea;
1-[(4R)-2,2-bis(fluoromethyl)-3,4-dihydro-2H-chromen-4-yl]-3-(1-methyl-2-oxo-1,2,3,4-tetrahydroquinazolin-5-yl)urea;
1-[(2S,4R)-2-(difluoromethyl)-2-methyl-3,4-dihydro-2H-chromen-4-yl]-3-(1-methyl-2-oxo-1,2,3,4-tetrahydroquinazolin-5-yl)urea;
1-[(4R)-3,4-dihydrospiro[chromene-2,1'-cyclopentan]-4-yl]-3-(1-methyl-2-oxo-1,2,3,4-tetrahydroquinazolin-5-yl)urea;
1-[(4R)-2,2-dimethyl-8-(trifluoromethyl)-3,4-dihydro-2H-chromen-4-yl]-3-(3-methyl-2-oxo-1,2,3,4-tetrahydroquinazolin-7-yl)urea;
1-(3-methyl-2-oxo-1,2,3,4-tetrahydroquinazolin-7-yl)-3-[(2R,4R)-2-methyl-2-(trifluoromethyl)-3,4-dihydro-2H-chromen-4-yl]urea;
1-[(4R)-6-fluoro-2,2-dimethyl-3,4-dihydro-2H-chromen-4-yl]-3-(1-methyl-2-oxo-1,2-dihydroquinolin-5-yl)urea;
1-(1-methyl-2-oxo-1,2-dihydroquinolin-5-yl)-3-[(2S,4R)-2-methyl-2-(trifluoromethyl)-3,4-dihydro-2H-chromen-4-yl]urea;
1-[(2S,4R)-2-(difluoromethyl)-2-methyl-3,4-dihydro-2H-chromen-4-yl]-3-(1-methyl-2-oxo-1,2-dihydroquinolin-5-yl)urea;
1-[(2R,4R)-2-(difluoromethyl)-2-methyl-3,4-dihydro-2H-chromen-4-yl]-3-(1-methyl-2-oxo-1,2-dihydroquinolin-5-yl)urea;
1-[(4R)-7-chloro-2,2-bis(fluoromethyl)-3,4-dihydro-2H-chromen-4-yl]-3-(3-oxo-3,4-dihydro-2H-1,4-benzoxazin-6-yl)urea;
1-[(2R,4R)-7-chloro-2-(difluoromethyl)-2-methyl-3,4-dihydro-2H-chromen-4-yl]-3-(2-oxo-1,2,3,4-tetrahydroquinolin-7-yl)urea;
1-[(4R)-7-chloro-2,2-bis(fluoromethyl)-3,4-dihydro-2H-chromen-4-yl]-3-(2-oxo-1,2,3,4-tetrahydroquinolin-7-yl)urea;
1-[(4R)-2,2-dimethyl-7-(trifluoromethyl)-3,4-dihydro-2H-chromen-4-yl]-3-(2-oxo-1,2,3,4-tetrahydroquinolin-7-yl)urea;
1-[(4R)-7,8-difluoro-2,2-dimethyl-3,4-dihydro-2H-chromen-4-yl]-3-(2-oxo-1,2,3,4-tetrahydroquinolin-7-yl)urea;
1-[(2R,4R)-2-methyl-2-(trifluoromethyl)-3,4-dihydro-2H-chromen-4-yl]-3-(2-oxo-1,2,3,4-tetrahydroquinolin-7-yl)urea;
1-(1-methyl-2-oxo-1,2,3,4-tetrahydroquinolin-7-yl)-3-[(4R)-7-(trifluoromethyl)-3,4-dihydro-2H-chromen-4-yl]urea;
1-[(4R)-7-fluoro-2,2-dimethyl-3,4-dihydro-2H-chromen-4-yl]-3-(3-oxo-3,4-dihydro-2H-1,4-benzoxazin-6-yl)urea; and
1-[(4R)-7-chloro-8-fluoro-2,2-dimethyl-3,4-dihydro-2H-chromen-4-yl]-3-(2-oxo-1,2,3,4-tetrahydroquinolin-7-yl)urea.

21. The compound or salt according to claim 1, wherein the compound is selected from the group consisting of:
1-[(4R)-7-chloro-2,2-bis(fluoromethyl)-3,4-dihydro-2H-chromen-4-yl]-3-(1-methyl-2-oxo-1,2,3,4-tetrahydroquinazolin-5-yl)urea;
1-[(4R)-8-chloro-7-fluoro-2,2-dimethyl-3,4-dihydro-2H-chromen-4-yl]-3-(1-methyl-2-oxo-1,2,3,4-tetrahydroquinazolin-5-yl)urea;
1-[(2R,4R)-7-chloro-2-(fluoromethyl)-2-methyl-3,4-dihydro-2H-chromen-4-yl]-3-(1-methyl-2-oxo-1,2,3,4-tetrahydroquinazolin-5-yl)urea;
1-[(4R)-2,2-dimethyl-3,4-dihydro-2H-chromen-4-yl]-3-(1-ethyl-2-oxo-1,2,3,4-tetrahydroquinazolin-5-yl)urea;

1-[(2R,4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea;
1-[(2S,4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea;
1-[(2R,4R)-2-(difluoromethyl)-2-methyl-3,4-dihydro-2H-chromen-4-yl]-3-(1-methyl-2-oxo-1,2,3,4-tetrahydroquinazolin-5-yl)urea;
1-[(2S,4R)-7-chloro-2-(fluoromethyl)-2-methyl-3,4-dihydro-2H-chromen-4-yl]-3-(1-methyl-2-oxo-1,2,3,4-tetrahydroquinazolin-5-yl)urea;
1-[(4R)-7-fluoro-2,2-dimethyl-3,4-dihydro-2H-chromen-4-yl]-3-(1-methyl-2-oxo-1,2-dihydroquinolin-5-yl)urea;
1-[(4R)-7-chloro-2,2-bis(fluoromethyl)-3,4-dihydro-2H-chromen-4-yl]-3-(1-methyl-2-oxo-1,2-dihydroquinolin-5-yl)urea;
1-[(4R)-7-chloro-8-fluoro-2,2-bis(fluoromethyl)-3,4-dihydro-2H-chromen-4-yl]-3-(1-methyl-2-oxo-1,2-dihydroquinolin-5-yl)urea;
1-[(4R)-8-chloro-7-fluoro-2,2-dimethyl-3,4-dihydro-2H-chromen-4-yl]-3-(1-methyl-2-oxo-1,2-dihydroquinolin-5-yl)urea;
1-[(4R)-7-chloro-2,2-dimethyl-3,4-dihydro-2H-chromen-4-yl]-3-(1-methyl-2-oxo-1,2-dihydroquinolin-5-yl)urea;
1-[(4R)-7-fluoro-2,2-bis(fluoromethyl)-3,4-dihydro-2H-chromen-4-yl]-3-(1-methyl-2-oxo-1,2-dihydroquinolin-5-yl)urea;
1-[(2R,4R)-7-chloro-2-(fluoromethyl)-2-methyl-3,4-dihydro-2H-chromen-4-yl]-3-(1-methyl-2-oxo-1,2-dihydroquinolin-5-yl)urea;
1-[(2S,4R)-7-chloro-2-(fluoromethyl)-2-methyl-3,4-dihydro-2H-chromen-4-yl]-3-(1-methyl-2-oxo-1,2-dihydroquinolin-5-yl)urea;
1-[(4R)-8-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;
1-[(4R)-7-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;
1-[(4R)-2,2-diethyl-8-fluoro-3,4-dihydro-2H-chromen-4-yl]-3-[3-(2-hydroxyethyl)-2-oxo-1,2,3,4-tetrahydroquinazolin-7-yl]urea;
1-[(4R)-2,2-diethyl-3,4-dihydro-2H-chromen-4-yl]-3-[3-(2-hydroxyethyl)-2-oxo-1,2,3,4-tetrahydroquinazolin-7-yl]urea;
1-[(4R)-2,2-diethyl-7-(trifluoromethyl)-3,4-dihydro-2H-chromen-4-yl]-3-[3-(2-hydroxyethyl)-2-oxo-1,2,3,4-tetrahydroquinazolin-7-yl]urea;
1-[(4R)-7-chloro-2,2-diethyl-3,4-dihydro-2H-chromen-4-yl]-3-[3-(2-hydroxyethyl)-2-oxo-1,2,3,4-tetrahydroquinazolin-7-yl]urea;
1-[(4R)-2,2-dimethyl-7-(trifluoromethyl)-3,4-dihydro-2H-chromen-4-yl]-3-[3-(2-hydroxyethyl)-2-oxo-1,2,3,4-tetrahydroquinazolin-7-yl]urea;
1-[(4R)-6-fluoro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea;
1-[(4R)-2,2-diethyl-6-fluoro-3,4-dihydro-2H-chromen-4-yl]-3-[3-(2-hydroxyethyl)-2-oxo-1,2,3,4-tetrahydroquinazolin-7-yl]urea;
1-[(4R)-6-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;
1-[(4R)-6-fluoro-3,4-dihydro-2H-chromen-4-yl]-3-[3-(2-hydroxyethyl)-2-oxo-1,2,3,4-tetrahydroquinazolin-7-yl]urea;
1-[3-(2-hydroxyethyl)-2-oxo-1,2,3,4-tetrahydroquinazolin-7-yl]-3-[(4R)-8-(trifluoromethyl)-3,4-dihydro-2H-chromen-4-yl]urea;
1-[3-(2-hydroxyethyl)-2-oxo-1,2,3,4-tetrahydroquinazolin-7-yl]-3-[(4R)-7-(trifluoromethyl)-3,4-dihydro-2H-chromen-4-yl]urea;
1-[(4S)-6-fluoro-3,4-dihydrospiro[chromene-2,1'-cyclobutan]-4-yl]-3-[3-(2-hydroxyethyl)-2-oxo-1,2,3,4-tetrahydroquinazolin-7-yl]urea;
1-[(4S)-6-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;
1-[(2S,4R)-2-(fluoromethyl)-2-methyl-7-(trifluoromethyl)-3,4-dihydro-2H-chromen-4-yl]-3-[3-(2-hydroxyethyl)-2-oxo-1,2,3,4-tetrahydroquinazolin-7-yl]urea;
1-[(2S,4R)-7-chloro-2-(fluoromethyl)-2-methyl-3,4-dihydro-2H-chromen-4-yl]-3-[3-(2-hydroxyethyl)-2-oxo-1,2,3,4-tetrahydroquinazolin-7-yl]urea;
1-[(2R,4R)-2-(difluoromethyl)-2-methyl-3,4-dihydro-2H-chromen-4-yl]-3-[3-(2-hydroxyethyl)-2-oxo-1,2,3,4-tetrahydroquinazolin-7-yl]urea;
1-[(4R)-7-chloro-8-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;
1-[(4R)-7-bromo-2,2-dimethyl-3,4-dihydro-2H-chromen-4-yl]-3-[3-(2-hydroxyethyl)-2-oxo-1,2,3,4-tetrahydroquinazolin-7-yl]urea;
1-(1-methyl-2-oxo-1,2-dihydroquinolin-5-yl)-3-[(4R)-7-(trifluoromethyl)-3,4-dihydro-2H-chromen-4-yl]urea;
1-[(4R)-3,4-dihydrospiro[chromene-2,1'-cyclopentan]-4-yl]-3-(1-methyl-2-oxo-1,2-dihydroquinolin-5-yl)urea;
1-[(4R)-2,2-diethyl-8-fluoro-3,4-dihydro-2H-chromen-4-yl]-3-(1-methyl-2-oxo-1,2-dihydroquinolin-5-yl)urea;
1-[(4R)-2,2-diethyl-3,4-dihydro-2H-chromen-4-yl]-3-(1-methyl-2-oxo-1,2-dihydroquinolin-5-yl)urea;
1-[(4R)-2,2-diethyl-7-(trifluoromethyl)-3,4-dihydro-2H-chromen-4-yl]-3-(1-methyl-2-oxo-1,2-dihydroquinolin-5-yl)urea;
1-[(4R)-7-chloro-2,2-diethyl-3,4-dihydro-2H-chromen-4-yl]-3-(1-methyl-2-oxo-1,2-dihydroquinolin-5-yl)urea;
1-[(4R)-6-fluoro-2,2-bis(fluoromethyl)-3,4-dihydro-2H-chromen-4-yl]-3-(1-methyl-2-oxo-1,2-dihydroquinolin-5-yl)urea;
1-[(4R)-6,8-difluoro-2,2-bis(fluoromethyl)-3,4-dihydro-2H-chromen-4-yl]-3-(1-methyl-2-oxo-1,2-dihydroquinolin-5-yl)urea;
1-[(4R)-6-fluoro-3,4-dihydrospiro[chromene-2,1'-cyclobutan]-4-yl]-3-(1-methyl-2-oxo-1,2-dihydroquinolin-5-yl)urea;
1-[(4R)-2,2-diethyl-6-fluoro-3,4-dihydro-2H-chromen-4-yl]-3-(1-methyl-2-oxo-1,2-dihydroquinolin-5-yl)urea;
1-[(4R)-8-fluoro-2,2-dipropyl-3,4-dihydro-2H-chromen-4-yl]-3-(1-methyl-2-oxo-1,2-dihydroquinolin-5-yl)urea;
1-[(4R)-2,2-diethyl-7-(trifluoromethoxy)-3,4-dihydro-2H-chromen-4-yl]-3-(1-methyl-2-oxo-1,2-dihydroquinolin-5-yl)urea;
1-[(4R)-2,2-dimethyl-3,4-dihydro-2H-chromen-4-yl]-3-(1-methyl-2-oxo-1,2-dihydroquinolin-5-yl)urea;
1-(1-methyl-2-oxo-1,2-dihydroquinolin-5-yl)-3-[(4S)-7-(trifluoromethoxy)-3,4-dihydro-2H-chromen-4-yl]urea;

1-[(4R)-6-fluoro-2,2-bis(methoxymethyl)-3,4-dihydro-2H-chromen-4-yl]-3-(1-methyl-2-oxo-1,2-dihydroquinolin-5-yl)urea;
1-[(4R)-2,2-bis(fluoromethyl)-3,4-dihydro-2H-chromen-4-yl]-3-(1-methyl-2-oxo-1,2-dihydroquinolin-5-yl)urea;
1-[(4R)-7,8-difluoro-2,2-dimethyl-3,4-dihydro-2H-chromen-4-yl]-3-(1-methyl-2-oxo-1,2-dihydroquinolin-5-yl)urea;
1-[(4R)-6-fluoro-3,4-dihydro-2H-chromen-4-yl]-3-(1-methyl-2-oxo-1,2-dihydroquinolin-5-yl)urea;
1-[(2S,4R)-2-(fluoromethyl)-2-methyl-7-(trifluoromethyl)-3,4-dihydro-2H-chromen-4-yl]-3-(1-methyl-2-oxo-1,2-dihydroquinolin-5-yl)urea;
1-[(4R)-7-chloro-8-fluoro-2,2-dimethyl-3,4-dihydro-2H-chromen-4-yl]-3-(1-methyl-2-oxo-1,2-dihydroquinolin-5-yl)urea;
1-(1-methyl-2-oxo-1,2-dihydroquinolin-5-yl)-3-[(4R)-7-(trifluoromethoxy)-3,4-dihydro-2H-chromen-4-yl]urea;
1-[(4S)-6-fluoro-3,4-dihydrospiro[chromene-2,1'-cyclobutan]-4-yl]-3-(1-methyl-2-oxo-1,2-dihydroquinolin-5-yl)urea;
1-[(4R)-7-bromo-2,2-dimethyl-3,4-dihydro-2H-chromen-4-yl]-3-(1-methyl-2-oxo-1,2-dihydroquinolin-5-yl)urea;
1-(1-methyl-2-oxo-1,2-dihydroquinolin-5-yl)-3-[(2R,4R)-2-methyl-2-(trifluoromethyl)-3,4-dihydro-2H-chromen-4-yl]urea;
1-[(4R)-2,2-dimethyl-7-(trifluoromethyl)-3,4-dihydro-2H-chromen-4-yl]-3-(1-methyl-2-oxo-1,2-dihydroquinolin-5-yl)urea;
1-[(4R)-2,2-bis(fluoromethyl)-7-(trifluoromethyl)-3,4-dihydro-2H-chromen-4-yl]-3-(1-methyl-2-oxo-1,2-dihydroquinolin-5-yl)urea;
1-[(4R)-2,2-dimethyl-8-(trifluoromethyl)-3,4-dihydro-2H-chromen-4-yl]-3-(1-methyl-2-oxo-1,2-dihydroquinolin-5-yl)urea;
1-[(4R)-8-fluoro-2,2-dimethyl-3,4-dihydro-2H-chromen-4-yl]-3-(1-methyl-2-oxo-1,2-dihydroquinolin-5-yl)urea;
1-[(4R)-8-fluoro-2,2-bis(fluoromethyl)-3,4-dihydro-2H-chromen-4-yl]-3-(1-methyl-2-oxo-1,2-dihydroquinolin-5-yl)urea;
1-(1-methyl-2-oxo-1,2-dihydroquinolin-5-yl)-3-[(4R)-8-(trifluoromethyl)-3,4-dihydro-2H-chromen-4-yl]urea;
1-[(4S)-6-fluoro-2,2-dimethyl-3,4-dihydro-2H-chromen-4-yl]-3-(1-methyl-2-oxo-1,2-dihydroquinolin-5-yl)urea;
1-[(4R)-7-chloro-2,2-bis(fluoromethyl)-3,4-dihydro-2H-chromen-4-yl]-3-(2-oxo-1,2-dihydroquinolin-5-yl)urea;
1-[(4R)-8-fluoro-2,2-dimethyl-3,4-dihydro-2H-chromen-4-yl]-3-(3-oxo-3,4-dihydro-2H-1,4-benzoxazin-6-yl)urea;
1-[(4R)-2,2-diethyl-8-fluoro-3,4-dihydro-2H-chromen-4-yl]-3-(3-oxo-3,4-dihydro-2H-1,4-benzoxazin-6-yl)urea;
1-[(4R)-2,2-diethyl-3,4-dihydro-2H-chromen-4-yl]-3-(3-oxo-3,4-dihydro-2H-1,4-benzoxazin-6-yl)urea;
1-[(4R)-2,2-diethyl-7-(trifluoromethyl)-3,4-dihydro-2H-chromen-4-yl]-3-(3-oxo-3,4-dihydro-2H-1,4-benzoxazin-6-yl)urea;
1-[(4R)-7-chloro-2,2-diethyl-3,4-dihydro-2H-chromen-4-yl]-3-(3-oxo-3,4-dihydro-2H-1,4-benzoxazin-6-yl)urea;
1-[(4R)-7,8-dichloro-2,2-diethyl-3,4-dihydro-2H-chromen-4-yl]-3-(3-oxo-3,4-dihydro-2H-1,4-benzoxazin-6-yl)urea;
1-[(4R)-2,2-dimethyl-7-(trifluoromethyl)-3,4-dihydro-2H-chromen-4-yl]-3-(3-oxo-3,4-dihydro-2H-1,4-benzoxazin-6-yl)urea;
1-[(4R)-6-fluoro-2,2-dipropyl-3,4-dihydro-2H-chromen-4-yl]-3-(3-oxo-3,4-dihydro-2H-1,4-benzoxazin-6-yl)urea;
1-[(4R)-6-fluoro-3,4-dihydrospiro[chromene-2,1'-cyclobutan]-4-yl]-3-(3-oxo-3,4-dihydro-2H-1,4-benzoxazin-6-yl)urea;
1-[(4R)-2,2-diethyl-6-fluoro-3,4-dihydro-2H-chromen-4-yl]-3-(3-oxo-3,4-dihydro-2H-1,4-benzoxazin-6-yl)urea;
1-[(4R)-8-fluoro-2,2-dipropyl-3,4-dihydro-2H-chromen-4-yl]-3-(3-oxo-3,4-dihydro-2H-1,4-benzoxazin-6-yl)urea;
1-[(4R)-2,2-diethyl-7-(trifluoromethoxy)-3,4-dihydro-2H-chromen-4-yl]-3-(3-oxo-3,4-dihydro-2H-1,4-benzoxazin-6-yl)urea;
1-[(4R)-2,2-dimethyl-3,4-dihydro-2H-chromen-4-yl]-3-(3-oxo-3,4-dihydro-2H-1,4-benzoxazin-6-yl)urea;
1-[(4R)-6-fluoro-2,2-dimethyl-3,4-dihydro-2H-chromen-4-yl]-3-(3-oxo-3,4-dihydro-2H-1,4-benzoxazin-6-yl)urea;
1-[(4R)-7-chloro-2,2-dimethyl-3,4-dihydro-2H-chromen-4-yl]-3-(3-oxo-3,4-dihydro-2H-1,4-benzoxazin-6-yl)urea;
1-(3-oxo-3,4-dihydro-2H-1,4-benzoxazin-6-yl)-3-[(4R)-7-(trifluoromethoxy)-3,4-dihydro-2H-chromen-4-yl]urea;
1-[(4R)-8-fluoro-2,2-bis(fluoromethyl)-3,4-dihydro-2H-chromen-4-yl]-3-(3-oxo-3,4-dihydro-2H-1,4-benzoxazin-6-yl)urea;
1-[(4R)-7,8-difluoro-2,2-dimethyl-3,4-dihydro-2H-chromen-4-yl]-3-(3-oxo-3,4-dihydro-2H-1,4-benzoxazin-6-yl)urea;
1-[(4R)-6-fluoro-3,4-dihydro-2H-chromen-4-yl]-3-(3-oxo-3,4-dihydro-2H-1,4-benzoxazin-6-yl)urea;
1-(3-oxo-3,4-dihydro-2H-1,4-benzoxazin-6-yl)-3-[(4R)-8-(trifluoromethyl)-3,4-dihydro-2H-chromen-4-yl]urea;
1-(3-oxo-3,4-dihydro-2H-1,4-benzoxazin-6-yl)-3-[(4R)-7-(trifluoromethyl)-3,4-dihydro-2H-chromen-4-yl]urea;
1-[(4S)-6-fluoro-3,4-dihydrospiro[chromene-2,1'-cyclobutan]-4-yl]-3-(3-oxo-3,4-dihydro-2H-1,4-benzoxazin-6-yl)urea;
1-[(4S)-6-fluoro-2,2-dimethyl-3,4-dihydro-2H-chromen-4-yl]-3-(3-oxo-3,4-dihydro-2H-1,4-benzoxazin-6-yl)urea;
1-[(4R)-3,4-dihydrospiro[chromene-2,1'-cyclopentan]-4-yl]-3-(3-oxo-3,4-dihydro-2H-1,4-benzoxazin-6-yl)urea;
1-[(2S,4R)-2-methyl-2-(trifluoromethyl)-3,4-dihydro-2H-chromen-4-yl]-3-(3-oxo-3,4-dihydro-2H-1,4-benzoxazin-6-yl)urea;
1-[(2R,4R)-2-methyl-2-(trifluoromethyl)-3,4-dihydro-2H-chromen-4-yl]-3-(3-oxo-3,4-dihydro-2H-1,4-benzoxazin-6-yl)urea;
1-[(2S,4R)-2-(fluoromethyl)-2-methyl-7-(trifluoromethyl)-3,4-dihydro-2H-chromen-4-yl]-3-(3-oxo-3,4-dihydro-2H-1,4-benzoxazin-6-yl)urea;
1-[(2R,4R)-2-(fluoromethyl)-2-methyl-7-(trifluoromethyl)-3,4-dihydro-2H-chromen-4-yl]-3-(3-oxo-3,4-dihydro-2H-1,4-benzoxazin-6-yl)urea;

1-[(2S,4R)-7-chloro-2-(fluoromethyl)-2-methyl-3,4-dihydro-2H-chromen-4-yl]-3-(3-oxo-3,4-dihydro-2H-1,4-benzoxazin-6-yl)urea;
1-[(2S,4R)-2-(difluoromethyl)-2-methyl-3,4-dihydro-2H-chromen-4-yl]-3-(3-oxo-3,4-dihydro-2H-1,4-benzoxazin-6-yl)urea;
1-[(2R,4R)-2-(difluoromethyl)-2-methyl-3,4-dihydro-2H-chromen-4-yl]-3-(3-oxo-3,4-dihydro-2H-1,4-benzoxazin-6-yl)urea;
1-[(4R)-7-chloro-2,2-bis(fluoromethyl)-3,4-dihydro-2H-chromen-4-yl]-3-[(2R)-2-methyl-3-oxo-3,4-dihydro-2H-1,4-benzoxazin-8-yl]urea;
1-[(4R)-8-fluoro-2,2-dimethyl-3,4-dihydro-2H-chromen-4-yl]-3-(1-methyl-2-oxo-1,2,3,4-tetrahydroquinazolin-5-yl)urea;
1-[(4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea;
1-[(4R)-2,2-dimethyl-7-(trifluoromethoxy)-3,4-dihydro-2H-chromen-4-yl]-3-(1-methyl-2-oxo-1,2,3,4-tetrahydroquinazolin-5-yl)urea;
1-(1-methyl-2-oxo-1,2,3,4-tetrahydroquinazolin-5-yl)-3-[(4R)-8-(trifluoromethoxy)-3,4-dihydro-2H-chromen-4-yl]urea;
1-[(4R)-2,2-diethyl-8-fluoro-3,4-dihydro-2H-chromen-4-yl]-3-(1-methyl-2-oxo-1,2,3,4-tetrahydroquinazolin-5-yl)urea;
1-[(4R)-2,2-diethyl-3,4-dihydro-2H-chromen-4-yl]-3-(1-methyl-2-oxo-1,2,3,4-tetrahydroquinazolin-5-yl)urea;
1-[(4R)-8-tert-butyl-3,4-dihydro-2H-chromen-4-yl]-3-(1-methyl-2-oxo-1,2,3,4-tetrahydroquinazolin-5-yl)urea;
1-[(4R)-2,2-diethyl-7-fluoro-3,4-dihydro-2H-chromen-4-yl]-3-(1-methyl-2-oxo-1,2,3,4-tetrahydroquinazolin-5-yl)urea;
1-[(4R)-2,2-diethyl-7-(trifluoromethyl)-3,4-dihydro-2H-chromen-4-yl]-3-(1-methyl-2-oxo-1,2,3,4-tetrahydroquinazolin-5-yl)urea;
1-[(4R)-7-chloro-2,2-diethyl-3,4-dihydro-2H-chromen-4-yl]-3-(1-methyl-2-oxo-1,2,3,4-tetrahydroquinazolin-5-yl)urea;
1-[(4R)-2,2-bis(fluoromethyl)-7-(trifluoromethyl)-3,4-dihydro-2H-chromen-4-yl]-3-(1-methyl-2-oxo-1,2,3,4-tetrahydroquinazolin-5-yl)urea;
1-[(4R)-7,8-dichloro-2,2-diethyl-3,4-dihydro-2H-chromen-4-yl]-3-(1-methyl-2-oxo-1,2,3,4-tetrahydroquinazolin-5-yl)urea;
1-[(4R)-8-chloro-2,2-bis(fluoromethyl)-3,4-dihydro-2H-chromen-4-yl]-3-(1-methyl-2-oxo-1,2,3,4-tetrahydroquinazolin-5-yl)urea;
1-[(4R)-2,2-bis(fluoromethyl)-7-(trifluoromethoxy)-3,4-dihydro-2H-chromen-4-yl]-3-(1-methyl-2-oxo-1,2,3,4-tetrahydroquinazolin-5-yl)urea;
1-[(4R)-2,2-dimethyl-7-(trifluoromethyl)-3,4-dihydro-2H-chromen-4-yl]-3-(1-methyl-2-oxo-1,2,3,4-tetrahydroquinazolin-5-yl)urea;
1-[(4R)-6-fluoro-2,2-dipropyl-3,4-dihydro-2H-chromen-4-yl]-3-(1-methyl-2-oxo-1,2,3,4-tetrahydroquinazolin-5-yl)urea;
1-[(4R)-6-fluoro-2,2-bis(fluoromethyl)-3,4-dihydro-2H-chromen-4-yl]-3-(1-methyl-2-oxo-1,2,3,4-tetrahydroquinazolin-5-yl)urea;
1-[(4R)-6,8-difluoro-2,2-bis(fluoromethyl)-3,4-dihydro-2H-chromen-4-yl]-3-(1-methyl-2-oxo-1,2,3,4-tetrahydroquinazolin-5-yl)urea;
1-[(4R)-6-fluoro-3,4-dihydrospiro[chromene-2,1'-cyclobutan]-4-yl]-3-(1-methyl-2-oxo-1,2,3,4-tetrahydroquinazolin-5-yl)urea;
1-[(4R)-2,2-diethyl-6-fluoro-3,4-dihydro-2H-chromen-4-yl]-3-(1-methyl-2-oxo-1,2,3,4-tetrahydroquinazolin-5-yl)urea;
1-[(4R)-8-fluoro-2,2-dipropyl-3,4-dihydro-2H-chromen-4-yl]-3-(1-methyl-2-oxo-1,2,3,4-tetrahydroquinazolin-5-yl)urea;
1-[(4R)-6-fluoro-2,2-dimethyl-3,4-dihydro-2H-chromen-4-yl]-3-(1-methyl-2-oxo-1,2,3,4-tetrahydroquinazolin-5-yl)urea;
1-[(4R)-7-fluoro-3,4-dihydro-2H-chromen-4-yl]-3-(1-methyl-2-oxo-1,2,3,4-tetrahydroquinazolin-5-yl)urea;
1-(1-methyl-2-oxo-1,2,3,4-tetrahydroquinazolin-5-yl)-3-[(4R)-7-(trifluoromethyl)-3,4-dihydro-2H-chromen-4-yl]urea;
1-[(4R)-7-chloro-2,2-bis(fluoromethyl)-3,4-dihydro-2H-chromen-4-yl]-3-(1-ethyl-2-oxo-1,2,3,4-tetrahydroquinazolin-5-yl)urea;
1-[(2R,4R)-2-(fluoromethyl)-2-methyl-3,4-dihydro-2H-chromen-4-yl]-3-(1-methyl-2-oxo-1,2,3,4-tetrahydroquinazolin-5-yl)urea;
1-[(2S,4R)-2-(fluoromethyl)-2-methyl-3,4-dihydro-2H-chromen-4-yl]-3-(1-methyl-2-oxo-1,2,3,4-tetrahydroquinazolin-5-yl)urea;
1-(1-methyl-2-oxo-1,2,3,4-tetrahydroquinazolin-5-yl)-3-[(2S,4R)-2-methyl-2-(trifluoromethyl)-3,4-dihydro-2H-chromen-4-yl]urea;
1-(1-methyl-2-oxo-1,2,3,4-tetrahydroquinazolin-5-yl)-3-[(2R,4R)-2-methyl-2-(trifluoromethyl)-3,4-dihydro-2H-chromen-4-yl]urea;
1-[(4R)-7-chloro-2,2-bis(fluoromethyl)-3,4-dihydro-2H-chromen-4-yl]-3-(1,3-dimethyl-2-oxo-1,2,3,4-tetrahydroquinazolin-5-yl)urea;
1-[(4R)-3,4-dihydro-2H-chromen-4-yl]-3-(1-methyl-2-oxo-1,2,3,4-tetrahydroquinazolin-5-yl)urea;
1-(1-methyl-2-oxo-1,2,3,4-tetrahydroquinazolin-5-yl)-3-[(4S)-7-(trifluoromethoxy)-3,4-dihydro-2H-chromen-4-yl]urea;
1-[(4R)-7-chloro-2,2-bis(fluoromethyl)-3,4-dihydro-2H-chromen-4-yl]-3-(3-methyl-2-oxo-1,2,3,4-tetrahydroquinazolin-7-yl)urea;
1-[(2S,4R)-2-(difluoromethyl)-2-methyl-3,4-dihydro-2H-chromen-4-yl]-3-(3-methyl-2-oxo-1,2,3,4-tetrahydroquinazolin-7-yl)urea;
1-[(4R)-8-chloro-7-fluoro-2,2-dimethyl-3,4-dihydro-2H-chromen-4-yl]-3-(3-methyl-2-oxo-1,2,3,4-tetrahydroquinazolin-7-yl)urea;
1-[(4R)-2,2-bis(fluoromethyl)-7-(trifluoromethyl)-3,4-dihydro-2H-chromen-4-yl]-3-(3-methyl-2-oxo-1,2,3,4-tetrahydroquinazolin-7-yl)urea;
1-[(4R)-3,4-dihydro-2H-chromen-4-yl]-3-(3-methyl-2-oxo-1,2,3,4-tetrahydroquinazolin-7-yl)urea;
1-[(4R)-7-fluoro-2,2-dimethyl-3,4-dihydro-2H-chromen-4-yl]-3-(3-methyl-2-oxo-1,2,3,4-tetrahydroquinazolin-7-yl)urea;
1-[(4R)-2,2-diethyl-8-fluoro-3,4-dihydro-2H-chromen-4-yl]-3-(3-methyl-2-oxo-1,2,3,4-tetrahydroquinazolin-7-yl)urea;
1-[(4R)-2,2-diethyl-3,4-dihydro-2H-chromen-4-yl]-3-(3-methyl-2-oxo-1,2,3,4-tetrahydroquinazolin-7-yl)urea;
1-[(4R)-2,2-diethyl-7-(trifluoromethyl)-3,4-dihydro-2H-chromen-4-yl]-3-(3-methyl-2-oxo-1,2,3,4-tetrahydroquinazolin-7-yl)urea;
1-[(4R)-7-chloro-2,2-diethyl-3,4-dihydro-2H-chromen-4-yl]-3-(3-methyl-2-oxo-1,2,3,4-tetrahydroquinazolin-7-yl)urea;

1-[(4R)-7,8-dichloro-2,2-diethyl-3,4-dihydro-2H-chromen-4-yl]-3-(3-methyl-2-oxo-1,2,3,4-tetrahydroquinazolin-7-yl)urea;
1-[(4R)-2,2-bis(fluoromethyl)-7-(trifluoromethoxy)-3,4-dihydro-2H-chromen-4-yl]-3-(3-methyl-2-oxo-1,2,3,4-tetrahydroquinazolin-7-yl)urea;
1-[(4R)-2,2-dimethyl-7-(trifluoromethyl)-3,4-dihydro-2H-chromen-4-yl]-3-(3-methyl-2-oxo-1,2,3,4-tetrahydroquinazolin-7-yl)urea;
1-[(4R)-6-fluoro-2,2-dipropyl-3,4-dihydro-2H-chromen-4-yl]-3-(3-methyl-2-oxo-1,2,3,4-tetrahydroquinazolin-7-yl)urea;
1-[(4R)-6-fluoro-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-6,8-difluoro-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-6-fluoro-3,4-dihydrospiro[chromene-2,1'-cyclobutan]-4-yl]-3-(3-methyl-2-oxo-1,2,3,4-tetrahydroquinazolin-7-yl)urea;
1-[(4R)-2,2-diethyl-6-fluoro-3,4-dihydro-2H-chromen-4-yl]-3-(3-methyl-2-oxo-1,2,3,4-tetrahydroquinazolin-7-yl)urea;
1-[(4R)-8-fluoro-2,2-dipropyl-3,4-dihydro-2H-chromen-4-yl]-3-(3-methyl-2-oxo-1,2,3,4-tetrahydroquinazolin-7-yl)urea;
1-[(4R)-2,2-diethyl-7-(trifluoromethoxy)-3,4-dihydro-2H-chromen-4-yl]-3-(3-methyl-2-oxo-1,2,3,4-tetrahydroquinazolin-7-yl)urea;
1-[(4R)-7-chloro-8-fluoro-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-2,2-dimethyl-3,4-dihydro-2H-chromen-4-yl]-3-(3-methyl-2-oxo-1,2,3,4-tetrahydroquinazolin-7-yl)urea;
1-(3-methyl-2-oxo-1,2,3,4-tetrahydroquinazolin-7-yl)-3-[(4S)-7-(trifluoromethoxy)-3,4-dihydro-2H-chromen-4-yl]urea;
1-(3-methyl-2-oxo-1,2,3,4-tetrahydroquinazolin-7-yl)-3-[(4R)-7-(trifluoromethoxy)-3,4-dihydro-2H-chromen-4-yl]urea;
1-[(4R)-6-fluoro-2,2-bis(methoxymethyl)-3,4-dihydro-2H-chromen-4-yl]-3-(3-methyl-2-oxo-1,2,3,4-tetrahydroquinazolin-7-yl)urea;
1-[(4R)-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-8-fluoro-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-6-fluoro-3,4-dihydro-2H-chromen-4-yl]-3-(3-methyl-2-oxo-1,2,3,4-tetrahydroquinazolin-7-yl)urea;
1-(3-methyl-2-oxo-1,2,3,4-tetrahydroquinazolin-7-yl)-3-[(4R)-8-(trifluoromethyl)-3,4-dihydro-2H-chromen-4-yl]urea;
1-(3-methyl-2-oxo-1,2,3,4-tetrahydroquinazolin-7-yl)-3-[(4R)-7-(trifluoromethyl)-3,4-dihydro-2H-chromen-4-yl]urea;
1-[(4S)-6-fluoro-3,4-dihydrospiro[chromene-2,1'-cyclobutan]-4-yl]-3-(3-methyl-2-oxo-1,2,3,4-tetrahydroquinazolin-7-yl)urea;
1-[(4S)-6-fluoro-2,2-dimethyl-3,4-dihydro-2H-chromen-4-yl]-3-(3-methyl-2-oxo-1,2,3,4-tetrahydroquinazolin-7-yl)urea;
1-[(4R)-3,4-dihydrospiro[chromene-2,1'-cyclopentan]-4-yl]-3-(3-methyl-2-oxo-1,2,3,4-tetrahydroquinazolin-7-yl)urea;
1-[(2R,4R)-2-(fluoromethyl)-2-methyl-7-(trifluoromethyl)-3,4-dihydro-2H-chromen-4-yl]-3-(3-methyl-2-oxo-1,2,3,4-tetrahydroquinazolin-7-yl)urea;
1-[(2R,4R)-2-(difluoromethyl)-2-methyl-3,4-dihydro-2H-chromen-4-yl]-3-(3-methyl-2-oxo-1,2,3,4-tetrahydroquinazolin-7-yl)urea;
1-[(4R)-7-fluoro-2,2-bis(fluoromethyl)-3,4-dihydro-2H-chromen-4-yl]-3-(3-methyl-2-oxo-1,2,3,4-tetrahydroquinazolin-7-yl)urea;
1-[(4R)-8-fluoro-2,2-dimethyl-3,4-dihydro-2H-chromen-4-yl]-3-(3-methyl-2-oxo-1,2,3,4-tetrahydroquinazolin-7-yl)urea;
1-[(4R)-2,2-bis(fluoromethyl)-7-(trifluoromethoxy)-3,4-dihydro-2H-chromen-4-yl]-3-(2-oxo-1,2,3,4-tetrahydroquinolin-7-yl)urea;
1-[(2S,4R)-7-chloro-2-(difluoromethyl)-2-methyl-3,4-dihydro-2H-chromen-4-yl]-3-(2-oxo-1,2,3,4-tetrahydroquinolin-7-yl)urea;
1-[(4R)-6-fluoro-2,2-bis(fluoromethyl)-3,4-dihydro-2H-chromen-4-yl]-3-(2-oxo-1,2,3,4-tetrahydroquinolin-7-yl)urea;
1-[(4R)-6,8-difluoro-2,2-bis(fluoromethyl)-3,4-dihydro-2H-chromen-4-yl]-3-(2-oxo-1,2,3,4-tetrahydroquinolin-7-yl)urea;
1-[(4R)-2,2-bis(fluoromethyl)-3,4-dihydro-2H-chromen-4-yl]-3-(2-oxo-1,2,3,4-tetrahydroquinolin-7-yl)urea;
1-[(4R)-8-fluoro-2,2-bis(fluoromethyl)-3,4-dihydro-2H-chromen-4-yl]-3-(2-oxo-1,2,3,4-tetrahydroquinolin-7-yl)urea;
1-[(4S)-7-chloro-2,2-bis(fluoromethyl)-3,4-dihydro-2H-chromen-4-yl]-3-(2-oxo-1,2,3,4-tetrahydroquinolin-7-yl)urea;
1-[(4R)-2,2-dimethyl-8-(trifluoromethyl)-3,4-dihydro-2H-chromen-4-yl]-3-(2-oxo-1,2,3,4-tetrahydroquinolin-7-yl)urea;
1-[(4R)-8-fluoro-2,2-dimethyl-3,4-dihydro-2H-chromen-4-yl]-3-(2-oxo-1,2,3,4-tetrahydroquinolin-7-yl)urea;
1-[(4R)-3,4-dihydro-2H-chromen-4-yl]-3-(2-oxo-1,2,3,4-tetrahydroquinolin-7-yl)urea;
1-[(4R)-7-fluoro-2,2-dimethyl-3,4-dihydro-2H-chromen-4-yl]-3-(2-oxo-1,2,3,4-tetrahydroquinolin-7-yl)urea;
1-[(4R)-2,2-diethyl-8-fluoro-3,4-dihydro-2H-chromen-4-yl]-3-(2-oxo-1,2,3,4-tetrahydroquinolin-7-yl)urea;
1-[(4R)-2,2-diethyl-3,4-dihydro-2H-chromen-4-yl]-3-(2-oxo-1,2,3,4-tetrahydroquinolin-7-yl)urea;
1-[(4R)-2,2-diethyl-7-(trifluoromethyl)-3,4-dihydro-2H-chromen-4-yl]-3-(2-oxo-1,2,3,4-tetrahydroquinolin-7-yl)urea;
1-[(4R)-7-chloro-2,2-diethyl-3,4-dihydro-2H-chromen-4-yl]-3-(2-oxo-1,2,3,4-tetrahydroquinolin-7-yl)urea;
1-[(4R)-7,8-dichloro-2,2-diethyl-3,4-dihydro-2H-chromen-4-yl]-3-(2-oxo-1,2,3,4-tetrahydroquinolin-7-yl)urea;
1-[(4R)-6-fluoro-2,2-dipropyl-3,4-dihydro-2H-chromen-4-yl]-3-(2-oxo-1,2,3,4-tetrahydroquinolin-7-yl)urea;
1-[(4R)-6-fluoro-3,4-dihydrospiro[chromene-2,1'-cyclobutan]-4-yl]-3-(2-oxo-1,2,3,4-tetrahydroquinolin-7-yl)urea;
1-[(4R)-2,2-diethyl-6-fluoro-3,4-dihydro-2H-chromen-4-yl]-3-(2-oxo-1,2,3,4-tetrahydroquinolin-7-yl)urea;
1-[(4R)-8-fluoro-2,2-dipropyl-3,4-dihydro-2H-chromen-4-yl]-3-(2-oxo-1,2,3,4-tetrahydroquinolin-7-yl)urea;

1-[(4R)-7-chloro-8-fluoro-2,2-bis(fluoromethyl)-3,4-dihydro-2H-chromen-4-yl]-3-(2-oxo-1,2,3,4-tetrahydroquinolin-7-yl)urea;
1-[(4R)-6-fluoro-2,2-dimethyl-3,4-dihydro-2H-chromen-4-yl]-3-(2-oxo-1,2,3,4-tetrahydroquinolin-7-yl)urea;
1-[(4R)-8-chloro-7-fluoro-2,2-dimethyl-3,4-dihydro-2H-chromen-4-yl]-3-(2-oxo-1,2,3,4-tetrahydroquinolin-7-yl)urea;
1-(2-oxo-1,2,3,4-tetrahydroquinolin-7-yl)-3-[(4S)-7-(trifluoromethoxy)-3,4-dihydro-2H-chromen-4-yl]urea;
1-[(4R)-7-chloro-2,2-dimethyl-3,4-dihydro-2H-chromen-4-yl]-3-(2-oxo-1,2,3,4-tetrahydroquinolin-7-yl)urea;
1-(2-oxo-1,2,3,4-tetrahydroquinolin-7-yl)-3-[(4R)-7-(trifluoromethoxy)-3,4-dihydro-2H-chromen-4-yl]urea;
1-[(4R)-6-fluoro-2,2-bis(methoxymethyl)-3,4-dihydro-2H-chromen-4-yl]-3-(2-oxo-1,2,3,4-tetrahydroquinolin-7-yl)urea;
1-(2-oxo-1,2,3,4-tetrahydroquinolin-7-yl)-3-[(4R)-8-(trifluoromethyl)-3,4-dihydro-2H-chromen-4-yl]urea;
1-(2-oxo-1,2,3,4-tetrahydroquinolin-7-yl)-3-[(4R)-7-(trifluoromethyl)-3,4-dihydro-2H-chromen-4-yl]urea;
1-[(2R,4R)-7-chloro-2-(fluoromethyl)-2-methyl-3,4-dihydro-2H-chromen-4-yl]-3-(2-oxo-1,2,3,4-tetrahydroquinolin-7-yl)urea;
1-[(4S)-6-fluoro-3,4-dihydrospiro[chromene-2,1'-cyclobutan]-4-yl]-3-(2-oxo-1,2,3,4-tetrahydroquinolin-7-yl)urea;
1-[(4S)-6-fluoro-2,2-dimethyl-3,4-dihydro-2H-chromen-4-yl]-3-(2-oxo-1,2,3,4-tetrahydroquinolin-7-yl)urea;
1-[(4R)-3,4-dihydrospiro[chromene-2,1'-cyclopentan]-4-yl]-3-(2-oxo-1,2,3,4-tetrahydroquinolin-7-yl)urea;
1-[(2S,4R)-2-methyl-2-(trifluoromethyl)-3,4-dihydro-2H-chromen-4-yl]-3-(2-oxo-1,2,3,4-tetrahydroquinolin-7-yl)urea;
1-[(2S,4R)-7-chloro-2-(fluoromethyl)-2-methyl-3,4-dihydro-2H-chromen-4-yl]-3-(2-oxo-1,2,3,4-tetrahydroquinolin-7-yl)urea;
1-[(2S,4R)-2-(difluoromethyl)-2-methyl-3,4-dihydro-2H-chromen-4-yl]-3-(2-oxo-1,2,3,4-tetrahydroquinolin-7-yl)urea;
1-[(2R,4R)-2-(difluoromethyl)-2-methyl-3,4-dihydro-2H-chromen-4-yl]-3-(2-oxo-1,2,3,4-tetrahydroquinolin-7-yl)urea;
1-[(4R)-7-fluoro-2,2-bis(fluoromethyl)-3,4-dihydro-2H-chromen-4-yl]-3-(2-oxo-1,2,3,4-tetrahydroquinolin-7-yl)urea;
1-[(4R)-7-chloro-2,2-bis(fluoromethyl)-3,4-dihydro-2H-chromen-4-yl]-3-(2-oxo-1,2,3,4-tetrahydroquinolin-7-yl)thiourea;
1-[(4R)-7-fluoro-2,2-dimethyl-3,4-dihydro-2H-chromen-4-yl]-3-(1-methyl-2-oxo-1,2,3,4-tetrahydroquinolin-7-yl)urea;
1-[(4R)-7-chloro-2,2-bis(fluoromethyl)-3,4-dihydro-2H-chromen-4-yl]-3-(1-methyl-2-oxo-1,2,3,4-tetrahydroquinolin-5-yl)urea;
1-[(4R)-7-chloro-2,2-bis(fluoromethyl)-3,4-dihydro-2H-chromen-4-yl]-3-(1-methyl-2-oxo-1,2,3,4-tetrahydroquinolin-7-yl)urea;
1-[(4R)-2,2-dimethyl-8-(trifluoromethyl)-3,4-dihydro-2H-chromen-4-yl]-3-(1-methyl-2-oxo-1,2,3,4-tetrahydroquinolin-7-yl)urea;
1-[(4R)-8-fluoro-2,2-dimethyl-3,4-dihydro-2H-chromen-4-yl]-3-(1-methyl-2-oxo-1,2,3,4-tetrahydroquinolin-7-yl)urea;
1-[(4R)-3,4-dihydro-2H-chromen-4-yl]-3-(1-methyl-2-oxo-1,2,3,4-tetrahydroquinolin-7-yl)urea;
1-[(4R)-2,2-diethyl-8-fluoro-3,4-dihydro-2H-chromen-4-yl]-3-(1-methyl-2-oxo-1,2,3,4-tetrahydroquinolin-7-yl)urea;
1-[(4R)-2,2-diethyl-3,4-dihydro-2H-chromen-4-yl]-3-(1-methyl-2-oxo-1,2,3,4-tetrahydroquinolin-7-yl)urea;
1-[(4R)-2,2-diethyl-7-(trifluoromethyl)-3,4-dihydro-2H-chromen-4-yl]-3-(1-methyl-2-oxo-1,2,3,4-tetrahydroquinolin-7-yl)urea;
1-[(4R)-7-chloro-2,2-diethyl-3,4-dihydro-2H-chromen-4-yl]-3-(1-methyl-2-oxo-1,2,3,4-tetrahydroquinolin-7-yl)urea;
1-[(4R)-2,2-bis(fluoromethyl)-7-(trifluoromethyl)-3,4-dihydro-2H-chromen-4-yl]-3-(1-methyl-2-oxo-1,2,3,4-tetrahydroquinolin-7-yl)urea;
1-[(4R)-7,8-dichloro-2,2-diethyl-3,4-dihydro-2H-chromen-4-yl]-3-(1-methyl-2-oxo-1,2,3,4-tetrahydroquinolin-7-yl)urea;
1-[(4R)-2,2-dimethyl-7-(trifluoromethyl)-3,4-dihydro-2H-chromen-4-yl]-3-(1-methyl-2-oxo-1,2,3,4-tetrahydroquinolin-7-yl)urea;
1-[(4R)-6-fluoro-2,2-dipropyl-3,4-dihydro-2H-chromen-4-yl]-3-(1-methyl-2-oxo-1,2,3,4-tetrahydroquinolin-7-yl)urea;
1-[(4R)-6-fluoro-2,2-bis(fluoromethyl)-3,4-dihydro-2H-chromen-4-yl]-3-(1-methyl-2-oxo-1,2,3,4-tetrahydroquinolin-7-yl)urea;
1-[(4R)-6,8-difluoro-2,2-bis(fluoromethyl)-3,4-dihydro-2H-chromen-4-yl]-3-(1-methyl-2-oxo-1,2,3,4-tetrahydroquinolin-7-yl)urea;
1-[(4R)-6-fluoro-3,4-dihydrospiro[chromene-2,1'-cyclobutan]-4-yl]-3-(1-methyl-2-oxo-1,2,3,4-tetrahydroquinolin-7-yl)urea;
1-[(4R)-2,2-diethyl-6-fluoro-3,4-dihydro-2H-chromen-4-yl]-3-(1-methyl-2-oxo-1,2,3,4-tetrahydroquinolin-7-yl)urea;
1-[(4R)-8-fluoro-2,2-dipropyl-3,4-dihydro-2H-chromen-4-yl]-3-(1-methyl-2-oxo-1,2,3,4-tetrahydroquinolin-7-yl)urea;
1-[(4R)-2,2-diethyl-7-(trifluoromethoxy)-3,4-dihydro-2H-chromen-4-yl]-3-(1-methyl-2-oxo-1,2,3,4-tetrahydroquinolin-7-yl)urea;
1-[(4R)-7-chloro-8-fluoro-2,2-bis(fluoromethyl)-3,4-dihydro-2H-chromen-4-yl]-3-(1-methyl-2-oxo-1,2,3,4-tetrahydroquinolin-7-yl)urea;
1-[(4R)-6-fluoro-2,2-dimethyl-3,4-dihydro-2H-chromen-4-yl]-3-(1-methyl-2-oxo-1,2,3,4-tetrahydroquinolin-7-yl)urea;
1-[(4R)-8-chloro-7-fluoro-2,2-dimethyl-3,4-dihydro-2H-chromen-4-yl]-3-(1-methyl-2-oxo-1,2,3,4-tetrahydroquinolin-7-yl)urea;
1-(1-methyl-2-oxo-1,2,3,4-tetrahydroquinolin-7-yl)-3-[(4S)-7-(trifluoromethoxy)-3,4-dihydro-2H-chromen-4-yl]urea;
1-[(4R)-7-chloro-2,2-dimethyl-3,4-dihydro-2H-chromen-4-yl]-3-(1-methyl-2-oxo-1,2,3,4-tetrahydroquinolin-7-yl)urea;
1-(1-methyl-2-oxo-1,2,3,4-tetrahydroquinolin-7-yl)-3-[(4R)-7-(trifluoromethoxy)-3,4-dihydro-2H-chromen-4-yl]urea;
1-[(4R)-6-fluoro-2,2-bis(methoxymethyl)-3,4-dihydro-2H-chromen-4-yl]-3-(1-methyl-2-oxo-1,2,3,4-tetrahydroquinolin-7-yl)urea;
1-[(4R)-2,2-bis(fluoromethyl)-3,4-dihydro-2H-chromen-4-yl]-3-(1-methyl-2-oxo-1,2,3,4-tetrahydroquinolin-7-yl)urea;

1-[(4R)-8-fluoro-2,2-bis(fluoromethyl)-3,4-dihydro-2H-chromen-4-yl]-3-(1-methyl-2-oxo-1,2,3,4-tetrahydroquinolin-7-yl)urea;

1-[(4R)-6-fluoro-3,4-dihydro-2H-chromen-4-yl]-3-(1-methyl-2-oxo-1,2,3,4-tetrahydroquinolin-7-yl)urea;

1-(1-methyl-2-oxo-1,2,3,4-tetrahydroquinolin-7-yl)-3-[(4R)-8-(trifluoromethyl)-3,4-dihydro-2H-chromen-4-yl]urea;

1-[(4S)-6-fluoro-3,4-dihydrospiro[chromene-2,1'-cyclobutan]-4-yl]-3-(1-methyl-2-oxo-1,2,3,4-tetrahydroquinolin-7-yl)urea;

1-[(4S)-6-fluoro-2,2-dimethyl-3,4-dihydro-2H-chromen-4-yl]-3-(1-methyl-2-oxo-1,2,3,4-tetrahydroquinolin-7-yl)urea;

1-[(4R)-3,4-dihydrospiro[chromene-2,1'-cyclopentan]-4-yl]-3-(1-methyl-2-oxo-1,2,3,4-tetrahydroquinolin-7-yl)urea;

1-[(2S,4R)-2-(fluoromethyl)-2-methyl-7-(trifluoromethyl)-3,4-dihydro-2H-chromen-4-yl]-3-(1-methyl-2-oxo-1,2,3,4-tetrahydroquinolin-7-yl)urea;

1-[(2R,4R)-2-(fluoromethyl)-2-methyl-7-(trifluoromethyl)-3,4-dihydro-2H-chromen-4-yl]-3-(1-methyl-2-oxo-1,2,3,4-tetrahydroquinolin-7-yl)urea;

1-[(2S,4R)-7-chloro-2-(fluoromethyl)-2-methyl-3,4-dihydro-2H-chromen-4-yl]-3-(1-methyl-2-oxo-1,2,3,4-tetrahydroquinolin-7-yl)urea;

1-[(2S,4R)-2-(difluoromethyl)-2-methyl-3,4-dihydro-2H-chromen-4-yl]-3-(1-methyl-2-oxo-1,2,3,4-tetrahydroquinolin-7-yl)urea;

1-[(2R,4R)-2-(difluoromethyl)-2-methyl-3,4-dihydro-2H-chromen-4-yl]-3-(1-methyl-2-oxo-1,2,3,4-tetrahydroquinolin-7-yl)urea;

1-[(4R)-7-chloro-8-fluoro-2,2-dimethyl-3,4-dihydro-2H-chromen-4-yl]-3-(1-methyl-2-oxo-1,2,3,4-tetrahydroquinolin-7-yl)urea;

1-[(4R)-7-fluoro-2,2-bis(fluoromethyl)-3,4-dihydro-2H-chromen-4-yl]-3-(1-methyl-2-oxo-1,2,3,4-tetrahydroquinolin-7-yl)urea;

1-[(4R)-7-bromo-2,2-dimethyl-3,4-dihydro-2H-chromen-4-yl]-3-(1-methyl-2-oxo-1,2,3,4-tetrahydroquinolin-7-yl)urea;

1-(1-methyl-2-oxo-1,2,3,4-tetrahydroquinolin-7-yl)-3-[(2S,4R)-2-methyl-2-(trifluoromethyl)-3,4-dihydro-2H-chromen-4-yl]urea;

1-[(4R)-7,8-difluoro-2,2-dimethyl-3,4-dihydro-2H-chromen-4-yl]-3-(1-methyl-2-oxo-1,2,3,4-tetrahydroquinolin-7-yl)urea;

1-[(4R)-7-chloro-2,2-bis(fluoromethyl)-3,4-dihydro-2H-chromen-4-yl]-3-[3-(morpholin-4-yl)-2-oxo-1,2,3,4-tetrahydroquinolin-7-yl]urea;

1-[(4R)-7-fluoro-2,2-dimethyl-3,4-dihydro-2H-chromen-4-yl]-3-[3-(morpholin-4-yl)-2-oxo-1,2,3,4-tetrahydroquinolin-7-yl]urea;

1-[(4R)-7-chloro-2,2-bis(fluoromethyl)-3,4-dihydro-2H-chromen-4-yl]-3-[3-(1,4-oxazepan-4-yl)-2-oxo-1,2,3,4-tetrahydroquinolin-7-yl]urea;

1-[(4R)-7-fluoro-2,2-dimethyl-3,4-dihydro-2H-chromen-4-yl]-3-[3-(1,4-oxazepan-4-yl)-2-oxo-1,2,3,4-tetrahydroquinolin-7-yl]urea;

1-[(4R)-7-chloro-2,2-bis(fluoromethyl)-3,4-dihydro-2H-chromen-4-yl]-3-{3-[(2-hydroxyethyl)(methyl)amino]-2-oxo-1,2,3,4-tetrahydroquinolin-7-yl}urea;

1-[(4R)-7-fluoro-2,2-dimethyl-3,4-dihydro-2H-chromen-4-yl]-3-{3-[(2-methoxyethyl)(methyl)amino]-2-oxo-1,2,3,4-tetrahydroquinolin-7-yl}urea;

1-[(4R)-7-chloro-2,2-bis(fluoromethyl)-3,4-dihydro-2H-chromen-4-yl]-3-{3-[(2-methoxyethyl)(methyl)amino]-2-oxo-1,2,3,4-tetrahydroquinolin-7-yl}urea;

1-[(4R)-2,2-dimethyl-8-(trifluoromethyl)-3,4-dihydro-2H-chromen-4-yl]-3-[3-(2-hydroxyethyl)-2-oxo-1,2,3,4-tetrahydroquinazolin-7-yl]urea;

1-[(4R)-3,4-dihydro-2H-chromen-4-yl]-3-[3-(2-hydroxyethyl)-2-oxo-1,2,3,4-tetrahydroquinazolin-7-yl]urea;

1-[(4R)-2,2-bis(fluoromethyl)-7-(trifluoromethyl)-3,4-dihydro-2H-chromen-4-yl]-3-[3-(2-hydroxyethyl)-2-oxo-1,2,3,4-tetrahydroquinazolin-7-yl]urea;

1-[(4R)-6-fluoro-2,2-dipropyl-3,4-dihydro-2H-chromen-4-yl]-3-[3-(2-hydroxyethyl)-2-oxo-1,2,3,4-tetrahydroquinazolin-7-yl]urea;

1-[(4R)-8-fluoro-2,2-dipropyl-3,4-dihydro-2H-chromen-4-yl]-3-[3-(2-hydroxyethyl)-2-oxo-1,2,3,4-tetrahydroquinazolin-7-yl]urea;

1-[(4R)-8-chloro-7-fluoro-2,2-dimethyl-3,4-dihydro-2H-chromen-4-yl]-3-[3-(2-hydroxyethyl)-2-oxo-1,2,3,4-tetrahydroquinazolin-7-yl]urea;

1-[(4R)-7-chloro-2,2-dimethyl-3,4-dihydro-2H-chromen-4-yl]-3-[3-(2-hydroxyethyl)-2-oxo-1,2,3,4-tetrahydroquinazolin-7-yl]urea;

1-[(4R)-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea;

1-[(4R)-8-fluoro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea;

1-[(4R)-7-chloro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea;

1-[(4R)-3,4-dihydrospiro[chromene-2,1'-cyclopentan]-4-yl]-3-[3-(2-hydroxyethyl)-2-oxo-1,2,3,4-tetrahydroquinazolin-7-yl]urea;

1-[(2S,4R)-2-(difluoromethyl)-2-methyl-3,4-dihydro-2H-chromen-4-yl]-3-[3-(2-hydroxyethyl)-2-oxo-1,2,3,4-tetrahydroquinazolin-7-yl]urea;

1-[(4R)-7-fluoro-2,2-bis(fluoromethyl)-3,4-dihydro-2H-chromen-4-yl]-3-[3-(2-hydroxyethyl)-2-oxo-1,2,3,4-tetrahydroquinazolin-7-yl]urea;

1-[(4R)-2,2-bis(fluoromethyl)-7-(trifluoromethyl)-3,4-dihydro-2H-chromen-4-yl]-3-(2-oxo-1,2,3,4-tetrahydroquinolin-7-yl)urea;

1-[(2R,4R)-7-chloro-2-(difluoromethyl)-2-methyl-3,4-dihydro-2H-chromen-4-yl]-3-(3-oxo-3,4-dihydro-2H-1,4-benzoxazin-6-yl)urea;

1-[(2S,4R)-7-chloro-2-(difluoromethyl)-2-methyl-3,4-dihydro-2H-chromen-4-yl]-3-(3-oxo-3,4-dihydro-2H-1,4-benzoxazin-6-yl)urea;

1-[(4R)-7-chloro-2,2-bis(fluoromethyl)-3,4-dihydro-2H-chromen-4-yl]-3-(3-oxo-3,4-dihydro-2H-1,4-benzoxazin-8-yl)urea;

1-[(4R)-2,2-bis(fluoromethyl)-7-(trifluoromethyl)-3,4-dihydro-2H-chromen-4-yl]-3-(3-oxo-3,4-dihydro-2H-1,4-benzoxazin-6-yl)urea;

1-[(4R)-7-chloro-8-fluoro-2,2-dimethyl-3,4-dihydro-2H-chromen-4-yl]-3-(3-oxo-3,4-dihydro-2H-1,4-benzoxazin-6-yl)urea;

1-(1-methyl-2-oxo-1,2,3,4-tetrahydroquinolin-7-yl)-3-[(2R,4R)-2-methyl-2-(trifluoromethyl)-3,4-dihydro-2H-chromen-4-yl]urea; and 1-[(2S,4R)-7-chloro-2-(difluoromethyl)-2-methyl-3,4-dihydro-2H-chromen-4-yl]-3-(1-methyl-2-oxo-1,2,3,4-tetrahydroquinazolin-5-yl)urea.

22. The compound of claim 1, or a salt thereof, wherein the compound when administered to a human subject produces an increase in average time for hand withdrawal from a temperature-controlled water bath relative to a vehicle control that is less than about 30 seconds.

23. The compound of claim 1, or a salt thereof, wherein the compound when tested in a rat tail immersion model of noxious thermosensation produces a percent increase in average response latency for tail withdrawal relative to a vehicle control that is less than about 20%.

24. The compound of claim 1, or a salt thereof, wherein the compound when contacted in vitro at a concentration of 10 µM with human TRPV1 receptor blocks intracellular calcium flux relative to intracellular calcium flux measured in vitro for human TRPV1 receptor at a pH of about 5.0 in the absence of such compound by less than about 75%.

25. The compound of claim 1, or a salt thereof, wherein the compound:
   (a) when tested in a rat tail immersion model of noxious thermosensation produces a percent increase in average response latency for tail withdrawal relative to a vehicle control that is less than about 20%; and
   (b) when contacted in vitro at a concentration of 10 µM with human TRPV1 receptor blocks intracellular calcium flux relative to intracellular calcium flux measured in vitro for human TRPV1 receptor at a pH of about 5.0 in the absence of such compound by less than about 75%.

26. A pharmaceutical composition comprising a therapeutically effective amount of a compound of formula (I-f) according to claim 1, or a pharmaceutically acceptable salt thereof, in combination with a pharmaceutically acceptable carrier.

27. The pharmaceutical composition according to claim 26 further comprising an analgesic or a nonsteroidal anti-inflammatory drug, or a combination thereof.

28. A method for treating pain comprising administering a therapeutically effective amount of a compound of formula (I-f) according to claim 1, or a pharmaceutically acceptable salt thereof, to a subject in need thereof.

29. The method according to claim 28 further comprising the step of co-administering with an analgesic or a nonsteroidal anti-inflammatory drug, or a combination thereof.

30. The method according to claim 29 wherein the nonsteroidal anti-inflammatory drug is ibuprofen.

31. A method for treating an inflammatory state selected from the group consisting of burns, rheumatoid arthritis, and osteoarthritis, the method comprising administering a therapeutically effective amount of a compound of formula (I-f) according to claim 1, or a pharmaceutically acceptable salt thereof, to a subject in need thereof.

\* \* \* \* \*